(12) United States Patent
Abe et al.

(10) Patent No.: US 9,708,320 B2
(45) Date of Patent: Jul. 18, 2017

(54) β-LACTAMASE INHIBITOR AND PROCESS FOR PREPARING THE SAME

(71) Applicant: MEIJI SEIKA PHARMA CO., LTD., Chuo-ku, Tokyo (JP)

(72) Inventors: Takao Abe, Kanagawa (JP); Takeshi Furuuchi, Kanagawa (JP); Yoshiaki Sakamaki, Kanagawa (JP); Seiichi Inamura, Kanagawa (JP); Akihiro Morinaka, Kanagawa (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/872,988

(22) Filed: Oct. 1, 2015

(65) Prior Publication Data

US 2016/0024090 A1    Jan. 28, 2016

Related U.S. Application Data

(62) Division of application No. 14/404,288, filed as application No. PCT/JP2013/064971 on May 30, 2013, now Pat. No. 9,181,250.

(30) Foreign Application Priority Data

May 30, 2012 (JP) .................. 2012-122603

(51) Int. Cl.
| C07D 211/06 | (2006.01) |
| C07D 295/00 | (2006.01) |
| C07D 471/08 | (2006.01) |
| C07D 211/60 | (2006.01) |
| A61K 45/06 | (2006.01) |
| A61K 31/43 | (2006.01) |
| A61K 31/545 | (2006.01) |
| A61K 31/546 | (2006.01) |
| A61K 31/439 | (2006.01) |
| A61K 31/444 | (2006.01) |
| A61K 31/4545 | (2006.01) |
| A61K 31/5377 | (2006.01) |
| A61K 31/437 | (2006.01) |
| A61K 31/407 | (2006.01) |
| A61K 31/4162 | (2006.01) |

(Continued)

(52) U.S. Cl.
CPC .......... *C07D 471/08* (2013.01); *A61K 31/407* (2013.01); *A61K 31/4162* (2013.01); *A61K 31/427* (2013.01); *A61K 31/43* (2013.01); *A61K 31/437* (2013.01); *A61K 31/439* (2013.01); *A61K 31/444* (2013.01); *A61K 31/4545* (2013.01); *A61K 31/5377* (2013.01); *A61K 31/545* (2013.01); *A61K 31/546* (2013.01); *A61K 45/06* (2013.01); *C07D 211/60* (2013.01); *C07F 7/0812* (2013.01); *Y02P 20/55* (2015.11)

(58) Field of Classification Search
CPC ............................. C07D 211/06; C07D 295/00
USPC ........................................................ 546/184
See application file for complete search history.

(56) References Cited

U.S. PATENT DOCUMENTS

| 7,112,592 B2 | 9/2006 | Lampilas et al. |
| 7,612,087 B2 | 11/2009 | Aszodi et al. |
| 7,638,529 B2 | 12/2009 | Lampilas et al. |

(Continued)

FOREIGN PATENT DOCUMENTS

| EP | 0213595 | 3/1987 |
| JP | 2004505088 A | 2/2004 |

(Continued)

OTHER PUBLICATIONS

U.S. Appl. No. 15/027,956; First Named Inventor: Takao Abe; Title: "Crystalline Forms of Diazabicyclooctane Derivative and Production Process Thereof"; filed Apr. 7, 2016.

(Continued)

*Primary Examiner* — Niloofar Rahmani
(74) *Attorney, Agent, or Firm* — Holtz, Holtz & Volek PC

(57) ABSTRACT

A diazabicyclooctane compound, which is a beta-lactame inhibitor, represented by the following formula (I):

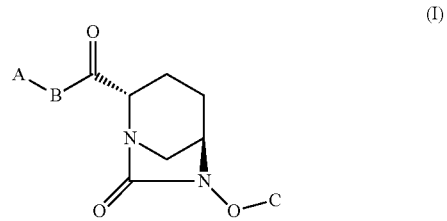

wherein A represents Ra(Rb)N— or RcO—; B represents NH or $NC_{1-6}$ alkyl; C represents benzyl, H or $SO_3M$, wherein M represents H, an inorganic or an organic cation; Ra and Rb represent H, $C_{1-6}$ alkyl or acyl; Rc represents $C_{1-6}$ alkyl or a heterocyclyl; A is unsubstituted or substituted with 0 to 4 substituents Fn1, wherein Fn1 represents $C_{1-6}$ alkyl, O=, or Rg-$(CH_2)_{0-3}$—, wherein Rg represents a heterocyclyl, phenyl, heteroaryl, acyl, $RdO_2S$—, Re(Rf)N—, Re(Rf)NCO—, ReO—, ReOCO— or a protective group, wherein Rd represents $C_{1-6}$ alkyl or MO—; Re and Rf represent H or $C_{1-6}$ alkyl, and a heterocycle having at least one nitrogen atom may be formed between Ra and Rb, between Rc and B, or between Re and Rf.

11 Claims, 3 Drawing Sheets

(51) Int. Cl.
*A61K 31/427* (2006.01)
*C07F 7/08* (2006.01)

(56) References Cited

U.S. PATENT DOCUMENTS

| | | | |
|---|---|---|---|
| 7,732,610 | B2 | 6/2010 | Lampilas et al. |
| 8,178,554 | B2 | 5/2012 | Lampilas et al. |
| 8,288,553 | B2 | 10/2012 | Priour et al. |
| 8,471,025 | B2 | 6/2013 | Dedhiya et al. |
| 8,487,093 | B2 | 7/2013 | Blizzard et al. |
| 8,772,490 | B2 | 7/2014 | Abe et al. |
| 8,796,257 | B2* | 8/2014 | Maiti .................. C07D 519/00 514/210.21 |
| 8,822,450 | B2* | 9/2014 | Patel .................. A61K 31/4545 514/119 |
| 8,829,191 | B2 | 9/2014 | Ronsheim et al. |
| 8,835,455 | B2 | 9/2014 | Dedhiya et al. |
| 8,877,743 | B2 | 11/2014 | Maiti et al. |
| 8,969,566 | B2 | 3/2015 | Ronsheim et al. |
| 9,006,230 | B2* | 4/2015 | Bhagwat .................. A61K 31/46 514/211.05 |
| 9,035,062 | B2 | 5/2015 | Abe et al. |
| 9,062,053 | B2 | 6/2015 | Dedhiya et al. |
| 9,284,273 | B2 | 3/2016 | Abe et al. |
| 9,284,314 | B2 | 3/2016 | Ronsheim et al. |
| 2003/0199541 | A1 | 10/2003 | Lampilas et al. |
| 2003/0220521 | A1 | 11/2003 | Reitz et al. |
| 2005/0020572 | A1 | 1/2005 | Aszodi et al. |
| 2005/0245505 | A1 | 11/2005 | Aszodi et al. |
| 2006/0046995 | A1 | 3/2006 | Lampilas et al. |
| 2006/0189652 | A1 | 8/2006 | Lampilas et al. |
| 2007/0299108 | A1 | 12/2007 | Aszodi et al. |
| 2009/0215747 | A1 | 8/2009 | Aszodi et al. |
| 2010/0048528 | A1 | 2/2010 | Aszodi et al. |
| 2010/0087648 | A1 | 4/2010 | Lampilas et al. |
| 2010/0197928 | A1 | 8/2010 | Priour et al. |
| 2011/0021772 | A1 | 1/2011 | Lampilas et al. |
| 2011/0046102 | A1 | 2/2011 | Ledoussal et al. |
| 2011/0152311 | A1 | 6/2011 | Dedhiya et al. |
| 2011/0213147 | A1 | 9/2011 | Lampilas et al. |
| 2011/0245254 | A1 | 10/2011 | Aszodi et al. |
| 2011/0294777 | A1 | 12/2011 | Blizzard et al. |
| 2012/0053350 | A1 | 3/2012 | Mangion et al. |
| 2013/0012712 | A1 | 1/2013 | Priour et al. |
| 2013/0267480 | A1 | 10/2013 | Dedhiya et al. |
| 2013/0274475 | A1 | 10/2013 | Mangion et al. |
| 2014/0221341 | A1 | 8/2014 | Maiti et al. |
| 2014/0288051 | A1 | 9/2014 | Maiti et al. |
| 2015/0246920 | A1 | 9/2015 | Dedhiya et al. |
| 2016/0264573 | A1* | 9/2016 | Abe .................. C07D 401/12 |
| 2016/0272641 | A1* | 9/2016 | Abe .................. A61K 31/439 |

FOREIGN PATENT DOCUMENTS

| | | | |
|---|---|---|---|
| JP | 2005518333 | A | 6/2005 |
| JP | 2005523897 | A | 8/2005 |
| JP | 2010138206 | A | 6/2010 |
| JP | 4515704 | B2 | 8/2010 |
| JP | 2010539147 | A | 12/2010 |
| JP | 2011510012 | A | 3/2011 |
| JP | 2011518871 | A | 6/2011 |
| JP | 2011207900 | A | 10/2011 |
| JP | 2012504593 | A | 2/2012 |
| JP | 5038509 | B2 | 10/2012 |
| WO | 0210172 | A1 | 2/2002 |
| WO | 02100860 | A2 | 12/2002 |
| WO | 03063864 | A2 | 8/2003 |
| WO | 2009090320 | A1 | 7/2009 |
| WO | 2009091856 | A2 | 7/2009 |
| WO | 2009133442 | A1 | 11/2009 |
| WO | 2010038115 | A1 | 4/2010 |
| WO | 2010126820 | A2 | 11/2010 |
| WO | 2011042560 | A1 | 4/2011 |
| WO | 2012086241 | A1 | 6/2012 |
| WO | 2012172368 | A1 | 12/2012 |
| WO | 2013030735 | A1 | 3/2013 |

OTHER PUBLICATIONS

U.S. Appl. No. 15/007,906, Title: "Compounds Useful for Producing an Optically Active Diazabicyclooctane Compound", filed Jan. 27, 2016, First Named Inventor: Takao Abe.

U.S. Appl. No. 15/023,976, Title: "Process for Producing Diazabicyclooctane Derivative and Intermediate Thereof", filed Mar. 22, 2016, First Named Inventor: Takao Abe.

Noriaki Hirayama, "Organic Compound Crystal Produced Handbook: Management and Know-How", Maruzen Co., Ltd., Jul. 25, 2008, pp. 57-84.

Baldwin, et al., "A Novel Entry to Carbenoid Species via β-Ketosulfoxonium Ylides", Journal of the Chemical Society, Chemical Communications, 1993, pp. 1434-1435.

Dolence, et al., "Synthesis and Siderophore Activity of Albomycin-like Peptides Derived from N5-Acetyl-N5-hydroxy-L-ornithine", Journal of Medicinal Chemistry, 1991, vol. 34, No. 3, pp. 956-968.

Freed, et al., "Synthesis of 5-Ketopipecolic Acid from Glutamic Acid", The Journal of Organic Chemistry, Dec. 1960, vol. 25, No. 12, pp. 2105-2107.

Jung, et al., "Diastereoselective synthesis of (2S,5S)- and (2S,5R)-N-benzyloxycarbonyl-5-hydroxypipecolic acids from trans-4-hydroxy-L-proline", Tetrahedron: Asymmetry 17 (2006), pp. 2479-2486.

King, et al., "The Chemistry of Extractives from Hardwoods. Part III. Baikiain, an Amino-acid Present in Baikiaea plurijuga", Journal of the Chemical Society, 1950, pp. 3590-3597.

Mangion, et al., "Iridium-Catalyzed X-H Insertions of Sulfoxonium Ylides", Organic Letters, 2009, vol. 11, No. 16, pp. 3566-3569.

Witkop, et al., "The Configuration of 5-Hydroxypipecolic Acid from Dates", Journal of the American Chemical Society, Jan. 5, 1957, vol. 79, No. 1, pp. 192-197.

Brown et al, "Some Active Derivatives of Penicillin", Applied Microbiology 1969, vol. 17, No. 3, pp. 339-343.

International Search Report issued in International Application No. PCT/JP2013/064971.

Mangion et al, "A Concise Synthesis of a β-Lactamase Inhibitor", Organic Letters, 2011, vol. 13, No. 20, pp. 5480-5483.

Cerfontain, et al., "Sulfur Trioxide", Encyclopedia of Reagents for Organic Synthesis, vol. 7, edited by Leo A. Paquette, 1995, John Wiley and Sons, pp. 4699-4702.

Knight, "N-Hydroxysuccinimide", Encyclopedia of Reagents for Organic Synthesis, vol. 4, Edited by Leo A. Paquette, 1995, John Wiley and Sons, pp. 2780-2781.

McIntosh, "Sulfur Troxide-1, 4-Dioxane", Encyclopedia of Reagents for Organic Synthesis, vol. 7, Edited by Leo A. Paquette, 1995, John Wiley and Sons, pp. 4702-4703.

Tidwell, "Sulfur Trioxide-Pyridine", Encyclopedia of Reagents for Organic Synthesis, vol. 7, Edited by Leo A Paquette, 1995, John Wiley and Sons, pp. 4703-4704.

Caira, "Crystalline Polymorphism of Organic Compounds", Topics in Current Chemistry, Springer, Berlin, DE, vol. 198, Jan. 1, 1998: pp. 163-208.

* cited by examiner

Antibacterial activities to 5 strains of AmpC constitutive expression, Enterobacteriaceae Antibacterial activities to 5 strains of IMP type metallo-β-lactamase producing strain, Enterobacteriaceae Antibacterial activities to 5 strains of CTX-M-15 (ESBL) producing strain, E. coli

β-LACTAMASE INHIBITOR AND PROCESS FOR PREPARING THE SAME

CROSS-REFERENCE TO RELATED APPLICATIONS

This application is a Divisional application of U.S. application Ser. No. 14/404,288, filed Nov. 26, 2014 (U.S. Pat. No. 9,181,250), which is a U.S. National Stage application of International Application No. PCT/JP2013/064971, filed May 30, 2013, which claims priority of Japanese Application No. 2012-122603, filed May 30, 2012, the entire contents of all of which are incorporated by reference herein.

TECHNICAL FIELD

The present invention relates to a novel diazabicyclooctane derivative represented by the formula (I), a pharmaceutically acceptable salt thereof or a solvate thereof. The present invention also relates to a process for preparing the same, and a use thereof as a β-lactamase inhibitor for the treatment of bacterial infection. The present invention further relates to a pharmaceutical composition and a method of treating bacterial infection using the compound of the present invention.

BACKGROUND ART

Penicillins and cephalosporins are β-lactam antibiotics which are most widely and frequently used in the clinic. However, the acquisition of resistance to β-lactam antibiotics by various pathogens severely has had a damaging effect on maintaining the effective treatment of bacterial infections. The most significant known mechanism related to the acquisition of bacterial resistance is the production of class A, C, and D β-lactamases having a serine residue at the active center. These enzymes decompose the β-lactam antibiotic, resulting in the loss of the antimicrobial activities. Class A β-lactamases preferentially hydrolyze penicillins while class C β-lactamases have a substrate profile favoring cephalosporins. As commercially available β-lactamase inhibitors, clavulanic acid, sulbactam, and tazobactam are known, and these inhibitors are effective mainly against class A β-lactamase producing bacteria, and used as a mixture with a penicillin antibiotic. However, 250 types or more of β-lactamases have been reported to date, and among them, in addition to the expansion of class C β-lactamases as well as extended-spectrum β-lactamase (ESBL) belonging to class A and D β-lactamases, further resistant bacteria which produce class A KPC-2 β-lactamase decomposing even carbapenem as a last resort for β-lactam antibiotic is being considered as a problem. The development of a novel inhibitor is strongly demanded as the commercially available inhibitors are ineffective against these β-lactamases.

Also, in recent years, infectious diseases caused by the above-mentioned resistant bacteria as pathogenic bacteria are found not only in severe infectious disease but also occasionally in community-acquired infectious disease, so that the development of a novel inhibitor which can be used in combination with the drug of first alternative (for example, penicillins or cephalosporins) in a city is strongly demanded. However, although there are a report of potential inhibitors and a report for treating severe infectious disease, there are only a few candidates under development.

In recent years, U.S. Pat. No. 7,112,592 (Patent document 1), U.S. Pat. No. 7,612,087 (Patent document 2) and WO 2009/091856 (Patent document 3) have disclosed that certain kinds of diazabicyclooctane derivatives are promising compounds in the treatment of infectious diseases as an antibiotic having non-β-lactam structure or a β-lactamase inhibitor. As a process for preparing the same, in addition to the above-mentioned documents, the process disclosed in WO 2010/126820 A2 (Patent document 4) has been known.

PRIOR ART DOCUMENTS

Patent Documents

[Patent document 1] U.S. Pat. No. 7,112,592
[Patent document 2] U.S. Pat. No. 7,612,087
[Patent document 3] WO 2009/091856 A2
[Patent document 4] WO 2010/126820 A2

DISCLOSURE OF THE INVENTION

Problems to be Solved by the Invention

The currently available β-lactamase inhibitors are insufficient to inhibit the incessantly increasing β-lactamase, and novel β-lactamase inhibitors have been required today for the difficult treatment for bacterial infectious diseases caused by resistant bacteria which produce class C β-lactamase, extended-spectrum β-lactamase (ESBL) belonging to class A and D, or class A KPC-2 decomposing even carbapenem as a last resort for β-lactam antibiotic.

Means for Solving the Problems

The present inventors have carried out research studies about a novel β-lactamase inhibitor effective for the β-lactamase producing bacteria presently causing the problems as mentioned above, particularly for the class A, class C and class D β-lactamases, and as a result, a novel diazabicyclooctane derivative represented by the formula (I) has been found. It has also been found that the compound of the present invention potently recover the antimicrobial activity of a β-lactam antibiotic against the resistant bacteria when used in combination with the β-lactam antibiotic.

Also, here has been established the preparation method of the compound represented by the formula (II), which is included in the formula (I) of the present invention:

[Chemical formula 1]

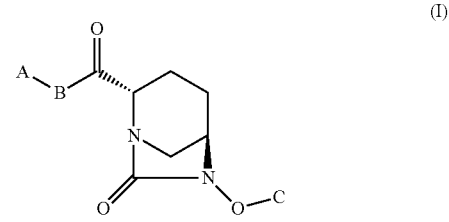

(I)

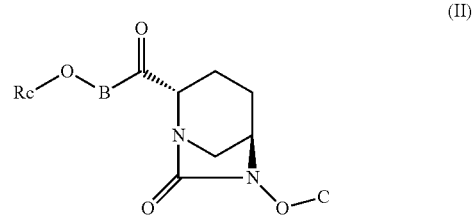

(II)

in the above formulae (I) and (II), A represents Ra(Rb)N— or RcO—; B represents NH or NC$_{1-6}$ alkyl; C represents benzyl, H or SO$_3$M, where M represents H, an inorganic cation or an organic cation; Ra and Rb each independently represent H, C$_{1-6}$ alkyl or acyl; Rc represents C$_{1-6}$ alkyl or a heterocyclyl; A may be modified by 0 to 4 substituents Fn1, where the substituent Fn1 may be substituted continuously; Fn1 represents C$_{1-6}$ alkyl, O= or Rg-(CH$_2$)$_{0-3}$—, where Rg represents a heterocyclyl, phenyl, heteroaryl, acyl, RdO$_2$S—, Re(Rf)N—, Re(Rf)NCO—, ReO—, ReOCO— or a protective group, where Rd represents C$_{1-6}$ alkyl or MO—; Re and Rf each independently represent H or C$_{1-6}$ alkyl, and further, between Ra and Rb, between Rc and B, and between Re and Rf may be closed by the bonding to form a heterocyclyl having at least one nitrogen atom.

At first, for the research of a preparation method to obtain the compound represented by the above-mentioned formula (II), even when the method in which a phosgene equivalent and an amine are used as disclosed in U.S. Pat. No. 7,112,592 or U.S. Pat. No. 7,612,087 or the method in which the compound is treated with triphosgene and a 10% aqueous phosphoric acid solution as disclosed in WO 2009/133442 A1 or WO 2010/126820 A2 is applied to the compound represented by the formula (IV-c):

[Chemical formula 2]

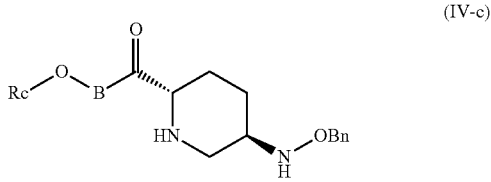

(IV-c)

in the above formula (IV-c), Rc and B have the same meanings as defined for the compound of the formula (II), and OBn represents benzyloxy, the compound represented by the above formula (IV-c) has N-alkoxycarbamoyl showing weak acidity in the side chain at the 2-position, so that the compound having a diazabicyclooctane structure represented by the following formula (IIa):

[Chemical formula 3]

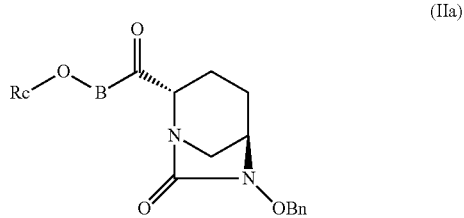

(IIa)

in the above formula (IIa), Rc and B have the same meanings as defined for the compound of the formula (II), and OBn represents benzyloxy, can be prepared only by an extremely minor yield.

Also, the method disclosed in WO 2009/133442 A1 or WO 2010/126820 A2 introduces the side chain at the 2-position at the initial stage of the preparation process, which is not so inexpensive, so that the method is not necessarily efficient as a commercial manufacturing process, and establishment of a preparation process which can be easily industrialized has been desired.

Thus, the present inventors have found the compounds represented by the following formula (IV-a2), (IV-a3) or (IV-a4):

[Chemical formula 4]

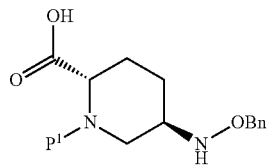

(IV-a2) P$^1$ = TFA
(IV-a3) P$^1$ = Boc
(IV-a4) P$^1$ = Teoc in the above formulae (IV-a2), (IV-a3) or (IV-a4), TFA represents trifluoroacetyl, Boc represents tert-butoxycarbonyl, Teoc represents 2-trimethylsilylethoxycarbonyl, and OBn represents benzyloxy,
as more useful starting materials, and earnestly studied to lead them to the compounds of the above formula (IV-c) and the above formula (IIa).

As a result, here has been established the process for preparing a compound represented by the following formula (III):

[Chemical formula 5]

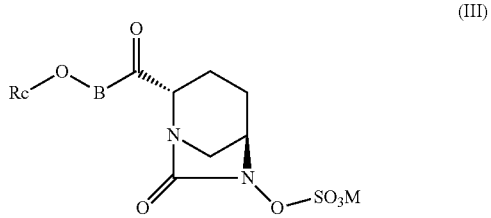

(III)

in the above formula (III), Rc, B and M have the same meanings as defined for the compound of the above formula (II),
which is included in the compound of the above formula (II).

That is, the present invention is directed to
(1) a diazabicyclooctane derivative represented by the following formula (I):

[Chemical formula 6]

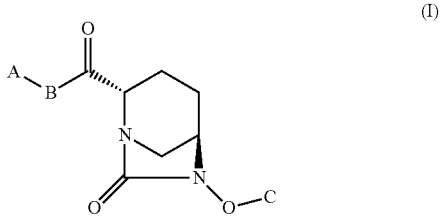

(I)

in the above formula (I), A represents Ra(Rb)N— or RcO—; B represents NH or NC$_{1-6}$ alkyl; C represents benzyl, H or SO$_3$M, where M represents H, an inorganic cation or an organic cation; Ra and Rb each independently represent H, C$_{1-6}$ alkyl or acyl; Rc represents C$_{1-6}$ alkyl or a heterocyclyl;

A may be modified by 0 to 4 substituents Fn1, where the substituent Fn1 may be substituted continuously; Fn1 represents $C_{1-6}$ alkyl, O= or Rg-$(CH_2)_{0-3}$—, where Rg represents a heterocyclyl, phenyl, heteroaryl, acyl, $RdO_2S$—, Re(Rf)N—, Re(Rf)NCO—, ReO—, ReOCO— or a protective group, where Rd represents $C_{1-6}$ alkyl or MO—; Re and Rf each independently represent H or $C_{1-6}$ alkyl, and further, between Ra and Rb, between Rc and B, and between Re and Rf may be closed by the bonding to form a heterocyclyl having at least one nitrogen atom, a pharmaceutically acceptable salt thereof, or a solvate thereof.

Also, according to the other embodiment of the present invention, it is directed to
(2) a diazabicyclooctane derivative represented by the following formula (II):

[Chemical formula 7]

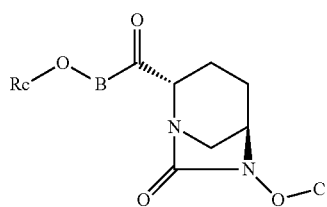

(II)

in the above formula (II), Rc represents $C_{1-6}$ alkyl or a heterocyclyl; B represents NH or $NC_{1-6}$ alkyl; C represents benzyl, H or $SO_3M$, where M represents H, an inorganic cation or an organic cation; Rc may be modified by 0 to 4 substituents Fn1, where the substituent Fn1 may be substituted continuously; Fn1 represents $C_{1-6}$ alkyl, O= or Rg-$(CH_2)_{0-3}$—, where Rg represents a heterocyclyl, phenyl, heteroaryl, acyl, $RdO_2S$—, Re(Rf)N—, Re(Rf)NCO—, ReO—, ReOCO— or a protective group, where Rd represents $C_{1-6}$ alkyl or MO—; Re and Rf each independently represent H or $C_{1-6}$ alkyl, and further, between Rc and B, and between Re and Rf may be closed by the bonding to form a heterocyclyl having at least one nitrogen atom,
a pharmaceutically acceptable salt thereof, or a solvate thereof,
which is included in the above formula (I).

Also, according to the further embodiment of the present invention, it is directed to
(3) a novel diazabicyclooctane derivative represented by the following formula (IIa):

[Chemical formula 8]

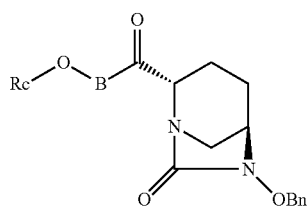

(IIa)

in the above formula (IIa), OBn represents benzyloxy, and Rc and B have the same meanings as defined for the above formula (II),
a pharmaceutically acceptable salt thereof or a solvate thereof,
which is included in the above formula (II).

Also, according to still further embodiment of the present invention, it is directed to
(4) a diazabicyclooctane derivative represented by the following formula (IIb):

[Chemical formula 9]

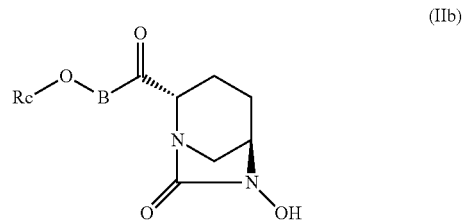

(IIb)

in the above formula (IIb), Rc and B have the same meanings as defined for the above formula (II),
a pharmaceutically acceptable salt thereof or a solvate thereof,
which is included in the above formula (II).

Also, according to still further embodiment of the present invention, it is directed to
(5) a diazabicyclooctane derivative represented by the following formula (III):

[Chemical formula 10]

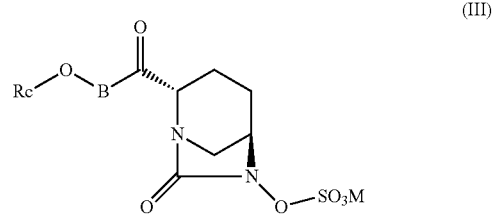

(III)

in the above formula (III), Rc, B and M have the same meanings as defined for the above formula (II),
a pharmaceutically acceptable salt thereof, or a solvate thereof,
which is included in the above formula (II).

Further, another embodiment of the present invention is directed to
(6) the compound of any one of the above (1) to (5), which is represented by one of the following formulae:

[Chemical formula 11]

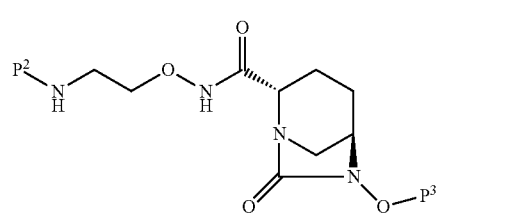

(II-059), (II-060), (II-109)

in the above formulae, P² represents tert-butoxycarbonyl (Boc), benzyloxycarbonyl (Cbz) or H; P³ represents benzyl (Bn), H or SO₃M; where M represents H, sodium, pyridinium or tetrabutylammonium, a pharmaceutically acceptable salt thereof or a solvate thereof.

Also, another embodiment of the present invention is directed to (7) the compound of any one of the above (1) to (3), which is (2S,5R)-N-(2-aminoethoxy)-7-oxo-6-(sulfooxy)-1,6-diazabicyclo[3.2.1]octane-2-carboxamide, (2S,5R)-N-[2-(methylamino)ethoxy]-7-oxo-6-(sulfooxy)-1,6-diazabicyclo[3.2.1]octane-2-carboxamide, (2S,5R)-7-oxo-N-[2-(propan-2-ylamino)ethoxy]-6-(sulfooxy)-1,6-diazabicyclo[3.2.1]-octane-2-carboxamide, (2S,5R)-N-[2-(dimethylamino)ethoxy]-7-oxo-6-(sulfooxy)-1,6-diazabicyclo[3.2.1]-octane-2-carboxamide, (2S,5R)-N-{[(2S)-2-aminopropyl]oxy}-7-oxo-6-(sulfooxy)-1,6-diazabicyclo[3.2.1]-octane-2-carboxamide, (2S,5R)-N-{[(2R)-2-aminopropyl]oxy}-7-oxo-6-(sulfooxy)-1,6-diazabicyclo[3.2.1]-octane-2-carboxamide, (2S,5R)-N-(3-aminopropoxy)-7-oxo-6-(sulfooxy)-1,6-diazabicyclo[3.2.1]octane-2-carboxamide, (2S,5R)-N-[(2S)-azetidin-2-ylmethoxy]-7-oxo-6-(sulfooxy)-1,6-diazabicyclo[3.2.1]-octane-2-carboxamide, (2S,5R)-7-oxo-N-[(2R)-pyrrolidin-2-ylmethoxy]-6-(sulfooxy)-1,6-diazabicyclo[3.2.1]-octane-2-carboxamide, (2S,5R)-7-oxo-N-[(2S)-piperidin-2-ylmethoxy]-6-(sulfooxy)-1,6-diazabicyclo[3.2.1]-octane-2-carboxamide, (2S,5R)-7-oxo-N-[(3S)-pyrrolidin-3-yloxy]-6-(sulfooxy)-1,6-diazabicyclo[3.2.1]octane-2-carboxamide, or (2S,5R)-N-(azetidin-3-ylmethoxy)-7-oxo-6-(sulfooxy)-1,6-diazabicyclo[3.2.1]octane-2-carboxamide, a pharmaceutically acceptable salt thereof, or a solvate thereof.

Also, according to another embodiment of the present invention, it is directed to (8) a pharmaceutical composition comprising the diazabicyclooctane derivative represented by the above formula (I), a pharmaceutically acceptable salt thereof or a solvate thereof, and, optionally, a pharmaceutically acceptable carrier.

Further, according to another embodiment of the present invention, it is directed to (9) a pharmaceutical composition according to (8) for administration in combination with a β-lactam antibiotic.

Moreover, according to another embodiment of the present invention, it is directed to (10) a pharmaceutical composition according to (8) or (9) for treating bacterial infection.

Also, according to still further embodiment of the present invention, it is directed to (11) a β-lactamase inhibitor comprising the diazabicyclooctane derivative represented by the above formula (I), a pharmaceutically acceptable salt thereof or a solvate thereof.

According to still further embodiment of the present invention, it is directed to (12) a pharmaceutical composition comprising the above β-lactamase inhibitor, a β-lactam antibiotics, and, optionally, a pharmaceutically acceptable carrier.

Moreover, according to still further embodiment of the present invention, provided is (13) a pharmaceutical composition comprising the above β-lactamase inhibitor, a β-lactam antibiotic selected from the group consisting of ampicillin, amoxicillin, piperacillin, ticarcillin, flomoxef, cefotaxim, ceftriaxone, ceftazidime, cefepime, ceftaroline, ceftolozane, imipenem, meropenem, biapenem, doripenem, ertapenem and aztreonam, and, optionally, a pharmaceutically acceptable carrier.

Also, according to still further embodiment of the present invention, it is directed to a method for treating bacterial infection, and provided (14) the method for treating bacterial infection which comprises administering the above β-lactamase inhibitor and a β-lactam antibiotic in combination.

Further, according to still further embodiment of the present invention, it is directed to a method for treating bacterial infection, and provided (15) the method for treating bacterial infection which comprises administering the β-lactamase inhibitor, and a β-lactam antibiotic selected from the group consisting of ampicillin, amoxicillin, piperacillin, ticarcillin, flomoxef, cefotaxim, ceftriaxone, ceftazidime, cefepime, ceftaroline, ceftolozane, imipenem, meropenem, biapenem, doripenem, ertapenem and aztreonam, in combination.

Moreover, according to another embodiment of the present invention, it is directed to a method for treating bacterial infection, and provided the method for treating a single or mixed bacterial infection caused by at least one of *Escherichia coli*, *Klebsiella pneumoniae*, *Enterobacter croacare*, *Citrobacter freundii*, *Serratia marcescens*, *Morganella morganii*, *Pseudomonas aeruginosa* and *Acinetobacter baumannii*, which comprises administering the β-lactamase inhibitor, and a β-lactam antibiotic selected from the group consisting of ampicillin, amoxicillin, piperacillin, ticarcillin, flomoxef, cefotaxim, ceftriaxone, ceftazidime, cefepime, ceftaroline, ceftolozane, imipenem, meropenem, biapenem, doripenem, ertapenem and aztreonam, in combination.

Further, according to another embodiment of the present invention, it is directed to a process for preparing the compound represented by the following formula (III):

[Chemical formula 12]

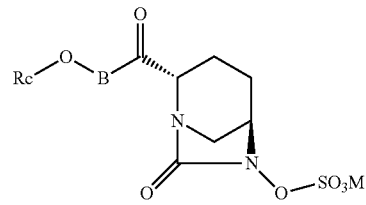

in the above formula (III), Rc, B and M have the same meanings as defined for the above formula (II), which is included in the above formula (II), which comprises (16) subjecting to coupling a compound represented by the following formula (IV-a):

[Chemical formula 13]

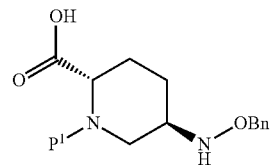

in the above formula (IV-a), P¹ represents a protective group which can be removed by an acid, a base or a nucleophilic agent; and OBn represents benzyloxy, with a compound: RcOBH using an active ester, an active amide or a dehydration condensing agent to prepare a compound represented by the following formula (IV-b):

[Chemical formula 14]

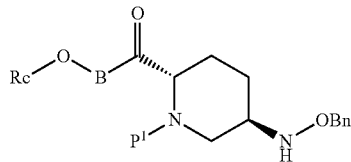

in the above formula (IV-b), P¹ represents a protective group which can be removed by an acid, a base or a nucleophilic agent; Rc and B have the same meanings as defined for the above formula (II), and OBn represents benzyloxy, deprotecting P¹ which is a protective group to prepare a compound represented by the following formula (IV-c):

[Chemical formula 15]

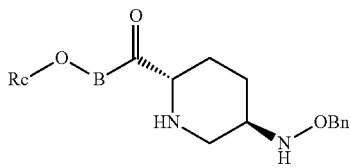

(IV-c)

in the above formula (IV-c), Rc and B have the same meanings as defined for the above formula (II), and OBn represents benzyloxy,
silylating the compound in the reaction system, and then, subjecting to intramolecular urea formation reaction to prepare a compound represented by the following formula (IIa):

[Chemical formula 16]

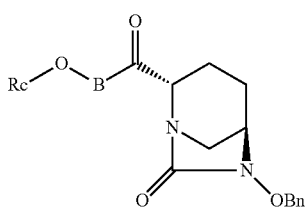

(IIa)

in the above formula (IIa), Rc and B have the same meanings as defined for the above formula (II), and OBn represents benzyloxy,
then, removing the benzyl of the benzyloxy at the 6-position using a hydrogenolysis catalyst under hydrogen atmosphere to prepare a compound represented by the following formula (IIb):

[Chemical formula 17]

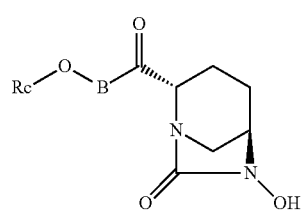

(IIb)

in the above formula (IIb), Rc and B have the same meanings as defined for the above formula (II),
and sulfating the hydroxyl group at the 6-position in the presence of a base, and, if necessary, deprotecting the protective group in the side chain: RcOB— to prepare the compound represented by the formula (III).

Moreover, according to another embodiment of the present invention, it is directed to a process for preparing the compound represented by the following formula (IIa):

[Chemical formula 18]

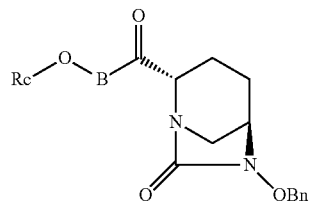

(IIa)

in the above formula (IIa), OBn represents benzyloxy, and Rc and B have the same meanings as defined for the above formula (II),
which is included in the above formula (II), which comprises (17) subjecting to coupling a compound represented by the following formula (IV-a):

[Chemical formula 19]

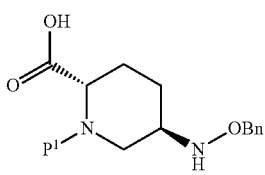

(IV-a)

in the above formula (IV-a), P¹ represents a protective group which can be removed by an acid, a base or a nucleophilic agent; and OBn represents benzyloxy,
with a compound: RcOBH using an active ester, an active amide or a dehydration condensing agent to prepare a compound represented by the following formula (IV-b):

[Chemical formula 20]

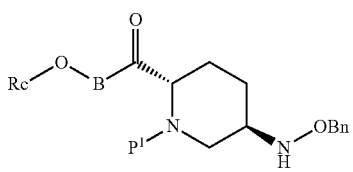

(IV-b)

in the above formula (IV-b), P¹ represents a protective group which can be removed by an acid, a base or a nucleophilic agent; Rc and B have the same meanings as defined for the above formula (II), and OBn represents benzyloxy,
deprotecting P¹ which is a protective group to prepare a compound represented by the following formula (IV-c):

[Chemical formula 21]

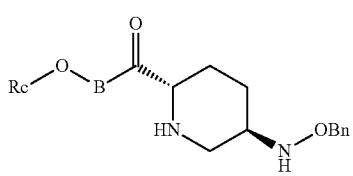

(IV-c)

in the above formula (IV-c), Rc and B have the same meanings as defined for the above formula (II), and OBn represents benzyloxy, silylating the compound in the reaction system, and then, subjecting to intramolecular urea formation reaction to prepare a compound represented by the formula (IIa).

Moreover, according to the other embodiment of the present invention, it is directed to a process for preparing the compound represented by the following formula (IIa):

[Chemical formula 22]

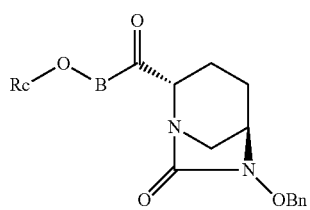

(IIa)

in the above formula (IIa), OBn represents benzyloxy, and Rc and B have the same meanings as defined for the above formula (II), which is included in the above formula (II), which comprises

(18) silylating the compound represented by the following formula (IV-c):

[Chemical formula 23]

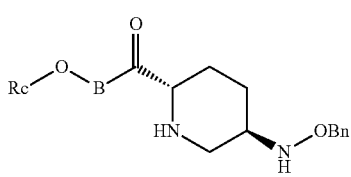

(IV-c)

in the above formula (IV-c), Rc and B have the same meanings as defined for the above formula (II), and OBn represents benzyloxy, in the reaction system, and then, subjecting to intramolecular urea formation reaction to prepare a compound represented by the formula (IIa).

Also, according to another embodiment of the present invention, it is directed to a process for preparing the compound represented by the following formula (III):

[Chemical formula 24]

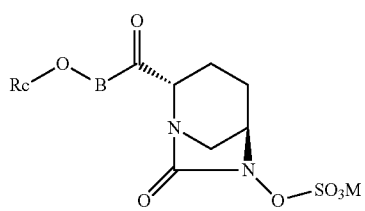

(III)

in the above formula (III), Rc, B and M have the same meanings as defined for the above formula (II), which is included in the above formula (II), which comprises

(19) removing the benzyl of the benzyloxy at the 6-position of a compound represented by the following formula (IIa):

[Chemical formula 25]

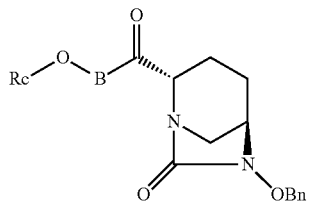

(IIa)

in the above formula (IIa), Rc and B have the same meanings as defined for the above formula (II), and OBn represents benzyloxy, using a hydrogenolysis catalyst under hydrogen atmosphere to prepare a compound represented by the following formula (IIb):

[Chemical formula 26]

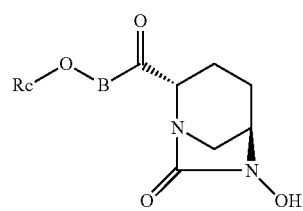

(IIb)

in the above formula (IIb), Rc and B have the same meanings as defined for the above formula (II), and sulfating the hydroxyl group at the 6-position in the presence of a base, and, if necessary, deprotecting the protective group in the side chain: RcOB— to prepare the compound represented by the formula (III).

Further, according to another embodiment of the present invention, it is directed to a process for preparing (2S,5R)-N-(2-aminoethoxy)-7-oxo-6-(sulfooxy)-1,6-diazabicyclo[3.2.1]octane-2-carboxamide represented by the following formula (III-059):

[Chemical formula 27]

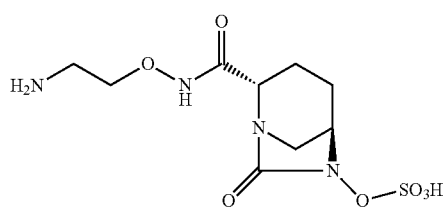

(III-059)

which comprises

(20) among the compounds represented by the following formulae (IV-a2), (IV-a3) and (IV-a4):

[Chemical formula 28]

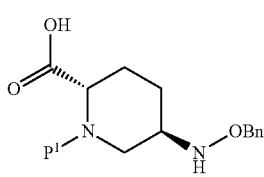

(IV-a2) P¹ = TFA
(IV-a3) P¹ = Boc
(IV-a4) P¹ = Teoc in the above formula (IV-a2), (IV-a3) or (IV-a4), TFA represents trifluoroacetyl, Boc represents tert-butoxycarbonyl, Teoc represents 2-trimethylsilylethoxycarbonyl, and OBn represents benzyloxy,
subjecting to coupling the compound represented by the formula (IV-a2) or (IV-a4) with tert-butyl 2-(aminooxy) ethylcarbamate using an active ester, an active amide or a dehydration condensing agent, or
subjecting to coupling the compound represented by the formula (IV-a3) with benzyl 2-(aminooxy)ethylcarbamate using an active ester, an active amide or a dehydration condensing agent,
to prepare a compound represented by the following formula (IV-b2-Boc-059), (IV-b3-Cbz-059) or (IV-b4-Boc-059):

[Chemical formula 29]

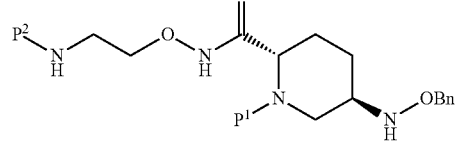

(IV-b2-Boc-059) P¹ = TFA, P² = Boc
(IV-b3-Cbz-059) P¹ = Boc, P² = Cbz
(IV-b4-Boc-059) P¹ = Teoc, P² = Boc in the above formula (IV-b2-Boc-059), (IV-b3-Cbz-059) or (IV-b4-Boc-059), TFA represents trifluoroacetyl, Boc represents tert-butoxycarbonyl, Cbz represents benzyloxycarbonyl, Teoc represents 2-trimethylsilylethoxycarbonyl, and OBn represents benzyloxy,
removing the trifluoroacetyl of the compound represented by the formula (IV-b2-Boc-059) by the treatment with a base to prepare a compound represented by the following formula (IV-c-Boc-059):

[Chemical formula 30]

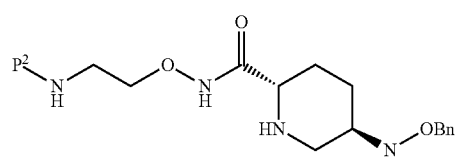

(IV-c-Boc-059) P² = Boc
(IV-c-Cbz-059) P² = Cbz in the above formula (IV-c-Boc-059) or (IV-c-Cbz-059), Boc represents tert-butoxycarbonyl, Cbz represents benzyloxycarbonyl, and OBn represents benzyloxy, removing the tert-butoxycarbonyl of the compound represented by the formula (IV-b3-Cbz-059) by an acid treatment to prepare a compound represented by the above formula (IV-c-Cbz-059), or removing the 2-trimethylsilylethoxycarbonyl of the compound represented by the formula (IV-b4-Boc-059) by a fluoride to prepare a compound represented by the above formula (IV-c-Boc-059), then, after silylating the above-mentioned (IV-c-Boc-059) or (IV-c-Cbz-059) in the reaction system, subjecting to intramolecular urea formation reaction to prepare a compound represented by the following formula (IIa-Boc-059) or (IIa-Cbz-059):

[Chemical formula 31]

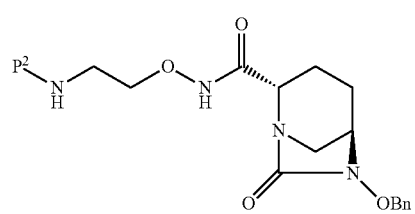

(IIa-Boc-059) P² = Boc
(IIa-Cbz-059) P² = Cbz in the above formula (IIa-Boc-059) or (IIa-Cbz-059), Boc represents tert-butoxycarbonyl, Cbz represents benzyloxycarbonyl, and OBn represents benzyloxy, removing the benzyl of the benzyloxy at the 6-position of the compound represented by the formula (IIa-Boc-059) using a hydrogenolysis catalyst under hydrogen atmosphere, or removing the benzyl of the benzyloxy at the 6-position of the compound represented by the formula (IIa-Cbz-059) using a hydrogenolysis catalyst under hydrogen atmosphere, and simultaneously tert-butoxycarbonylating the same in the presence of di-tert-butoxydicarbonate to prepare a compound represented by the following formula (IIb-Boc-059):

[Chemical formula 32]

(IIb-Boc-059)

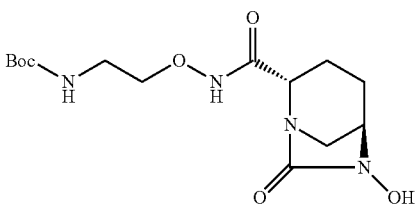

in the above formula (IIb-Boc-059), Boc represents tert-butoxycarbonyl, sulfating the hydroxyl group at the 6-position to prepare a compound represented by the following formula (III-Boc-059):

[Chemical formula 33]

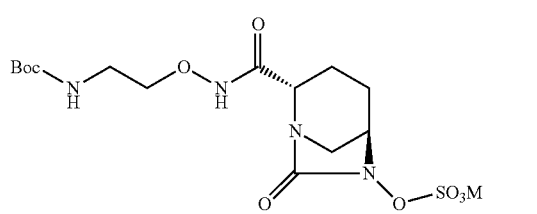

(III-Boc-059)

in the above formula (III-Boc-059), Boc represents tert-butoxycarbonyl, and M represents H, pyridinium, sodium, or tetrabutylammonium, and deprotecting the tert-butoxycarbonyl by an acid treatment to prepare the compound represented by the formula (III-059).

Also, according to another embodiment of the present invention, it is directed to a process for preparing tert-butyl {2-[({[(2S,5R)-6-benzyloxy-7-oxo-1,6-diazabicyclo[3.2.1]octo-2-yl]carbonyl}amino)oxy]ethyl}carbamate, or benzyl {2-[({[(2S,5R)-6-benzyloxy-7-oxo-1,6-diazabicyclo[3.2.1]octo-2-yl]carbonyl}amino)oxy]-ethyl}carbamate represented by the following formula (IIa-Boc-059) or (IIa-Cbz-059):

[Chemical formula 34]

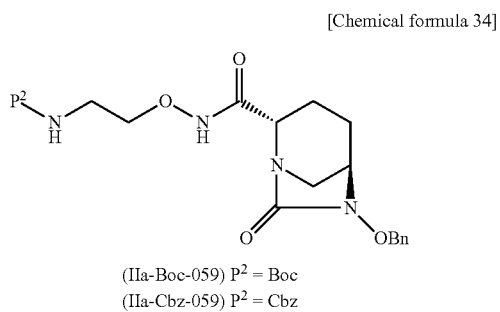

(IIa-Boc-059) $P^2$ = Boc
(IIa-Cbz-059) $P^2$ = Cbz in the above formula (IIa-Boc-059) or (IIa-Cbz-059), Boc represents tert-butoxycarbonyl, Cbz represents benzyloxycarbonyl, and OBn represents benzyloxy, which comprises (21) among the compounds represented by the following formulae (IV-a2), (IV-a3) and (IV-a4):

[Chemical formula 35]

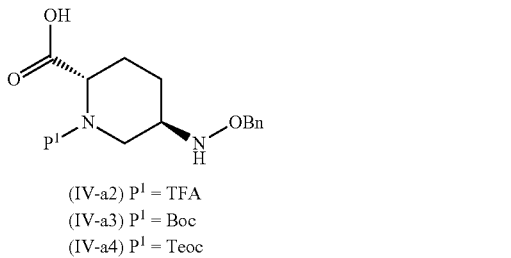

(IV-a2) $P^1$ = TFA
(IV-a3) $P^1$ = Boc
(IV-a4) $P^1$ = Teoc in the above formula (IV-a2), (IV-a3) or (IV-a4), TFA represents trifluoroacetyl, Boc represents tert-butoxycarbonyl, Teoc represents 2-trimethylsilylethoxycarbonyl, and OBn represents benzyloxy, subjecting to coupling each of the compounds represented by the formulae (IV-a2) and (IV-a4) using tert-butyl 2-(aminooxy)ethylcarbamate, 1-ethyl-3-(3-dimethylamino-propyl)carbodiimide hydrochloride and 1-hydroxybenzotriazole.monohydrate in combination, subjecting to coupling the compound represented by the formula (IV-a3) using benzyl 2-(aminooxy)ethylcarbamate, 1-ethyl-3-(3-dimethylaminopropyl)carbodiimide hydrochloride and 1-hydroxybenzotriazole.monohydrate in combination, to prepare a compound represented by the following formula (IV-b2-Boc-059), (IV-b3-Cbz-059) or (IV-b4-Boc-059):

[Chemical formula 36]

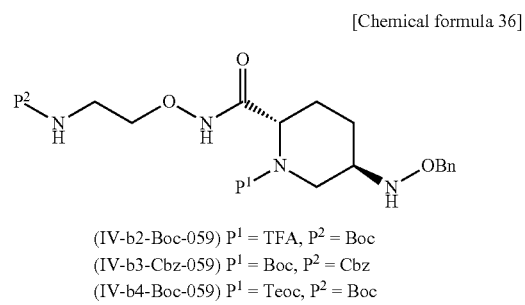

(IV-b2-Boc-059) $P^1$ = TFA, $P^2$ = Boc
(IV-b3-Cbz-059) $P^1$ = Boc, $P^2$ = Cbz
(IV-b4-Boc-059) $P^1$ = Teoc, $P^2$ = Boc in the above formula (IV-b2-Boc-059), (IV-b3-Cbz-059) or (IV-b4-Boc-059), TFA represents trifluoroacetyl, Boc represents tert-butoxycarbonyl, Cbz represents benzyloxycarbonyl, Teoc represents 2-trimethylsilylethoxycarbonyl, and OBn represents benzyloxy, removing the trifluoroacetyl of the compound represented by the formula (IV-b2-Boc-059) by using a base selected from lithium hydroxide, sodium hydroxide and potassium hydroxide to prepare a compound represented by the following formula (IV-c-Boc-059):

[Chemical formula 37]

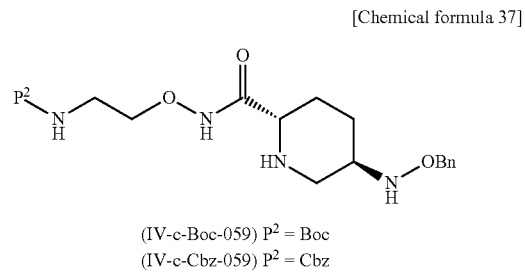

(IV-c-Boc-059) $P^2$ = Boc
(IV-c-Cbz-059) $P^2$ = Cbz in the above formula (IV-c-Boc-059) or (IV-c-Cbz-059), Boc represents tert-butoxycarbonyl, Cbz represents benzyloxycarbonyl, and OBn represents benzyloxy, removing the tert-butoxycarbonyl of the compound represented by the formula (IV-b3-Cbz-059) using an acid selected from hydrochloric acid, sulfuric acid, methanesulfonic acid and trifluoroacetic acid to prepare a compound represented by the above formula (IV-c-Cbz-059), or removing the 2-trimethylsilylethoxycarbonyl of the compound represented by the formula (IV-b4-Boc-059) using tetrabutylammonium fluoride to prepare a compound represented by the above formula (IV-c-Boc-059), and silylating the compound represented by the above formula (IV-c-Boc-059) or (IV-c-Cbz-059) using chlorotrialkylsilane in the reaction system and subsequently subjecting to intramolecular urea formation reaction using phosgene or diphosgene to prepare the compound represented by the formula (IIa-Boc-059) or (IIa-Cbz-059).

According to another embodiment of the present invention, it is directed to a process for preparing tert-butyl {2-[({[(2S,5R)-6-benzyloxy-7-oxo-1,6-diazabicyclo-[3.2.1]octo-2-yl]carbonyl}amino)oxy]ethyl}carbamate, or benzyl {2-[({[(2S,5R)-6-benzyloxy-7-oxo-1,6-diazabicyclo[3.2.1]oct-2-yl]carbonyl}amino)oxy]ethyl}carbamate represented by the following formula (IIa-Boc-059) or (IIa-Cbz-059):

[Chemical formula 38]

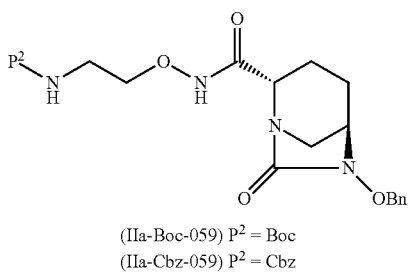

(IIa-Boc-059) P² = Boc
(IIa-Cbz-059) P² = Cbz in the above formula (IIa-Boc-059) or (IIa-Cbz-059), Boc represents tert-butoxycarbonyl, Cbz represents benzyloxycarbonyl, and OBn represents benzyloxy, which comprises

(22) silylating a compound represented by the following formula (IV-c-Boc-059) or (IV-c-Cbz-059):

[Chemical formula 39]

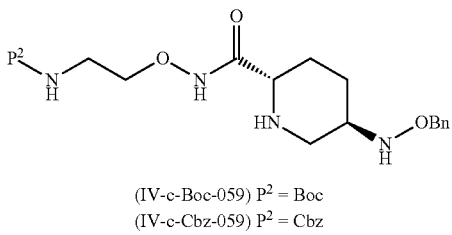

(IV-c-Boc-059) P² = Boc
(IV-c-Cbz-059) P² = Cbz in the above formula (IV-c-Boc-059) or (IV-c-Cbz-059), Boc represents tert-butoxycarbonyl, Cbz represents benzyloxycarbonyl, and OBn represents benzyloxy, using chlorotrimethylsilane in the reaction system, and subsequently subjecting to intramolecular urea formation reaction using phosgene or diphosgene to prepare the compound represented by the formula (IIa-Boc-059) or (IIa-Cbz-059).

Further, according to another embodiment of the present invention, it is directed to a process for preparing (2S,5R)-N-(2-aminoethoxy)-7-oxo-6-(sulfooxy)-1,6-diazabicyclo[3.2.1]octane-2-carboxamide represented by the following formula (III-059):

[Chemical formula 40]

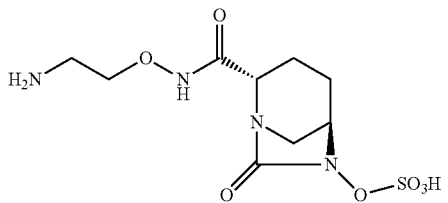

(III-059)

which comprises

(23) among the compounds represented by the following formulae (IIa-Boc-059) and (IIa-Cbz-059):

[Chemical formula 41]

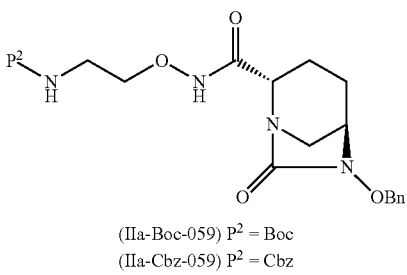

(IIa-Boc-059) P² = Boc
(IIa-Cbz-059) P² = Cbz in the above formula (IIa-Boc-059) or (IIa-Cbz-059), Boc represents tert-butoxycarbonyl, Cbz represents benzyloxycarbonyl, and OBn represents benzyloxy, removing the benzyl of the benzyloxy at the 6-position of the compound represented by the formula (IIa-Boc-059) using palladium-carbon under hydrogen atmosphere, or removing the benzyl of the benzyloxy at the 6-position of the compound represented by the formula (IIa-Cbz-059) using palladium-carbon under hydrogen atmosphere in the presence of di-tert-butoxydicarbonate, and simultaneously subjecting to tert-butoxycarbonylation to prepare a compound represented by the following formula (IIb-Boc-059);

[Chemical formula 42]

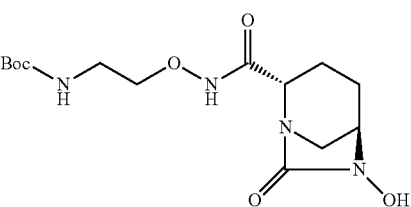

(IIb-Boc-059)

in the above formula (IIb-Boc-059), Boc represents tert-butoxycarbonyl, sulfating the hydroxyl group at the 6-position by a sulfur trioxide-pyridine complex in the presence of pyridine, 2-picoline or 2,6-lutidine, to prepare a compound represented by the following formula (III-Boc-059):

[Chemical formula 43]

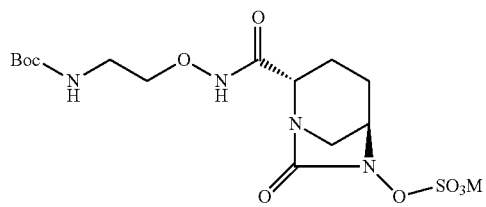

(III-Boc-059)

in the above formula (III-Boc-059), Boc represents tert-butoxycarbonyl, and M represents H, pyridinium, sodium or tetrabutylammonium,
and deprotecting the tert-butoxycarbonyl by an acid selected from hydrochloric acid, sulfuric acid, methanesulfonic acid, trifluoroacetic acid and tetrafluoroboric acid to prepare the compound represented by the formula (III-059).

Also, according to another embodiment of the present invention, it is directed to a process for preparing tert-butyl {2-[({[(2S,5R)-6-benzyloxy-7-oxo-1,6-diazabicyclo[3.2.1]oct-2-yl]carbonyl}amino)oxy]ethyl}carbamate represented by the following formula (IIa-Boc-059):

[Chemical formula 44]

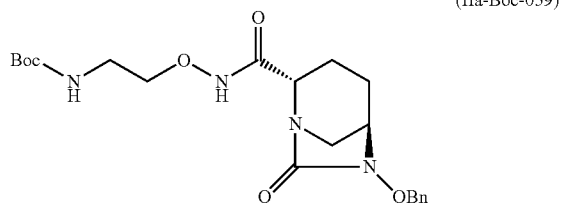

(IIa-Boc-059)

in the above formula (IIa-Boc-059), Boc represents tert-butoxycarbonyl, and OBn represents benzyloxy,
which comprises
(24) silylating a compound represented by the following formula (IV-c-Boc-059):

[Chemical formula 45]

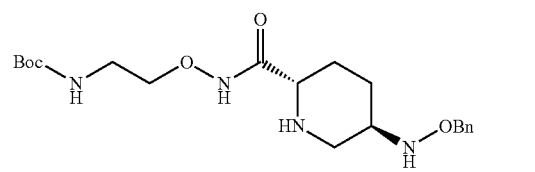

(IV-c-Boc-059)

in the above formula (IV-c-Boc-059), Boc represents tert-butoxycarbonyl, and OBn represents benzyloxy,
using triethylamine and chlorotrimethylsilane in the reaction system, and subsequently subjecting to intramolecular urea formation reaction using phosgene or diphosgene with a catalytic amount of 4-dimethylaminepyridine to prepare the compound represented by the formula (IIa-Boc-059).

In addition, according to the other embodiment of the present invention, it is directed to a process for preparing (2S,5R)-N-(2-aminoethoxy)-7-oxo-6-(sulfooxy)-1,6-diazabicyclo[3.2.1]octane-2-carboxamide represented by the following formula (III-059):

[Chemical formula 46]

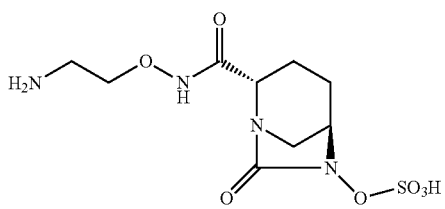

(III-059)

which comprises,
(25) removing the benzyl of the benzyloxy at the 6-position of a compound represented by the following formula (IIa-Boc-059):

[Chemical formula 47]

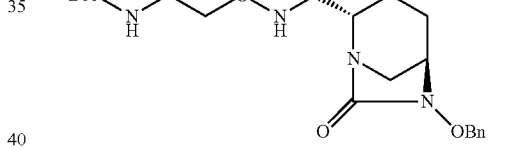

(IIa-Boc-059)

in the above formula (IIa-Boc-059), Boc represents tert-butoxycarbonyl, and OBn represents benzyloxy,
using palladium-carbon under hydrogen atmosphere to prepare a compound represented by the following formula (IIb-Boc-059):

[Chemical formula 48]

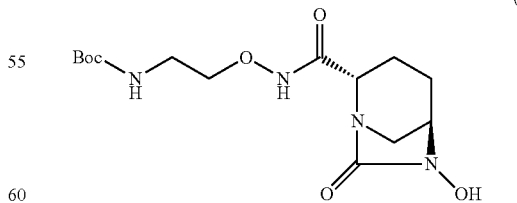

(IIb-Boc-059)

in the above formula (IIb-Boc-059), Boc represents tert-butoxycarbonyl, sulfating the hydroxyl group at the 6-position using a sulfur trioxide-pyridine complex in the presence of pyridine, 2-picoline or 2,6-lutidine to prepare a compound represented by the following formula (III-Boc-059):

[Chemical formula 49]

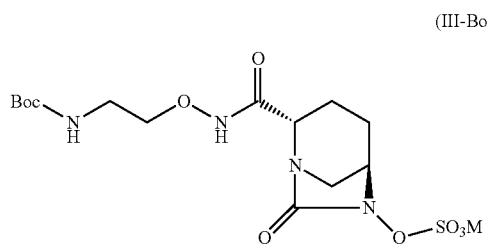

in the above formula (III-Boc-059), Boc represents tert-butoxycarbonyl, and M represents H, pyridinium, sodium or tetrabutylammonium, and deprotecting the tert-butoxycarbonyl with an acid selected from hydrochloric acid, sulfuric acid, methanesulfonic acid, trifluoroacetic acid and tetrafluoroboric acid to prepare the compound represented by the formula (III-059).

Also, another embodiment of the present invention is directed to a process for preparing (2S,5R)-methyl 5-(benzyloxyamino)piperidine-2-carboxylate or a hydrochloride thereof, which comprises (26) subjecting (2S,5S)-5-hydroxypiperidine-2-carboxylic acid or a hydrochloride thereof to methyl esterification, trifluoroacetylation, benzyloxyamination of the C5 hydroxyl group and removal of trifluoroacetyl each without subjecting to purification, followed by crystallization as a hydrochloride thereby isolating and purifying (2S,5R)-methyl 5-(benzyloxyamino)piperidine-2-carboxylate or a hydrochloride thereof.

Further, another embodiment of the present invention is directed to (27) the compounds represented by the formulae:

[Chemical formula 50]

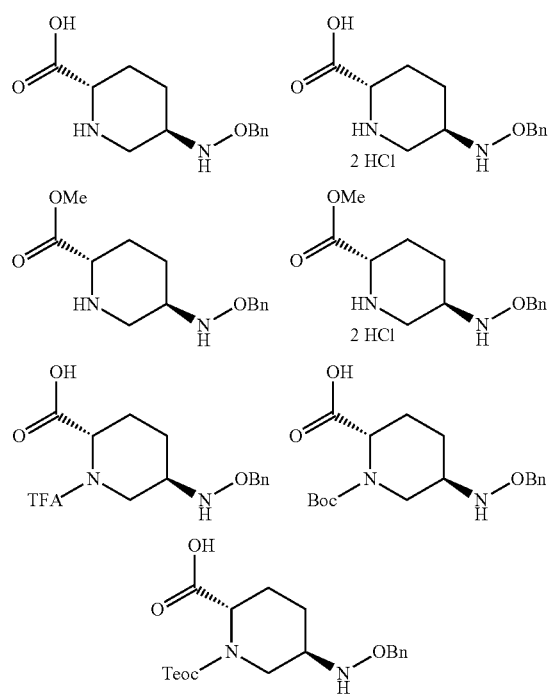

in the above formulae, TFA represents trifluoroacetyl, OMe represents methoxy, Boc represents tert-butoxycarbonyl, Teoc represents 2-trimethylsilylethoxycarbonyl, and OBn represents benzyloxy.

Effects of the Invention

The novel diazabicyclooctane derivatives represented by the above formula (I) provided by the present invention show potent inhibitory activity against various kinds of β-lactamases. In particular, it shows potent inhibitory activity against class A, class C and class D β-lactamases. More specifically, it shows potent inhibitory activity against class C β-lactamase, extended-spectrum β-lactamase (ESBL), and KPC-2 β-lactamase, and antimicrobial activity of the existing β-lactam antibiotic against the bacteria producing these β-lactamases resistant to the β-lactam antibiotic can be potently recovered in combination with the compound of this invention.

In addition, the process for preparing the compound represented by the following formula (II):

[Chemical formula 51]

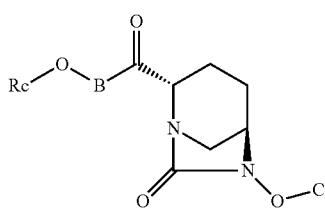

(II)

in the above formula (II), Rc represents $C_{1-6}$ alkyl or a heterocyclyl; B represents NH or $NC_{1-6}$ alkyl; C represents benzyl, H or $SO_3M$, where M represents H, an inorganic cation or an organic cation; Rc may be modified by 0 to 4 substituents Fn1, where the substituent Fn1 may be substituted continuously; Fn1 represents $C_{1-6}$ alkyl, O= or Rg-$(CH_2)_{0-3}$—, where Rg represents a heterocyclyl, phenyl, heteroaryl, acyl, $RdO_2S$—, Re(Rf)N—, Re(Rf)NCO—, ReO—, ReOCO— or a protective group, where Rd represents $C_{1-6}$ alkyl or MO—; Re and Rf each independently represent H or $C_{1-6}$ alkyl, and further, between Rc and B, and between Re and Rf may be closed by the bonding to form a heterocyclyl having at least one nitrogen atom,
which is included in the compound of the formula (I) provided by the present invention, is a preparation process having higher usefulness as a preparation process for commercialization.

MODE FOR CARRYING OUT THE INVENTION

Figure 1:
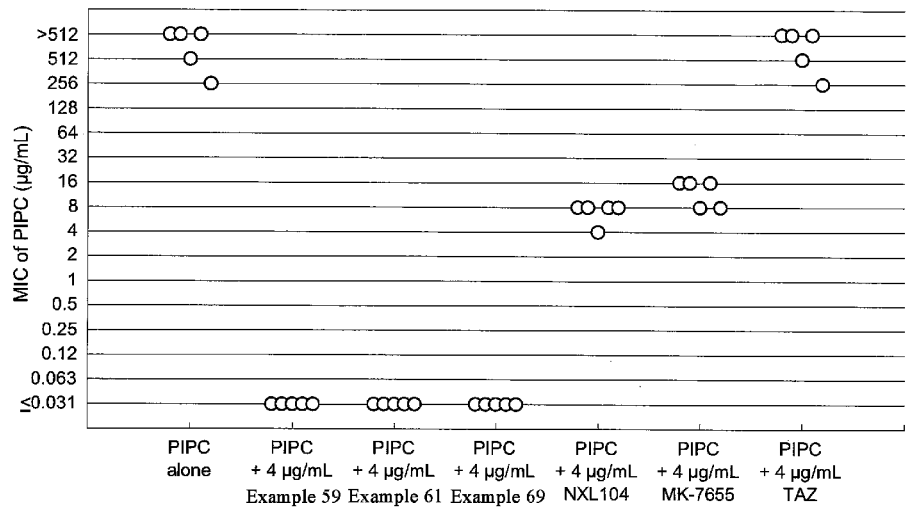
FIG. 1 shows antibacterial activities to 5 strains of KPC-2 or 3 producing strain, *K. pneumoniae*.
Figure 2:
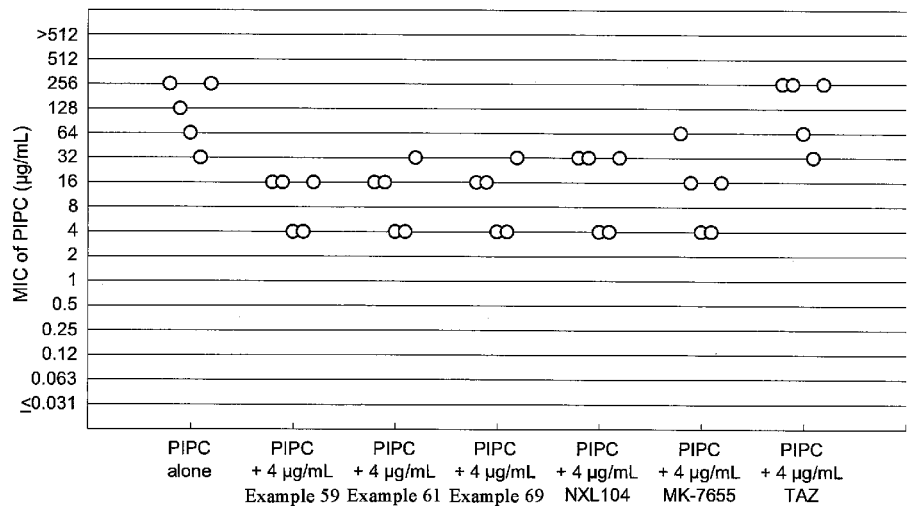
FIG. 2 shows antibacterial activities to 5 strains of AmpC constitutive expression, *P. aeruginosa*.
Figure 3:
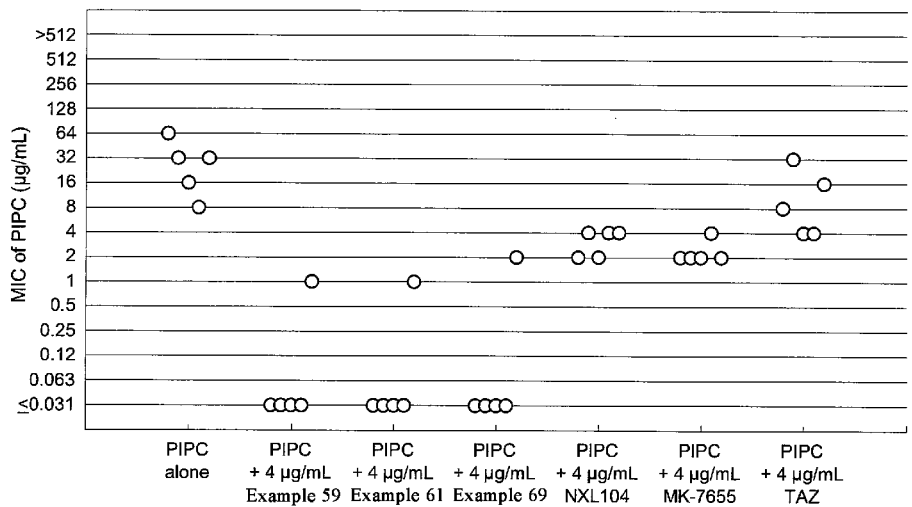
FIG. 3 shows antibacterial activities to 5 strains of AmpC constitutive expression, Enterobacteriaceae.
Figure 4:
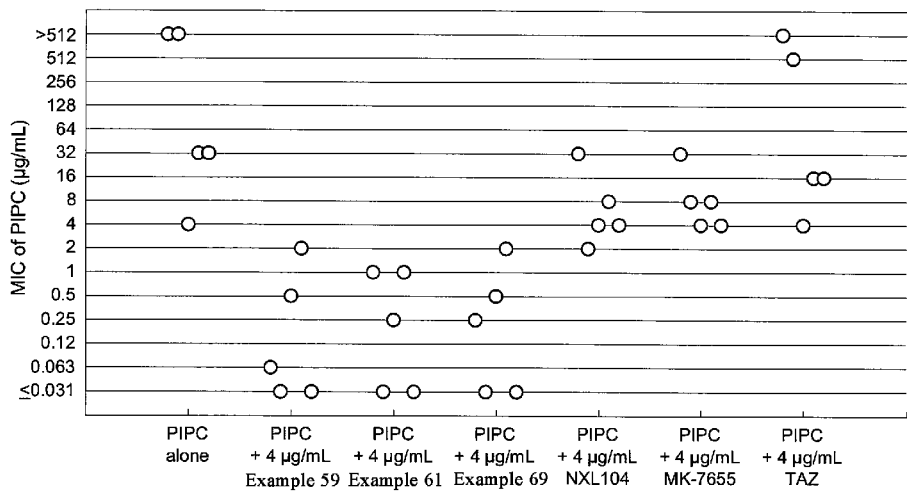
FIG. 4 shows antibacterial activities to 5 strains of IMP type metallo-β-lactamase producing strain, Enterobacteriaceae.
Figure 5:
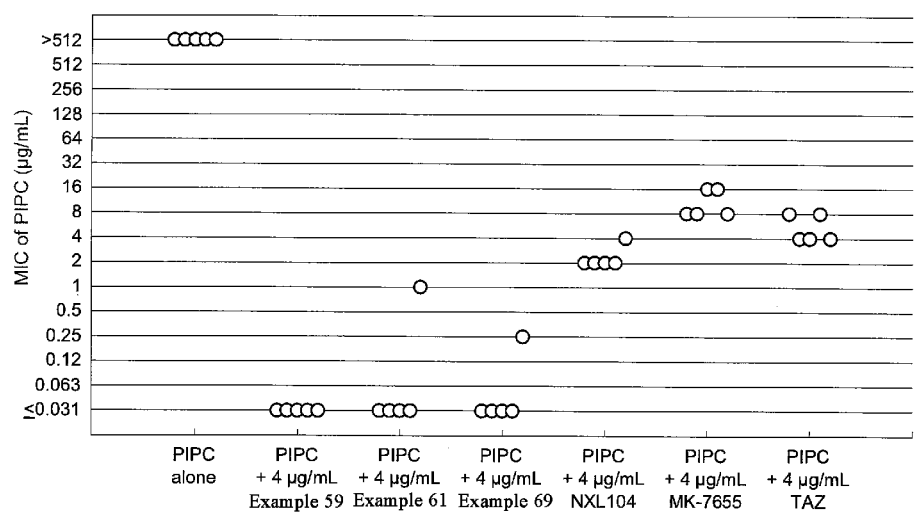
FIG. 5 shows antibacterial activities to 5 strains of CTX-M-15 (ESBL) producing strain, *E. coli*.

As mentioned above, the present invention is to provide a novel diazabicyclooctane derivative represented by the following formula (I), a pharmaceutically acceptable salt thereof, or a solvate thereof, and a (β-lactamase inhibitor comprising the compound of the formula (I):

[Chemical formula 52]

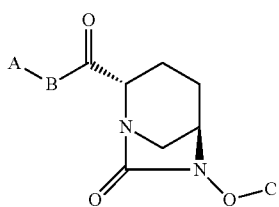

(I)

in the above formula (I), A represents Ra(Rb)N— or RcO—; B represents NH or $NC_{1-6}$ alkyl; C represents benzyl, H or $SO_3M$, where M represents H, an inorganic cation or an organic cation; Ra and Rb each independently represent H, $C_{1-6}$ alkyl or acyl; Rc represents $C_{1-6}$ alkyl or a heterocyclyl; A may be modified by 0 to 4 substituents Fn1, where the substituent Fn1 may be substituted continuously; Fn1 represents $C_{1-6}$ alkyl, O= or Rg-$(CH_2)_{0-3}$—, where Rg represents a heterocyclyl, phenyl, heteroaryl, acyl, $RdO_2S$—, Re(Rf)N—, Re(Rf)NCO—, ReO—, ReOCO— or a protective group, where Rd represents $C_{1-6}$ alkyl or MO—; Re and Rf each independently represent H or $C_{1-6}$ alkyl, and further, between Ra and Rb, between Rc and B, and between Re and Rf may be closed by the bonding to form a heterocyclyl having at least one nitrogen atom.

In the following, the novel diazabicyclooctane derivatives represented by the formula (I) of the present invention and a process for preparing the same, a β-lactamase inhibitor, and a use of the compound of this invention for the treatment of the bacterial infection will be explained in detail, but the present invention is not limited by the scope of the designated specific examples.

The term "salt" used in the present specification means a pharmaceutically acceptable salt, and there are a base-added salt comprising an inorganic base or an organic base, and an acid-added salt comprising an inorganic acid or an organic acid.

The terms "inorganic cation" mean an alkali metal or an alkaline earth metal, etc., and the terms "organic cation" mean an ammonium salt formed from mono- to tri-substituted amine, and a quaternary ammonium salt formed from tetra-substituted amine or by substituted heteroaromatic ring.

When "M" is H and the compound of the present invention has an amino group, cyclic amines or aromatic amines which can be protonated in the molecule, the amino group, cyclic amines or aromatic amines in the molecule behave as a protonated ammonium salt, and it can take the form of an intramolecular salt, which is also deemed to be a part of the compound of the present invention. Further, when "M" is an organic cation and present in the molecule of the compound of the present invention as a quaternary ammonium salt, it can also take the form of an intramolecular salt, which is also deemed to be a part of the compound of the present invention.

The term "modified" means to exchange H in A or in the substituent Fn1 and bind with or by the substituent Fn1.

The terms "A may be modified by 0 to 4 substituents Fn1, and the substituent Fn1 may be substituted continuously." mean that Fn1 which modifies A may be further modified by Fn1, and there may be mentioned A-(Fn1)$_{0-4}$, A-(Fn1)(Fn1)$_{0-3}$, A-(Fn1)$_2$(Fn1)$_{0-2}$, and A-(Fn1)$_3$(Fn1)$_{0-1}$, etc.

Specific examples of the "protective group" may be mentioned a trialkylsilyl and a carbamate type protective group, preferably triisopropylsilyl, tert-butyldimethylsilyl, tert-butoxycarbonyl or benzyloxycarbonyl, which is a protective group for an amino group and a hydroxyl group disclosed in Protective Groups in Organic Synthesis (T. W. Greene et al., Wiley, New York (1999)).

The solvent contained in the "solvate" may be water, methanol, ethanol, isopropanol, acetone and methyl ethyl ketone, more preferably water.

The terms "$C_{1-6}$ alkyl" mean an alkyl group having 1 to 6 carbon atoms, which may be straight, branched or cyclic.

The terms "acyl" mean formyl, benzoyl, phenylacetyl, $C_{1-6}$ alkylcarbonyl, heterocyclylcarbonyl, and heteroarylcarbonyl.

The terms "heterocyclyl" mean a 3 to 7-membered monocyclic saturated heterocyclic ring or non-aromatic ring having 1 to 3 nitrogen atom(s), oxygen atom(s) and/or sulfur atom(s) in total.

The terms "heteroaryl" mean a 5 to 6-membered monocyclic heteroaromatic ring having 1 to 4 nitrogen atom(s), oxygen atom(s) and/or sulfur atom(s) in total.

The terms "Ra(Rb)N—" and "Re(Rf)N—" mean an amino group substituted by Ra and Rb, or Re and Rf.

The term "RcO—" means oxy bonded to Rc, i.e., alkoxy or heterocyclyloxy, and the term "ReO—" means oxy bonded to Re, i.e., alkoxy or hydroxy.

The term "$RdO_2S$—" means sulfonyl bonded to Rd.

The term "Re(Rf)NCO—" means carbonyl bonded to Re(Rf)N—.

The term "ReOCO—" means carbonyl bonded to ReO—.

The term "O═" means an oxo group.

Specific examples of the bases which form the "base-added salt" may be mentioned lithium hydroxide, sodium hydroxide, potassium hydroxide, sodium hydrogen carbonate, potassium hydrogen carbonate, sodium carbonate, potassium carbonate, lithium carbonate, calcium carbonate, sodium acetate, potassium acetate, trisodium citrate, sodium dihydrogen citrate, tripotassium citrate, potassium dihydrogen citrate, ammonia, methylamine, ethylamine, dimethylamine, diethylamine, trimethylamine, triethylamine, N-methylmorpholine, ethanolamine and triethanolamine, etc., preferably sodium hydroxide, sodium hydrogen carbonate, sodium carbonate, sodium acetate, trisodium citrate, sodium dihydrogen citrate and triethanolamine, etc.

Specific examples of the acids which form the "acid-added salt" may be mentioned hydrochloric acid, hydrobromic acid, hydroiodic acid, sulfuric acid, sulfuric acid, hemisulfuric acid, thiocyanic acid, acetic acid, butyric acid, propionic acid, cyclopentanepropionic acid, pivalic acid, heptanoic acid, hexanoic acid, 3-phenyl-propionic acid, undecanoic acid, lactic acid, oxalic acid, malonic acid, succinic acid, citric acid, tartaric acid, malic acid, maleic acid, fumaric acid, adipic acid, alginic acid, aspartic acid, benzoic acid, digluconic acid, nicotinic acid, pamoic acid, pectic acid, glucoheptanoic acid, glycerophosphoric acid, benzenesulfonic acid, tosylic acid, methanesulfonic acid, ethanesulfonic acid, camphorsulfonic acid, dodecylsulfuric acid, 2-hydroxyethanesulfonic acid and 2-naphthalenesulfonic acid, etc., preferably hydrochloric acid, sulfuric acid, acetic acid, lactic acid, malic acid, citric acid, methanesulfonic acid and tosylic acid, etc.

Specific examples of the "inorganic cation" include sodium, potassium, lithium, calcium, etc., preferably sodium and potassium.

Specific examples of the "organic cation" includes methylammonium, ethylammonium, dimethylammonium, diethylammonium, diisopropylammonium, pyridinium, trimethylammonium, triethylammonium, cyclohexylammonium, dicyclohexylammonium, diisopropylethylammonium, pyridinium, tetramethylammonium, tetraethylammonium, tetrabutylammonium, triethylbenzylammonium, N,N'-dimethylimidazolium, N-methylpyridinium, etc., preferably pyridinium and tetrabutylammonium.

Specific examples of the "$C_{1-6}$ alkyl" include a $C_{1-6}$ alkyl group such as methyl, ethyl, propyl, isopropyl, butyl, tert-butyl, s-butyl, isobutyl, pentyl, 1,1-dimethylpropyl, 1,2-dimethylpropyl, neopentyl, 1-methylbutyl, 2-methylbutyl, isopentyl and hexyl, a $C_{3-6}$ cycloalkyl group such as cyclopropyl, cyclobutyl, cyclopentyl and cyclohexyl, or a methyl group substituted by a $C_{3-5}$ cycloalkyl group such as cyclopropylmethyl, cyclobutylmethyl, cyclopentylmethyl, preferably methyl, ethyl, propyl, isopropyl, butyl, tert-butyl, cyclopropyl, cyclobutyl, cyclopropylmethyl and cyclobutylmethyl.

Specific examples of the "heterocyclyl" include a group derived from aziridine, oxirane, thiirane, azetidine, oxetane, thietane, pyrrolidine, tetrahydrofuran, tetrahydrothiophene, imidazolidine, oxazolidine, thiazolidine, pyrazolidine, piperidine, tetrahydro-2H-pyran, tetrahydro-2H-thiopyran, hexahydropyridazine, piperazine, morpholine, thiomorpholine, 1,2-oxazolidine, 1,2-oxazinane, 1,4-dioxane, 1,2-thiazinane, azepane, oxepane, thiepane, 1,4-diazepane, 1,4-oxazepane, 1,4-thiazepane, 1,2,5-triazepane, 1,4,5-oxadiazepane, 1,2,5-oxadiazepane, 1,4,5-thiadiazepane, 1,5,2-dioxazepane, 1,5,2-oxathiazepane, 3,4-dihydro-2H-pyrrole, 4,5-dihydro-1H-pyrazole, 4,5-dihydro-1H-imidazole, 4,5-dihydro-1,2-oxazole, 4,5-dihydro-1,3-oxazole, 4,5-dihydro-1,3-thiazole, 2,3,4,5-tetrahydropyridine, 1,2,3,6-tetrahydropyrazine, 5,6-dihydro-4H-1,2-oxazine, 3,6-dihydro-2-H-1,4-oxazine, etc., preferably a group derived from azetidine, pyrrolidine, tetrahydrofuran, piperidine, tetrahydro-2H-pyran, imidazolidine, oxazolidine, 1,2-oxazolidine, hexahydropyridazine, piperazine, morpholine, 1,2-oxazinane, azepane, 1,4-diazepane and 1,2-oxazepane.

Specific examples of the protective group for the "heterocyclyl" to which "tert-butoxycarbonyl or benzyloxycarbonyl is bonded" include a group derived from 1-(tert-butoxycarbonyl)azetidine, 1-(tert-butoxycarbonyl)pyrrolidine, 1,3-di(tert-butoxycarbonyl)imidazolidine, 3-(tert-butoxycarbonyl)oxazolidine, 1,3-di(tert-butoxycarbonyl)pyrazolidine, 1-(tert-butoxycarbonyl)piperidine, 1,2-di(tert-butoxycarbonyl)hexahydropyridazine, 1,4-di(tert-butoxycarbonyl)piperazine, 4-(tert-butoxycarbonyl)morpholine, 2-(tert-butoxycarbonyl)-1,2-oxazolidine, 2-(tert-butoxycarbonyl)-1,2-oxazinane, 1-(tert-butoxycarbonyl)azepane, 1,4-di(tert-butoxycarbonyl)-1,4-diazepane, 1-(benzyloxycarbonyl)azetidine, 1-(benzyloxycarbonyl)pyrrolidine, 1,3-di(benzyloxycarbonyl)imidazolidine, 3-(benzyloxycarbonyl)oxazolidine, 1,3-di(benzyloxycarbonyl)pyrazolidine, 1-(benzyloxycarbonyl)piperidine, 1,2-di(benzyloxycarbonyl)hexahydropyridazine, 1,4-di(benzyloxycarbonyl)piperazine, 4-(benzyloxycarbonyl)morpholine, 2-(benzyloxycarbonyl)-1,2-oxazolidine, 2-(benzyloxycarbonyl)-1,2-oxazinane, 1-(benzyloxycarbonyl)azepane, 1,4-di(benzyloxycarbonyl)-1,4-diazepane, etc., and it is natural that specific examples having the above protective group are included in the specific examples having heterocyclyl to be described later.

Specific examples of the "heteroaryl" include a group derived from pyrrole, furan, thiophene, pyrazole, imidazole, 1,2-oxazole, 1,3-oxazole, 1,2-thiazole, 1,3-thiazole, 1,2,3-triazole, 1,2,4-triazole, 1,2,3-oxadiazole, 1,3,4-oxadiazole, 1,2,3-thiadiazole, 1,3,4-thiadiazole, tetrazole, pyridine, pyridazine, pyrimidine, pyrazine, 1,2,4-triazine, 1,3,5-triazine, etc., preferably a group derived from pyrrole, furan, imidazole, oxazole and pyridine.

Specific examples of the protective group for the "heteroaryl" to which "tert-butoxycarbonyl or benzyloxycarbonyl is bonded" include a group derived from 1-tert-butoxycarbonylpyrrole, 1-tert-butoxycarbonylpyrazole, 1-tert-butoxycarbonylimidazole, 1-tert-butoxycarbonyl-1,2,3-triazole, 1-tert-butoxycarbonyl-1,2,4-triazole, 1-tert-butoxycarbonyltetrazole, 1-benzyloxycarbonylpyrrole, 1-benzyloxycarbonylpyrazole, 1-benzyloxycarbonylimidazole, 1-benzyloxycarbonyl-1,2,3-triazole, 1-benzyloxycarbonyl-1,2,4-triazole, 1-benzyloxycarbonyltetrazole, etc., and it is natural that specific examples having the above protective group are included in the specific examples having heteroaryl to be described later.

Specific examples of the "$C_{1-6}$ alkylcarbonyl" include acetyl, propanoyl, butanoyl, isobutanoyl, pentanoyl, 2,2-dimethylpropanoyl, 2-methylbutanoyl, 3-methylbutanoyl, hexanoyl, cyclopropanecarbonyl, cyclobutanecarbonyl, cyclopentanecarbonyl, cyclohexanecarbonyl, 2-cyclopropylacetyl, 2-cyclobutylacetyl, 2-cyclopentylacetyl, etc.

Specific examples of the "heterocyclylcarbonyl" include aziridin-2-ylcarbonyl, oxiran-2-ylcarbonyl, thiiran-2-ylcarbonyl, azetidin-2-ylcarbonyl, azetidin-3-ylcarbonyl, oxetan-2-ylcarbonyl, oxetan-3-ylcarbonyl, thietan-2-ylcarbonyl, thietan-3-ylcarbonyl, pyrrolidin-2-ylcarbonyl, pyrrolidin-3-ylcarbonyl, tetrahydrofuran-2-ylcarbonyl, tetrahydrofuran-3-ylcarbonyl, tetrahydrothiophen-2-ylcarbonyl, tetrahydrothiophen-3-ylcarbonyl, pyrazolidin-3-ylcarbonyl, pyrazolidin-4-ylcarbonyl, 1,2-oxazolidin-3-ylcarbonyl, 1,2-oxazolidin-4-ylcarbonyl, 1,2-oxazolidin-5-ylcarbonyl, piperidin-2-ylcarbonyl, piperidin-3-ylcarbonyl, piperidin-4-ylcarbonyl, tetrahydro-2H-pyran-2-ylcarbonyl, tetrahydro-2H-pyran-3-ylcarbonyl, tetrahydro-2H-pyran-4-ylcarbonyl, tetrahydro-2H-thiopyran-2-ylcarbonyl, tetrahydro-2H-thiopyran-3-ylcarbonyl, tetrahydro-2H-thiopyran-4-ylcarbonyl, hexahydropyridazin-3-ylcarbonyl, hexahydropyridazin-4-ylcarbonyl, piperazin-2-ylcarbonyl, morpholin-2-ylcarbonyl, morpholin-3-ylcarbonyl, thiomorpholin-2-ylcarbonyl, thiomorpholin-3-ylcarbonyl, 1,2-oxazinan-3-ylcarbonyl, 1,2-oxazinan-4-ylcarbonyl, 1,2-oxazinan-5-ylcarbonyl, 1,2-oxazinan-6-ylcarbonyl, 1,4-dioxan-2-ylcarbonyl, 1,2-thiazinan-3-ylcarbonyl, 1,2-thiazinan-4-ylcarbonyl, 1,2-thiazinan-5-ylcarbonyl, 1,2-thiazinan-6-ylcarbonyl, azepan-2-ylcarbonyl, azepan-3-ylcarbonyl, azepan-4-ylcarbonyl, oxepan-2-ylcarbonyl, oxepan-3-ylcarbonyl, oxepan-4-ylcarbonyl, thiepan-2-ylcarbonyl, thiepan-3-ylcarbonyl, thiepan-4-ylcarbonyl, 1,4-diazepan-2-ylcarbonyl, 1,4-diazepan-5-ylcarbonyl, 1,4-diazepan-6-ylcarbonyl, 1,4-oxazepan-2-ylcarbonyl, 1,4-oxazepan-3-ylcarbonyl, 1,4-oxazepan-5-ylcarbonyl, 1,4-oxazepan-6-ylcarbonyl, 1,4-oxazepan-7-ylcarbonyl, 1,4-thiazepan-2-ylcarbonyl, 1,4-thiazepan-3-ylcarbonyl, 1,4-thiazepan-5-ylcarbonyl, 1,4-thiazepan-6-ylcarbonyl, 1,4-thiazepan-7-ylcarbonyl, 1,2,5-triazepan-3-ylcarbonyl, 1,2,5-triazepan-4-ylcarbonyl, 1,4,5-oxadiazepan-2-ylcarbonyl, 1,4,5-oxadiazepan-3-ylcarbonyl, 1,2,5-oxadiazepan-3-ylcarbonyl, 1,2,5-oxadiazepan-4-ylcarbonyl, 1,2,5-oxadiazepan-6-ylcarbonyl, 1,2,5-oxadiazepan-7-ylcarbonyl, 1,4,5-thiadiazepan-2-ylcarbonyl, 1,4,5-thiadiazepan-3-ylcarbonyl, 1,5,2-dioxazepan-3-ylcarbonyl, 1,5,2-dioxazepan-4-ylcarbonyl, 1,5,2-dioxazepan-6-ylcarbonyl, 1,5,2-dioxazepan-7-ylcarbonyl, 1,5,2-oxathiazepan-3-ylcarbonyl, 1,5,2-oxathiazepan-4-ylcarbonyl, 1,5,2-oxathiazepan-6-ylcarbonyl, 1,5,2-oxathiazepan-7-ylcarbonyl, etc. It is natural that above specific examples include those to which tert-butoxycarbonyl or benzyloxycarbonyl is bonded as a protective group.

Specific examples of the "heteroarylcarbonyl" include pyrrol-2-ylcarbonyl, pyrrol-3-ylcarbonyl, furan-2-ylcarbonyl, furan-3-ylcarbonyl, thiophen-2-ylcarbonyl, thiophen-3-ylcarbonyl, pyrazol-3-ylcarbonyl, pyrazol-4-ylcarbonyl, imidazol-2-ylcarbonyl, imidazol-4-ylcarbonyl, 1,2-oxazol-3-ylcarbonyl, 1,2-oxazol-4-ylcarbonyl, 1,2-oxazol-5-ylcarbonyl, 1,3-oxazol-2-ylcarbonyl, 1,3-oxazol-4-ylcarbonyl, 1,3-oxazol-5-ylcarbonyl, 1,2-thiazol-3-ylcarbonyl, 1,2-thiazol-4-ylcarbonyl, 1,2-thiazol-5-ylcarbonyl, 1,3-thiazol-2-ylcarbonyl, 1,3-thiazol-4-ylcarbonyl, 1,3-thiazol-5-ylcarbonyl, 1,2,3-triazol-4-ylcarbonyl, 1,2,3-oxadiazol-4-ylcarbonyl, 1,2,3-oxadiazol-5-ylcarbonyl, 1,2,3-thiadiazol-4-ylcarbonyl, 1,2,3-thiadiazol-5-ylcarbonyl, 1,2,4-triazol-3-ylcarbonyl, 1,3,4-oxadiazol-2-ylcarbonyl, 1,3,4-thiadiazol-2-ylcarbonyl, tetrazol-5-ylcarbonyl, pyridin-2-ylcarbonyl, pyridin-3-ylcarbonyl, pyridin-4-ylcarbonyl, pyridazin-3-ylcarbonyl, pyridazin-4-ylcarbonyl, pyrimidin-2-ylcarbonyl, pyrimidin-4-ylcarbonyl, pyrimidin-5-ylcarbonyl, pyrazin-2-ylcarbonyl, 1,2,4-triazin-3-ylcarbonyl, 1,2,4-triazin-5-ylcarbonyl, 1,2,4-triazin-6-ylcarbonyl, 1,3,5-triazin-2-ylcarbonyl, etc. It is natural that above specific examples include those to which tert-butoxycarbonyl or benzyloxycarbonyl is bonded as a protective group.

To the above "acyl", formyl, benzoyl, or phenylacetyl is added, and preferred are formyl, benzoyl, acetyl, phenylacetyl, propanoyl, butanoyl, 2-methylpropanoyl, 2,2-dimethylpropanoyl, azetidin-2-ylcarbonyl, azetidin-3-ylcarbonyl, pyrrolidin-2-ylcarbonyl, pyrrolidin-3-ylcarbonyl, tetrahydrofuran-3-ylcarbonyl, piperidin-2-ylcarbonyl, piperidin-3-ylcarbonyl, piperidin-4-ylcarbonyl, tetrahydro-2H-pyran-2-ylcarbonyl, tetrahydro-2H-pyran-3-ylcarbonyl, tetrahydro-2H-pyran-4-ylcarbonyl, furan-2-ylcarbonyl, 1,3-oxazol-2-ylcarbonyl, 1,3-oxazol-4-ylcarbonyl, pyridin-2-ylcarbonyl, pyridin-3-ylcarbonyl, and pyridin-4-ylcarbonyl.

Specific examples of Re(Rf)N— include amino, methylamino, ethylamino, propylamino, isopropylamino, butylamino, tert-butylamino, s-butylamino, isobutylamino, pentylamino, 1,1-dimethylpropylamino, 1,2-dimethylpropylamino, neopentylamino, 1-methylbutylamino, 2-methylbutylamino, isopentylamino, hexylamino, N,N-dimethylamino, N,N-diethylamino, N,N-dipropylamino, N,N-di(isopropyl)amino, N,N-dibutylamino, N,N-di(tert-butyl)amino, N,N-di(s-butyl)amino, N,N-di(isobutyl)amino, N,N-dipentylamino, N,N-di(1,1-dimethylpropyl)amino, N,N-di(1,2-dimethylpropyl)amino, N,N-di(neopentyl)amino, N,N-di(1-methylbutyl)amino, N,N-di(2-methylbutyl)amino, N,N-di(isopentyl)amino, N,N-di(hexyl)amino, etc., preferably amino, methylamino, ethylamino, propylamino, isopropylamino, N,N-dimethylamino, and N,N-diethylamino. It is natural that the above specific examples include those protected by tert-butoxycarbonyl or benzyloxycarbonyl as a protective group.

Specific examples of Re(Rf)NCO— include aminocarbonyl, methylaminocarbonyl, ethylaminocarbonyl, propylaminocarbonyl, isopropylaminocarbonyl, butylaminocarbonyl, tert-butylaminocarbonyl, s-butylaminocarbonyl, isobutylaminocarbonyl, pentylaminocarbonyl, 1,1-dimethylpropylaminocarbonyl, 1,2-dimethylpropylaminocarbonyl, neopentylaminocarbonyl, 1-methylbutylaminocarbonyl, 2-methylbutylaminocarbonyl, isopentylaminocarbonyl, hexylaminocarbonyl, N,N-dimethylaminocarbonyl, N,N-diethylaminocarbonyl, N,N-dipropylaminocarbonyl, N,N-di(isopropyl)aminocarbonyl, N,N-dibutylaminocarbonyl, N,N-di(tert-butyl)aminocarbonyl, N,N-di(s-butyl)aminocarbonyl, N,N-di(isobutyl)aminocarbonyl, N,N-dipentylaminocarbonyl, N,N-di(1,1-dimethylpropyl)aminocarbonyl, N,N-di(1,2-dimethylpropyl)aminocarbonyl, N,N-di(neopentyl)aminocarbonyl, N,N-di(1-methyl-butyl)aminocarbonyl, N,N-di(2-methylbutyl)aminocarbonyl, N,N-di(isopentyl)aminocarbonyl, etc., which are derived from specific examples of Re(Rf)N— described above, preferably dimethylaminocarbonyl or diethylaminocarbonyl.

Specific examples of ReO— include hydroxy, methoxy, ethoxy, propoxy, isopropoxy, butoxy, tert-butoxy, s-butoxy, isobutoxy, pentoxy, 1,1-dimethylpropoxy, 1,2-dimethylpropoxy, neopentoxy, 1-methylbutoxy, 2-methylbutoxy, isopentoxy, hexyloxy, benzyloxy, cyclopropoxy, cyclobutoxy, cyclopentyloxy, cyclohexyloxy, cyclopropylmethoxy, cyclobutylmethoxy, cyclopentylmethoxy, etc., preferably hydroxy, methoxy, ethoxy, propoxy, isopropoxy, tert-butoxy, cyclopropoxy and cyclobutylmethoxy. It is natural that the above hydroxy includes those to which triisopropylsilyl included in trialkylsilyloxy as a protective group is bonded.

Specific examples of ReOCO— include methoxycarbonyl, ethoxycarbonyl, propoxycarbonyl, isopropoxycarbonyl, butoxycarbonyl, tert-butoxycarbonyl, s-butoxycarbonyl, isobutoxycarbonyl, pentoxycarbonyl, 1,1-dimethylpropoxycarbonyl, 1,2-dimethylpropoxycarbonyl, neopentoxycarbonyl, 1-methylbutoxycarbonyl, 2-methylbutoxycarbonyl, isopentoxycarbonyl, hexyloxycarbonyl, etc., which are derived from the specific examples of ReO— described above, preferably methoxycarbonyl, ethoxycarbonyl, tert-butoxycarbonyl, and benzyloxycarbonyl, methoxycarbonyl modified by phenyl which is defined by Fn1.

Specific examples of RdO$_2$S— include methylsulfonyl, ethylsulfonyl, propylsulfonyl, isopropylsulfonyl, butylsulfonyl, tert-butylsulfonyl, s-butylsulfonyl, isobutylsulfonyl, pentylsulfonyl, 1,1-dimethylpropylsulfonyl, 1,2-dimethylpropylsulfonyl, neopentylsulfonyl, 1-methylbutylsulfonyl, 2-methylbutylsulfonyl, isopentylsulfonyl, hexylsulfonyl, cyclopropanesulfonyl, cyclobutanesulfonyl, cyclopentylsulfonyl, cyclohexylsulfonyl, cyclopropylmethanesulfonyl, cyclobutylmethanesulfonyl, cyclopentylmethanesulfonyl, etc., preferably sulfoxy and methanesulfonyl.

Among specific examples of Ra(Rb)N— comprising the above C$_{1-6}$ alkyl, acyl and Re(Rf)N—, preferred are amino, methylamino, ethylamino, propylamino, isopropylamino, tert-butylamino, isobutylamino, N,N-dimethylamino, N,N-diethylamino, N,N-di(isopropyl)amino, acetylamino, propanoylamino, isobutanoylamino, phenylacetylamino, benzoylamino, [(azetidin-2-yl)carbonyl]amino, [(azetidin-3-yl)carbonyl]amino, [(pyrrolidin-2-yl)carbonyl]amino, [(pyrrolidin-3-yl)carbonyl]amino, [(tetrahydrofuran-3-yl)carbonyl]amino, [(tetrahydrothiophen-3-yl)carbonyl]amino, [(pyrazolidin-3-yl)carbonyl]amino, [(pyrazolidin-4-yl)carbonyl]amino, [(1,2-oxazolidin-3-yl)carbonyl]amino, [(piperidin-2-yl)carbonyl]-amino, [(piperidin-3-yl)carbonyl]amino, [(piperidin-4-yl)carbonyl]amino, [(tetrahydro-2H-pyran-2-yl)carbonyl]amino, [(tetrahydro-2H-pyran-4-yl)carbonyl]amino, [(tetrahydro-2H-thiopyran-4-yl)carbonyl]amino, [(hexahydropyridazin-3-yl)carbonyl]-amino, [(hexahydropyridazin-4-yl)carbonyl]amino, [(piperazin-2-yl)carbonyl]amino, [(morpholin-2-yl)carbonyl]amino, [(morpholin-3-yl)carbonyl]amino, [(thiomorpholin-2-yl)carbonyl]amino, [(thiomorpholin-3-yl)carbonyl]amino, [(1,2-oxazinan-3-yl)carbonyl]amino, [(azepan-2-yl)carbonyl]amino, [(azepan-4-yl)carbonyl]amino, [(oxepan-2-yl)carbonyl]amino, [(oxepan-4-yl)carbonyl]amino, [(1,4-diazepan-2-yl)carbonyl]amino, [(1,4-diazepan-6-yl)carbonyl]amino, pyrrol-2-ylcarbonylamino, pyrrol-3-ylcarbonylamino, furan-2-ylcarbonylamino, furan-3-ylcarbonylamino, pyrazol-3-ylcarbonylamino, pyrazol-4-ylcarbonylamino, imidazol-2-ylcarbonylamino, imidazol-4-ylcarbonylamino, 1,2-oxazol-3-ylcarbonylamino, 1,2-oxazol-4-ylcarbonylamino, 1,2-oxazol-5-ylcarbonylamino, 1,3-oxazol-2-ylcarbonylamino, 1,3-oxazol-4-ylcarbonylamino, 1,3-oxazol-5-ylcarbonylamino, 1,3-thiazol-2-ylcarbonylamino, 1,3-thiazol-4-ylcarbonylamino, 1,3-thiazol-5-ylcarbonylamino, 1,2,3-triazol-4-ylcarbonylamino, 1,2,3-triazol-5-ylcarbonylamino, 1,2,3-oxadiazol-4-ylcarbonylamino, 1,2,3-oxadiazol-5-ylcarbonylamino, 1,2,4-triazol-3-ylcarbonylamino, 1,3,4-oxadiazol-3-ylcarbonylamino, tetrazol-5-ylcarbonylamino, pyridin-2-ylcarbonylamino, pyridin-3-ylcarbonylamino, pyridin-4-ylcarbonylamino, pyridazin-3-ylcarbonylamino, pyridazin-4-ylcarbonylamino, pyrimidin-2-ylcarbonylamino, pyrimidin-4-ylcarbonylamino, pyrazin-2-ylcarbonylamino, 1,2,4-triazin-3-ylcarbonylamino, 1,2,4-triazin-5-ylcarbonylamino, 1,2,4-triazin-6-ylcarbonylamino, 1,3,5-triazin-2-ylcarbonylamino, etc. In addition, specific examples in the case where Ra and Rb of Ra(Rb)N— are bonded to form a heterocyclyl include azetidin-1-yl, pyrrolidin-1-yl, piperidin-1-yl, azepan-1-yl, 2-oxoazetidin-1-yl, 2-oxopyrrolidin-1-yl, 2-oxopiperidin-1-yl, 2-oxoazepan-1-yl, etc. It is natural that the above specific examples include those to which tert-butoxycarbonyl or benzyloxycarbonyl is bonded as a protective group.

Among specific examples of C$_{1-6}$ alkoxy exemplified by specific examples of the above ReO—, and RcO— to be obtained from heterocyclyl, preferred are methoxy, ethoxy, propoxy, isopropoxy, cyclobutylmethoxy, azetidin-3-yloxy, oxetan-3-yloxy, thietan-3-yloxy, pyrrolidin-3-yloxy, tetrahydrofuran-3-yloxy, tetrahydrothiophen-3-yloxy, pyrazolidin-4-yloxy, piperidin-3-yloxy, piperidin-4-yloxy, tetrahydro-2H-pyran-3-yloxy, tetrahydro-2H-pyran-4-yloxy, tetrahydro-2H-thiopyran-3-yloxy, tetrahydro-2H-thiopyran-4-yloxy, hexahydropyridazin-4-yloxy, 1,2-oxazolidin-4-yloxy, 1,2-oxazinan-4-yloxy, 1,2-oxazinan-5-yloxy, 1,2-thiazinan-4-yloxy, 1,2-thiazinan-5-yloxy, azepan-3-yloxy, azepan-4-yloxy, oxepan-3-yloxy, oxepan-4-yloxy, thiepan-3-yloxy, thiepan-4-yloxy, 1,4-diazepan-6-yloxy, 1,4-oxazepan-6-yloxy, 1,4-thiazepan-6-yloxy, etc. In addition, in RcO—B—, specific examples of heterocyclyl formed by the bonding of ring Rc and B include 1,2-oxazolidine, 1,2-oxazinane, 1,2-oxazepane, etc. It is natural that the specific examples include those to which tert-butoxycarbonyl or benzyloxycarbonyl is bonded as a protective group.

In the following, specific examples in the case where C$_{1-6}$ alkyl, acyl, or heterocyclyl which form the above Ra(Rb)N— or RcO— is modified by C$_{1-6}$ alkyl, O=, Rg-(CH$_2$)$_{0-3}$—, heterocyclyl, phenyl, heteroaryl, acyl, RdO$_2$S—, Re(Rf)N—, Re(Rf)NCO—, ReO— and ReOCO—, which are defined by Fn1, or by a protective group will be described in detail by way of representative examples, but it is natural that the examples are not limited to the scope of the specific examples which are illustrated.

Specific example of C$_{1-6}$ alkyl modified by amino (H$_2$N—) which is a representative example of Re(Rf)N— include 2-aminoethyl, 2-aminopropyl, 3-aminopropyl, 2-amino-1-methylethyl, 2-aminobutyl, 3-aminobutyl, 4-aminobutyl, 2-amino-1,1-dimethylethyl, 2-amino-1-methylpropyl, 3-amino-2-methylpropyl, etc. It is natural that those to which a protective tert-butoxycarbonyl or benzyloxycarbonyl which is included in ReOCO— is bonded is included in the above specific examples.

In addition, CH$_2$ to which amino is bonded in 2-aminoethyl in the above specific examples is modified by O= (oxo) to obtain an aminocarbonylalkyl derivative included in Re(Rf)NCO— include 2-(amino)-2-oxoethyl, 2-(methylamino)-2-oxoethyl, 2-(ethylamino)-2-oxoethyl, 2-oxo-2-(propylamino)ethyl, 2-(isopropylamino)-2-oxoethyl, 2-(tert-butylamino)-2-oxoethyl, 2-(isobutylamino)-2-oxoethyl, etc.

In addition, specific examples in which the above 2-aminoethyl derivative is modified by methylsulfonyl as a representative example of RdO$_2$S—, acetyl as a representative example of acyl or carbamoyl (H$_2$NCO—) as a representative example of Re(Rf)NCO— include 2-(methylsulfonylamino)ethyl, 2-(methylsulfonylamino)propyl, 3-(methylsulfonylamino)propyl, 2-(methylsulfonylamino)-1-methylethyl, 2-(methyl-sulfonylamino)butyl, 3-(methylsulfonylamino)butyl, 4-(methylsulfonylamino)butyl, 2-(methylsulfonylamino)-1,1-dimethylethyl, 2-(methylsulfonylamino)-1-methylpropyl, 3-(methylsulfonylamino)-2-methylpropyl, 2-(acetylamino)ethyl, 2-(acetylamino)propyl, 3-(acetylamino)propyl, 2-(acetylamino)-1-methylethyl, 2-(acetylamino)butyl, 3-(acetylamino)butyl, 4-(acetylamino)butyl, 2-(acetylamino)-1,1-dimethylethyl, 2-(acetylamino)-1-methylpropyl, 3-(acetylamino)-2-methylpropyl, 2-(carbamoylamino)-ethyl, 2-(carbamoylamino)propyl, 3-(carbamoylamino)propyl, 2-(carbamoylamino)-1-methylethyl, 2-(carbamoylamino)butyl, 3-(carbamoylamino)butyl, 4-(carbamoylamino)-butyl, 2-(carbamoylamino)-1,1-dimethylethyl, 2-(carbamoylamino)-1-methylpropyl, 3-(carbamoylamino)-2-methylpropyl, etc.

Specific examples in which C$_{1-6}$ alkyl is modified by hydroxy (HO—) as a representative example of ReO— include 2-hydroxyethyl, 2-hydroxypropyl, 3-hydroxypropyl, 2-hydroxy-1-methylethyl, 2-hydroxybutyl, 3-hydroxybutyl, 4-hydroxybutyl, 1,1-dimethyl-2-hydroxyethyl, 2-hydroxy-1-methylpropyl, 3-hydroxy-2-methylpropyl, etc. It is natural that the above specific examples include those in which hydroxy is protected by triisopropylsilyl included in trialkylsilyl.

Specific example in the case where ethyl as a representative example of $C_{1-6}$ alkyl is modified by methylsulfonyl as the representative example of $RdO_2S$— includes 2-(methylsulfonyl)ethyl.

Specific examples of $C_{1-6}$ alkylcarbonyl, phenylacetyl or benzoyl modified by amino ($H_2N$—) as the representative example of Re(Rf)N— include 2-aminoacetyl, 2-aminopropanoyl, 3-aminopropanoyl, 2-aminobutanoyl, 3-aminobutanoyl, 4-aminobutanoyl, 3-amino-2-methylpropanoyl, 2-(2-aminophenyl)acetyl, 2-(3-aminophenyl)-acetyl, 2-(4-aminophenyl)acetyl, 2-[2-(aminomethyl)phenyl]acetyl, 2-[3-(amino-methyl)phenyl]acetyl, 2-[4-(aminomethyl)phenyl]acetyl, 2-aminobenzoyl, 3-aminobenzoyl, 4-aminobenzoyl, 2-(aminomethyl)benzoyl, 3-(aminomethyl)benzoyl, 4-(aminomethyl)benzoyl, etc. It is natural that those to which tert-butoxycarbonyl or benzyloxycarbonyl is bonded as a protective group are included as specific example.

Specific examples of $C_{1-6}$ alkylcarbonyl, phenylacetyl, benzoyl modified by hydroxyl (HO—) as the representative example of ReO— include 2-hydroxyacetyl, 2-hydroxypropanoyl, 3-hydroxypropanoyl, 2-hydroxybutanoyl, 3-hydroxybutanoyl, 4-hydroxybutanoyl, 3-hydroxy-2-methylpropanoyl, 2-(2-hydroxyphenyl)acetyl, 2-(3-hydroxyphenyl)acetyl, 2-(4-hydroxyphenyl)acetyl, 2-hydroxybenzoyl, 3-hydroxybenzoyl, 4-hydroxybenzoyl, etc. It is natural that those in which hydroxy is protected by triisopropylsilyl included in trialkylsilyl are included in the above specific examples.

Specific examples in which methyl or ethyl as the representative example of $C_{1-6}$ alkyl is modified by heterocyclyl include azetidin-2-ylmethyl, azetidin-3-ylmethyl, pyrrolidin-2-ylmethyl, pyrrolidin-3-ylmethyl, tetrahydrofuran-3-ylmethyl, tetrahydrothiophen-3-ylmethyl, pyrazolidin-4-ylmethyl, 1,2-oxazolidin-3-ylmethyl, piperidin-2-ylmethyl, piperidin-3-ylmethyl, piperidin-4-ylmethyl, tetrahydro-2H-pyran-4-ylmethyl, tetrahydro-2H-thiopyran-4-ylmethyl, hexahydropyridazin-4-ylmethyl, piperazin-2-ylmethyl, 1,2-oxazinan-3-ylmethyl, morpholin-2-ylmethyl, morpholin-3-ylmethyl, thiomorpholin-2-ylmethyl, thiomorpholin-3-ylmethyl, azepan-2-ylmethyl, azepan-4-ylmethyl, oxepan-2-ylmethyl, oxepan-4-ylmethyl, 1,4-diazepan-2-ylmethyl, 1,4-diazepan-6-ylmethyl, 2-(azetidin-1-yl)ethyl, 2-(pyrrolidin-1-yl)ethyl, 2-(pyrazolidin-1-yl)ethyl, 2-(piperidin-1-yl)ethyl, 2-(hexahydropyridazin-1-yl)ethyl, 2-(piperazin-1-yl)ethyl, 2-(morpholin-4-yl)ethyl, 2-(thiomorpholin-4-yl)ethyl, 2-(1,2-oxazolidin-2-yl)ethyl, 2-(1,2-oxazinan-2-yl)ethyl, 2-(azepan-1-yl)ethyl, 2-(1,4-diazepan-1-yl)ethyl, etc. It is natural that the above specific examples include those to which tert-butoxycarbonyl or benzyloxycarbonyl is bonded as a protective group.

In addition, specific examples in which ethyl of the above heterocyclyl-ethyl derivative is further modified by O= (oxo) to form aminocarbonyl included in Re(Rf)NCO— include 2-(azetidin-1-yl)-2-oxoethyl, 2-oxo-(pyrrolidin-1-yl)ethyl, 2-oxo-(pyrazolidin-1-yl)ethyl, 2-oxo-(piperidin-1-yl)ethyl, 2-(hexahydropyridazin-1-yl)-2-oxoethyl, 2-oxo-(piperazin-1-yl)ethyl, 2-(morpholin-4-yl)-2-oxoethyl, 2-oxo-(thiomorpholin-4-yl)ethyl, 2-(1,2-oxazolidin-2-yl)-2-oxoethyl, 2-(1,2-oxazinan-2-yl)-2-oxoethyl, 2-(azepan-1-yl)-2-oxoethyl, 2-(1,4-diazepan-1-yl)-2-oxoethyl, etc. It is natural that the above specific examples include those to which tert-butoxycarbonyl or benzyloxycarbonyl is bonded as a protective group.

Specific examples in which, among Re(Rf)NCO—, Re and Rf modified by Fn1 are bonded to form a heterocyclyl include azetidin-1-ylcarbonyl, pyrrolidin-1-ylcarbonyl, 1,2-oxazolidin-2-ylcarbonyl, pyrazolidin-1-ylcarbonyl, piperidin-1-ylcarbonyl, hexahydropyridazin-1-ylcarbonyl, piperazin-1-ylcarbonyl, morpholin-4-ylcarbonyl, thiomorpholin-4-ylcarbonyl, 1,2-oxazinan-2-ylcarbonyl, azepan-1-ylcarbonyl, 1,4-diazepan-1-ylcarbonyl, etc.

Specific examples in the case where methyl or ethyl as the representative example of $C_{1-6}$ alkyl is modified by heteroaryl include pyrrol-2-ylmethyl, furan-2-ylmethyl, pyrazol-3-ylmethyl, pyrazol-4-ylmethyl, imidazol-2-ylmethyl, imidazol-4-ylmethyl, 1,2-oxazol-3-ylmethyl, 1,3-oxazol-2-ylmethyl, 1,3-oxazol-4-ylmethyl, 1,3-thiazol-2-ylmethyl, 1,3-thiazol-4-ylmethyl, 1,2,3-triazol-4-ylmethyl, 1,2,3-oxadiazol-4-ylmethyl, 1,2,4-triazol-3-ylmethyl, 1,3,4-oxadiazol-2-ylmethyl, tetrazol-5-ylmethyl, pyridin-2-ylmethyl, pyridin-3-ylmethyl, pyridin-4-ylmethyl, pyridazin-3-ylmethyl, pyridazin-4-ylmethyl, pyrimidin-2-ylmethyl, pyrimidin-4-ylmethyl, pyrazin-2-ylmethyl, 1,2,4-triazin-3-ylmethyl, 1,2,4-triazin-5-ylmethyl, 1,3,5-triazin-2-ylmethyl, 2-(pyrrol-1-yl)ethyl, 2-(pyrazol-1-yl)ethyl, 2-(imidazol-1-yl)ethyl, 2-(1,2,3-triazol-1-yl)ethyl, 2-(1,2,4-triazol-1-yl)ethyl, 2-(tetrazol-1-yl)ethyl, etc. It is natural that the above specific examples include those to which tert-butoxycarbonyl or benzyloxycarbonyl is bonded as a protective group.

Specific examples in which heterocyclyl is modified by methyl as the representative example of $C_{1-6}$ alkyl include 1-methylazetidine, 3-methylazetidine, 1-methylpyrrolidine, 3-methylpyrrolidine, 1-methylimidazolidine, 3-methyloxazolidine, 1-methylpyrazolidine, 1-methylpiperidine, 4-methylpiperidine, 2-methyltetrahydro-2H-pyran, 4-methyltetrahydro-2H-pyran, 1-methylpiperazine, 1,4-dimethylpiperazine, 4-methylmorpholine, 4-methyl-thiomorpholine, 1-methylazepane, 1-methyl-1,4-diazepane, 1,4-dimethyl-1,4-diazepane, etc. It is natural that the above specific examples include those to which tert-butoxycarbonyl or benzyloxycarbonyl is bonded as a protective group.

Specific examples of heterocyclyl modified by O= (oxo) include 2-oxoazetidine, 2-oxopyrrolidine, 3-oxopyrazolidine, 2-oxoimidazolidine, 3-oxo-1,2-oxazolidine, 2-oxooxazolidine, 2-oxopiperidine, 3-oxo-hexahydropyridazine, 2-oxopiperazine, 3-oxomorpholine, 3-oxo-1,2-oxazinane, 2-oxoazepane, 2-oxo-1,4-diazepane, 5-oxo-1,4-diazepane, etc.

Specific examples in the case where ethyl as the representative example of $C_{1-6}$ alkyl described above is modified by heterocyclyl and further heterocyclyl is modified by O= (oxo) include 2-(2-oxoazetidin-1-yl)ethyl, 2-(2-oxopyrrolidin-1-yl)ethyl, 2-(2-oxoimidazolidin-3-yl)ethyl, 2-(2-oxooxazolidin-3-yl)ethyl, 2-(3-oxopyrazolidin-1-yl)ethyl, 2-(2-oxopiperidin-1-yl)ethyl, 2-(3-oxo-hexahydropyridazin-1-yl)ethyl, 2-(2-oxopiperazin-1-yl)ethyl, 2-(3-oxomorpholin-4-yl)ethyl, 2-(3-oxo-1,2-oxazolidin-2-yl)ethyl, 2-(3-oxo-1,2-oxazinan-2-yl)ethyl, 2-(2-oxoazepan-1-yl)ethyl, 2-(2-oxo-1,4-diazepan-1-yl)ethyl, 2-(5-oxo-1,4-diazepan-1-yl)ethyl, etc.

Specific examples of the heterocyclylcarbonyl in which the heterocyclyl is modified by O= (oxo) include 4-oxoazetidin-2-ylcarbonyl, 5-oxopyrrolidin-2-ylcarbonyl, 2-oxoimidazolidin-4-ylcarbonyl, 2-oxooxazolidin-4-ylcarbonyl, 5-oxopyrazolidin-3-ylcarbonyl, 6-oxopiperidin-2-ylmethyl, 2-oxopiperidin-4-ylcarbonyl, 6-oxo-hexahydropyridazin-3-ylcarbonyl, 3-oxo-hexahydropyridazin-4-ylcarbonyl, 5-oxopiperazin-2-ylcarbonyl, 6-oxopiperazin-2-ylcarbonyl, 5-oxomorpholin-2-ylcarbonyl, 5-oxomorpholin-3-ylcarbonyl, 3-oxothiomorpholin-2-ylcarbonyl, 5-oxothiomorpholin-3-ylcarbonyl, 7-oxoazepan-2-ylcarbonyl, 2-oxoazepan-4-ylcarbonyl, 7-oxo-1,4-diazepan-2-ylcarbonyl, 2-oxo-1,4-diazepan-6-ylcarbonyl, etc. It is natural that the above specific examples include those to which tert-butoxycarbonyl or benzyloxycarbonyl is bonded as protective group.

Specific examples of heterocyclyl modified by amino ($H_2N$—) as the representative example of Re(Rf)N— include a group derived from 3-aminoazetidine, 3-aminopyrrolidine, 3-amino-tetrahydrofuran, 3-amino-tetrahydrothiophene, 4-aminopyrazolidine, 4-aminopiperidine, 4-amino-tetrahydro-2H-pyran, 4-amino-tetrahydro-2H-thiopyran, 4-amino-hexahydropyridazine, 4-amino-1,2-oxazolidine, 4-amino-1,2-oxazinane, 4-aminoazepane, 4-aminooxepane, 6-amino-1,4-diazepane, etc. It is natural that the above specific examples include those to which tert-butoxycarbonyl or benzyloxycarbonyl is bonded as a protective group.

Specific examples of heterocyclyl modified by hydroxy (HO—) as the representative example of ReO— include a group derived from 3-hydroxyazetidine, 3-hydroxypyrrolidine, 4-hydroxypyrazolidine, 4-hydroxytetrahydrofuran, 4-hydroxytetrahydrothiophene, 3-hydroxypiperidine, 4-hydroxypiperidine, 4-hydroxytetrahydro-2H-thiopyran, 4-hydroxy-hexahydropyridazine, 4-hydroxy-1,2-oxazolidine, 4-hydroxy-1,2-oxazinane, 4-hydroxyazepane, 6-hydroxy-1,4-diazepane, etc. It is natural that the above specific examples include those in which hydroxy is protected by triisopropylsilyl, heterocyclyl is protected by tert-butoxycarbonyl or benzyloxycarbonyl.

Specific examples of heteroaryl modified by methyl as the representative example of $C_{1-6}$ alkyl include a group derived from 1-methylpyrrole, 2-methylpyrrole, 3-methylpyrrole, 1-methylpyrazole, 3-methylpyrazole, 4-methylpyrazole, 2-methylimidazole, 4-methylimidazole, 4-methyl-1,2-oxazole, 5-methyl-1,2-oxazole, 2-methyl-1,3-oxazole, 4-methyl-1,3-oxazole, 5-methyl-1,3-oxazole, 1-methyl-1,2,3-triazole, 4-methyl-1,2,3-triazole, 1-methyl-1,2,4-triazole, 3-methyl-1,2,4-triazole, 1-methyltetrazole, 5-methyltetrazole, 2-methyl-1,3,4-oxadiazole, 2-methylpyridine, 3-methylpyridine, 4-methylpyridine, 3-methylpyridazine, 4-methylpyridazine, 2-methylpyrimidine, 4-methylpyrimidine, 2-methylpyrazine, 3-methyl-1,2,4-triazine, 5-methyl-1,2,4-triazine, 6-methyl-1,2,4-triazine, 2-methyl-1,3,5-triazine, etc. It is natural that the specific examples include those to which tert-butoxycarbonyl or benzyloxycarbonyl is bonded as a protective group.

Specific examples of heteroaryl modified by amino ($H_2N$—) as the representative example of Re(Rf)N— include a group derived from 2-aminopyrrole, 3-aminopyrrole, 2-aminofuran, 3-aminofuran, 3-aminopyrazole, 4-aminopyrazole, 2-aminoimidazole, 3-amino-1,2-oxazole, 2-amino-1,3-oxazole, 2-aminothiazole, 4-amino-1,2,3-triazole, 3-amino-1,2,4-triazole, 2-amino-1,3,4-thiadiazole, 5-aminotetrazole, 2-amino-1,3,4-oxadiazole, 2-aminopyridine, 3-aminopyridazine, 2-aminopyrimidine, 3-amino-1,2,4-triazine, 2-amino-1,3,5-triazine, etc. It is natural that the specific examples include those to which tert-butoxycarbonyl or benzyloxycarbonyl is bonded as a protective group.

Specific examples of heteroaryl modified by hydroxy (OH—) as the representative example of ReO— include a group derived from 2-hydroxypyrrole, 3-hydroxypyrrole, 2-hydroxyfuran, 3-hydroxyfuran, 3-hydroxypyrazole, 4-hydroxypyrazole, 2-hydroxyimidazole, 3-hydroxy-1,2-oxazole, 2-hydroxy-1,3-oxazole, 2-hydroxythiazole, 4-hydroxy-1,2,3-triazole, 3-hydroxy-1,2,4-triazole, 5-hydroxytetrazole, 2-hydroxy-1,3,4-oxadiazole, 2-hydroxypyridine, 3-hydroxypyridazine, 2-hydroxypyrimidine, 3-hydroxy-1,2,4-triazine, 2-hydroxy-1,3,5-triazine, etc. It is natural that the specific examples include those in which hydroxy is protected by triisopropylsilyl, and heteroaryl is protected by tert-butoxycarbonyl or benzyloxycarbonyl.

As the specific examples of Ra(Rb)N— comprising the above $C_{1-6}$ alkyl or acyl, preferred are amino, methylamino, ethylamino, propylamino, isopropylamino, dimethylamino, diethylamino, phenylamino, acetylamino, propanoylamino, butanoylamino, 2-methylpropanoylamino, 2,2-dimethylpropanoylamino, 2-aminoacetylamino, 3-aminopropanoylamino, 2-methoxyacetylamino, phenylacetylamino, 2-(4-aminophenyl)acetylamino, 2-(4-aminomethylphenyl)acetylamino, benzoylamino, 4-aminobenzoylamino, 4-aminomethylbenzoylamino, [(azetidin-2-yl)carbonyl]amino, [(pyrrolidin-2-yl)carbonyl]amino, [(pyrrolidin-3-yl)carbonyl]amino, [(piperidin-2-yl)carbonyl]amino, [(piperidin-3-yl)carbonyl]amino, [(piperidin-4-yl)carbonyl]amino, [(4-cyclopentylmethylpiperidin-2-yl)carbonyl]amino, [(tetrahydro-2H-pyran-4-yl)carbonyl]amino, [(5-oxopyrrolidin-2-yl)carbonyl]amino, furan-2-ylcarbonylamino, 1,3-oxazol-4-ylcarbonylamino, pyridin-2-ylcarbonylamino, pyridin-3-ylcarbonylamino, pyridin-4-ylcarbonylamino, methanesulfonylamino, dimethylaminocarbonylamino, diethylaminocarbonylamino, phenylaminocarbonylamino, morpholin-4-ylcarbonylamino, methoxycarbonylamino, ethoxycarbonylamino, tert-butoxycarbonylamino, etc. In addition, specific examples in the case where among Ra(Rb)N—, Ra and Rb modified by Fn1 are bonded to form a heterocyclyl include azetidin-1-yl, pyrrolidin-1-yl, piperidin-1-yl, piperazin-1-yl, morpholin-4-yl, thiomorpholin-4-yl, azepan-1-yl, 1,4-diazepan-1-yl, 2-oxoazetidin-1-yl, 2-oxopyrrolidin-1-yl, 2-oxopiperidin-1-yl, 2-oxo-piperazin-1-yl, 3-oxo-morpholin-4-yl, 2-oxoazepan-1-yl, 2-oxo-1,4-diazepan-1-yl, etc. It is natural that free NH or HO modified by a protective group such as tert-butoxycarbonyl, benzyloxycarbonyl, or triisopropylsilyl is included in the above Ra(Rb)N—, if necessary.

In addition, specific examples of RcO— comprising the above $C_{1-6}$ alkoxy and heterocyclyloxy include preferably methoxy, ethoxy, propoxy, isopropoxy, cyclobutylmethoxy, azetidin-3-yloxy, pyrrolidin-3-yloxy, tetrahydrofuran-3-yloxy, tetrahydrothiophen-3-yloxy, pyrazolidin-4-yloxy, piperidin-3-yloxy, piperidin-4-yloxy, tetrahydro-2H-pyran-4-yloxy, tetrahydro-2H-thiopyran-4-yloxy, 1,2-oxazolidin-4-yloxy, 1,2-oxazinan-4-yloxy, 1,2-oxazinan-5-yloxy, azepan-3-yloxy, azepan-4-yloxy, 1,4-diazepan-6-yloxy, 1,4-oxazepane-6-yloxy, 2-aminoethoxy, 2-(methylamino)ethoxy, 2-(propylamino)ethoxy, 2-(isopropylamino)ethoxy, 2-(dimethylamino)ethoxy, 2-hydroxyethoxy, 2-methoxyethoxy, 2-aminopropoxy, 3-aminopropoxy, 2-amino-1-methylethoxy, 2-amino-2-oxo-ethoxy, 2-(dimethylamino)-2-oxo-ethoxy, 2-(methylsulfonyl)ethoxy, (azetidin-2-yl)methoxy, (azetidin-3-yl)methoxy, (pyrrolidin-2-yl)methoxy, (pyrrolidin-3-yl)methoxy, (piperidin-2-yl)methoxy, (piperidin-3-yl)methoxy, (piperidin-4-yl)methoxy, (4-oxoazetidin-2-yl)methoxy, (5-oxopyrrolidin-2-yl)methoxy, (6-oxopiperidin-2-yl)methoxy, 2-(azetidin-1-yl)ethoxy, 2-(pyrrolidin-1-yl)ethoxy, 2-(piperidin-1-yl)ethoxy, 2-(morpholin-4-yl)ethoxy, 2-(piperazin-1-yl)ethoxy, 2-(1,4-diazepan-1-yl)ethoxy, 2-(azetidin-1-yl)-2-oxoethoxy, 2-oxo-2-(pyrrolidin-1-yl)ethoxy, 2-oxo-2-(piperidin-1-yl)ethoxy, 2-oxo-2-(piperazin-1-yl)ethoxy, 2-(morpholin-4-yl)-2-oxoethoxy, 2-(1,4-diazepan-1-yl)-2-oxoethoxy, 2-(2-oxoazetidin-1-yl)ethoxy, 2-(2-oxopyrrolidin-1-yl)ethoxy, 2-(2-oxopiperidin-1-yl)ethoxy, 2-(2-oxoimidazolidin-1-yl)ethoxy, 2-(2-oxo-1, 3-oxazolidin-3-yl)ethoxy, 2-(pyrrol-1-yl)ethoxy, 2-(imidazol-1-yl)ethoxy, 2-(2-sulfonate-1H-imidazol-1-ium-1-yl)ethoxy. In addition, specific examples of heterocyclyl formed by bondage of Rc and B or Rc and B modified by Fn1 in RcO—B— include 1,2-oxazolidin-2-yl, 1,2-oxazinan-2-yl, 1,2-oxazepan-2-yl, 1,2,5-oxadiazepan-2-yl, 1,5,2-dioxazepan-5-yl, etc. It is natural that free NH or HO modified by a protective group such as tert-butoxycarbonyl, benzyloxycarbonyl, or triisopropylsilyl is included in the above RcO—, if necessary.

More specific examples of compounds provided by the present invention preferably include compounds as follows:

(2S,5R)-7-oxo-6-(sulfooxy)-1,6-diazabicyclo[3.2.1]octane-2-carbohydrazide,
tert-butyl 2-{[(2S,5R)-6-benzyloxy-7-oxo-1,6-diazabicyclo[3.2.1]oct-2-yl]carbonyl}-hydrazinecarboxylate,
tert-butyl 2-{[(2S,5R)-6-hydroxy-7-oxo-1,6-diazabicyclo[3.2.1]oct-2-yl]carbonyl}-hydrazinecarboxylate,
tetrabutylammonium tert-butyl 2-{[(2S,5R)-7-oxo-6-(sulfooxy)-1,6-diazabicyclo[3.2.1]-oct-2-yl]carbonyl}hydrazinecarboxylate,
sodium tert-butyl 1-methyl-2-{[(2S,5R)-7-oxo-6-(sulfooxy)-1,6-diazabicyclo[3.2.1]oct-2-yl]carbonyl}hydrazinecarboxylate,
tert-butyl 2-{[(2S,5R)-6-benzyloxy-7-oxo-1,6-diazabicyclo[3.2.1]oct-2-yl]carbonyl}-1-methylhydrazinecarboxylate,
tert-butyl 2-{[(2S,5R)-6-hydroxy-7-oxo-1,6-diazabicyclo[3.2.1]oct-2-yl]carbonyl}-1-methylhydrazinecarboxylate,
pyridinium tert-butyl 2-{[(2S,5R)-7-oxo-6-(sulfooxy)-1,6-diazabicyclo[3.2.1]oct-2-yl]carbonyl}-1-methylhydrazinecarboxylate,
(2S,5R)-N'-methyl-7-oxo-6-(sulfooxy)-1,6-diazabicyclo[3.2.1]octane-2-carbohydrazide,
sodium (2S,5R)-N',N'-dimethyl-7-oxo-6-(sulfooxy)-1,6-diazabicyclo[3.2.1]octane-2-carbohydrazide,
(2S,5R)-6-benzyloxy-N',N'-dimethyl-7-oxo-1,6-diazabicyclo[3.2.1]octane-2-carbohydrazide,
(2S,5R)-N',N'-dimethyl-6-hydroxy-7-oxo-1,6-diazabicyclo[3.2.1]octane-2-carbohydrazide,
pyridinium (2S,5R)-N',N'-dimethyl-7-oxo-6-(sulfooxy)-1,6-diazabicyclo[3.2.1]octane-2-carbohydrazide,
sodium (2S,5R)-N'-acetyl-7-oxo-6-(sulfooxy)-1,6-diazabicyclo[3.2.1]octane-2-carbohydrazide,
(2S,5R)-N'-acetyl-6-benzyloxy-7-oxo-1,6-diazabicyclo[3.2.1]octane-2-carbohydrazide,
(2S,5R)-N'-acetyl-6-hydroxy-7-oxo-1,6-diazabicyclo[3.2.1]octane-2-carbohydrazide,
tetrabutylammonium (2S,5R)-N'-acetyl-7-oxo-6-(sulfooxy)-1,6-diazabicyclo[3.2.1]-octane-2-carbohydrazide,
sodium (2S,5R)-7-oxo-N'-propanoyl-6-(sulfooxy)-1,6-diazabicyclo[3.2.1]octane-2-carbohydrazide,
(2S,5R)-6-benzyloxy-7-oxo-N'-propanoyl-1,6-diazabicyclo[3.2.1]octane-2-carbohydrazide,
(2S,5R)-6-hydroxy-7-oxo-N'-propanoyl-1,6-diazabicyclo[3.2.1]octane-2-carbohydrazide,
pyridinium (2S,5R)-7-oxo-N'-propanoyl-6-(sulfooxy)-1,6-diazabicyclo[3.2.1]octane-2-carbohydrazide,
sodium (2S,5R)-N'-(2-methylpropanoyl)-7-oxo-6-(sulfooxy)-1,6-diazabicyclo[3.2.1]-octane-2-carbohydrazide,
(2S,5R)-6-benzyloxy-N'-(2-methylpropanoyl)-7-oxo-1,6-diazabicyclo[3.2.1]octane-2-carbohydrazide,
(2S,5R)-6-hydroxy-N'-(2-methylpropanoyl)-7-oxo-1,6-diazabicyclo[3.2.1]octane-2-carbohydrazide,
pyridinium (2S,5R)-N'-(2-methylpropanoyl)-7-oxo-6-(sulfooxy)-1,6-diazabicyclo[3.2.1]octane-2-carbohydrazide,
sodium (2S,5R)-N'-(2,2-dimethylpropanoyl)-7-oxo-6-(sulfooxy)-1,6-diazabicyclo[3.2.1]octane-2-carbohydrazide,
(2S,5R)-6-benzyloxy-N'-(2,2-dimethylpropanoyl)-7-oxo-1,6-diazabicyclo[3.2.1]octane-2-carbohydrazide,
(2S,5R)-N'-(2,2-dimethylpropanoyl)-6-hydroxy-7-oxo-1,6-diazabicyclo[3.2.1]octane-2-carbohydrazide,
pyridinium (2S,5R)-N'-(2,2-dimethylpropanoyl)-7-oxo-6-(sulfooxy)-1,6-diazabicyclo-[3.2.1]octane-2-carbohydrazide,
sodium (2S,5R)-N'-acetyl-N'-methyl-7-oxo-6-(sulfooxy)-1,6-diazabicyclo[3.2.1]octane-2-carbohydrazide,
(2S,5R)-N'-acetyl-6-benzyloxy-N'-methyl-7-oxo-1,6-diazabicyclo[3.2.1]octane-2-carbohydrazide,
(2S,5R)-N'-acetyl-6-hydroxy-N'-methyl-7-oxo-1,6-diazabicyclo[3.2.1]octane-2-carbohydrazide,
pyridinium (2S,5R)-N'-acetyl-N'-methyl-7-oxo-6-(sulfooxy)-1,6-diazabicyclo[3.2.1]-octane-2-carbohydrazide,
(2S,5R)-N'-(aminoacetyl)-7-oxo-6-(sulfooxy)-1,6-diazabicyclo[3.2.1]octane-2-carbohydrazide,
tert-butyl[2-(2-{[(2S,5R)-6-benzyloxy-7-oxo-1,6-diazabicyclo[3.2.1]oct-2-yl]carbonyl}hydrazinyl)-2-oxoethyl]carbamate,
tert-butyl[2-(2-{[(2S,5R)-6-hydroxy-7-oxo-1,6-diazabicyclo[3.2.1]oct-2-yl]carbonyl}-hydrazinyl)-2-oxoethyl]carbamate,
pyridinium tert-butyl[2-(2-{[(2S,5R)-7-oxo-6-(sulfooxy)-1,6-diazabicyclo[3.2.1]oct-2-yl]carbonyl}hydrazinyl)-2-oxoethyl]carbamate,
(2S,5R)-N'-(3-aminopropanoyl)-7-oxo-6-(sulfooxy)-1,6-diazabicyclo[3.2.1]octane-2-carbohydrazide,
tert-butyl[3-(2-{[(2S,5R)-6-benzyloxy-7-oxo-1,6-diazabicyclo[3.2.1]oct-2-yl]carbonyl}hydrazinyl)-3-oxopropyl]carbamate,
tert-butyl[3-(2-{[(2S,5R)-6-hydroxy-7-oxo-1,6-diazabicyclo[3.2.1]oct-2-yl]carbonyl}-hydrazinyl)-3-oxopropyl]carbamate,
pyridinium tert-butyl[3-(2-{[(2S,5R)-7-oxo-6-(sulfooxy)-1,6-diazabicyclo[3.2.1]oct-2-yl]carbonyl}hydrazinyl)-3-oxopropyl]carbamate,
(2S,5R)-N'-[(4-aminophenyl)acetyl]-7-oxo-6-(sulfooxy)-1,6-diazabicyclo[3.2.1]octane-2-carbohydrazide,
tert-butyl {4-[2-(2-{[(2S,5R)-6-benzyloxy-7-oxo-1,6-diazabicyclo[3.2.1]oct-2-yl]carbonyl}hydrazinyl)-2-oxoethyl]phenyl}carbamate,
tert-butyl {4-[2-(2-{[(2S,5R)-6-hydroxy-7-oxo-1,6-diazabicyclo[3.2.1]oct-2-yl]carbonyl}hydrazinyl)-2-oxoethyl]phenyl}carbamate,
tetrabutylammonium tert-butyl {4-[2-(2-{[(2S,5R)-7-oxo-6-(sulfooxy)-1,6-diazabicyclo[3.2.1]oct-2-yl]carbonyl}hydrazinyl)-2-oxoethyl]phenyl}carbamate,
sodium (2S,5R)-N'-(methoxyacetyl)-7-oxo-6-(sulfooxy)-1,6-diazabicyclo[3.2.1]octane-2-carbohydrazide,
(2S,5R)-6-benzyloxy-N'-(methoxyacetyl)-7-oxo-1,6-diazabicyclo[3.2.1]octane-2-carbohydrazide,
(2S,5R)-6-hydroxy-N'-(methoxyacetyl)-7-oxo-1,6-diazabicyclo[3.2.1]octane-2-carbohydrazide,
pyridinium (2S,5R)-N'-(methoxyacetyl)-7-oxo-6-(sulfooxy)-1,6-diazabicyclo[3.2.1]-octane-2-carbohydrazide,
sodium (2S,5R)-N'-benzoyl-7-oxo-6-(sulfooxy)-1,6-diazabicyclo[3.2.1]octane-2-carbohydrazide,
(2S,5R)-N'-benzoyl-6-benzyloxy-7-oxo-1,6-diazabicyclo[3.2.1]octane-2-carbohydrazide,
(2S,5R)-N'-benzoyl-6-hydroxy-7-oxo-1,6-diazabicyclo[3.2.1]octane-2-carbohydrazide,
pyridinium (2S,5R)-N'-benzoyl-7-oxo-6-(sulfooxy)-1,6-diazabicyclo[3.2.1]octane-2-carbohydrazide,
(2S,5R)-N'-(4-aminobenzoyl)-7-oxo-6-(sulfooxy)-1,6-diazabicyclo[3.2.1]octane-2-carbohydrazide, tert-butyl {4-[(2-{[(2S,5R)-6-benzyloxy-7-oxo-1,6-diazabicyclo[3.2.1]oct-2-yl]carbonyl}hydrazinyl)carbonyl]phenyl}carbamate,
tert-butyl {4-[(2-{[(2S,5R)-6-hydroxy-7-oxo-1,6-diazabicyclo[3.2.1]oct-2-yl]carbonyl}hydrazinyl)carbonyl]phenyl}carbamate,
tetrabutylammonium tert-butyl {4-[(2-{[(2S,5R)-7-oxo-6-(sulfooxy)-1,6-diazabicyclo-[3.2.1]oct-2-yl]carbonyl}hydrazinyl)carbonyl]phenyl}carbamate,
(2S,5R)-N'-(4-(aminomethyl)benzoyl)-7-oxo-6-(sulfooxy)-1,6-diazabicyclo[3.2.1]-octane-2-carbohydrazide,
tert-butyl {4-[(2-{[(2S,5R)-6-benzyloxy-7-oxo-1,6-diazabicyclo[3.2.1]oct-2-yl]carbonyl}hydrazinyl)carbonyl]benzyl}carbamate,
tert-butyl {4-[(2-{[(2S,5R)-6-hydroxy-7-oxo-1,6-diazabicyclo[3.2.1]oct-2-yl]carbonyl}hydrazinyl)carbonyl]benzyl}carbamate,
pyridinium tert-butyl {4-[(2-{[(2S,5R)-7-oxo-6-(sulfooxy)-1,6-diazabicyclo[3.2.1]oct-2-yl]carbonyl}hydrazinyl)carbonyl]benzyl}carbamate,
sodium (2S,5R)-7-oxo-N-(2-oxopyrrolidin-1-yl)-6-(sulfooxy)-1,6-diazabicyclo[3.2.1]-octane-2-carboxamide,
(2S,5R)-6-benzyloxy-7-oxo-N-(2-oxopyrrolidin-1-yl)-1,6-diazabicyclo[3.2.1]octane-2-carboxamide,
(2S,5R)-6-hydroxy-7-oxo-N-(2-oxopyrrolidin-1-yl)-1,6-diazabicyclo[3.2.1]octane-2-carboxamide,
pyridinium (2S,5R)-7-oxo-N-(2-oxopyrrolidin-1-yl)-6-(sulfooxy)-1,6-diazabicyclo-[3.2.1]octane-2-carboxamide,
sodium (2S,5R)-7-oxo-6-(sulfooxy)-N'-(tetrahydro-2H-pyran-4-ylcarbonyl)-1,6-diazabicyclo[3.2.1]octane-2-carbohydrazide,
(2S,5R)-6-benzyloxy-7-oxo-N'-(tetrahydro-2H-pyran-4-ylcarbonyl)-1,6-diazabicyclo-[3.2.1]octane-2-carbohydrazide,
(2S,5R)-6-hydroxy-7-oxo-N'-(tetrahydro-2H-pyran-4-ylcarbonyl)-1,6-diazabicyclo-[3.2.1]octane-2-carbohydrazide,
pyridinium (2S,5R)-7-oxo-6-(sulfooxy)-N'-(tetrahydro-2H-pyran-4-ylcarbonyl)-1,6-diazabicyclo[3.2.1]octane-2-carbohydrazide,
(2S,5R)-7-oxo-N'-(piperidin-4-ylcarbonyl)-6-(sulfooxy)-1,6-diazabicyclo[3.2.1]octane-2-carbohydrazide,
tert-butyl 4-[(2-{[(2S,5R)-6-benzyloxy-7-oxo-1,6-diazabicyclo[3.2.1]oct-2-yl]carbonyl}hydrazinyl)carbonyl]piperidine-1-carboxylate,
tert-butyl 4-[(2-{[(2S,5R)-6-hydroxy-7-oxo-1,6-diazabicyclo[3.2.1]oct-2-yl]carbonyl-hydrazinyl)carbonyl]piperidine-1-carboxylate,
pyridinium tert-butyl 4-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate,
(2S,5R)-7-oxo-N'-[(2S)-piperidin-2-ylcarbonyl]-6-(sulfooxy)-1,6-diazabicyclo[3.2.1]-octane-2-carbohydrazide,
tert-butyl (2S)-2-[(2-{[(2S,5R)-6-benzyloxy-7-oxo-1,6-diazabicyclo[3.2.1]oct-2-yl]carbonyl}hydrazinyl)carbonyl]piperidine-1-carboxylate,
tert-butyl (2S)-2-[(2-{[(2S,5R)-6-hydroxy-7-oxo-1,6-diazabicyclo[3.2.1]oct-2-yl]carbonyl}hydrazinyl)carbonyl]piperidine-1-carboxylate,
tetrabutylammonium tert-butyl (2S)-2-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate,
(2S,5R)-7-oxo-N'-[(2R)-piperidin-2-ylcarbonyl]-6-(sulfooxy)-1,6-diazabicyclo[3.2.1]octane-2-carbohydrazide,
tert-butyl (2R)-2-[(2-{[(2S,5R)-6-benzyloxy-7-oxo-1,6-diazabicyclo[3.2.1]oct-2-yl]carbonyl}hydrazinyl)carbonyl]piperidine-1-carboxylate,
tert-butyl (2R)-2-[(2-{[(2S,5R)-6-hydroxy-7-oxo-1,6-diazabicyclo[3.2.1]oct-2-yl]carbonyl}hydrazinyl)carbonyl]piperidine-1-carboxylate,
tetrabutylammonium tert-butyl (2R)-2-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate,
(2S,5R)-7-oxo-N'-[(2S)-pyrrolidin-2-ylcarbonyl]-6-(sulfooxy)-1,6-diazabicyclo[3.2.1]-octane-2-carbohydrazide,
tert-butyl (2S)-2-[(2-{[(2S,5R)-6-benzyloxy-7-oxo-1,6-diazabicyclo[3.2.1]oct-2-yl]carbonyl}hydrazinyl)carbonyl]pyrrolidine-1-carboxylate,
tert-butyl (2S)-2-[(2-{[(2S,5R)-6-hydroxy-7-oxo-1,6-diazabicyclo[3.2.1]oct-2-yl]carbonyl}hydrazinyl)carbonyl]pyrrolidine-1-carboxylate,
tetrabutylammonium tert-butyl (2S)-2-[(2-{[(2S,5R)-7-oxo-6-(sulfooxy)-1,6-diazabicyclo[3.2.1]oct-2-yl]carbonyl}hydrazinyl)carbonyl]pyrrolidine-1-carboxylate,
(2S,5R)-7-oxo-N'-[(2R)-pyrrolidin-2-ylcarbonyl]-6-(sulfooxy)-1,6-diazabicyclo[3.2.1]-octane-2-carbohydrazide,
tert-butyl (2R)-2-[(2-{[(2S,5R)-6-benzyloxy-7-oxo-1,6-diazabicyclo[3.2.1]oct-2-yl]carbonyl}hydrazinyl)carbonyl]pyrrolidine-1-carboxylate,
tert-butyl (2R)-2-[(2-{[(2S,5R)-6-hydroxy-7-oxo-1,6-diazabicyclo[3.2.1]oct-2-yl]carbonyl}hydrazinyl)carbonyl]pyrrolidine-1-carboxylate,
tetrabutylammonium tert-butyl (2R)-2-[(2-{[(2S,5R)-7-oxo-6-(sulfooxy)-1,6-diazabicyclo[3.2.1]oct-2-yl]carbonyl}hydrazinyl)carbonyl]pyrrolidine-1-carboxylate,
(2S,5R)-N'-{[(2S,4R)-4-cyclopropylmethylpiperidin-2-yl]carbonyl}-7-oxo-6-(sulfooxy)-1,6-diazabicyclo[3.2.1]octane-2-carbohydrazide,
tert-butyl (2S,4R)-2-[(2-{[(2S,5R)-6-benzyloxy-7-oxo-1,6-diazabicyclo[3.2.1]oct-2-yl]carbonyl}hydrazinyl)carbonyl]-4-cyclopropylmethylpiperidine-1-carboxylate,
tert-butyl (2S,4R)-4-cyclopropylmethyl-2-[(2-{[(2S,5R)-6-hydroxy-7-oxo-1,6-diazabicyclo[3.2.1]oct-2-yl]carbonyl}hydrazinyl)carbonyl]piperidine-1-carboxylate,
tetrabutylammonium tert-butyl (2S,4R)-4-cyclopropylmethyl-2-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate,
sodium (2S,5R)-7-oxo-N'-{[(2S)-5-oxopyrrolidin-2-yl]carbonyl}-6-(sulfooxy)-1,6-diazabicyclo[3.2.1]octane-2-carbohydrazide,
tert-butyl (2S)-2-[(2-{[(2S,5R)-6-benzyloxy-7-oxo-1,6-diazabicyclo[3.2.1]oct-2-yl]carbonyl}hydrazinyl)carbonyl]-5-oxopyrrolidine-1-carboxylate,
tert-butyl (2S)-2-[(2-{[(2S,5R)-6-hydroxy-7-oxo-1,6-diazabicyclo[3.2.1]oct-2-yl]carbonyl}hydrazinyl)carbonyl]-5-oxopyrrolidine-1-carboxylate,
tetrabutylammonium tert-butyl (2S)-2-[(2-{[(2S,5R)-7-oxo-6-(sulfooxy)-1,6-diazabicyclo[3.2.1]oct-2-yl]carbonyl}hydrazinyl)carbonyl]-5-oxopyrrolidine-1-carboxylate,
sodium (2S,5R)-7-oxo-N'-{[(2R)-5-oxopyrrolidin-2-yl]carbonyl}-6-(sulfooxy)-1,6-diazabicyclo[3.2.1]octane-2-carbohydrazide,
tert-butyl (2R)-2-[(2-{[(2S,5R)-6-benzyloxy-7-oxo-1,6-diazabicyclo[3.2.1]oct-2-yl]carbonyl}hydrazinyl)carbonyl]-5-oxopyrrolidine-1-carboxylate,
tert-butyl (2R)-2-[(2-{[(2S,5R)-6-hydroxy-7-oxo-1,6-diazabicyclo[3.2.1]oct-2-yl]carbonyl}hydrazinyl)carbonyl]-5-oxopyrrolidine-1-carboxylate,
tetrabutylammonium tert-butyl (2R)-2-[(2-{[(2S,5R)-7-oxo-6-(sulfooxy)-1,6-diazabicyclo[3.2.1]oct-2-yl]carbonyl}hydrazinyl)carbonyl]-5-oxopyrrolidine-1-carboxylate, sodium (2S,5R)-N'-(furan-2-ylcarbonyl)-7-oxo-6-(sulfooxy)-1,6-diazabicyclo[3.2.1]-octane-2-carbohydrazide,
(2S,5R)-6-benzyloxy-N'-(furan-2-ylcarbonyl)-7-oxo-1,6-diazabicyclo[3.2.1]octane-2-carbohydrazide,
(2S,5R)-N'-(furan-2-ylcarbonyl)-6-hydroxy-7-oxo-1,6-diazabicyclo[3.2.1]octane-2-carbohydrazide,
pyridinium (2S,5R)-N'-(furan-2-ylcarbonyl)-7-oxo-6-(sulfooxy)-1,6-diazabicyclo-[3.2.1]octane-2-carbohydrazide,
sodium (2S,5R)-N'-(1,3-oxazol-4-ylcarbonyl)-7-oxo-6-(sulfooxy)-1,6-diazabicyclo-[3.2.1]octane-2-carbohydrazide,
(2S,5R)-6-benzyloxy-N'-(1,3-oxazol-4-ylcarbonyl)-7-oxo-1,6-diazabicyclo[3.2.1]-octane-2-carbohydrazide,
(2S,5R)-6-hydroxy-N'-(1,3-oxazol-4-ylcarbonyl)-7-oxo-1,6-diazabicyclo[3.2.1]octane-2-carbohydrazide,
pyridinium (2S,5R)-N'-(1,3-oxazol-4-ylcarbonyl)-7-oxo-6-(sulfooxy)-1,6-diazabicyclo-[3.2.1]octane-2-carbohydrazide,
sodium (2S,5R)-7-oxo-N'-(pyridin-3-ylcarbonyl)-6-(sulfooxy)-1,6-diazabicyclo[3.2.1]-octane-2-carbohydrazide,
(2S,5R)-6-benzyloxy-7-oxo-N'-(pyridin-3-ylcarbonyl)-1,6-diazabicyclo[3.2.1]octane-2-carbohydrazide,
(2S,5R)-6-hydroxy-7-oxo-N'-(pyridin-3-ylcarbonyl)-1,6-diazabicyclo[3.2.1]octane-2-carbohydrazide,
pyridinium (2S,5R)-7-oxo-N'-(pyridin-3-ylcarbonyl)-6-(sulfooxy)-1,6-diazabicyclo-[3.2.1]octane-2-carbohydrazide,
sodium (2S,5R)-7-oxo-N'-(pyridin-4-ylcarbonyl)-6-(sulfooxy)-1,6-diazabicyclo[3.2.1]-octane-2-carbohydrazide,
(2S,5R)-6-benzyloxy-7-oxo-N'-(pyridin-4-ylcarbonyl)-1,6-diazabicyclo[3.2.1]octane-2-carbohydrazide,
(2S,5R)-6-hydroxy-7-oxo-N'-(pyridin-4-ylcarbonyl)-1,6-diazabicyclo[3.2.1]octane-2-carbohydrazide,
pyridinium (2S,5R)-7-oxo-N'-(pyridin-4-ylcarbonyl)-6-(sulfooxy)-1,6-diazabicyclo-[3.2.1]octane-2-carbohydrazide,
sodium N,N-dimethyl-2-{[(2S,5R)-7-oxo-6-(sulfooxy)-1,6-diazabicyclo[3.2.1]oct-2-yl]carbonyl}hydrazinecarboxamide,
2-{[(2S,5R)-6-benzyloxy-7-oxo-1,6-diazabicyclo[3.2.1]oct-2-yl]carbonyl}-N,N-dimethylhydrazinecarboxamide,
2-{[(2S,5R)-6-hydroxy-7-oxo-1,6-diazabicyclo[3.2.1]oct-2-yl]carbonyl}-N,N-dimethylhydrazinecarboxamide,
pyridinium 2-{[(2S,5R)-7-oxo-6-(sulfooxy)-1,6-diazabicyclo[3.2.1]oct-2-yl]carbonyl}-N,N-dimethylhydrazinecarboxamide,
sodium N,N-diethyl-2-{[(2S,5R)-7-oxo-6-(sulfooxy)-1,6-diazabicyclo[3.2.1]oct-2-yl]carbonyl}hydrazinecarboxamide,
2-{[(2S,5R)-6-benzyloxy-7-oxo-1,6-diazabicyclo[3.2.1]oct-2-yl]carbonyl}-N,N-diethylhydrazinecarboxamide,
N,N-diethyl-2-{[(2S,5R)-6-hydroxy-7-oxo-1,6-diazabicyclo[3.2.1]oct-2-yl]carbonyl}-hydrazinecarboxamide,
pyridinium N,N-diethyl-2-{[(2S,5R)-7-oxo-6-(sulfooxy)-1,6-diazabicyclo[3.2.1]oct-2-yl]carbonyl}hydrazinecarboxamide,
sodium 2-{[(2S,5R)-7-oxo-6-(sulfooxy)-1,6-diazabicyclo[3.2.1]oct-2-yl]carbonyl}-N-phenylhydrazinecarboxamide,
2-{[(2S,5R)-6-benzyloxy-7-oxo-1,6-diazabicyclo[3.2.1]oct-2-yl]carbonyl}-N-phenylhydrazinecarboxamide,
2-{[(2S,5R)-6-hydroxy-7-oxo-1,6-diazabicyclo[3.2.1]oct-2-yl]carbonyl}-N-phenylhydrazinecarboxamide,
pyridinium 2-{[(2S,5R)-7-oxo-6-(sulfooxy)-1,6-diazabicyclo[3.2.1]oct-2-yl]carbonyl}-N-phenylhydrazinecarboxamide,
sodium (2S,5R)-N'-(morpholin-4-ylcarbonyl)-7-oxo-6-(sulfooxy)-1,6-diazabicyclo-[3.2.1]octane-2-carbohydrazide,
(2S,5R)-6-benzyloxy-N'-(morpholin-4-ylcarbonyl)-7-oxo-1,6-diazabicyclo[3.2.1]-octane-2-carbohydrazide,
(2S,5R)-6-hydroxy-N'-(morpholin-4-ylcarbonyl)-7-oxo-1,6-diazabicyclo[3.2.1]octane-2-carbohydrazide,
pyridinium (2S,5R)-N'-(morpholin-4-ylcarbonyl)-7-oxo-6-(sulfooxy)-1,6-diazabicyclo-[3.2.1]octane-2-carbohydrazide,
sodium methyl 2-{[(2S,5R)-7-oxo-6-(sulfooxy)-1,6-diazabicyclo[3.2.1]oct-2-yl]carbonyl}hydrazinecarboxylate,
methyl 2-{[(2S,5R)-6-benzyloxy-7-oxo-1,6-diazabicyclo[3.2.1]oct-2-yl]carbonyl}-hydrazinecarboxylate,
methyl 2-{[(2S,5R)-6-hydroxy-7-oxo-1,6-diazabicyclo[3.2.1]oct-2-yl]carbonyl}-hydrazinecarboxylate,
tetrabutylammonium methyl 2-{[(2S,5R)-7-oxo-6-(sulfooxy)-1,6-diazabicyclo[3.2.1]oct-2-yl]carbonyl}hydrazinecarboxylate,
sodium ethyl 2-{[(2S,5R)-7-oxo-6-(sulfooxy)-1,6-diazabicyclo[3.2.1]oct-2-yl]carbonyl}hydrazinecarboxylate,
ethyl 2-{[(2S,5R)-6-benzyloxy-7-oxo-1,6-diazabicyclo[3.2.1]oct-2-yl]carbonyl}-hydrazinecarboxylate,
ethyl 2-{[(2S,5R)-6-hydroxy-7-oxo-1,6-diazabicyclo[3.2.1]oct-2-yl]carbonyl}-hydrazinecarboxylate,
pyridinium ethyl 2-{[(2S,5R)-7-oxo-6-(sulfooxy)-1,6-diazabicyclo[3.2.1]oct-2-yl]carbonyl}hydrazinecarboxylate,
sodium tert-butyl 2-{[(2S,5R)-7-oxo-6-(sulfooxy)-1,6-diazabicyclo[3.2.1]oct-2-yl]carbonyl}hydrazinecarboxylate,
tert-butyl 2-{[(2S,5R)-6-benzyloxy-7-oxo-1,6-diazabicyclo[3.2.1]oct-2-yl]carbonyl}-hydrazinecarboxylate,
tert-butyl 2-{[(2S,5R)-6-hydroxy-7-oxo-1,6-diazabicyclo[3.2.1]oct-2-yl]carbonyl}-hydrazinecarboxylate,
pyridinium tert-butyl 2-{[(2S,5R)-7-oxo-6-(sulfooxy)-1,6-diazabicyclo[3.2.1]oct-2-yl]carbonyl}hydrazinecarboxylate,
sodium (2S,5R)-N'-(methylsulfonyl)-7-oxo-6-(sulfooxy)-1,6-diazabicyclo[3.2.1]octane-2-carbohydrazide,
(2S,5R)-6-benzyloxy-N'-(methylsulfonyl)-7-oxo-1,6-diazabicyclo[3.2.1]octane-2-carbohydrazide,
(2S,5R)-6-hydroxy-N'-(methylsulfonyl)-7-oxo-1,6-diazabicyclo[3.2.1]octane-2-carbohydrazide,
pyridinium (2S,5R)-N'-(methylsulfonyl)-7-oxo-6-(sulfooxy)-1,6-diazabicyclo[3.2.1]-octane-2-carbohydrazide,
sodium (2S,5R)-N-(morpholin-4-yl)-7-oxo-6-(sulfooxy)-1,6-diazabicyclo[3.2.1]octane-2-carboxamide,
(2S,5R)-6-benzyloxy-N-(morpholin-4-yl)-7-oxo-1,6-diazabicyclo[3.2.1]octane-2-carboxamide,
(2S,5R)-6-hydroxy-N-(morpholin-4-yl)-7-oxo-1,6-diazabicyclo[3.2.1]octane-2-carboxamide,
pyridinium (2S,5R)-N-(morpholin-4-yl)-7-oxo-6-(sulfooxy)-1,6-diazabicyclo[3.2.1]-octane-2-carboxamide,
sodium (2S,5R)-N-methoxy-7-oxo-6-(sulfooxy)-1,6-diazabicyclo[3.2.1]octane-2-carboxamide,
(2S,5R)-6-benzyloxy-N-methoxy-7-oxo-1,6-diazabicyclo[3.2.1]octane-2-carboxamide,
(2S,5R)-6-hydroxy-N-methoxy-7-oxo-1,6-diazabicyclo[3.2.1]octane-2-carboxamide,
tetrabutylammonium (2S,5R)-N-methoxy-7-oxo-6-(sulfooxy)-1,6-diazabicyclo[3.2.1]-octane-2-carboxamide,
sodium (2S,5R)-N-ethoxy-7-oxo-6-(sulfooxy)-1,6-diazabicyclo[3.2.1]octane-2-carboxamide,
(2S,5R)-6-benzyloxy-N-ethoxy-7-oxo-1,6-diazabicyclo[3.2.1]octane-2-carboxamide,
(2S,5R)-N-ethoxy-6-hydroxy-7-oxo-1,6-diazabicyclo[3.2.1]octane-2-carboxamide,
pyridinium (2S,5R)-N-ethoxy-7-oxo-6-(sulfooxy)-1,6-diazabicyclo[3.2.1]octane-2-carboxamide,
sodium (2S,5R)-N-(cyclobutylmethoxy)-7-oxo-6-(sulfooxy)-1,6-diazabicyclo[3.2.1]-octane-2-carboxamide, (2S,5R)-6-benzyloxy-N-(cyclobutylmethoxy)-7-oxo-1,6-diazabicyclo[3.2.1]octane-2-carboxamide,
(2S,5R)-N-(cyclobutylmethoxy)-6-hydroxy-7-oxo-1,6-diazabicyclo[3.2.1]octane-2-carboxamide,
pyridinium (2S,5R)-N-(cyclobutylmethoxy)-7-oxo-6-(sulfooxy)-1,6-diazabicyclo[3.2.1]octane-2-carboxamide,
(2S,5R)-N-(2-aminoethoxy)-7-oxo-6-(sulfooxy)-1,6-diazabicyclo[3.2.1]octane-2-carboxamide,
tert-butyl {2-[({[(2S,5R)-6-benzyloxy-7-oxo-1,6-diazabicyclo[3.2.1]oct-2-yl]carbonyl}-amino)oxy]ethyl}carbamate,
tert-butyl {2-[({[(2S,5R)-6-hydroxy-7-oxo-1,6-diazabicyclo[3.2.1]oct-2-yl]carbonyl}-amino)oxy]ethyl}carbamate,
tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}carbamate,
pyridinium tert-butyl {2-[({[(2S,5R)-7-oxo-6-(sulfooxy)-1,6-diazabicyclo[3.2.1]oct-2-yl]carbonyl}amino)oxy]ethyl}carbamate,
sodium tert-butyl {2-[({[(2S,5R)-7-oxo-6-(sulfooxy)-1,6-diazabicyclo[3.2.1]oct-2-yl]carbonyl}amino)oxy]ethyl}carbamate,
(2S,5R)-N-[2-(methylamino)ethoxy]-7-oxo-6-(sulfooxy)-1,6-diazabicyclo[3.2.1]octane-2-carboxamide,
tert-butyl {2-[({[(2S,5R)-6-benzyloxy-7-oxo-1,6-diazabicyclo[3.2.1]oct-2-yl]carbonyl}amino)oxy]ethyl}methylcarbamate,
tert-butyl {2-[({[(2S,5R)-6-hydroxy-7-oxo-1,6-diazabicyclo[3.2.1]oct-2-yl]carbonyl}-amino)oxy]ethyl}methylcarbamate,
tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}methylcarbamate,
(2S,5R)-N-[2-(ethylamino)ethoxy]-7-oxo-6-(sulfooxy)-1,6-diazabicyclo[3.2.1]octane-2-carboxamide,
tert-butyl {2-[({[(2S,5R)-6-benzyloxy-7-oxo-1,6-diazabicyclo[3.2.1]oct-2-yl]carbonyl}amino)oxy]ethyl}ethylcarbamate,
tert-butyl ethyl {2-[({[(2S,5R)-6-hydroxy-7-oxo-1,6-diazabicyclo[3.2.1]oct-2-yl]carbonyl}amino)oxy]ethyl}carbamate,
tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}ethylcarbamate,
(2S,5R)-7-oxo-N-[2-(propylamino)ethoxy]-6-(sulfooxy)-1,6-diazabicyclo[3.2.1]octane-2-carboxamide,
tert-butyl {2-[({[(2S,5R)-6-benzyloxy-7-oxo-1,6-diazabicyclo[3.2.1]oct-2-yl]carbonyl}amino)oxy]ethyl}propylcarbamate,
tert-butyl {2-[({[(2S,5R)-6-hydroxy-7-oxo-1,6-diazabicyclo[3.2.1]oct-2-yl]carbonyl}-amino)oxy]ethyl}propylcarbamate,
tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}propylcarbamate,
(2S,5R)-7-oxo-N-[2-(propan-2-ylamino)ethoxy]-6-(sulfooxy)-1,6-diazabicyclo[3.2.1]-octane-2-carboxamide,
tert-butyl {2-[({[(2S,5R)-6-benzyloxy-7-oxo-1,6-diazabicyclo[3.2.1]oct-2-yl]carbonyl}amino)oxy]ethyl}propan-2-ylcarbamate,
tert-butyl {2-[({[(2S,5R)-6-hydroxy-7-oxo-1,6-diazabicyclo[3.2.1]oct-2-yl]carbonyl}-amino)oxy]ethyl}propan-2-ylcarbamate,
tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}propan-2-ylcarbamate,
(2S,5R)-N-[2-(dimethylamino)ethoxy]-7-oxo-6-(sulfooxy)-1,6-diazabicyclo[3.2.1]-octane-2-carboxamide,
(2S,5R)-6-benzyloxy-N-[2-(dimethylamino)ethoxy]-7-oxo-1,6-diazabicyclo[3.2.1]-octane-2-carboxamide,
(2S,5R)-N-[2-(dimethylamino)ethoxy]-6-hydroxy-7-oxo-1,6-diazabicyclo[3.2.1]octane-2-carboxamide,
pyridinium (2S,5R)-N-[2-(dimethylamino)ethoxy]-7-oxo-6-(sulfooxy)-1,6-diazabicyclo[3.2.1]octane-2-carboxamide,
(2S,5R)-N-{[(2S)-2-aminopropyl]oxy}-7-oxo-6-(sulfooxy)-1,6-diazabicyclo[3.2.1]-octane-2-carboxamide,
tert-butyl {(2S)-1-[({[(2S,5R)-6-benzyloxy-7-oxo-1,6-diazabicyclo[3.2.1]oct-2-yl]carbonyl}amino)oxy]propan-2-yl}carbamate,
tert-butyl {(2S)-1-[({[(2S,5R)-6-hydroxy-7-oxo-1,6-diazabicyclo[3.2.1]oct-2-yl]carbonyl}amino)oxy]propan-2-yl}carbamate,
tetrabutylammonium tert-butyl {(2S)-1-[({[(2S,5R)-7-oxo-6-(sulfooxy)-1,6-diazabicyclo[3.2.1]oct-2-yl]carbonyl}amino)oxy]propan-2-yl}carbamate,
(2S,5R)-N-{[(2R)-2-aminopropyl]oxy}-7-oxo-6-(sulfooxy)-1,6-diazabicyclo[3.2.1]-octane-2-carboxamide,
tert-butyl {(2R)-1-[({[(2S,5R)-6-benzyloxy-7-oxo-1,6-diazabicyclo[3.2.1]oct-2-yl]carbonyl}amino)oxy]propan-2-yl}carbamate,
tert-butyl {(2R)-1-[({[(2S,5R)-6-hydroxy-7-oxo-1,6-diazabicyclo[3.2.1]oct-2-yl]carbonyl}amino)oxy]propan-2-yl}carbamate,
tetrabutylammonium tert-butyl {(2R)-1-[({[(2S,5R)-7-oxo-6-(sulfooxy)-1,6-diazabicyclo[3.2.1]oct-2-yl]carbonyl}amino)oxy]propan-2-yl}carbamate,
(2S,5R)-N-{[(2S)-1-aminopropan-2-yl]oxy}-7-oxo-6-(sulfooxy)-1,6-diazabicyclo-[3.2.1]octane-2-carboxamide,
tert-butyl {(2S)-2-[({[(2S,5R)-6-benzyloxy-7-oxo-1,6-diazabicyclo[3.2.1]oct-2-yl]carbonyl}amino)oxy]propyl}carbamate,
tert-butyl {(2S)-2-[({[(2S,5R)-6-hydroxy-7-oxo-1,6-diazabicyclo[3.2.1]oct-2-yl]carbonyl}amino)oxy]propyl}carbamate,
tetrabutylammonium tert-butyl {(2S)-2-[({[(2S,5R)-7-oxo-6-(sulfooxy)-1,6-diazabicyclo[3.2.1]oct-2-yl]carbonyl}amino)oxy]propyl}carbamate,
(2S,5R)-N-(3-aminopropoxy)-7-oxo-6-(sulfooxy)-1,6-diazabicyclo[3.2.1]octane-2-carboxamide,
tert-butyl {3-[({[(2S,5R)-6-benzyloxy-7-oxo-1,6-diazabicyclo[3.2.1]oct-2-yl]carbonyl}amino)oxy]propyl}carbamate,
tert-butyl {3-[({[(2S,5R)-6-hydroxy-7-oxo-1,6-diazabicyclo[3.2.1]oct-2-yl]carbonyl}-amino)oxy]propyl}carbamate,
tetrabutylammonium tert-butyl {3-[({[(2S,5R)-7-oxo-6-(sulfooxy)-1,6-diazabicyclo-[3.2.1]oct-2-yl]carbonyl}amino)oxy]propyl}carbamate,
sodium (2S,5R)-2-(1,2-oxazolidin-2-ylcarbonyl)-6-(sulfooxy)-1,6-diazabicyclo[3.2.1]-octan-7-one,
(2S,5R)-6-benzyloxy-2-(1,2-oxazolidin-2-ylcarbonyl)-1,6-diazabicyclo[3.2.1]octan-7-one,
(2S,5R)-6-hydroxy-2-(1,2-oxazolidin-2-ylcarbonyl)-1,6-diazabicyclo[3.2.1]octan-7-one,
pyridinium (2S,5R)-2-(1,2-oxazolidin-2-ylcarbonyl)-6-(sulfooxy)-1,6-diazabicyclo-[3.2.1]octan-7-one,
sodium (2S,5R)-2-(1,2-oxazinan-2-ylcarbonyl)-6-(sulfooxy)-1,6-diazabicyclo[3.2.1]-octan-7-one,
(2S,5R)-6-benzyloxy-2-(1,2-oxazinan-2-ylcarbonyl)-1,6-diazabicyclo[3.2.1]octan-7-one,
(2S,5R)-6-hydroxy-2-(1,2-oxazinan-2-ylcarbonyl)-1,6-diazabicyclo[3.2.1]octan-7-one,
pyridinium (2S,5R)-2-(1,2-oxazinan-2-ylcarbonyl)-6-(sulfooxy)-1,6-diazabicyclo[3.2.1]octan-7-one, sodium (2S,5R)-N-[2-(morpholin-4-yl)ethoxy]-7-oxo-6-(sulfooxy)-1,6-diazabicyclo-[3.2.1]octane-2-carboxamide, (2S,5R)-6-benzyloxy-N-[2-(morpholin-4-yl)ethoxy]-7-oxo-1,6-diazabicyclo[3.2.1]-octane-2-carboxamide, (2S,5R)-6-hydroxy-N-[2-(morpholin-4-yl)ethoxy]-7-oxo-1,6-diazabicyclo[3.2.1]octane-2-carboxamide, pyridinium (2S,5R)-N-[2-(morpholin-4-yl)ethoxy]-7-oxo-6-(sulfooxy)-1,6-diazabicyclo[3.2.1]octane-2-carboxamide, (2S,5R)-7-oxo-N-[2-(piperazin-1-yl)ethoxy]-6-(sulfooxy)-1,6-diazabicyclo[3.2.1]octane-2-carboxamide, tert-butyl 4-{2-[({[(2S,5R)-6-benzyloxy-7-oxo-1,6-diazabicyclo[3.2.1]oct-2-yl]carbonyl}amino)oxy]ethyl}piperazine-1-carboxylate, tert-butyl 4-{2-[({[(2S,5R)-6-hydroxy-7-oxo-1,6-diazabicyclo[3.2.1]oct-2-yl]carbonyl}-amino)oxy]ethyl}piperazine-1-carboxylate, tetrabutylammonium tert-butyl 4-{2-[({[(2S,5R)-7-oxo-6-(sulfooxy)-1,6-diazabicyclo-[3.2.1]oct-2-yl]carbonyl}amino)oxy]ethyl}piperazine-1-carboxylate, (2S,5R)-7-oxo-N-[2-(1,4-diazepan-1-yl)ethoxy]-6-(sulfooxy)-1,6-diazabicyclo[3.2.1]-octane-2-carboxamide, tert-butyl 4-{2-[({[(2S,5R)-6-benzyloxy-7-oxo-1,6-diazabicyclo[3.2.1]oct-2-yl]carbonyl}amino)oxy]ethyl}-1,4-diazepane-1-carboxylate, tert-butyl 4-{2-[({[(2S,5R)-6-hydroxy-7-oxo-1,6-diazabicyclo[3.2.1]oct-2-yl]carbonyl}-amino)oxy]ethyl}-1,4-diazepane-1-carboxylate, pyridinium tert-butyl 4-{2-[({[(2S,5R)-7-oxo-6-(sulfooxy)-1,6-diazabicyclo[3.2.1]oct-2-yl]carbonyl}amino)oxy]ethyl}-1,4-diazepane-1-carboxylate, (2S,5R)-N-[(2S)-azetidin-2-ylmethoxy]-7-oxo-6-(sulfooxy)-1,6-diazabicyclo[3.2.1]-octane-2-carboxamide, tert-butyl (2S)-2-{[({[(2S,5R)-6-benzyloxy-7-oxo-1,6-diazabicyclo[3.2.1]oct-2-yl]carbonyl}amino)oxy]methyl}azetidine-1-carboxylate, tert-butyl (2S)-2-{[({[(2S,5R)-6-hydroxy-7-oxo-1,6-diazabicyclo[3.2.1]oct-2-yl]carbonyl}amino)oxy]methyl}azetidine-1-carboxylate, tetrabutylammonium tert-butyl (2S)-2-{[({[(2S,5R)-7-oxo-6-(sulfooxy)-1,6-diazabicyclo[3.2.1]oct-2-yl]carbonyl}amino)oxy]methyl}azetidine-1-carboxylate, (2S,5R)-7-oxo-N-[(2S)-pyrrolidin-2-ylmethoxy]-6-(sulfooxy)-1,6-diazabicyclo[3.2.1]-octane-2-carboxamide, tert-butyl (2S)-2-{[({[(2S,5R)-6-benzyloxy-7-oxo-1,6-diazabicyclo[3.2.1]oct-2-yl]carbonyl}amino)oxy]methyl}pyrrolidine-1-carboxylate, tert-butyl (2S)-2-{[({[(2S,5R)-6-hydroxy-7-oxo-1,6-diazabicyclo[3.2.1]oct-2-yl]carbonyl}amino)oxy]methyl}pyrrolidine-1-carboxylate, pyridinium tert-butyl (2S)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate, (2S,5R)-7-oxo-N-[(2R)-pyrrolidin-2-ylmethoxy]-6-(sulfooxy)-1,6-diazabicyclo[3.2.1]-octane-2-carboxamide, tert-butyl (2R)-2-{[({[(2S,5R)-6-benzyloxy-7-oxo-1,6-diazabicyclo[3.2.1]oct-2-yl]carbonyl}amino)oxy]methyl}pyrrolidine-1-carboxylate, tert-butyl (2R)-2-{[({[(2S,5R)-6-hydroxy-7-oxo-1,6-diazabicyclo[3.2.1]oct-2-yl]carbonyl}amino)oxy]methyl}pyrrolidine-1-carboxylate, tetrabutylammonium tert-butyl (2R)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate, (2S,5R)-7-oxo-N-[(2S)-piperidin-2-ylmethoxy]-6-(sulfooxy)-1,6-diazabicyclo[3.2.1]-octane-2-carboxamide, tert-butyl (2S)-2-{[({[(2S,5R)-6-benzyloxy-7-oxo-1,6-diazabicyclo[3.2.1]oct-2-yl]carbonyl}amino)oxy]methyl}piperidine-1-carboxylate, tert-butyl (2S)-2-{[({[(2S,5R)-6-hydroxy-7-oxo-1,6-diazabicyclo[3.2.1]oct-2-yl]carbonyl}amino)oxy]methyl}piperidine-1-carboxylate, tetrabutylammonium tert-butyl (2S)-2-{[({[(2S,5R)-7-oxo-6-(sulfooxy)-1,6-diazabicyclo[3.2.1]oct-2-yl]carbonyl}amino)oxy]methyl}piperidine-1-carboxylate, (2S,5R)-N-(azetidin-3-yloxy)-7-oxo-6-(sulfooxy)-1,6-diazabicyclo[3.2.1]octane-2-carboxamide, tert-butyl 3-[({[(2S,5R)-6-benzyloxy-7-oxo-1,6-diazabicyclo[3.2.1]oct-2-yl]carbonyl}amino)oxy]azetidine-1-carboxylate, tert-butyl 3-[({[(2S,5R)-6-hydroxy-7-oxo-1,6-diazabicyclo[3.2.1]oct-2-yl]carbonyl}-amino)oxy]azetidine-1-carboxylate, tetrabutylammonium tert-butyl 3-[({[(2S,5R)-7-oxo-6-(sulfooxy)-1,6-diazabicyclo-[3.2.1]oct-2-yl]carbonyl}amino)oxy]azetidine-1-carboxylate, (2S,5R)-7-oxo-N-[(3R)-pyrrolidin-3-yloxy]-6-(sulfooxy)-1,6-diazabicyclo[3.2.1]octane-2-carboxamide, tert-butyl (3R)-3-[({[(2S,5R)-6-benzyloxy-7-oxo-1,6-diazabicyclo[3.2.1]oct-2-yl]carbonyl}amino)oxy]pyrrolidine-1-carboxylate, tert-butyl (3R)-3-[({[(2S,5R)-6-hydroxy-7-oxo-1,6-diazabicyclo[3.2.1]oct-2-yl]carbonyl}amino)oxy]pyrrolidine-1-carboxylate, tetrabutylammonium tert-butyl (3R)-3-[({[(2S,5R)-7-oxo-6-(sulfooxy)-1,6-diazabicyclo[3.2.1]oct-2-yl]carbonyl}amino)oxy]pyrrolidine-1-carboxylate, (2S,5R)-7-oxo-N-[(3S)-pyrrolidin-3-yloxy]-6-(sulfooxy)-1,6-diazabicyclo[3.2.1]octane-2-carboxamide, tert-butyl (3S)-3-[({[(2S,5R)-6-benzyloxy-7-oxo-1,6-diazabicyclo[3.2.1]oct-2-yl]carbonyl}amino)oxy]pyrrolidine-1-carboxylate, tert-butyl (3S)-3-[({[(2S,5R)-6-hydroxy-7-oxo-1,6-diazabicyclo[3.2.1]oct-2-yl]carbonyl}amino)oxy]pyrrolidine-1-carboxylate, tetrabutylammonium tert-butyl (3S)-3-[({[(2S,5R)-7-oxo-6-(sulfooxy)-1,6-diazabicyclo[3.2.1]oct-2-yl]carbonyl}amino)oxy]pyrrolidine-1-carboxylate, (2S,5R)-N-(azetidin-3-ylmethoxy)-7-oxo-6-(sulfooxy)-1,6-diazabicyclo[3.2.1]octane-2-carboxamide, tert-butyl 3-{[({[(2S,5R)-6-benzyloxy-7-oxo-1,6-diazabicyclo[3.2.1]oct-2-yl]carbonyl}amino)oxy]methyl}azetidine-1-carboxylate, tert-butyl 3-{[({[(2S,5R)-6-hydroxy-7-oxo-1,6-diazabicyclo[3.2.1]oct-2-yl]carbonyl}amino)oxy]methyl}azetidine-1-carboxylate, tetrabutylammonium tert-butyl 3-{[({[(2S,5R)-7-oxo-6-(sulfooxy)-1,6-diazabicyclo-[3.2.1]oct-2-yl]carbonyl}amino)oxy]methyl}azetidine-1-carboxylate, (2S,5R)-7-oxo-N-[(3R)-piperidin-3-ylmethoxy]-6-(sulfooxy)-1,6-diazabicyclo[3.2.1]-octane-2-carboxamide, tert-butyl (3R)-3-{[({[(2S,5R)-6-benzyloxy-7-oxo-1,6-diazabicyclo[3.2.1]oct-2-yl]carbonyl}amino)oxy]methyl}piperidine-1-carboxylate, tert-butyl (3R)-3-{[({[(2S,5R)-6-hydroxy-7-oxo-1,6-diazabicyclo[3.2.1]oct-2-yl]carbonyl}amino)oxy]methyl}piperidine-1-carboxylate, tetrabutylammonium tert-butyl (3R)-3-{[({[(2S,5R)-7-oxo-6-(sulfooxy)-1,6-diazabicyclo[3.2.1]oct-2-yl]carbonyl}amino)oxy]methyl}piperidine-1-carboxylate, (2S,5R)-7-oxo-N-(piperidin-4-yloxy)-6-(sulfooxy)-1,6-diazabicyclo[3.2.1]octane-2-carboxamide, tert-butyl 4-[({[(2S,5R)-6-benzyloxy-7-oxo-1,6-diazabicyclo[3.2.1]oct-2-yl]carbonyl}amino)oxy]piperidine-1-carboxylate,
tert-butyl 4-[({[(2S,5R)-6-hydroxy-7-oxo-1,6-diazabicyclo[3.2.1]oct-2-yl]carbonyl}amino)oxy]piperidine-1-carboxylate,
tetrabutylammonium tert-butyl 4-[({[(2S,5R)-7-oxo-6-(sulfooxy)-1,6-diazabicyclo-[3.2.1]oct-2-yl]carbonyl}amino)oxy]piperidine-1-carboxylate,
(2S,5R)-7-oxo-N-(piperidin-4-ylmethoxy)-6-(sulfooxy)-1,6-diazabicyclo[3.2.1]octane-2-carboxamide,
tert-butyl 4-{[({[(2S,5R)-6-benzyloxy-7-oxo-1,6-diazabicyclo[3.2.1]oct-2-yl]carbonyl}amino)oxy]methyl}piperidine-1-carboxylate,
tert-butyl 4-{[({[(2S,5R)-6-hydroxy-7-oxo-1,6-diazabicyclo[3.2.1]oct-2-yl]carbonyl}-amino)oxy]methyl}piperidine-1-carboxylate,
tetrabutylammonium tert-butyl 4-{[({[(2S,5R)-7-oxo-6-(sulfooxy)-1,6-diazabicyclo-[3.2.1]oct-2-yl]carbonyl}amino)oxy]methyl}piperidine-1-carboxylate,
sodium (2S,5R)-N-[2-(1H-imidazol-1-yl)ethoxy]-7-oxo-6-(sulfooxy)-1,6-diazabicyclo-[3.2.1]octane-2-carboxamide,
(2S,5R)-6-benzyloxy-N-[2-(1H-imidazol-1-yl)ethoxy]-7-oxo-1,6-diazabicyclo[3.2.1]-octane-2-carboxamide,
(2S,5R)-6-hydroxy-N-[2-(1H-imidazol-1-yl)ethoxy]-7-oxo-1,6-diazabicyclo[3.2.1]-octane-2-carboxamide,
pyridinium (2S,5R)-N-[2-(1H-imidazol-1-yl)ethoxy]-7-oxo-6-(sulfooxy)-1,6-diazabicyclo[3.2.1]octane-2-carboxamide,
sodium (2S,5R)-7-oxo-N-[2-(1H-pyrrol-1-yl)ethoxy]-6-(sulfooxy)-1,6-diazabicyclo-[3.2.1]octane-2-carboxamide,
(2S,5R)-6-benzyloxy-7-oxo-N-[2-(1H-pyrrol-1-yl)ethoxy]-1,6-diazabicyclo[3.2.1]-octane-2-carboxamide,
(2S,5R)-6-hydroxy-7-oxo-N-[2-(1H-pyrrol-1-yl)ethoxy]-1,6-diazabicyclo[3.2.1]octane-2-carboxamide,
pyridinium (2S,5R)-7-oxo-N-[2-(1H-pyrrol-1-yl)ethoxy]-6-(sulfooxy)-1,6-diazabicyclo-[3.2.1]octane-2-carboxamide,
disodium 1-{2-[({[(2S,5R)-7-oxo-6-(sulfonateoxy)-1,6-diazabicyclo[3.2.1]oct-2-yl]carbonyl}amino)oxy]ethyl}-1H-imidazole-2-sulfonate,
(2S,5R)-6-benzyloxy-N-[2-(1H-imidazol-1-yl)ethoxy]-7-oxo-1,6-diazabicyclo[3.2.1]-octane-2-carboxamide,
(2S,5R)-6-hydroxy-N-[2-(1H-imidazol-1-yl)ethoxy]-7-oxo-1,6-diazabicyclo[3.2.1]-octane-2-carboxamide,
pyridinium 1-{2-[({[(2S,5R)-7-oxo-6-(sulfonateoxy)-1,6-diazabicyclo[3.2.1]oct-2-yl]carbonyl}amino)oxy]ethyl}-1H-imidazole-1-ium-2-sulfonate,
sodium (2S,5R)-N-[2-(dimethylamino)-2-oxoethoxy]-7-oxo-6-(sulfooxy)-1,6-diazabicyclo[3.2.1]octane-2-carboxamide,
(2S,5R)-6-benzyloxy-N-[2-(dimethylamino)-2-oxoethoxy]-7-oxo-1,6-diazabicyclo-[3.2.1]octane-2-carboxamide,
(2S,5R)-N-[2-(dimethylamino)-2-oxoethoxy]-6-hydroxy-7-oxo-1,6-diazabicyclo[3.2.1]-octane-2-carboxamide,
pyridinium (2S,5R)-N-[2-(dimethylamino)-2-oxoethoxy]-7-oxo-6-(sulfooxy)-1,6-diazabicyclo[3.2.1]octane-2-carboxamide,
(2S,5R)-7-oxo-N-[2-oxo-2-(piperazin-1-yl)ethoxy]-6-(sulfooxy)-1,6-diazabicyclo[3.2.1]octane-2-carboxamide,
tert-butyl 4-{[({[(2S,5R)-6-benzyloxy-7-oxo-1,6-diazabicyclo[3.2.1]oct-2-yl]carbonyl}-amino)oxy]acetyl}piperazine-1-carboxylate,
tert-butyl 4-{[({[(2S,5R)-6-hydroxy-7-oxo-1,6-diazabicyclo[3.2.1]oct-2-yl]carbonyl}-amino)oxy]acetyl}piperazine-1-carboxylate,
tetrabutylammonium tert-butyl 4-{[({[(2S,5R)-7-oxo-6-(sulfooxy)-1,6-diazabicyclo-[3.2.1]oct-2-yl]carbonyl}amino)oxy]acetyl}piperazine-1-carboxylate,
sodium (2S,5R)-N-[2-(morpholin-4-yl)-2-oxoethoxy]-7-oxo-6-(sulfooxy)-1,6-diazabicyclo[3.2.1]octane-2-carboxamide,
(2S,5R)-6-benzyloxy-N-[2-(morpholin-4-yl)-2-oxoethoxy]-7-oxo-1,6-diazabicyclo-[3.2.1]octane-2-carboxamide,
(2S,5R)-6-hydroxy-N-[2-(morpholin-4-yl)-2-oxoethoxy]-7-oxo-1,6-diazabicyclo-[3.2.1]octane-2-carboxamide,
pyridinium (2S,5R)-N-[2-(morpholin-4-yl)-2-oxoethoxy]-7-oxo-6-(sulfooxy)-1,6-diazabicyclo[3.2.1]octane-2-carboxamide,
(2S,5R)-N-[2-(1,4-diazepan-1-yl)-2-oxoethoxy]-7-oxo-6-(sulfooxy)-1,6-diazabicyclo-[3.2.1]octane-2-carboxamide,
tert-butyl 4-{[({[(2S,5R)-6-benzyloxy-7-oxo-1,6-diazabicyclo[3.2.1]oct-2-yl]carbonyl}-amino)oxy]acetyl}-1,4-diazepane-1-carboxylate,
tert-butyl 4-{[({[(2S,5R)-6-hydroxy-7-oxo-1,6-diazabicyclo[3.2.1]oct-2-yl]carbonyl}-amino)oxy]acetyl}-1,4-diazepane-1-carboxylate,
tetrabutylammonium tert-butyl 4-{[({[(2S,5R)-7-oxo-6-(sulfooxy)-1,6-diazabicyclo-[3.2.1]oct-2-yl]carbonyl}amino)oxy]acetyl}-1,4-diazepane-1-carboxylate,
sodium (2S,5R)-7-oxo-N-[2-(2-oxopyrrolidin-1-yl)ethoxy]-6-(sulfooxy)-1,6-diazabicyclo[3.2.1]octane-2-carboxamide,
(2S,5R)-6-benzyloxy-7-oxo-N-[2-(2-oxopyrrolidin-1-yl)ethoxy]-1,6-diazabicyclo-[3.2.1]octane-2-carboxamide,
(2S,5R)-6-hydroxy-7-oxo-N-[2-(2-oxopyrrolidin-1-yl)ethoxy]-1,6-diazabicyclo-[3.2.1]octane-2-carboxamide,
pyridinium (2S,5R)-7-oxo-N-[2-(2-oxopyrrolidin-1-yl)ethoxy]-6-(sulfooxy)-1,6-diazabicyclo[3.2.1]octane-2-carboxamide,
sodium (2S,5R)-7-oxo-N-[2-(2-oxoimidazolidin-1-yl)ethoxy]-6-(sulfooxy)-1,6-diazabicyclo[3.2.1]octane-2-carboxamide,
(2S,5R)-6-benzyloxy-7-oxo-N-[2-(2-oxoimidazolidin-1-yl)ethoxy]-1,6-diazabicyclo-[3.2.1]octane-2-carboxamide,
(2S,5R)-6-hydroxy-7-oxo-N-[2-(2-oxoimidazolidin-1-yl)ethoxy]-1,6-diazabicyclo-[3.2.1]octane-2-carboxamide,
pyridinium (2S,5R)-7-oxo-N-[2-(2-oxoimidazolidin-1-yl)ethoxy]-6-(sulfooxy)-1,6-diazabicyclo[3.2.1]octane-2-carboxamide,
sodium (2S,5R)-N-(2-hydroxyethoxy)-7-oxo-6-(sulfooxy)-1,6-diazabicyclo[3.2.1]octane-2-carboxamide,
(2S,5R)-6-benzyloxy-7-oxo-N-(2-triisopropylsilyloxyethoxy)-1,6-diazabicyclo[3.2.1]-octane-2-carboxamide,
(2S,5R)-6-hydroxy-7-oxo-N-(2-triisopropylsilyloxyethoxy)-1,6-diazabicyclo[3.2.1]-octane-2-carboxamide,
tetrabutylammonium (2S,5R)-7-oxo-6-(sulfooxy)-N-(2-triisopropylsilyloxyethoxy)-1,6-diazabicyclo[3.2.1]octane-2-carboxamide,
sodium (2S,5R)-N-(2-methoxyethoxy)-7-oxo-6-(sulfooxy)-1,6-diazabicyclo[3.2.1]-octane-2-carboxamide,
(2S,5R)-6-benzyloxy-N-(2-methoxyethoxy)-7-oxo-1,6-diazabicyclo[3.2.1]octane-2-carboxamide,
(2S,5R)-6-hydroxy-N-(2-methoxyethoxy)-7-oxo-1,6-diazabicyclo[3.2.1]octane-2-carboxamide,
pyridinium (2S,5R)-N-(2-methoxyethoxy)-7-oxo-6-(sulfooxy)-1,6-diazabicyclo[3.2.1]-octane-2-carboxamide, sodium (2S,5R)-N-[2-(methylsulfonyl)ethoxy]-7-oxo-6-(sulfooxy)-1,6-diazabicyclo-[3.2.1]octane-2-carboxamide, (2S,5R)-6-benzyloxy-N-[2-(methylsulfonyl)ethoxy]-7-oxo-1,6-diazabicyclo[3.2.1]-octane-2-carboxamide, (2S,5R)-6-hydroxy-N-[2-(methylsulfonyl)ethoxy]-7-oxo-1,6-diazabicyclo[3.2.1]octane-2-carboxamide, pyridinium (2S,5R)-N-[2-(methylsulfonyl)ethoxy]-7-oxo-6-(sulfooxy)-1,6-diazabicyclo[3.2.1]octane-2-carboxamide, benzyl {2-[({[(2S,5R)-6-benzyloxy-7-oxo-1,6-diazabicyclo[3.2.1]oct-2-yl]carbonyl}-amino)oxy]ethyl}carbamate, and tert-butyl {2-[({[(2S,5R)-6-hydroxy-7-oxo-1,6-diazabicyclo[3.2.1]oct-2-yl]carbonyl}-amino)oxy]ethyl}carbamate.

Also, as the specific examples of the compounds of the present invention, the following compound groups are preferably mentioned.

[Chemical formula 53]

(II-017)

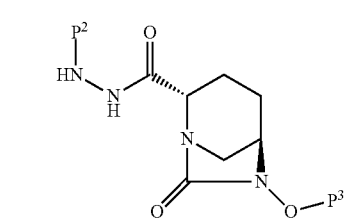

(II-018), (II-019)

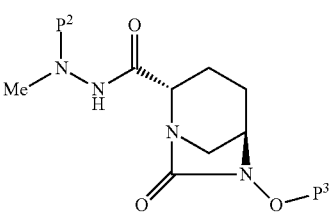

(II-020)

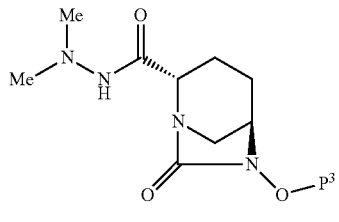

(II-021)

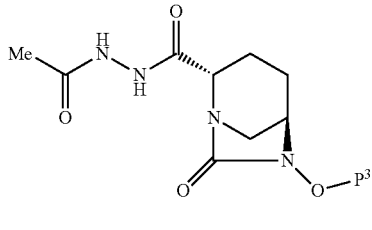

(II-022)

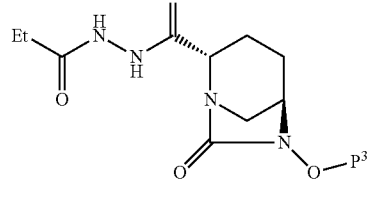

(II-023)

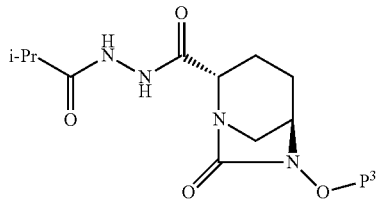

(II-024)

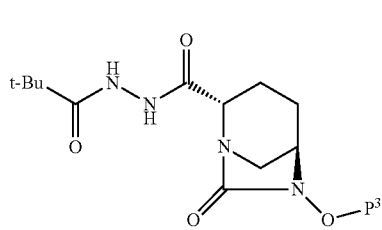

(II-025)

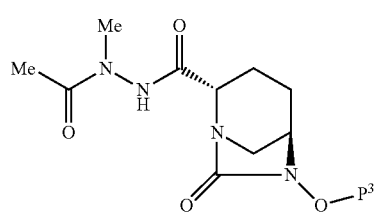

(II-026)

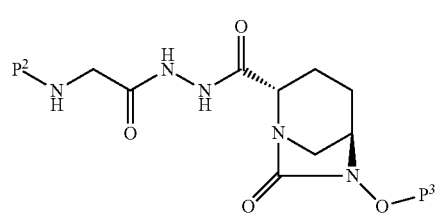

(II-027)

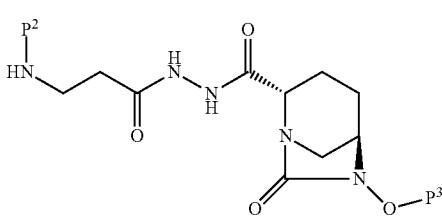

(II-028)

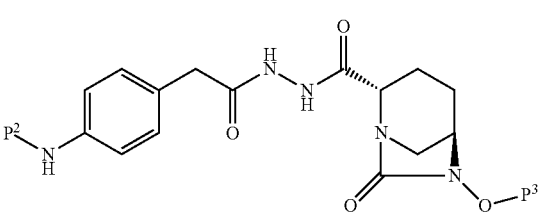

(II-029)

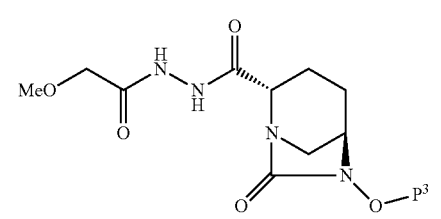

(II-030)
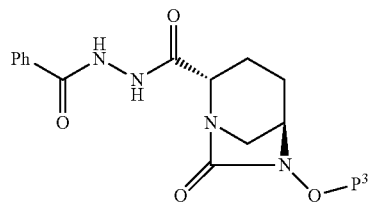
(II-031)
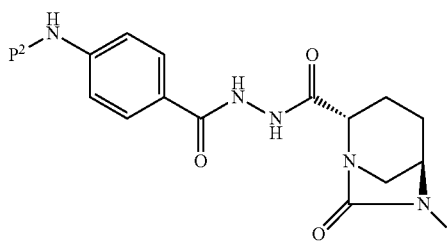
(II-032)
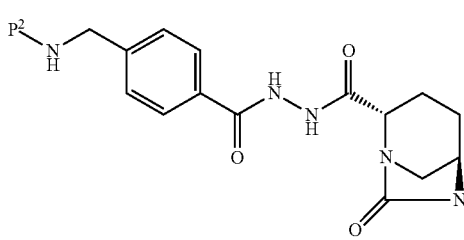
(II-033)
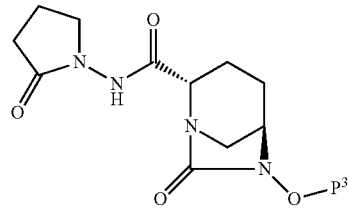
(II-034)
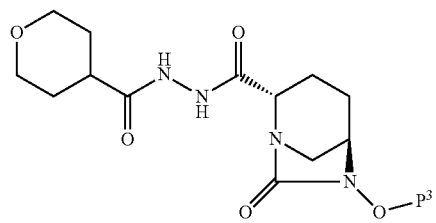
(II-035)
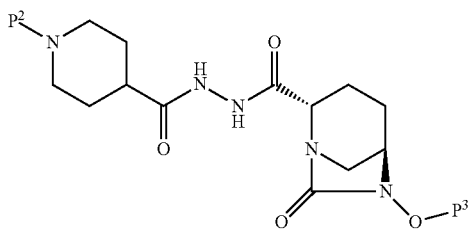
(II-036)
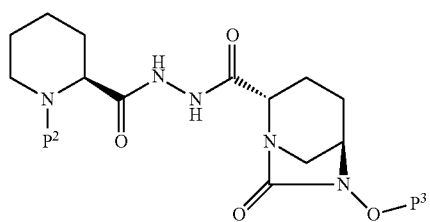
(II-037)
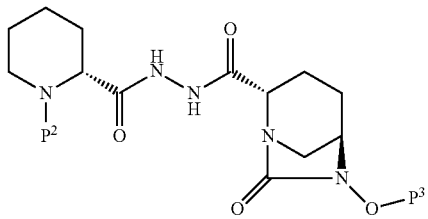
(II-038)
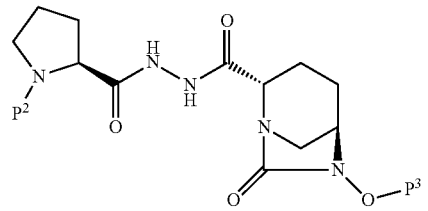
(II-039)
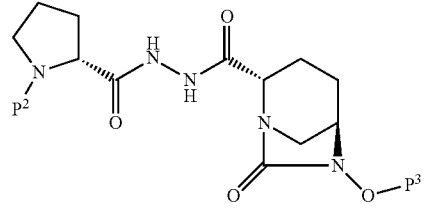
(II-040)
(II-041)
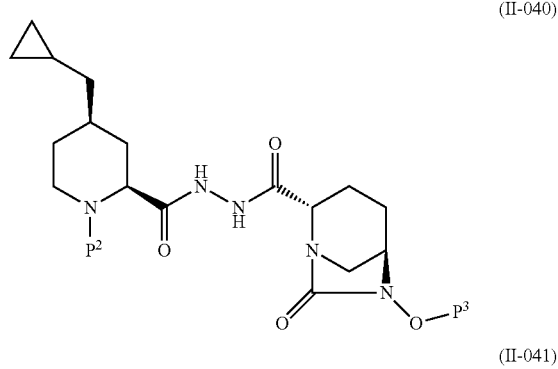
(II-042)
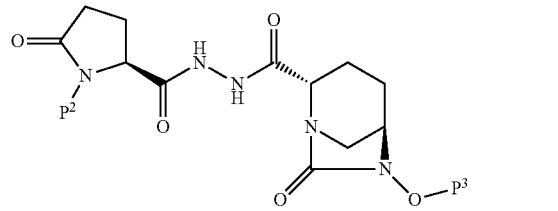
in the above formulae, $P^2$ represents tert-butoxycarbonyl (Boc), benzyloxycarbonyl (Cbz), or H; $P^3$ represents benzyl (Bn), H or $SO_3M$; where M represents H, sodium, pyridinium or tetrabutylammonium.

[Chemical formula 54]
(II-043) 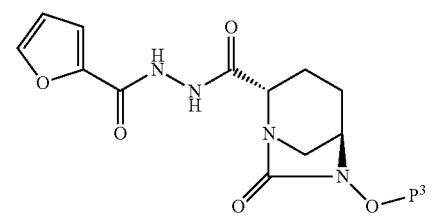
(II-044) 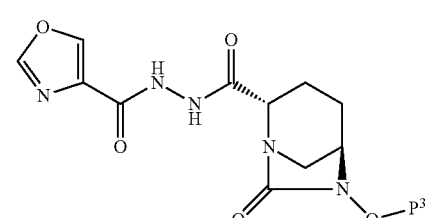
(II-045) 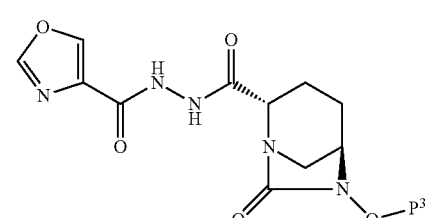
(II-046) 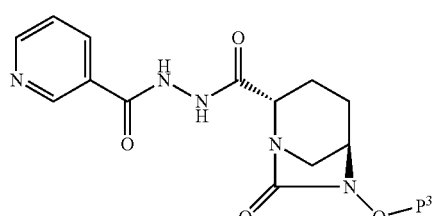
(II-047) 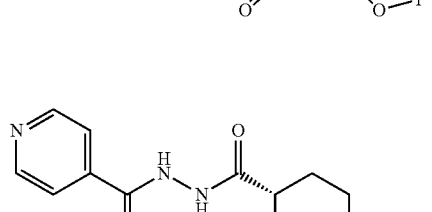
(II-048) 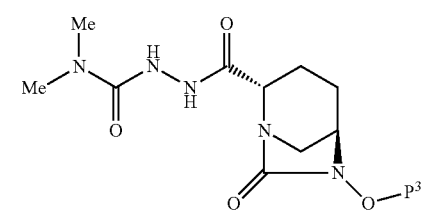
(II-049) 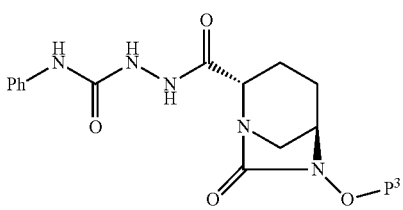
(II-050) 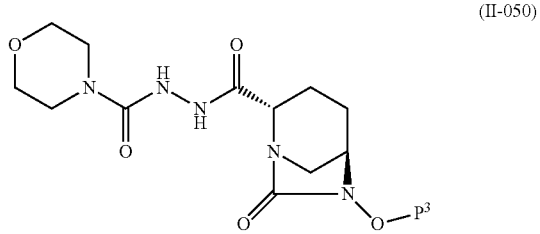
(II-051) 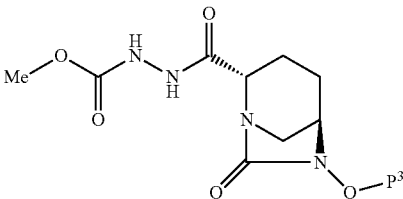
(II-052) 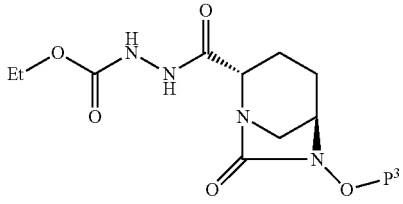
(II-053) 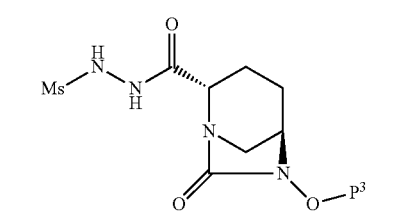
(II-054) 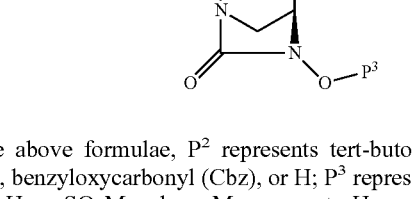
(II-055) 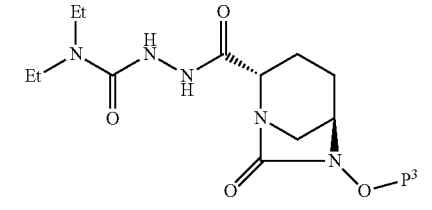
in the above formulae, $P^2$ represents tert-butoxycarbonyl (Boc), benzyloxycarbonyl (Cbz), or H; $P^3$ represents benzyl (Bn), H or $SO_3M$; where M represents H, sodium, pyridinium or tetrabutylammonium, and Ms represents methylsulfonyl.

[Chemical formula 55]
(II-056) 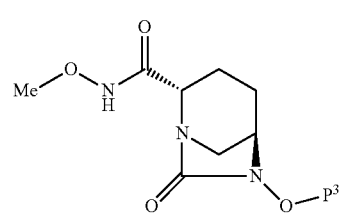
(II-057) 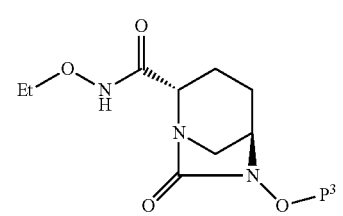
(II-058) 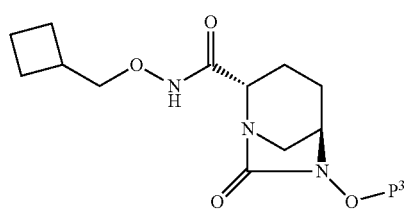
(II-059), (II-060), (II-109) 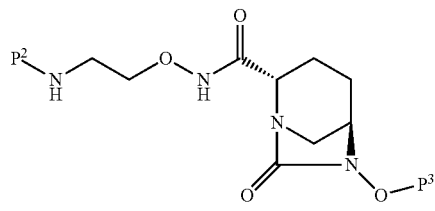
(II-061) 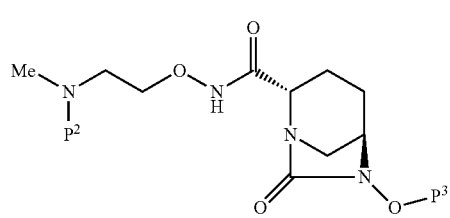
(II-062) 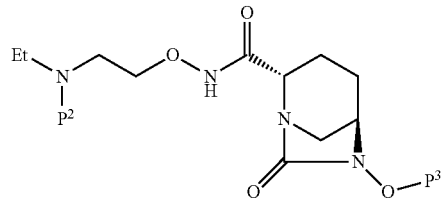
(II-063) 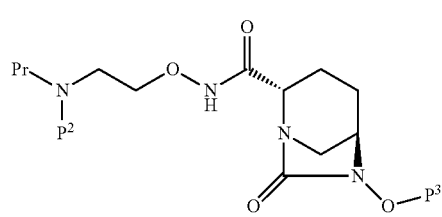
-continued
(II-064) 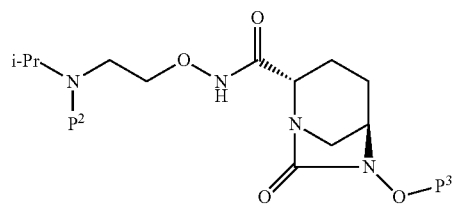
(II-065) 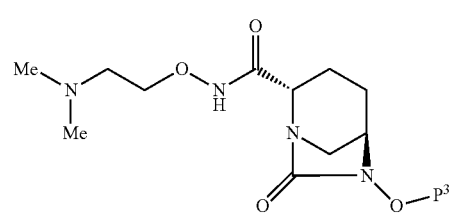
(II-066) 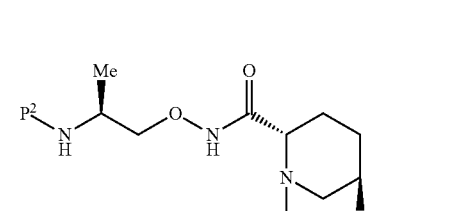
(II-067) 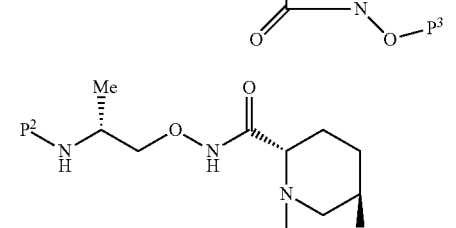
(II-068) 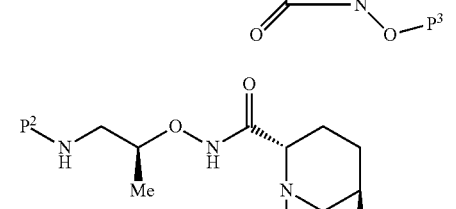
(II-069) 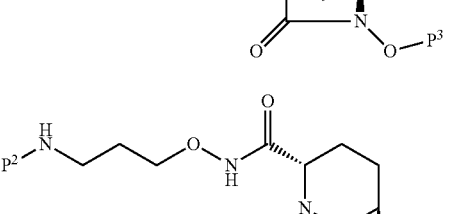
(II-070) 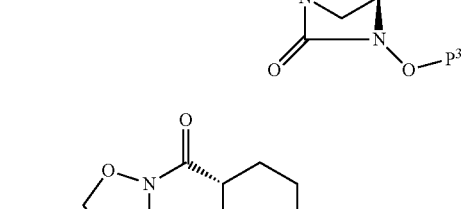

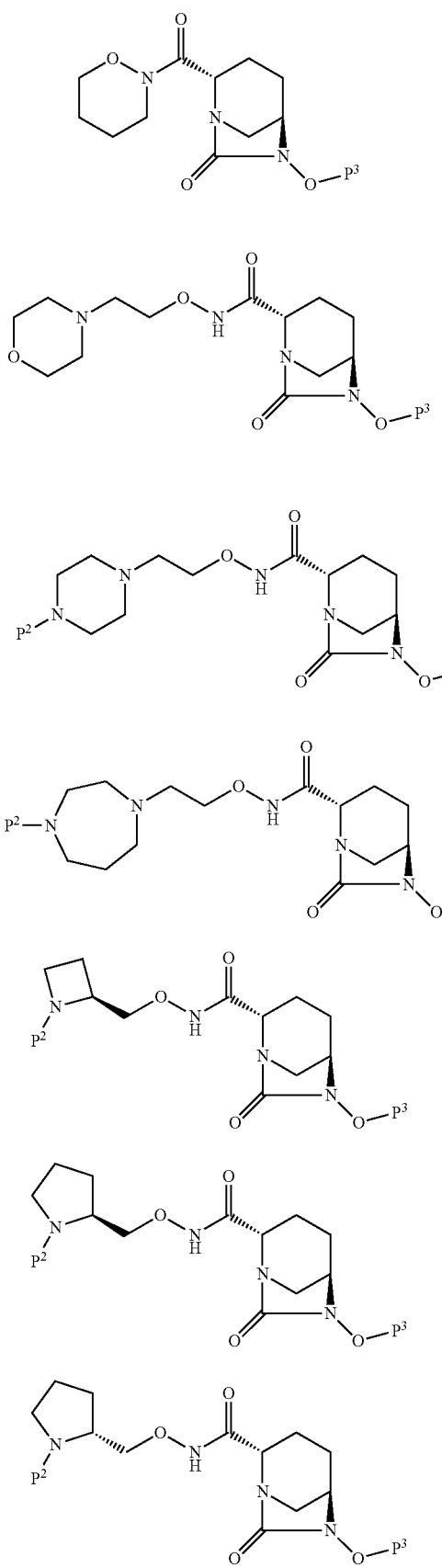
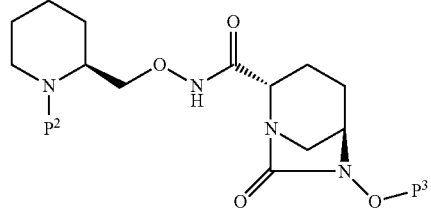
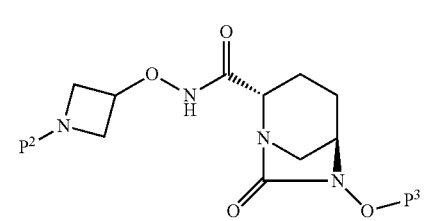
in the above formulae, P² represents tert-butoxycarbonyl (Boc), benzyloxycarbonyl (Cbz), or H; P³ represents benzyl (Bn), H or SO₃M; where M represents H, sodium, pyridinium or tetrabutylammonium.
[Chemical formula 56]

(II-084) 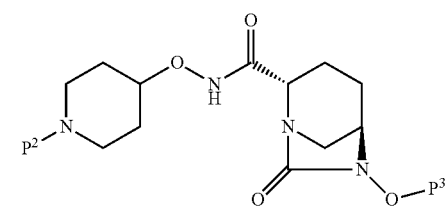
(II-085) 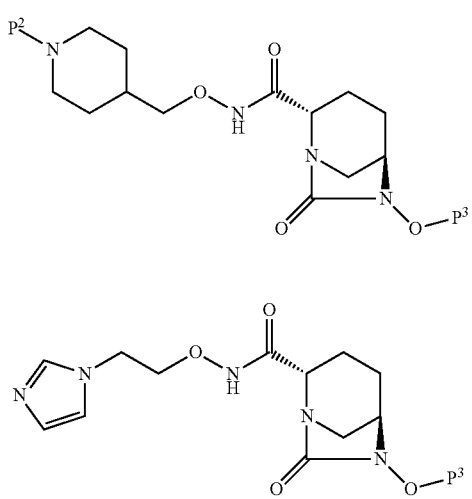
(II-086)
(II-087) 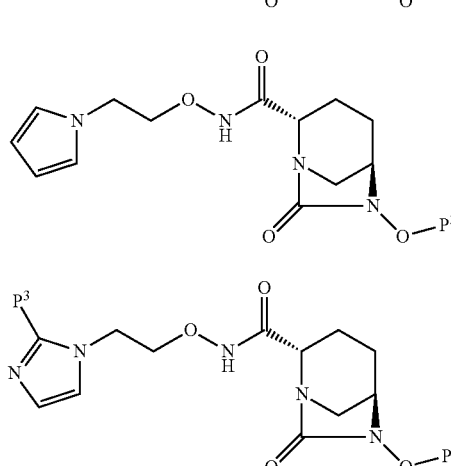
(II-088) 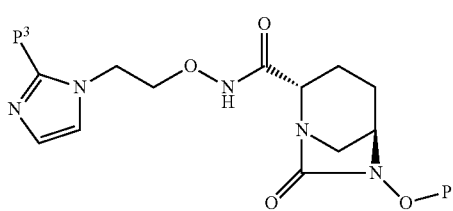
(II-089) 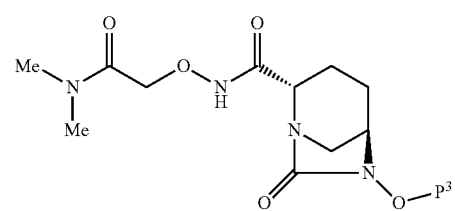
(II-090) 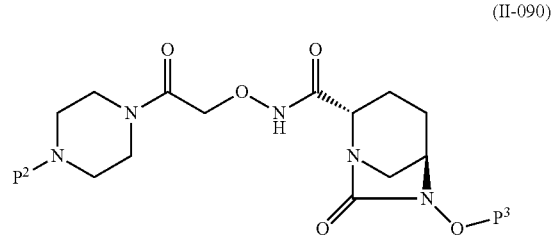
(II-091) 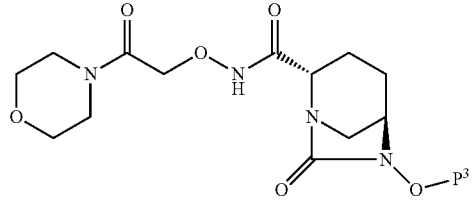
(II-092) 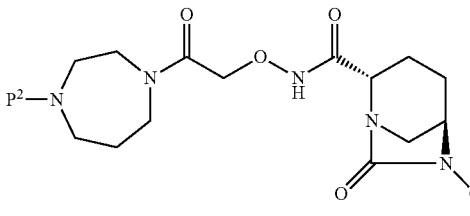
(II-093) 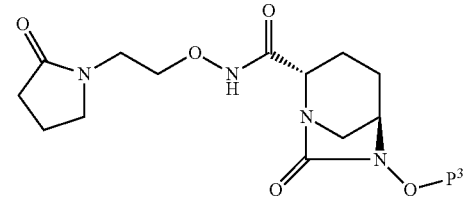
(II-094) 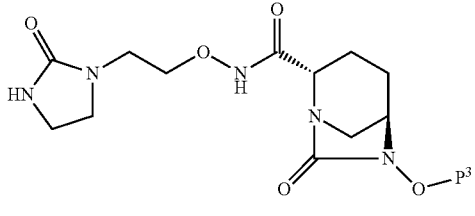
(II-095) 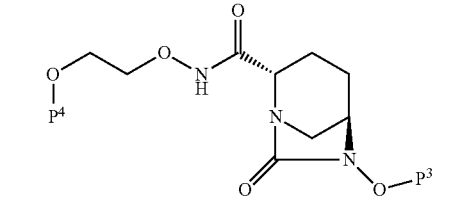
(II-096) 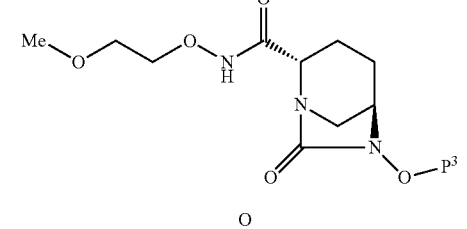
(II-097) 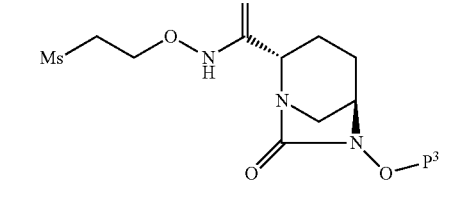
in the above formulae, $P^2$ represents tert-butoxycarbonyl (Boc), benzyloxycarbonyl (Cbz), or H; $P^3$ represents benzyl (Bn), H or $SO_3M$; where M represents H, sodium, pyridinium or tetrabutylammonium; and $P^4$ represents triisopropylsilyl or H.

More preferably, the specific examples include:

tert-butyl {2-[({[(2S,5R)-6-benzyloxy-7-oxo-1,6-diazabicyclo[3.2.1]oct-2-yl]carbonyl}-amino)oxy]ethyl}carbamate, tert-butyl {2-[({[(2S,5R)-6-hydroxy-7-oxo-1,6-diazabicyclo[3.2.1]oct-2-yl]carbonyl}-amino)oxy]ethyl}carbamate, pyridinium tert-butyl {2-[({[(2S,5R)-7-oxo-6-(sulfooxy)-1,6-diazabicyclo[3.2.1]oct-2-yl]carbonyl}amino)oxy]ethyl}carbamate, sodium tert-butyl {2-[({[(2S,5R)-7-oxo-6-(sulfooxy)-1,6-diazabicyclo[3.2.1]oct-2-yl]carbonyl}amino)oxy]ethyl}carbamate, tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}carbamate, (2S,5R)-N-(2-aminoethoxy)-7-oxo-6-(sulfooxy)-1,6-diazabicyclo[3.2.1]octane-2-carboxamide, benzyl {2-[({[(2S,5R)-6-benzyloxy-7-oxo-1,6-diazabicyclo[3.2.1]oct-2-yl]carbonyl}-amino)oxy]ethyl}carbamate, (2S,5R)-N-[2-(methylamino)ethoxy]-7-oxo-6-(sulfooxy)-1,6-diazabicyclo[3.2.1]octane-2-carboxamide, tert-butyl {2-[({[(2S,5R)-6-benzyloxy-7-oxo-1,6-diazabicyclo[3.2.1]oct-2-yl]carbonyl}amino)oxy]ethyl}methylcarbamate, tert-butyl {2-[({[(2S,5R)-6-hydroxy-7-oxo-1,6-diazabicyclo[3.2.1]oct-2-yl]carbonyl}-amino)oxy]ethyl}methylcarbamate, tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}methylcarbamate, (2S,5R)-7-oxo-N-[2-(propan-2-ylamino)ethoxy]-6-(sulfooxy)-1,6-diazabicyclo[3.2.1]-octane-2-carboxamide, tert-butyl {2-[({[(2S,5R)-6-benzyloxy-7-oxo-1,6-diazabicyclo[3.2.1]oct-2-yl]carbonyl}amino)oxy]ethyl}propan-2-ylcarbamate, tert-butyl {2-[({[(2S,5R)-6-hydroxy-7-oxo-1,6-diazabicyclo[3.2.1]oct-2-yl]carbonyl}-amino)oxy]ethyl}propan-2-ylcarbamate, tetrabutylammonium tert-butyl {2-[({[(2S,5R)-7-oxo-6-(sulfooxy)-1,6-diazabicyclo-[3.2.1]oct-2-yl]carbonyl}amino)oxy]ethyl}propan-2-ylcarbamate, (2S,5R)-N-[2-(dimethylamino)ethoxy]-7-oxo-6-(sulfooxy)-1,6-diazabicyclo[3.2.1]-octane-2-carboxamide, (2S,5R)-6-benzyloxy-N-[2-(dimethylamino)ethoxy]-7-oxo-1,6-diazabicyclo[3.2.1]-octane-2-carboxamide, (2S,5R)-N-[2-(dimethylamino)ethoxy]-6-hydroxy-7-oxo-1,6-diazabicyclo[3.2.1]octane-2-carboxamide, pyridinium (2S,5R)-N-[2-(dimethylamino)ethoxy]-7-oxo-6-(sulfooxy)-1,6-diazabicyclo[3.2.1]octane-2-carboxamide, (2S,5R)-N-{[(2S)-2-aminopropyl]oxy}-7-oxo-6-(sulfooxy)-1,6-diazabicyclo[3.2.1]-octane-2-carboxamide, tert-butyl {(2S)-1-[({[(2S,5R)-6-benzyloxy-7-oxo-1,6-diazabicyclo[3.2.1]oct-2-yl]carbonyl}amino)oxy]propan-2-yl}carbamate, tert-butyl {(2S)-1-[({[(2S,5R)-6-hydroxy-7-oxo-1,6-diazabicyclo[3.2.1]oct-2-yl]carbonyl}amino)oxy]propan-2-yl}carbamate, tetrabutylammonium tert-butyl {(2S)-1-[({[(2S,5R)-7-oxo-6-(sulfooxy)-1,6-diazabicyclo[3.2.1]oct-2-yl]carbonyl}amino)oxy]propan-2-yl}carbamate, (2S,5R)-N-{[(2R)-2-aminopropyl]oxy}-7-oxo-6-(sulfooxy)-1,6-diazabicyclo[3.2.1]-octane-2-carboxamide, tert-butyl {(2R)-1-[({[(2S,5R)-6-benzyloxy-7-oxo-1,6-diazabicyclo[3.2.1]oct-2-yl]carbonyl}amino)oxy]propan-2-yl}carbamate, tert-butyl {(2R)-1-[({[(2S,5R)-6-hydroxy-7-oxo-1,6-diazabicyclo[3.2.1]oct-2-yl]carbonyl}amino)oxy]propan-2-yl}carbamate, tetrabutylammonium tert-butyl {(2R)-1-[({[(2S,5R)-7-oxo-6-(sulfooxy)-1,6-diazabicyclo[3.2.1]oct-2-yl]carbonyl}amino)oxy]propan-2-yl}carbamate, (2S,5R)-N-(3-aminopropoxy)-7-oxo-6-(sulfooxy)-1,6-diazabicyclo[3.2.1]octane-2-carboxamide, tert-butyl {3-[({[(2S,5R)-6-benzyloxy-7-oxo-1,6-diazabicyclo[3.2.1]oct-2-yl]carbonyl}-amino)oxy]propyl}carbamate, tert-butyl {3-[({[(2S,5R)-6-hydroxy-7-oxo-1,6-diazabicyclo[3.2.1]oct-2-yl]carbonyl}-amino)oxy]propyl}carbamate, tetrabutylammonium tert-butyl {3-[({[(2S,5R)-7-oxo-6-(sulfooxy)-1,6-diazabicyclo-[3.2.1]oct-2-yl]carbonyl}amino)oxy]propyl}carbamate, (2S,5R)-N-[(2S)-azetidin-2-ylmethoxy]-7-oxo-6-(sulfooxy)-1,6-diazabicyclo[3.2.1]-octane-2-carboxamide, tert-butyl (2S)-2-{[({[(2S,5R)-6-benzyloxy-7-oxo-1,6-diazabicyclo[3.2.1]oct-2-yl]carbonyl}amino)oxy]methyl}azetidine-1-carboxylate, tert-butyl (2S)-2-{[({[(2S,5R)-6-hydroxy-7-oxo-1,6-diazabicyclo[3.2.1]oct-2-yl]carbonyl}amino)oxy]methyl}azetidine-1-carboxylate, tetrabutylammonium tert-butyl (2S)-2-{[({[(2S,5R)-7-oxo-6-(sulfooxy)-1,6-diazabicyclo[3.2.1]oct-2-yl]carbonyl}amino)oxy]methyl}azetidine-1-carboxylate, (2S,5R)-7-oxo-N-[(2R)-pyrrolidin-2-ylmethoxy]-6-(sulfooxy)-1,6-diazabicyclo[3.2.1]-octane-2-carboxamide, tert-butyl (2R)-2-{[({[(2S,5R)-6-benzyloxy-7-oxo-1,6-diazabicyclo[3.2.1]oct-2-yl]carbonyl}amino)oxy]methyl}pyrrolidine-1-carboxylate, tert-butyl (2R)-2-{[({[(2S,5R)-6-hydroxy-7-oxo-1,6-diazabicyclo[3.2.1]oct-2-yl]carbonyl}amino)oxy]methyl}pyrrolidine-1-carboxylate, tetrabutylammonium tert-butyl (2R)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate, (2S,5R)-7-oxo-N-[(2S)-piperidin-2-ylmethoxy]-6-(sulfooxy)-1,6-diazabicyclo[3.2.1]-octane-2-carboxamide, tert-butyl (2S)-2-{[({[(2S,5R)-6-benzyloxy-7-oxo-1,6-diazabicyclo[3.2.1]oct-2-yl]carbonyl}amino)oxy]methyl}piperidine-1-carboxylate, tert-butyl (2S)-2-{[({[(2S,5R)-6-hydroxy-7-oxo-1,6-diazabicyclo[3.2.1]oct-2-yl]carbonyl}amino)oxy]methyl}piperidine-1-carboxylate, tetrabutylammonium tert-butyl (2S)-2-{[({[(2S,5R)-7-oxo-6-(sulfooxy)-1,6-diazabicyclo[3.2.1]oct-2-yl]carbonyl}amino)oxy]methyl}piperidine-1-carboxylate, (2S,5R)-7-oxo-N-[(3S)-pyrrolidin-3-yloxy]-6-(sulfooxy)-1,6-diazabicyclo[3.2.1]octane-2-carboxamide, tert-butyl (3S)-3-[({[(2S,5R)-6-benzyloxy-7-oxo-1,6-diazabicyclo[3.2.1]oct-2-yl]carbonyl}amino)oxy]pyrrolidine-1-carboxylate, tert-butyl (3S)-3-[({[(2S,5R)-6-hydroxy-7-oxo-1,6-diazabicyclo[3.2.1]oct-2-yl]carbonyl}amino)oxy]pyrrolidine-1-carboxylate, tetrabutylammonium tert-butyl (3S)-3-[({[(2S,5R)-7-oxo-6-(sulfooxy)-1,6-diazabicyclo-[3.2.1]oct-2-yl]carbonyl}amino)oxy]pyrrolidine-1-carboxylate, (2S,5R)-N-(azetidin-3-ylmethoxy)-7-oxo-6-(sulfooxy)-1,6-diazabicyclo[3.2.1]octane-2-carboxamide, tert-butyl 3-{[({[(2S,5R)-6-benzyloxy-7-oxo-1,6-diazabicyclo[3.2.1]oct-2-yl]carbonyl}amino)oxy]methyl}azetidine-1-carboxylate, tert-butyl 3-{[({[(2S,5R)-6-hydroxy-7-oxo-1,6-diazabicyclo[3.2.1]oct-2-yl]carbonyl}-amino)oxy]methyl}azetidine-1-carboxylate, and tetrabutylammonium tert-butyl 3-{[({[(2S,5R)-7-oxo-6-(sulfooxy)-1,6-diazabicyclo-[3.2.1]oct-2-yl]carbonyl}amino)oxy]methyl}azetidine-1-carboxylate, and the following compound group may be mentioned.

[Chemical formula 57]

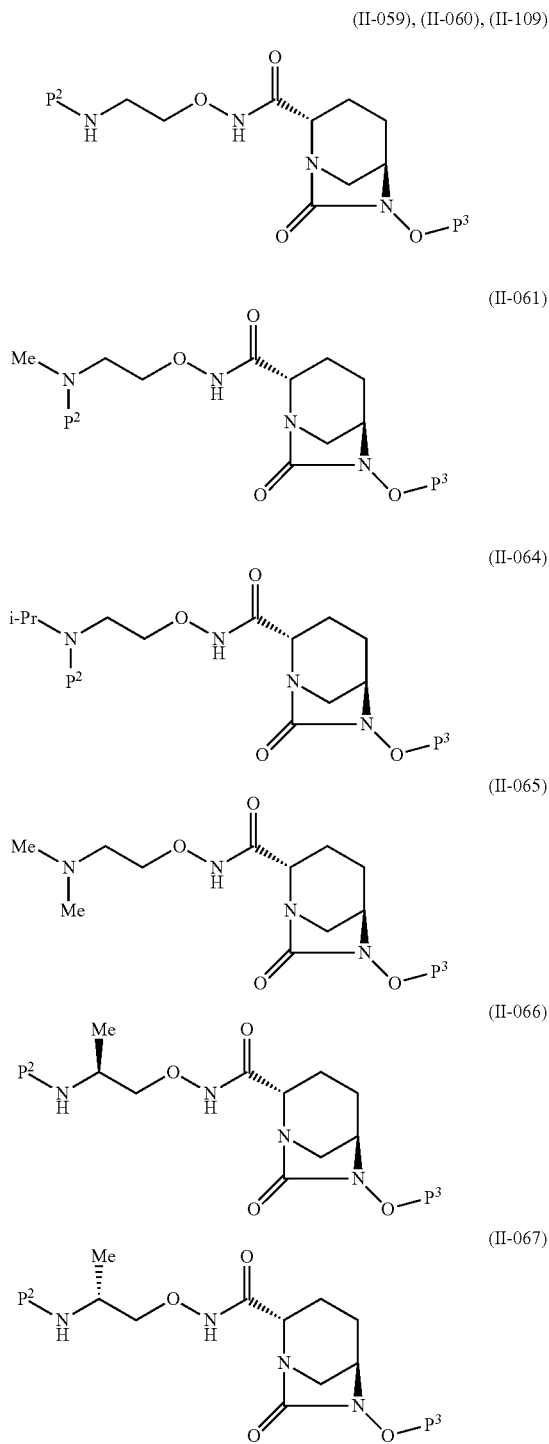

in the above formulae, $P^2$ represents tert-butoxycarbonyl (Boc), benzyloxycarbonyl (Cbz) or H; $P^3$ represents benzyl (Bn), H or $SO_3M$; where M represents H, sodium, pyridinium or tetrabutylammonium.

Most preferably, (2S,5R)-N-(2-aminoethoxy)-7-oxo-6-(sulfooxy)-1,6-diazabicyclo[3.2.1]octane-2-carboxamide, (2S,5R)-N-[2-(methylamino)ethoxy]-7-oxo-6-(sulfooxy)-1,6-diazabicyclo[3.2.1]octane-2-carboxamide, (2S,5R)-7-oxo-N-[2-(propan-2-ylamino)ethoxy]-6-(sulfooxy)-1,6-diazabicyclo[3.2.1]-octane-2-carboxamide, (2S,5R)-N-[2-(dimethylamino)ethoxy]-7-oxo-6-(sulfooxy)-1,6-diazabicyclo[3.2.1]-octane-2-carboxamide, (2S,5R)-N-{[(2S)-2-aminopropyl]oxy}-7-oxo-6-(sulfooxy)-1,6-diazabicyclo[3.2.1]-octane-2-carboxamide,
(2S,5R)-N-{[(2R)-2-aminopropyl]oxy}-7-oxo-6-(sulfooxy)-1,6-diazabicyclo[3.2.1]-octane-2-carboxamide,
(2S,5R)-N-(3-aminopropoxy)-7-oxo-6-(sulfooxy)-1,6-diazabicyclo[3.2.1]octane-2-carboxamide,
(2S,5R)-N-[(2S)-azetidin-2-ylmethoxy]-7-oxo-6-(sulfooxy)-1,6-diazabicyclo[3.2.1]-octane-2-carboxamide,
(2S,5R)-7-oxo-N-[(2R)-pyrrolidin-2-ylmethoxy]-6-(sulfooxy)-1,6-diazabicyclo[3.2.1]-octane-2-carboxamide,
(2S,5R)-7-oxo-N-[(2S)-piperidin-2-ylmethoxy]-6-(sulfooxy)-1,6-diazabicyclo[3.2.1]-octane-2-carboxamide,
(2S,5R)-7-oxo-N-[(3S)-pyrrolidin-3-yloxy]-6-(sulfooxy)-1,6-diazabicyclo[3.2.1]octane-2-carboxamide, and
(2S,5R)-N-(azetidin-3-ylmethoxy)-7-oxo-6-(sulfooxy)-1,6-diazabicyclo[3.2.1]octane-2-carboxamide are mentioned.

The medicament provided by the present invention comprises a substance selected from the group consisting of the compound represented by the formula (I), (II) or (III) and a pharmaceutically acceptable salt thereof, and a hydrate thereof or a solvate thereof as an effective ingredient, is administered orally or parenterally, and preferably administered parenterally. The compound of the present invention and a (β-lactam antibiotic can be administered by the method in which individually prepared respective medicaments at the time of use are administered simultaneously or separately in combination, or the method in which both of the medicaments are previously mixed generally by using one or more additives (carrier) for preparation to prepare a pharmaceutical composition and administering the same.

Specific examples of the pharmaceutical composition for oral administration may include a tablet, a capsule, a granule, powder, a pill, an aqueous or non-aqueous solution for oral administration and a suspension.

As an administration route for the parenteral administration, there may be mentioned intranasal, eye drops, ear drops, percutaneous, tracheobronchial, endorectal, in urinary organ, subcutaneous, intramuscular and intravenous.

Specific examples of the pharmaceutical composition for the parenteral administration as an intravenous administration may include an injection solution for the intravenous administration in which a powdered form of the pharmaceutical composition is dissolved in an acceptable solvent. The acceptable solvent may be mentioned, for example, steric water for injection, physiological saline solution, glucose liquid, Ringer's solution, bacteriostatic water for injection containing methylparaben and propylparaben, or bacteriostatic water for injection containing benzyl alcohol.

The pharmaceutical composition in the powder form for the parenteral administration can be manufactured by subjecting to sterilization process the compound of the present invention which is an active body and a (β-lactam antibiotic, dispensing in a sealed vial and subjecting to lyophilization, or dispensing the pharmaceutical composition in the state of sterilized powder into a sealed vial. Specific methods for the sterilization process may be preferably mentioned:

a method in which an individual or mixed solution is subjected to removal of endotoxin, filtration of insoluble matter, then, crystallization, filling in a sealed vial and gamma ray irradiation;

a method in which an individual or mixed solution is subjected to removal of endotoxin, aseptic filtration, final sterilization such as steam sterilization under pressure and pulsed-light radiation, and lyophilization;

a method in which individual solution is subjected to removal of endotoxin, aseptic filtration under aseptic atmosphere, successively filling in a sealed vial, freezing and overlaying, and then, lyophilization;

a method in which each solution of the compound is individually subjected to removal of endotoxin, aseptic filtration, and crystallization under aseptic atmosphere;

a method in which either of the medicament in the state of sterilized powder crystallized under aseptic atmosphere is overlaid under aseptic atmosphere on another medicament in the state of sterilized powder which has been lyophilized in a sealed vial; and a method in which either of the medicament in the state of sterilized powder lyophilized and the other medicine in the state of sterilized powder crystallized under aseptic atmosphere are mixed under aseptic atmosphere.

More preferred are the method in which an individual solution is subjected to removal of endotoxin, aseptic filtration under aseptic atmosphere, successively filling in a sealed vial, freezing and overlaying, and then, lyophilization, or the method in which each solution of the compound is individually subjected to removal of endotoxin, aseptic filtration, and crystallization under aseptic atmosphere.

The above-mentioned pharmaceutical composition can be stored at a room temperature or lower until it is prepared as an intravenous injection solution, and used by dissolving therein at the time of use. The concentration of the compound of the present invention in the reconstituted intravenous injection solution is in the range of, for example, 1 mg/mL to 50 mg/mL.

The administration dose and the number of administration of the pharmaceutical composition of the present invention are not specifically limited, and the administration dose and the number of administration can be optionally determined depending on the various conditions such as the purpose of the treatment or prophylaxis, kind of the diseases, age, body weight and symptom of the patient. The effective blood concentration of the compound of the present invention to be used in combination with the β-lactam antibiotic is so adjusted that it preferably maintains 1 µg/mL or more during the administration of the β-lactam antibiotic. The administration dose of the compound according to the present invention for intravenous administration is preferably 2 to 75 mg/kg per each time, and for oral administration is preferably 4 to 300 mg/kg, in several times per day depending on the number of administration times of the β-lactam antibiotic, preferably administered 2 to 6 times.

Here, the β-lactam antibiotic which can be used in combination with the compound of the present invention may be mentioned penicillin, cephem and carbapenem.

Specific examples of penicillins include benzylpenicillin, phenethicillin, cloxacillin, dicloxacillin, ampicillin, cyclacillin, amoxycillin, talampicillin, becampicillin, lenampicillin, aspoxicillin, piperacillin, sulbenicillin, pivmecillinam, sultamicillin, phenoxymethylpenicillin, carbenicillin, azidocillin, propicillin, epicillin, ticarcillin, pirbenicilin, azlocillin, mezlocillin, and other known penicillins.

Specific examples of cephems include cefaclor, cefazolin, cefatrizine, cefadroxil, cephapirin, cefamandole, nafate, cephradine, cephalexin, cephalothin, cefepime, cefoxitin, cefixime, ceftazidime, cefditoren, cefdinir, cefsulodin, cefoselis, cefozopran, cefotaxime, ceftazidime, ceftaroline, cefotiam, ceftizoxime, ceftibuten, ceftezole, cefteram, ceftriaxone, cefonicid, cefpiramide, cefpirome, cefbuperazone, cefprozil, cefoperazone, cefpodoxime, cefminox, cefmetazole, cefmenoxime, cefradine, cefroxadine, cefuroxime, ceftolozane (CXA101, (6R,7R)-3-[5-amino-4-[3-(2-aminoethyl)ureido]-1-methyl-1H-pyrazole-2-ium-2-ylmethyl]-7-[2-(5-amino-1,2,4-thiadiazol-3-yl)-2-[(Z)-1-carboxy-1- methylethoxyimino]acetamide]-3-cephem-4-carboxylic acid hydrogen sulfate) and other known cephems.

Examples of the carbapenem may be mentioned imipenem, panipenem, meropenem, biapenem, doripenem, ertapenem and tebipenem, and a DHP-1 inhibitor such as sodium cilastatin may be used in combination, if necessary.

Examples of the β-lactam antibiotics other than the carbapenems, penicillins and cephems may be mentioned a β-lactam antibiotic such as aztreonam, carumonam, latamoxef, flomoxef, loracarbef, faropenem and ritipenem.

Examples of the penicillins which are particularly suitable for using in combination with the compound of the present invention may be mentioned ampicillin, amoxicillin, carbenicillin, piperacillin, azlocillin, mezlocillin and ticarcillin. Such penicillins may be used, for example, in the form of a pharmaceutically acceptable salt such as a sodium salt. As the other embodiment, ampicillin or amoxicillin can be used in combination with the compound of the formula (I) in the form of a suspension for injection or amphoteric ion type (ampicillin.trihydrate or amoxicillin, trihydrate) fine particles for a suspension for injection.

Particularly suitable cephems for combined administration with the compound of the present invention are cefotaxime, ceftriaxone, ceftazidime, cefepime, etc., and these can be used in the form of a pharmaceutically acceptable salt such as a sodium salt.

Particularly suitable carbapenems for combined administration with the compound of the present invention are imipenem, meropenem, biapenem, doripenem and ertapenem.

An example of the particularly suitable β-lactam antibiotic for combined administration with the compound of the present invention other than the carbapenems, penicillins and cephems is aztreonam.

By using the compound of the present invention and a β-lactam antibiotic in combination, it can be used for the treatment of infectious disease caused by class A and class C β-lactamase producing strains, and ESBL and KPC2 carbapenemase producing strains, in addition to bacterial infection included in the antimicrobial spectrum of the antibiotics.

The class A and class C β-lactamase producing strains, and ESBL and KPC2 carbapenemase producing strains include *Escherichia coli, Klebsiella pneumoniae, Enterobacter croacare, Citrobacter freundii, Serratia marcescens, Morganella morganii, Pseudomonas aeruginosa* and *Acinetobacter baumannii.*

In the following, general preparation process of the compound of the present application will be explained.

The compounds applied to investigation and evaluation of the present invention can be synthesized by using the side chain-forming compound (A-BH) and the carboxylic acid represented by the formula (6b) according to the following scheme 1:

Scheme 1

[Chemical formula 58]

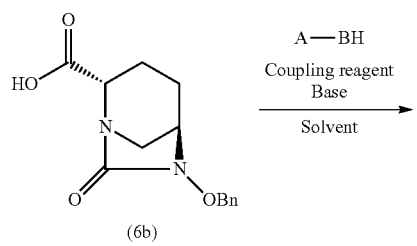

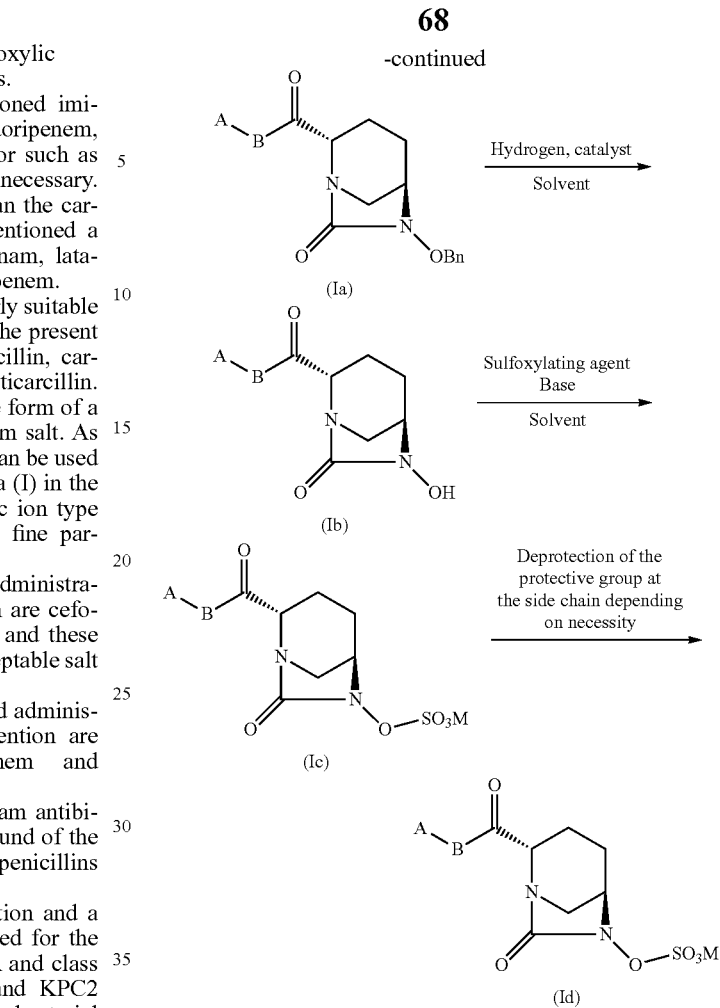

in the above scheme, OBn represents benzyloxy, including the method disclosed in U.S. Pat. No. 7,112,592, by carrying out modification and improvement of the reaction conditions, post-treatment and purification step in view of the reactivity specific for the respective functional groups or the stability specific for the respective compounds.

That is, an optically active carboxylic acid represented by the formula (6b) and the side chain-forming compound (A-BH) are treated by a method selected from the mixed acid anhydride method, the active esterifying method, the active amidating method or the dehydration condensing agent in the presence of a base to prepare a compound represented by the formula (Ia), the benzyl of the benzyloxy of the formula (Ia) is subjected to hydrogenolysis reaction under hydrogen atmosphere in the presence of a catalyst selected from platinum oxide, palladium oxide, palladium black and palladium-carbon, and if necessary, in the presence of di-tert-butoxydicarbonate, to prepare a compound represented by the formula (Ib), the hydroxyl group of the formula (Ib) is sulfated by a sulfating agent selected from sulfur trioxide-pyridine complex, sulfur trioxide-dimethylformamide complex and chlorosulfonic acid in the presence of a base selected from pyridine, 2-picoline, 2,6-lutidine and 2,4,6-collidine to prepare a compound represented by the formula (Ic), and if necessary, the protective group for the amino group (for example, tert-butoxycarbonyl group (Boc)) on the side chain is gently treated with an acid (for example, selected from hydrochloric acid, sulfuric acid, methanesulfonic acid, p-toluenesulfonic acid, trifluoromethanesulfonic acid, trifluoroacetic acid or tetrafluoroboric acid, etc.) to deprotect it, and then, the compound represented by the formula (Id) is purified by octadecyl silica gel column chromatography, column chromatography using a synthetic resin such as DIAION HP21 (available from Mitsubishi Chemical Corporation), SEPABEADS SP207 (available from Mitsubishi Chemical Corporation) or preparative HPLC, etc., at a suitable pH, etc., whereby the objective compound can be synthesized.

The optically active carboxylic acid represented by the above formula (6b) can be synthesized by the following scheme 2:

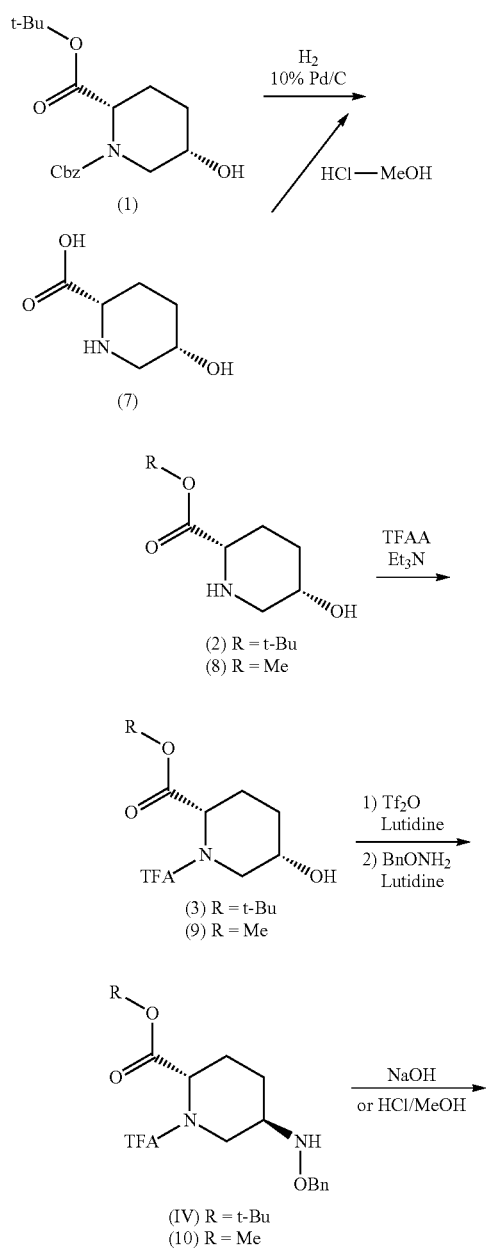

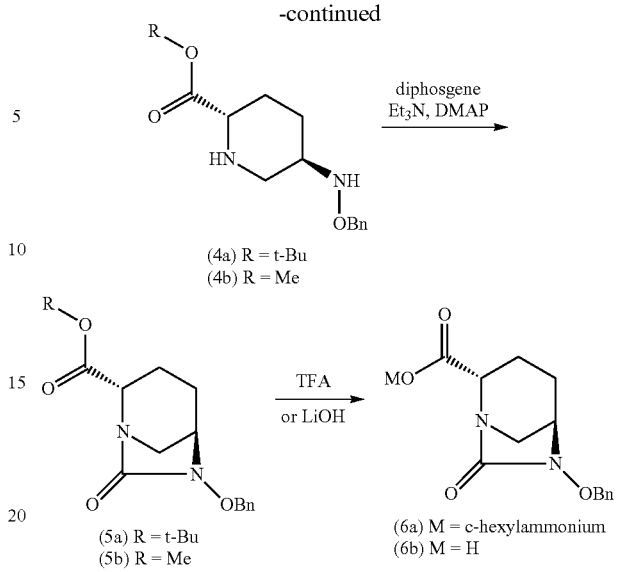

in the above scheme, Cbz represents benzyloxycarbonyl, t-Bu represents a tert-butyl, TFAA represents trifluoroacetic acid anhydride, TFA bonded to the compound represents trifluoroacetyl, $Tf_2O$ represents trifluoromethanesulfonic acid anhydride, $BnONH_2$ represents benzyloxyamine, DMAP represents 4-dimethylaminopyridine, TFA solely described in the scheme represents trifluoroacetic acid, OBn represents benzyloxy, and LiOH represents lithium hydroxide, and the method shown in the Examples of the present invention.

That is, the benzyloxycarbonyl of the known compound represented by the formula (1) is removed by the hydrogenolysis reaction in the presence of a catalyst such as palladium-carbon under hydrogen atmosphere to prepare a compound represented by the formula (2); converting it by reacting with trifluoroacetic acid anhydride in the presence of triethylamine to prepare a compound represented by the formula (3); reacting the hydroxyl group at the 5-position thereof with trifluoromethanesulfonic acid anhydride in the presence of 2,6-lutidine, subsequently with benzyloxyamine to prepare a compound represented by the formula (IV); removing the trifluoroacetyl by using sodium hydroxide to prepare a compound represented by the formula (4a), or subjecting to removal of the trifluoroacetyl by using hydrogen chloride-methanol and an ester exchange reaction simultaneously to prepare a compound represented by the formula (4b); reacting them with diphosgene or phosgene in the presence of triethylamine or 4-dimethylaminopyridine to prepare a compound represented by the formula (5a) or (5b); and cleaving the ester at the 2-position by an acid treatment using trifluoroacetic acid, etc., or a base treatment using lithium hydroxide, etc., to prepare (2S,5R)-6-(benzyloxy)-7-oxo-1,6-diazabicyclo[3.2.1]octane-2-carboxylic acid represented by the formula (6b). Or else, commercially available (2S,5S)-5-hydroxypiperidine-2-carboxylic acid represented by the formula (7) or a hydrochloride thereof is derived to the compound represented by the formula (10) or (4b) according to the similar method as mentioned above without purification, and isolated as a hydrochloride thereof, and further the procedure is carried out to obtain (2S,5R)-6-(benzyloxy)-7-oxo-1,6-diazabicyclo[3.2.1]octane-2-carboxylic acid represented by the formula (6b).

Among the side chain-forming compound A-BH, the specific hydrazine derivative represented by Ra(Rb)N—BH can be synthesized by the following scheme 3:

Scheme 3

[Chemical formula 60]

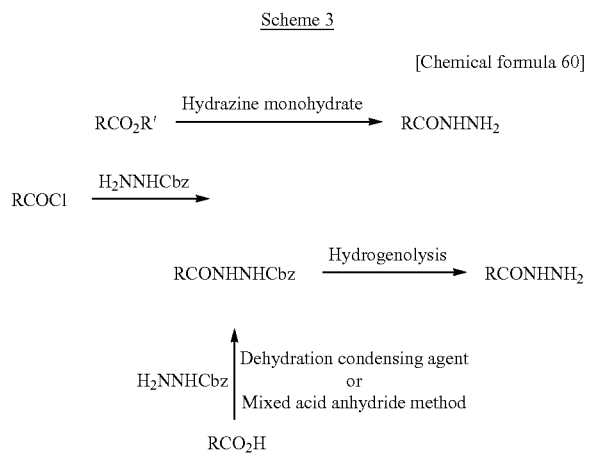

in the above scheme, Cbz represents benzyloxycarbonyl. That is, it can be easily synthesized by subjecting to the reaction of an ester and hydrazine.monohydrate, amidating an acid chloride and N-benzyloxycarbonyl hydrazine in the presence of a suitable base, or amidating a carboxylic acid and N-benzyloxycarbonyl hydrazine by a dehydration condensing agent or by the mixed acid anhydride method, and then, subjecting the benzyloxycarbonyl group to hydrogenolysis in the presence of a catalyst such as palladium-carbon.

Also, a specific alkoxyamine represented by RcOBH is synthesized by the method shown in the following scheme 4:

Scheme 4

[Chemical formula 61]

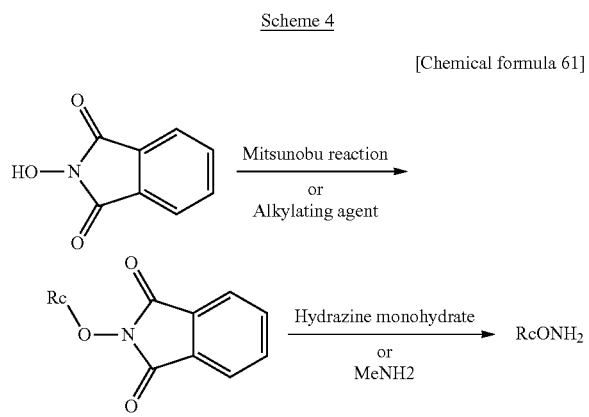

That is, it can be easily synthesized by subjecting N-hydroxyphthalimide and a suitable alcohol derivative to coupling according to Mitsunobu reaction, or reacting with an alkylating agent having a leaving group such as alkyl halide and a methylsulfonyloxy group, then, deprotecting the phthalimide by an organic base such as hydrazine.monohydrate or methylamine.

In the following, a process for preparing the compound represented by the following formula (III):

[Chemical formula 62]

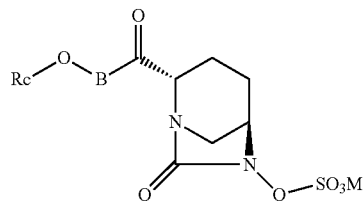

(III)

in the above formula (III), Rc represents a $C_{1-6}$ alkyl or a heterocyclyl; B represents NH or $NC_{1-6}$ alkyl; M represents H, an inorganic cation or an organic cation; Rc may be modified by 0 to 4 substituents Fn1, where the substituent Fn1 may be substituted continuously; Fn1 represents $C_{1-6}$ alkyl, O= or Rg-$(CH_2)_{0-3}$—, where Rg represents a heterocyclyl, phenyl, heteroaryl, acyl, $RdO_2S$—, Re(Rf)N—, Re(Rf)NCO—, ReO—, ReOCO— or a protective group, where Rd represents $C_{1-6}$ alkyl or MO—; Re and Rf each independently represent H or $C_{1-6}$ alkyl; and between Rc-B, and between Re-Rf may be closed by the bonding to form a heterocyclyl having at least one nitrogen atom, to be provided in the present invention will be explained in more detail.

In the preparation process of the present invention, as the suitable protective group represented by $P^1$ in a starting material represented by the following formula (IV-a):

[Chemical formula 63]

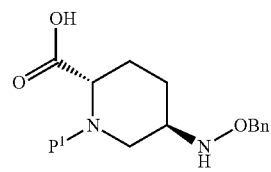

(IV-a)

in the above formula (IV-a), $P^1$ represents a protective group which can be removed by an acid, a base or a nucleophilic agent; and OBn represents benzyloxy, the protective group for an amino group capable of deprotecting by an acid, a base or a nucleophilic agent described in Protective Groups in Organic Synthesis (T. W. Greene et al., Wiley, New York (1999)) can be employed. More specifically, there may be mentioned tert-butoxycarbonyl, 2-trimethylsilylethoxycarbonyl, 1,1-dimethylpropinyl-oxycarbonyl, 1-methyl-1-(4-biphenylyl)ethoxycarbonyl, 1-methylcyclobutoxycarbonyl, 1-adamantyloxycarbonyl, diphenylmethoxycarbonyl, 9-fluorenylmethoxycarbonyl, 1,1-dimethyl-2-cyanoethoxycarbonyl, formyl, trichloroacetyl, trifluoroacetyl, benzenesulphenyl, 2-nitrobenzenesulphenyl, 2-trimethylsilylethanesulfonyl, 2-nitrobenzenesulfonyl, 4-nitrobenzenesulfonyl, 2,4-dinitrobenzenesulfonyl, 2-naphthalenesulfonyl, 9-anthrathenesulfonyl and benzenethiazole sulfonyl, preferably tert-butoxycarbonyl, 2-trimethylsilylethoxycarbonyl, trifluoroacetyl, 9-fluorenylmethoxycarbonyl, 2-nitrobenzenesulfonyl or 4-nitrobenzenesulfonyl.

The step of obtaining a compound represented by the following formula (IV-b):

[Chemical formula 64]

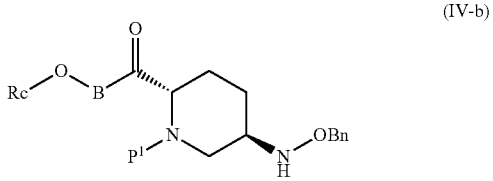

(IV-b)

in the above formula (IV-b), P¹ represents a protective group which can be removed by an acid, a base or a nucleophilic agent, Rc and B have the same meanings as defined for the compound represented by the formula (III), and OBn represents benzyloxy, by coupling the compound represented by the formula (IV-a) with the side chain-forming compound: RcOBH, can be carried out by the method where the compound represented by the formula (IV-a) is treated by using an active ester, an active amide or the dehydration condensing agent in a suitable solvent.

Coupling using the dehydration condensing agent is carried out in many cases by adding an active ester group or an active amide group as a catalyst to form an active ester or an active amide in the reaction system, and the specific examples are mentioned and explained below.

The solvent to be used for the dehydration condensing agent may be mentioned water, methanol, ethanol, isopropanol, ethyl acetate, toluene, tetrahydrofuran, dioxane, acetonitrile, dichloromethane, chloroform, dimethylformamide, dimethylacetamide, etc., preferably ethyl acetate, tetrahydrofuran, dichloromethane, acetonitrile, dimethylformamide, dimethylacetamide, which can be used singly or in admixture.

When the active esterifying agent or the active amidating agent is used, the reaction is carried out in the presence of a base, if necessary. The base to be used in the reaction may be mentioned triethylamine, diisopropylethylamine, tributylamine, N-methylmorpholine and 4-dimethylaminopyridine, preferably triethylamine, and used in the range of 1 to 3 equivalents depending on necessity based on the compound represented by the formula (IV-a), preferably 1 to 1.5 equivalents.

As the dehydration condensing agent, there may be used carbodiimide alone such as N,N'-diisopropylcarbodiimide, N,N'-dicyclohexylcarbodiimide and 1-ethyl-3-(3-dimethylaminopropyl)carbodiimide hydrochloride, or in combination with an active amide group or an active ester group such as imidazole, 1-hydroxybenzotriazole.monohydrate, N-hydroxysuccinimide and 2-hydroxypyridine-N-oxide, and further there may be mentioned an active esterifying agent or an active amidating agent such as carbonyldiimidazole, benzotriazol-1-yloxy-tris(dimethylamino)phosphonium hexafluorophosphate, 2-chloro-1-methylpyridinium iodide and 4-(4,6-dimethoxy-1,3,5-triazin-2-yl)-4-methylmorpholinium chloride, preferably 1-ethyl-3-(3-dimethylaminopropyl)carbodiimide hydrochloride in combination with 1-hydroxybenzotriazole.monohydrate, or selected 2-chloro-1-methylpyridinium iodide, and the agent is used in the range of 1.0 to 2.0 equivalents based on the compound represented by the formula (IV-a), more preferably 1.0 to 1.5 equivalents. The reaction temperature is in the range of −40° C. to room temperature, preferably in the range of −20° C. to room temperature. The reaction is carried out with a time in the range of 30 minutes to 1 day, preferably in the range of 2 hours to 16 hours.

The compound represented by the formula (IV-b) can be isolated by diluting the reaction mixture with a suitable solvent after completion of the reaction, washing successively with water, a diluted acid, an aqueous base solution (for example, diluted hydrochloric acid, potassium monohydrogen sulfate, citric acid, or an aqueous sodium bicarbonate solution, saturated saline solution), and evaporating the solvent to concentrate the reaction mixture. The organic solvent to be used for dilution may be mentioned diethyl ether, ethyl acetate, butyl acetate, toluene, dichloromethane and chloroform, preferably ethyl acetate.

Subsequently, the step of deprotecting the compound represented by the above formula (IV-b) to prepare a compound represented by the following formula (IV-c):

[Chemical formula 65]

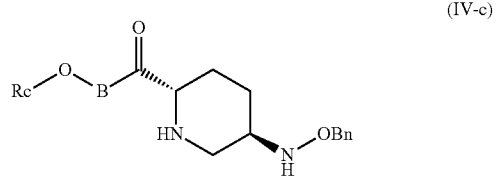

(IV-c)

in the above formula (IV-c), Rc and B have the same meanings as defined for the compound represented by the formula (III), and OBn represents benzyloxy, can be carried out as follows.

The solvent to be used for deprotecting under the acidic conditions may be mentioned water, methanol, ethanol, isopropanol, ethyl acetate, tetrahydrofuran, dioxane, dichloromethane, chloroform, 1,2-dichloroethane, 2,2,2-trifluoroethanol, etc., preferably water, methanol, ethanol, ethyl acetate, dioxane and dichloromethane, which can be used singly or in admixture.

The acid to be used for deprotecting under the acidic conditions may be mentioned hydrochloric acid, sulfuric acid, phosphoric acid, formic acid, trifluoroacetic acid, methanesulfonic acid, trifluoromethanesulfonic acid, chloromethanesulfonic acid, tetrafluoroboric acid, etc., preferably hydrochloric acid, sulfuric acid, trifluoroacetic acid, methanesulfonic acid and tetrafluoroboric acid, more preferably hydrochloric acid or trifluoroacetic acid. The acid is used in the range of 1 equivalent to a solvent amount based on the compound represented by the formula (IV-b), preferably 5-fold amount to a solvent amount. The reaction temperature is in the range of −25 to 50° C., preferably in the range of −10 to 30° C. The reaction is carried out with a time in the range of 30 minutes to 16 hours, preferably in the range of 30 minutes to 5 hours.

The solvent to be used for deprotecting under basic conditions or by the nucleophilic agent may be mentioned water, methanol, ethanol, isopropanol, tetrahydrofuran, dioxane, acetonitrile, dimethylformamide, dimethylacetamide, 2,2,2-trifluoroethanol, etc., preferably water, methanol, tetrahydrofuran and dioxane, which can be used singly or in admixture.

The base to be used for deprotecting under basic conditions may be mentioned lithium hydroxide, sodium hydroxide, potassium hydroxide, cesium hydroxide, lithium carbonate, sodium carbonate, potassium carbonate, cesium carbonate, etc., preferably lithium hydroxide, sodium hydroxide and potassium hydroxide, and is used in the range of 2 to 5 equivalents based on the compound represented by the formula (IV-b), preferably in the range of 2 to 4 equivalents. The reaction temperature is in the range of −25 to 50° C., preferably 0 to 10° C. The reaction is carried out with a time in the range of 30 minutes to 16 hours, preferably in the range of 30 minutes to 5 hours.

The nucleophilic agent to be used for deprotecting by the nucleophilic agent may be mentioned a thiol such as ethanethiol, thioglycolic acid and thiophenol; and a fluoride such as hydrogen fluoride pyridine, sodium fluoride, potassium fluoride, cesium fluoride and tetrabutylammonium fluoride, preferably tetrabutylammonium fluoride, and is used in the range of 2 to 4 equivalents based on the compound represented by the formula (IV-b), preferably 2 to 3 equivalents. The reaction temperature is selected from the range of 0 to 100° C., preferably 25 to 60° C. The reaction is carried out with a time in the range of 2 hours to 48 hours, preferably 8 hours to 24 hours.

The compound represented by the formula (IV-c) having the RcONHCO group with a weak acidic property is an amphoteric substance, so that there is an optimum pH range for obtaining the compound as a free base. The optimum pH is in the range of pH6 to 9, preferably in the range of pH6 to 8.

The compound represented by the formula (IV-c) can be isolated by diluting the reaction mixture with an organic solvent, adjusting the optimum pH as mentioned above, and extracting with a solvent. The organic solvent to be used for diluting the basic reaction mixture may be mentioned diethyl ether, ethyl acetate, butyl acetate, toluene, dichloromethane and chloroform, preferably ethyl acetate or dichloromethane.

Subsequently, the step of silylating the compound represented by the above formula (IV-c) in the reaction system, and continuously subjecting to intramolecular urea formation reaction to obtain a compound represented by the following formula (IIa):

[Chemical formula 66]

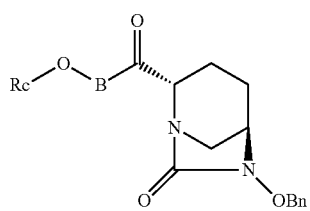

(IIa)

in the above formula (IIa), Rc and B have the same meanings as defined for the compound represented by the formula (III), and OBn represents benzyloxy, can be carried out as follows.

The solvent to be used for the reaction may be mentioned ethyl acetate, tetrahydrofuran, dioxane, acetonitrile, dimethylformamide, dimethylacetamide, etc., preferably acetonitrile is selected.

The base to be used for the reaction may be mentioned triethylamine, diisopropylethylamine, tributylamine and N-methylmorpholine, preferably triethylamine, and is used in the range of 3 to 6 equivalents based on the compound represented by the formula (IV-c), preferably 3 to 4 equivalents.

The silylating agent to be used for the reaction may be mentioned a chlorotrialkylsilane such as chlorotrimethylsilane, chlorotriethylsilane, chlorotriisopropylsilane and chloro-tert-butyldimethylsilane; trimethylsilyl trifluoromethanesulfonate and tert-butyldimethylsilyl trifluoromethanesulfonate, preferably a chlorotrialkylsilane such as chlorotrimethylsilane, and is used in the range of 1 to 3 equivalents based on the compound represented by the formula (IV-c), preferably 1 to 1.5 equivalents.

The urea-forming agent to be used for the reaction may be mentioned phosgene, diphosgene, triphosgene and carbonyldiimidazole, preferably phosgene and diphosgene, and is used in the range of 0.5 to 2 equivalents based on the compound represented by the formula (IV-c), preferably 0.5 to 1.0 equivalent. At that time, to complete the urea formation, a catalytic amount of 4-dimethylaminopyridine is used in the range of 0.1 to 1 equivalent based on the compound represented by the formula (IV-c), preferably 0.1 to 0.2 equivalent.

The reaction temperature is in the range of −25 to 50° C., preferably −15 to 30° C. The reaction is carried out with a time in the range of 10 minutes to 24 hours, preferably 1 hour to 16 hours.

The formed compound represented by the formula (V-2) can be isolated by the conventional post-treatment such as evaporating the organic solvent of the reaction mixture to concentrate the same, diluting with a solvent, washing with an acid and a base, drying, evaporating the solvent to concentrate the same, and precipitation.

Subsequently, the step of preparing a compound represented by the following formula (IIb):

[Chemical formula 67]

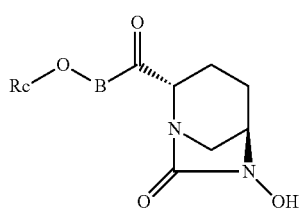

(IIb)

in the above formula (IIb), Rc and B have the same meanings as defined for the compound represented by the formula (III), by cleaving the benzyl group of the benzyloxy group at the 6-position of the compound represented by the above formula (IIa) using a hydrogenolysis catalyst under hydrogen atmosphere can be carried out as follows.

The solvent to be used for the reaction may be mentioned water, methanol, ethanol, isopropanol, ethyl acetate, tetrahydrofuran and dioxane, preferably methanol or tetrahydrofuran, which can be used singly or in admixture.

The hydrogenolysis catalyst may be mentioned platinum oxide, palladium hydroxide, palladium black or palladium-carbon, preferably palladium-carbon.

An amount of the catalyst is employed in the range of 5 to 100 wt % based on the compound represented by the formula (IIa), preferably 5 to 30 wt %.

A supply source of the hydrogen to be used for the hydrogenolysis is a hydrogen gas, and a hydrogen pressure is selected in the range of atmospheric pressure to 1 MPa, preferably atmospheric pressure to 0.5 MPa. As the supply source of the hydrogen, ammonium formate, cyclohexene or cyclohexadiene can be used as the other method. An amount of the hydrogen to be supplied is used at least stoichiometric amount.

The reaction temperature of the hydrogenolysis is in the range of 10 to 50° C., preferably in the range of 15 to 30° C. The reaction is carried out with a time in the range of 0.5 to 3 hours, preferably in the range of 0.5 to 2 hours.

When the amino group and the benzyloxycarbonyl group as the protective group therefor are present in the side chain Rc of the compound represented by the formula (IIa), they can be protected again by the tert-butoxycarbonyl group in the presence of di-tert-butoxycarbonyldicarbonate simultaneously with the above-mentioned hydrogenolysis reaction.

An amount of the di-tert-butoxycarbonyldicarbonate to be added is 1 to 2 equivalents based on the compound represented by the formula (IIa), preferably 1 to 1.2 equivalents. After completion of the reaction, the compound represented by the formula (IIb) can be isolated by the usual operations such as filtration of the catalyst, and evaporation of the solvent to concentrate the mixture.

Subsequently, the step of leading to the compound represented by the above formula (III) by sulfating the hydroxyl group at the 6-position of the compound represented by the above formula (IIb) in the presence of a base, and deprotecting the protective group at the side chain (RcO), if necessary, can be carried out as follows.

The solvent to be used for sulfation may be mentioned water, methanol, ethanol, isopropanol, dichloromethane, chloroform, 1,2-dichloroethane, pyridine, acetonitrile and dimethylformamide, preferably dichloromethane, pyridine and acetonitrile, which can be used singly or in admixture.

The base to be used for the reaction may be mentioned triethylamine, tributylamine, diisopropylethylamine, N-methylmorpholine, pyridine, 2-picoline, 3-picoline, 2,6-lutidine, 2,4,6-collidine, 4-dimethylaminopiperidine and N-methylimidazole, preferably pyridine, 2-picoline and 2,6-lutidine, and is used in the range of 1.0 to a solvent amount based on the compound represented by the formula (IIb), preferably in the range of 3.0 to a solvent amount.

The material to be used as the sulfating agent may be mentioned chlorosulfonic acid, sulfur trioxide-pyridine complex, sulfur trioxide-dimethylformamide complex, sulfur trioxide-trimethylamine complex and sulfur trioxide-triethylamine complex, preferably sulfur trioxide-pyridine complex or sulfur trioxide-dimethylformamide complex, and is used in the range of 1 to 4 equivalents based on the compound represented by the formula (IIb), preferably 2 to 3 equivalents. The reaction temperature is in the range of 0 to 50° C., preferably 10 to 30° C. The reaction is carried out with a time in the range of 12 to 48 hours, preferably in the range of 12 to 24 hours.

After completion of the reaction, the compound represented by the formula (III) can be obtained as a sulfonic acid pyridinium salt by filtration and evaporation of the solvent to concentrate the reaction mixture, and by making a treatment with an aqueous inorganic base solution containing sodium such as an aqueous sodium bicarbonate solution to give a sodium salt, by adding 1 to 3 mol equivalents of tetrabutylammonium hydrogen sulfate to the aqueous solution of the sodium salt, and extracting with an organic solvent such as ethyl acetate to give a tetrabutylammonium salt, and the above-mentioned aqueous solution is adjusted to the optimum pH to give an intramolecular salt, to provide to the next step or the product is purified to prepare a compound represented by the formula (III) as a final form.

Here, the optimum pH means the pH range at which the compound represented by the formula (III) can be present stably as an intramolecular salt. The range of pH4 to 7 is selected to isolate the compound as an intramolecular salt, more preferably in the range of pH5 to 6.

When the protective group (for example, a tert-butoxycarbonyl group) is present at the side chain (RcO) of the formula (III), it is further applied to the deprotection step.

As the step of deprotecting the tert-butoxycarbonyl group in the side chain (RcO), deprotection under acidic conditions is employed.

The solvent to be used for the reaction may be mentioned water, methanol, ethanol, isopropanol, ethyl acetate, tetrahydrofuran, dioxane, dichloromethane, chloroform, 1,2-dichloroethane, 2,2,2-trifluoroethanol, etc., preferably dichloromethane, ethyl acetate or 2,2,2-trifluoroethanol.

The acid to be used for deprotection under acidic conditions may be mentioned hydrochloric acid, sulfuric acid, phosphoric acid, formic acid, trifluoroacetic acid, methanesulfonic acid, trifluoromethanesulfonic acid, chloromethanesulfonic acid, tetrafluoroboric acid, etc., preferably hydrochloric acid, sulfuric acid, trifluoroacetic acid, methanesulfonic acid and tetrafluoroboric acid, more preferably hydrochloric acid, sulfuric acid and trifluoroacetic acid. The acid is used in the range of 1 equivalent to a solvent amount based on the compound represented by the formula (III), preferably 3-fold amount to a solvent amount. The reaction temperature is in the range of −25 to 50° C., preferably −10 to 30° C. The reaction is carried out with a time in the range of 30 minutes to 5 hours, preferably in the range of 30 minutes to 1 hour.

After completion of the deprotection, the solvent of the reaction mixture is evaporated to concentrate the mixture or a poor solvent is added to precipitate the crude product and then the mixture is made to an aqueous solution with the optimum pH in the range of pH5 to 6, and is subjected to precipitation again, or purification by using octadecyl silica (ODS), a synthetic resin such as DIAION HP-20 and SEPA-BEADS SP207, and an ion-exchange resin such as DOWEX 50W-X8 (Na type), further reprecipitation or lyophilization to obtain a compound represented by the formula (III) as a final form.

Moreover, the preparation process of the compound represented by the above formula (III) and (2S,5R)-7-oxo-N-(2-aminoethoxy)-6-sulfooxy-1,6-diazabicyclo[3.2.1]octane-2-carboxamide represented by the formula (III-059):

[Chemical formula 68]

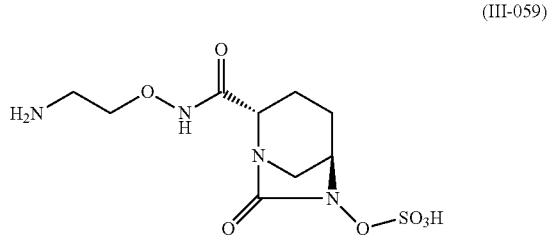

(III-059)

will be explained in detail.

The step of preparing (2S,5R)-methyl 5-(benzyloxyamino)piperidine-2-carboxylate represented by the above formula (4b) or a hydrochloride thereof can be carried out as follows.

Methyl esterification of the commercially available (2S, 5S)-5-hydroxypiperidine-2-carboxylic acid represented by the formula (7) or a hydrochloride thereof is carried out in methanol under heating in the presence of a suitable acid. The acid to be used may be mentioned hydrogen chloride, sulfuric acid, perchloric acid, methanesulfonic acid and p-toluenesulfonic acid, preferably hydrogen chloride. When hydrogen chloride is used, it is used in an amount of 3 to 6 equivalents, preferably 4 to 5 equivalents based on an amino acid molar number/weight ratio obtained from an acid/base consuming amount of the compound represented by the formula (7). The reaction is carried out under reflux for 2 to 4 hours, preferably 3 hours. After completion of the reaction, the residue obtained by concentrating the reaction mixture is made basic, and extracted with a suitable organic solvent to isolate (2S,5S)-methyl 5-hydroxypiperidine-2-carboxylate represented by the formula (8). The base to be used may be mentioned sodium hydroxide, sodium carbonate and potassium carbonate, preferably potassium carbonate. The solvent to be used for extraction may be mentioned diethyl ether, ethyl acetate, dichloromethane, chloroform, preferably ethyl acetate. The isolated compound represented by the formula (8) can be applied to the next step without further purification.

Trifluoroacetylation of (2S,5S)-methyl 5-hydroxypiperidine-2-carboxylate represented by the formula (8) is carried out by the reaction with trifluoroacetic anhydride in the presence of triethylamine. The trifluoroacetic anhydride is used in an amount of 0.9 to 1.3 equivalents, preferably 1.0 equivalent based on the sum total of a molar number/weight ratio of the compound represented by the formula (8) obtained by the pre-labeled HPLC method and an amino acid molar number/weight ratio obtained from an acid consuming amount. Also, triethylamine is used in an amount double as much of that of trifluoroacetic anhydride. The reaction solvent is selected from dichloromethane, chloroform, dichloroethane, ethyl acetate and tetrahydrofuran, preferably ethyl acetate. The reaction is carried out at a temperature in the range of −70° C. to 0° C., preferably −40° C. to 0° C., and a reaction time in the range of 60 to 120 minutes, preferably 60 to 90 minutes. (2S,5S)-methyl 5-hydroxy-1-(2,2,2-trifluoroacetyl)piperidine-2-carboxylate represented by the formula (9) can be isolated by adding water to the reaction mixture to hydrolyze the trifluoroacetoxy group at the 5-position alone, then washing with usual acid/base and concentrating the mixture under reduced pressure. The isolated compound represented by the formula (9) can be applied to the next step without further purification.

The step of benzyloxyamination of the hydroxyl group at the 5-position of (2S,5S)-methyl 5-hydroxy-1-(2,2,2-trifluoroacetyl)piperidine-2-carboxylate represented by the formula (9) can be carried out by reacting it with trifluoromethanesulfonic anhydride in an amount of 1 to 1.1 equivalents, preferably 1 equivalent in the presence of 2,6-lutidine in an amount of 1 to 1.2 equivalents, preferably 1.1 equivalents based on the HPLC titer of the compound represented by the formula (9) in the reaction system to prepare a trifluoromethanesulfonic acid ester, subsequently reacting the resulting compound with benzyloxyamine in an amount of 1 to 3 equivalents, preferably 2 equivalents in the presence of 2,6-lutidine in an amount of 1 to 1.2 equivalents, preferably 1.1 equivalents. The reaction solvent is selected from dichloromethane, chloroform, 1,2-dichloromethane, tetrahydrofuran and acetonitrile, preferably acetonitrile. The reaction is carried out at a temperature in the range of −50° C. to 50° C., preferably −35° C. to 0° C., and a reaction time in the range of 1 to 5 days, preferably 2 to 3 days. (2S,5R)-methyl 5-(benzyloxyamino)-1-(2,2,2-trifluoroacetyl)piperidine-2-carboxylate represented by the formula (10) can be isolated and purified by concentrating the reaction mixture under reduced pressure, diluting the residue with a solvent such as ethyl acetate, etc., washing with usual acid/base, and concentrating the mixture under reduced pressure to prepare a crude compound represented by the formula (10), then, dissolving the crude product in ethyl acetate and adding a hydrogen chloride-ethyl acetate solution thereto to obtain a hydrochloride of the compound represented by the formula (10).

Removal of the 2,2,2-trifluoroacetyl group of (2S,5R)-methyl 5-(benzyloxyamino)-1-(2,2,2-trifluoroacetyl)piperidine-2-carboxylate represented by the formula (10) can be carried out in methanol under heating in the presence of a suitable acid. The acid to be used is suitably hydrogen chloride, sulfuric acid, perchloric acid, methanesulfonic acid and p-toluenesulfonic acid, preferably hydrogen chloride. An amount of hydrogen chloride to be used is in the range of 10 to 20 equivalents, preferably 13 to 18 equivalents based on the amount of the compound represented by the formula (10). The reaction time is 1 to 4 days, preferably 1 to 3 days. When an acid other than hydrogen chloride is used, the residue obtained by concentrating the reaction mixture under reduced pressure is made basic, a free base of (2S,5R)-5-(benzyloxyamino)piperidine-2-carboxylate represented by the formula (4b) is once extracted with a suitable organic solvent, and then, an acid selected from oxalic acid and hydrogen chloride is added thereto to isolate and purify the objective compound as a salt. When hydrogen chloride is used, the reaction mixture is concentrated and ethyl acetate is added as a poor solvent to isolate and purify a hydrochloride of the compound represented by the formula (4b).

Here, the compound represented by the formula (4b) can be easily isolated and purified as a hydrochloride by crystallization so that it is an intermediate industrially extremely advantageous.

The compound represented by the following formula (IV-a2), (IV-a3) or (IV-a4):

[Chemical formula 69]

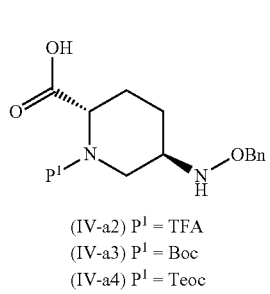

(IV-a2) P¹ = TFA
(IV-a3) P¹ = Boc
(IV-a4) P¹ = Teoc in the above formula (IV-a2), (IV-a3) or (IV-a4), TFA represents trifluoroacetyl, Boc represents tert-butoxycarbonyl, Teoc represents 2-trimethylsilylethoxycarbonyl, and OBn represents benzyloxy,
can be prepared by the following scheme 5:

in the above scheme, the free TFA represents trifluoroacetic acid, TFA bonded to the chemical formula represents trifluoroacetyl, t-Bu represents tert-butyl, OBn represents benzyloxy, Boc₂O represents di-tert-butoxydicarbonate, TeocO-Su represents N-(2-trimethylsilylethoxycarbonyloxy)succinimide, Boc represents tert-butoxycarbonyl, and Teoc represents 2-trimethylsilylethoxycarbonyl,
from the compound represented by the formula (IV) or the formula (4b) in the synthetic scheme 2 of the optically active carboxylic acid (6b), and by the method shown in Examples.

That is, the compound represented by the formula (IV-a2) can be prepared by cleaving the tert-butoxy ester of the compound represented by the formula (IV) with a solvent amount of trifluoroacetic acid in a halogen series solvent such as dichloromethane and chloroform.

Also, the compound represented by the formula (IV-a1) can be obtained by removing the trifluoroacetyl of the compound represented by the formula (IV) with a base selected from sodium hydroxide and potassium hydroxide in hydrated dioxane, cleaving the tert-butoxy ester by an acid selected from hydrochloric acid, sulfuric acid, trifluoroacetic acid or methanesulfonic acid to prepare a salt of the compound represented by the formula (IV-a1), which can be used in the next step after isolation or without isolation. In addition, the methyl ester of the hydrochloride of the compound represented by the formula (4b) is cleaved under the similar basic conditions to prepare a solution of the compound represented by the formula (IV-a1) and the compound can be used in the next step without isolation.

Scheme 5

[Chemical formula 70]

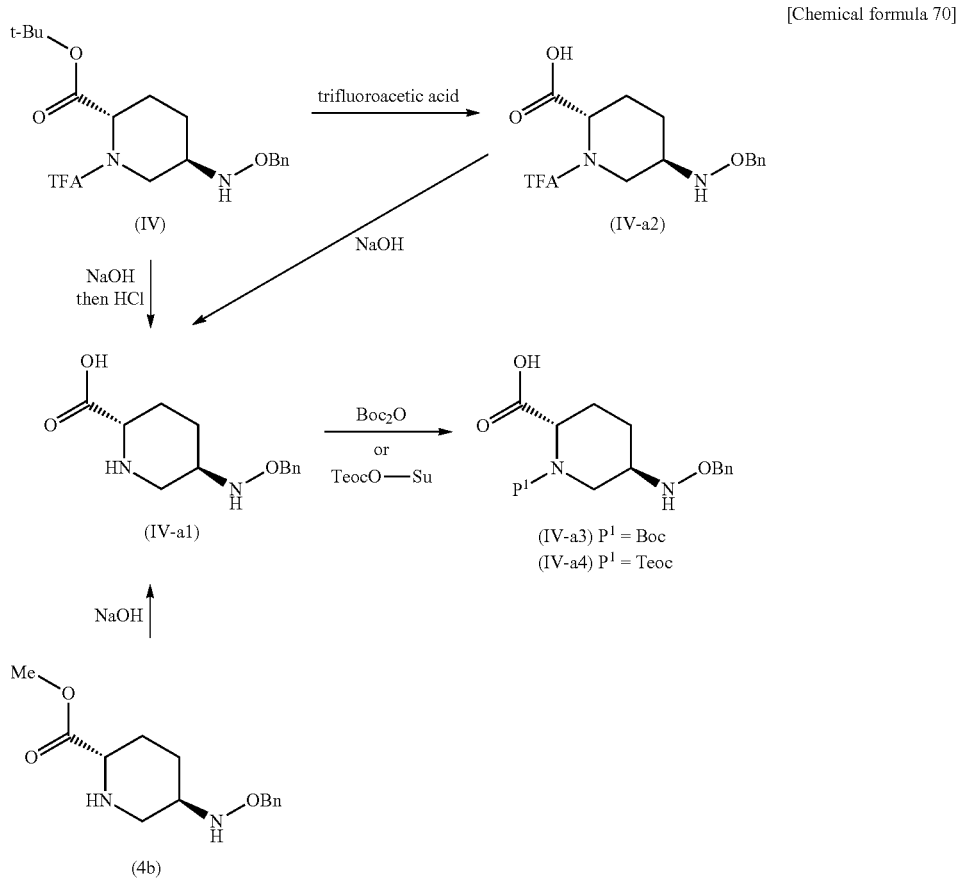

The compounds represented by the formulae (IV-a3) and (IV-a4) can be prepared by dissolving the compound represented by the formula (IV-a1) in aqueous dioxane or aqueous tetrahydrofuran, and reacting with a tert-butoxycarbonylating agent selected from Boc$_2$O (di-tert-butoxydicarbonate), Boc-ON (2-(tert-butoxycarbonyloxy-imino)-2-phenylacetonitrile) and Boc-OSu (N-(tert-butoxycarbonyloxy)succinimide), or with N-(2-trimethylsilylethoxycarbonyloxy) succinimide in the presence of a base selected from sodium hydroxide, sodium carbonate, potassium carbonate and triethylamine.

(2S,5R)-5-(benzyloxyamino)piperidin-2-carboxylic acid,
(2S,5R)-5-(benzyloxyamino)-1-(2,2,2-trifluoroacetyl)piperidin-2-carboxylic acid,
(2S,5R)-5-(benzyloxyamino)-1-(tert-butoxycarbonyl)piperidin-2-carboxylic acid, and
(2S,5R)-5-(benzyloxyamino)-1-((2-(trimethylsilyl)ethoxy)carbonyl)piperidin-2-carboxylic acid, which are the formulae (IV-a1), (IV-a2), (IV-a3) and (IV-a4), respectively, in the above scheme 5 are each novel compound, and they have usefulness not only in the field of the present invention but also general starting materials.

Among the above formulae (IV-a2), (IV-a3) and (IV-a4), the step of obtaining the compound represented by the following formula (IV-b2-Boc-059), (IV-b3-Cbz-059), (IV-b4-Boc-059):

[Chemical formula 71]

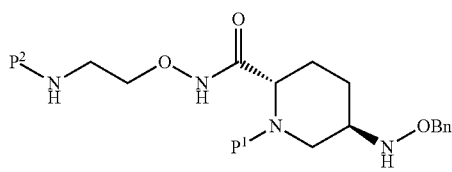

(IV-b2-Boc-059) P$^1$ = TFA, P$^2$ = Boc
(IV-b3-Cbz-059) P$^1$ = Boc, P$^2$ = Cbz
(IV-b4-Boc-059) P$^1$ = Teoc, P$^2$ = Boc in the above formula (IV-b2-Boc-059), (IV-b3-Cbz-059), (IV-b4-Boc-059), TFA represents trifluoroacetyl, Boc represents tert-butoxycarbonyl, Cbz represents benzyloxycarbonyl, Teoc represents 2-trimethylsilylethoxycarbonyl, and OBn represents benzyloxy, by subjecting to coupling the compounds represented by the formulae (IV-a2) and (IV-a4) by the method of using tert-butyl 2-(aminooxy)ethylcarbamate and an active ester, an active amide or a dehydration condensing agent, and by subjecting to coupling the compound represented by the formula (IV-a3) by the method of using benzyl 2-(aminooxy)ethylcarbamate and an active ester, an active amide or a dehydration condensing agent can be carried out as follows.

An amount of the tert-butyl 2-(aminooxy)ethylcarbamate or benzyl 2-(aminooxy)ethylcarbamate to be used is 1 to 2 equivalents based on the compound represented by the formula (IV-a2), (IV-a3) or (IV-a4), preferably 1.0 to 1.5 equivalents.

Coupling using the dehydration condensing agent is carried out in many cases by adding an active ester group or an active amide group as a catalyst to form an active ester or an active amide in the reaction system, and the specific examples are mentioned and explained below.

The solvent to be used when the dehydration condensing agent is used may be mentioned ethyl acetate, toluene, tetrahydrofuran, dioxane, acetonitrile, dichloromethane, chloroform, dimethylformamide, dimethylacetamide, etc., preferably ethyl acetate, tetrahydrofuran, dichloromethane, acetonitrile, dimethylformamide and dimethylacetamide.

When an active esterifying agent or an active amidating agent is used, the reaction is carried out in the presence of a base, if necessary. The base to be used for the reaction may be mentioned triethylamine, diisopropylethylamine, tributylamine, N-methylmorpholine and 4-dimethylaminopyridine, preferably triethylamine, and is used in the range of 1 to 3 equivalents based on the compound represented by the formula (IV-b2-Boc-059), (IV-b3-Cbz-059) or (IV-b4-Boc-059) depending on necessity, preferably 1 to 1.5 equivalents.

The dehydration condensing agent may be used carbodiimide alone such as N,N'-diisopropylcarbodiimide, N,N'-dicyclohexylcarbodiimide and 1-ethyl-3-(3-dimethylaminopropyl)carbodiimide hydrochloride, or a combination with an active ester group such as 1-hydroxybenzotriazole.monohydrate, N-hydroxysuccinimide and 2-hydroxypyridine-N-oxide, and further an active amidating agent or an active esterifying agent such as carbonyldiimidazole, benzotriazol-1-yloxy-tris(dimethylamino)phosphonium hexafluorophosphate, 2-chloro-1-methylpyridinium iodide and 4-(4,6-dimethoxy-1,3,5-triazin-2-yl)-4-methylmorpholinium chloride, preferably 1-ethyl-3-(3-dimethylaminopropyl)carbodiimide hydrochloride in combination with 1-hydroxybenzotriazole.monohydrate, or selected 2-chloro-1-methylpyridinium iodide, and 1-ethyl-3-(3-dimethylaminopropyl) carbodiimide hydrochloride is used in the range of 1 to 2 mol equivalents and 1-hydroxybenzotriazole.monohydrate in the range of 1 to 2 equivalents based on the compound represented by the formula (IV-a2), (IV-a3) or (IV-a4), preferably 1 to 1.3 equivalents of 1-ethyl-3-(3-dimethylaminopropyl) carbodiimide hydrochloride and 0.1 to 0.3 equivalent of 1-hydroxybenzotriazole.monohydrate. The reaction temperature is in the range of −40° C. to room temperature, preferably in the range of −20° C. to room temperature. The reaction is carried out with a time in the range of 30 minutes to 1 day, preferably 2 hours to 16 hours.

The compound of the formula (IV-b2-Boc-059), (IV-b3-Cbz-059) or (IV-b4-Boc-059) which is a coupling product can be isolated after completion of the reaction, by diluting the reaction mixture with a suitable solvent, washing successively with water, a diluted acid, an aqueous base solution (for example, diluted hydrochloric acid, potassium monohydrogen sulfate, citric acid, or an aqueous sodium bicarbonate solution), and evaporating the solvent to concentrate the reaction mixture. The organic solvent to be used for dilution may be mentioned diethyl ether, ethyl acetate, butyl acetate, toluene, dichloromethane and chloroform, preferably ethyl acetate.

Then, the step of removing the trifluoroacetyl group of the compound represented by the above formula (IV-b2-Boc-059) by a base treatment to prepare a compound represented by the following formula (IV-c-Boc-059):

[Chemical formula 72]

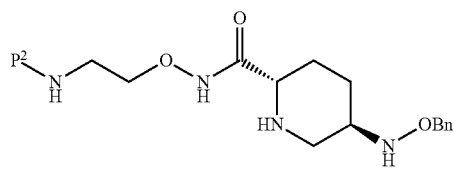

(IV-c-Boc-059) P$^2$ = Boc
(IV-c-Cbz-059) P$^2$ = Cbz in the above formula (IV-c-Boc-059) or (IV-c-Cbz-059), Boc represents tert-butoxycarbonyl, Cbz represents benzyloxycarbonyl, and OBn represents benzyloxy, can be carried out as follows.

The solvent to be used for removal of the trifluoroacetyl group may be mentioned water, methanol, ethanol, isopropanol, tetrahydrofuran, dioxane, dichloromethane, chloroform, 1,2-dichloroethane, etc., preferably water, methanol, tetrahydrofuran and dioxane, which may be used singly or in admixture, more preferably aqueous dioxane or tetrahydrofuran.

The base to be used may be mentioned lithium hydroxide, sodium hydroxide, potassium hydroxide, cesium hydroxide, lithium carbonate, sodium carbonate, potassium carbonate, cesium carbonate, etc., preferably lithium hydroxide, sodium hydroxide and potassium hydroxide, more preferably sodium hydroxide, and is used in the range of 2 to 4 equivalents based on the compound represented by the formula (IV-b2), preferably 2 to 3 equivalents.

The reaction temperature is in the range of −20 to 30° C., preferably in the range of 0 to 10° C. The reaction is carried out with a time in the range of 1 to 16 hours, preferably in the range of 1 to 3 hours.

The compound represented by the formula (IV-c-Boc-059) having the RcONHCO group which shows a weak acidic property is an amphoteric substance, so that there is an optimum pH range for obtaining the compound as a free base. The optimum pH is in the range of pH6 to 9, preferably in the range of pH6 to 8.

The compound represented by the formula (IV-c-Boc-059) can be isolated by diluting the reaction mixture with an organic solvent, adjusting the mixture to the optimum pH, and extracting the mixture with a solvent. The organic solvent to be used for diluting the basic reaction mixture may be mentioned diethyl ether, ethyl acetate, butyl acetate, toluene, dichloromethane and chloroform, preferably ethyl acetate or dichloromethane.

Also, the step of removing the tert-butoxycarbonyl group of the compound represented by the above formula (IV-b3-Cbz-059) by an acid treatment to prepare a compound represented by the above formula (IV-c-Cbz-059) can be carried out as follows.

The solvent to be used for removal of the tert-butoxycarbonyl group may be mentioned water, methanol, ethanol, isopropanol, ethyl acetate, dioxane, dichloromethane, chloroform, 1,2-dichloroethane and 2,2,2-trifluoroethanol, preferably methanol, ethanol, ethyl acetate, dioxane and dichloromethane, which may be used singly or in admixture.

The acid to be used for the reaction may be mentioned hydrochloric acid, sulfuric acid, phosphoric acid, formic acid, trifluoroacetic acid, methanesulfonic acid, trifluoromethanesulfonic acid, chloromethanesulfonic acid and tetrafluoroboric acid, preferably hydrochloric acid, sulfuric acid, methanesulfonic acid and trifluoroacetic acid, more preferably hydrochloric acid or trifluoroacetic acid. The acid is used in the range of 1 equivalent to a solvent amount based on the compound represented by the formula (IV-b3-Cbz-059), preferably 5-fold amount to a solvent amount.

The reaction temperature is in the range of −25 to 50° C., preferably in the range of −10 to 30° C. The reaction is carried out with a time in the range of 1 to 6 hours, preferably in the range of 1 to 3 hours.

The compound represented by the formula (IV-c-Cbz-059) having the RcONHCO group which shows a weak acidic property is an amphoteric substance, so that there is an optimum pH range for obtaining the compound as a free base. The optimum pH is in the range of pH6 to 9, preferably in the range of pH6 to 8.

The compound represented by the formula (IV-c-Cbz-059) can be isolated by diluting the reaction mixture with an organic solvent, adjusting the mixture to the optimum pH, and extracting the mixture with a solvent. The organic solvent to be used for diluting the basic reaction mixture may be mentioned diethyl ether, ethyl acetate, butyl acetate, toluene, dichloromethane and chloroform, preferably ethyl acetate or dichloromethane.

The step of removing the 2-trimethylsilylethoxycarbonyl of the compound represented by the above formula (IV-b4-Boc-059) by a fluoride to prepare a compound represented by the above formula (IV-c-Boc-059) can be carried out as follows.

The solvent to be used for removal of the 2-trimethylsilylethoxycarbonyl may be mentioned water, methanol, ethanol, isopropanol, ethyl acetate, dioxane, tetrahydrofuran, acetonitrile, dimethylformamide and dimethylacetamide, preferably dioxane, tetrahydrofuran and acetonitrile.

The fluoride to be used for the reaction may be mentioned sodium fluoride, potassium fluoride, cesium fluoride, hydrofluoric acid, hydrogen fluoride-pyridine, tetrabutylammonium fluoride, preferably tetrabutylammonium fluoride, and is used 2 to 6 equivalents based on the compound represented by the formula (IV-b4-Boc-059), preferably 2 to 3 equivalents.

The reaction temperature is in the range of 0 to 100° C., preferably in the range of 25 to 60° C. The reaction is carried out with a time in the range of 1 to 48 hours, preferably in the range of 12 to 24 hours.

The compound represented by the formula (IV-c-Boc-059) can be isolated by diluting the reaction mixture with an organic solvent, adjusting the mixture to the optimum pH, and extracting the mixture with a solvent in the same manner as in the formula (IV-b2-Boc-059). The organic solvent to be used for diluting the basic reaction mixture may be mentioned diethyl ether, ethyl acetate, butyl acetate, toluene, dichloromethane and chloroform, preferably ethyl acetate.

Next, the step of preparing a compound represented by the following formula (IIa-Boc-059) or (IIa-Cbz-059):

[Chemical formula 73]

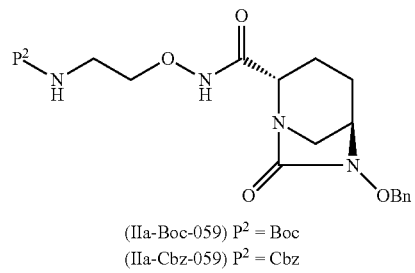

(IIa-Boc-059) $P^2$ = Boc
(IIa-Cbz-059) $P^2$ = Cbz in the above formula (IIa-Boc-059) or (IIa-Cbz-059), Boc represents tert-butoxycarbonyl, Cbz represents benzyloxycarbonyl, and OBn represents benzyloxy, by silylating the compound represented by the above formula (IV-c-Boc-059) or (IV-c-Cbz-059) in the reaction system, continuously subjecting to intramolecular urea formation reaction can be carried out as follows.

The solvent to be used for the reaction may be mentioned ethyl acetate, tetrahydrofuran, dioxane, acetonitrile, dimethylformamide, dimethylacetamide, dichloromethane, chloroform, 1,2-dichloroethane, etc., preferably acetonitrile.

The organic base to be used for the reaction may be mentioned triethylamine, diisopropylethylamine, tributylamine, N-methylmorpholine, etc., preferably triethylamine, and is used in the range of 3 to 6 equivalents based on the compound represented by the formula (IV-c-Boc-059) or the formula (IV-c-Cbz-059), preferably 3 to 4 equivalents.

The silylating agent to be used for the reaction may be mentioned a chlorotrialkylsilane such as chlorotrimethylsilane, chlorotriethylsilane, chlorotriisopropylsilane and chloro-tert-butyldimethylsilane; trimethylsilyl trifluoromethanesulfonate and tert-butyldimethylsilyl trifluoromethanesulfonate, preferably chlorotrimethylsilane, and is used in the range of 1 to 3 equivalents based on the compound represented by the formula (IV-c-Boc-059) or the formula (IV-c-Cbz-059), preferably 1 to 2 equivalents.

The urea-forming agent to be used for the reaction may be mentioned phosgene, diphosgene, triphosgene and carbonyldiimidazole, preferably phosgene and diphosgene, and is used in the range of 0.5 to 2 equivalents based on the compound represented by the formula (IV-c-Boc-059) or the formula (IV-c-Cbz-059), preferably 0.5 to 1.0 equivalent. At that time, to complete the urea formation, a catalytic amount of 4-dimethylaminopyridine is used in the range of 0.1 to 1 equivalent based on the compound represented by the formula (IV-c), preferably 0.1 to 0.2 equivalent. The reaction temperature is in the range of −25 to 50° C., preferably −15 to 30° C. The reaction is carried out with a time in the range of 10 minutes to 24 hours, preferably in the range of 10 minutes to 16 hours.

The formed compound represented by the formula (IIa-Boc-059) or (IIa-Cbz-059) can be isolated by the conventional post-treatment such as evaporating the organic solvent of the reaction mixture to concentrate the same, diluting with a solvent, washing with an acid and a base, drying, and evaporating the solvent to concentrate the same.

Next, the step of preparing a compound represented by the following formula (IIb-Boc-059):

[Chemical formula 74]

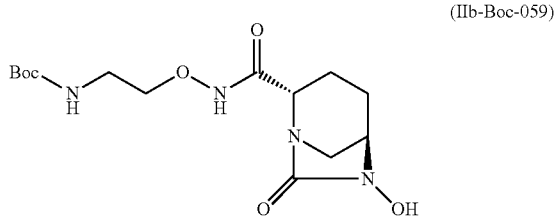

(IIb-Boc-059)

in the above formula (IIb-Boc-059), Boc represents tert-butoxycarbonyl, by cleaving the benzyl of the benzyloxy at the 6-position of the compound represented by the formula (IIa-Boc-059) using a hydrogenolysis catalyst under hydrogen atmosphere, or
removing the benzyl of the benzyloxy at the 6-position of the compound represented by the formula (IIa-Cbz-059) using a hydrogenolysis catalyst under hydrogen atmosphere, and simultaneously subjecting to tert-butoxycarbonylation can be carried out as follows.

The solvent to be used for the reaction may be mentioned water, methanol, ethanol, isopropanol, ethyl acetate, tetrahydrofuran and dioxane, preferably methanol or tetrahydrofuran, which may be used singly or in admixture.

The hydrogenolysis catalyst may be mentioned platinum oxide, palladium hydroxide, palladium black or palladium-carbon, preferably palladium-carbon.

An amount of the catalyst is employed in the range of 5 to 50 wt % in the dry weight based on the compound represented by the formula (V-2), preferably 5 to 20 wt %.

A supply source of the hydrogen to be used for the hydrogenolysis is a hydrogen gas, and a hydrogen pressure is selected in the range of atmospheric pressure to 1 MPa, more preferably atmospheric pressure to 0.5 MPa. As the supply source of the hydrogen, ammonium formate, cyclohexene or cyclohexadiene can be used as another method. An amount of the hydrogen to be supplied is used at least stoichiometric amount.

The reaction temperature of the hydrogenolysis is in the range of 10 to 50° C., preferably in the range of 15 to 30° C. The reaction is carried out with a time in the range of 0.5 to 3 hours, preferably in the range of 0.5 to 2 hours. As in the compound represented by the formula (IIa-Cbz-059), when the compound has benzyloxycarbonyl separating from the benzyloxy at the 6-position, it can be protected again by the tert-butoxycarbonyl in the presence of di-tert-butoxycarbonyldicarbonate simultaneously with the above-mentioned hydrogenolysis reaction.

An amount of the di-tert-butoxycarbonyldicarbonate to be added is 1 to 2 equivalents based on the compound represented by the formula (IIa-Cbz-059), preferably 1 to 1.2 equivalents. After completion of the reaction, the compound represented by the formula (IIb-Boc-059) formed in the reaction system can be isolated by the usual operations such as filtration of the catalyst, and evaporation of the solvent to concentrate the mixture.

Next, the step of preparing a compound represented by the following formula (III-Boc-059):

[Chemical formula 75]

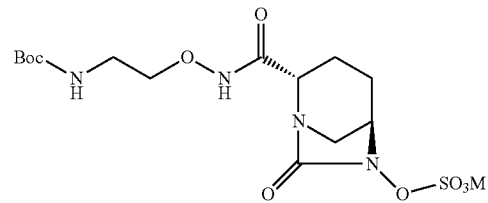

(III-Boc-059)

in the above formula (III-Boc-059), Boc represents tert-butoxycarbonyl, and M represents H, pyridinium, sodium or tetrabutylammonium, by sulfating the hydroxyl group at the 6-position of the compound represented by the formula (IIb-Boc-059) in the presence of an organic base can be carried out as follows.

The solvent to be used for sulfation may be mentioned water, methanol, ethanol, isopropanol, dichloromethane, chloroform, 1,2-dichloroethane, pyridine, acetonitrile, dimethylformamide, etc., preferably dichloromethane, pyridine or acetonitrile.

The organic base to be used for the reaction may be mentioned triethylamine, tributylamine, diisopropylethylamine, N-methylmorpholine, pyridine, 2-picoline, 3-picoline, 2,6-lutidine, 2,4,6-collidine, 4-dimethylaminopiperidine and N-methylimidazole, preferably pyridine, 2-picoline and 2,6-lutidine, and is used in the range of 1.0 to a solvent amount based on the compound represented by the formula (IIb-Boc-059), preferably in the range of 3.0 to a solvent amount.

The material to be used as a sulfating reagent may be mentioned chlorosulfonic acid, sulfur trioxide-pyridine complex, sulfur trioxide-dimethylformamide complex, sulfur trioxide-trimethylamine complex and sulfur trioxide-triethylamine complex preferably sulfur trioxide-pyridine complex, and is used in the range of 1 to 4 equivalents based on the compound represented by the formula (IIb-Boc-059), preferably 1 to 3 equivalents.

The reaction temperature is in the range of 0 to 50° C., preferably 10 to 30° C. The reaction is carried out with a time in the range of 12 to 48 hours, preferably in the range of 12 to 24 hours.

After completion of the reaction, the compound represented by the formula (III-Boc-059) can be obtained as a sulfonic acid pyridinium salt by filtration and evaporation of the solvent to concentrate the reaction mixture, and by treating it with an aqueous inorganic base solution containing sodium such as an aqueous sodium bicarbonate solution to give a sodium salt, removing an excessive organic base by washing with a solvent and by adding 1 to 3 mol equivalents, preferably 1 to 2 equivalents of tetrabutylammonium hydrogen sulfate, and extracting with an organic solvent such as ethyl acetate to give a tetrabutylammonium salt, which can be applied to the next step without purification.

Next, the step of preparing the above-mentioned (III-059) by deprotecting the tert-butoxycarbonyl of the compound represented by the formula (III-Boc-059) with an acid selected from hydrochloric acid, sulfuric acid, methanesulfonic acid, trifluoroacetic acid and tetrafluoroboric acid can be carried out as follows.

The solvent to be used for the reaction may be mentioned water, methanol, ethanol, isopropanol, ethyl acetate, tetrahydrofuran, dioxane, dichloromethane, chloroform, 1,2-dichloroethane, 2,2,2-trifluoroethanol, etc., preferably dichloromethane or 2,2,2-trifluoroethanol.

The acid to be used for deprotection under acidic conditions may be mentioned hydrochloric acid, sulfuric acid, phosphoric acid, formic acid, trifluoroacetic acid, methanesulfonic acid, trifluoromethanesulfonic acid, chloromethanesulfonic acid, tetrafluoroboric acid, etc., preferably hydrochloric acid, sulfuric acid, trifluoroacetic acid, methanesulfonic acid and tetrafluoroboric acid. The acid is used in the range of 1 equivalent to a solvent amount based on the compound represented by the formula (III-Boc-059), preferably 5-fold amount to a solvent amount. The reaction is carried out in the range of −25 to 50° C., preferably −10 to 30° C. The reaction is carried out with a time in the range of 30 minutes to 5 hours, preferably in the range of 30 minutes to 1 hour.

After completion of the deprotection, the solvent of the reaction mixture is evaporated to concentrate the mixture, the obtained residue is made an aqueous solution with an optimum pH, and subjected to purification with octadecyl silica (ODS), a synthetic resin such as HP-20 and SP207, or an ion exchange resin such as DOWEX 50W-X8 (Na type), evaporation of the solvent to concentrate the mixture and reprecipitation or lyophilization to give the compound represented by the formula (III-059).

Here, the optimum pH means the pH range in which the compound represented by the formula (III-059) is capable of existing stably as an intramolecular salt. The range of pH 4 to 7 is selected to isolate the compound as an intramolecular salt, more preferably in the range of pH 5 to 6.

EXAMPLES

Hereinafter, the present invention will be illustrated in more detail by examples, but the present invention is not intended to be limited by examples, with various modifications being possible.

Reference Example 1

(2S,5S)-1-Benzyl 2-tert-butyl 5-hydroxypiperidine-1,2-dicarboxylate (1)

Step 1: (S)-1-Benzyl 2-tert-butyl 5-oxopyrrolidine-1,2-dicarboxylate (S)-1-(Benzyloxycarbonyl)-5-oxopyrrolidine-2-carboxylic acid (100 g) was dissolved in dehydrated methylene chloride (2 L), and under ice cooling, concentrated sulfuric acid (10 mL) and isobutene (213 g) were added, followed by stirring overnight at +20° C. or less. The reaction mixture was added to cold aqueous sodium carbonate solution while paying attention to effervescence, followed by liquid separation of the organic phase, washing with saturated brine and drying over anhydrous magnesium sulfate, then the solvent was concentrated under reduced pressure. The residue was subjected to silica gel column chromatography (hexane/ethyl acetate=7/3), and crystallized with hexane/ethyl acetate to afford 80 g of the title compound as a colorless crystalline powder (yield 67%). Enantiomeric excess 99.9% ee or more (CHIRALPAK AD-H, 4.6×150 mm, UV 210 nm, hexane/ethanol=2/1, flow rate 1 mL/min., retention time 4.2 min.).

$[\alpha]^{20}_D$ −43.30 (c 0.52 in CHCl$_3$), according to Non-Patent Document [Journal of Medicinal Chemistry 1991, 34(3), 956-968. Dolence, E K.; Lin, C E.; Miller, M J.; Payne, S M. "Synthesis and siderophore activity of albomycin-like peptides derived from N5-acetyl-N5-hydroxy-L-ornithine"] −41.8° (c 6.71, CHCl$_3$); $^1$H NMR (400 MHz, CDCl$_3$) δ 1.39 (s, 9H), 2.04 (m, 1H), 2.32 (m, 1H), 2.51 (ddd, J=17.6, 9.5, 3.2 Hz, 1H), 2.62 (ddd, J=17.6, 10.5, 9.5 Hz, 1H), 4.55 (dd, J=9.5, 2.7 Hz, 1H), 5.25 (d, J=12.2 Hz, 1H), 5.30 (d, J=12.2 Hz, 1H), 7.26-7.41 (m, 5H); MS m/z 320 (M+H).

Step 2: (S)-tert-Butyl 2-(benzyloxycarbonylamino)-5-oxo-6-dimethylsulfoxonium hexanoate To a solution of trimethylsulfoxonium iodide (70.2 g) in dehydrated N,N-dimethylformamide (585 mL), under an argon atmosphere, was added potassium tert-butoxide (36.8 g, 279 mmol), followed by stirring at room temperature for 1 hour. Then, at 5° C. or less, (S)-1-benzyl 2-tert-butyl 5-oxopyrrolidine-1,2-dicarboxylate (87.0 g) was added within 20 minutes (washed with dehydrated N,N-dimethylformamide (87 mL)), followed by allowing to react at the same temperature for 1 hour. The reaction mixture was added to ice-cold water (2.6 L), saturated with sodium chloride, extracted with ethyl acetate (2.6 L×once, 1.3 L×twice, 650 mL×4 times), and the solvent of the organic layer was distilled off under reduced pressure. The resulting residue was subjected to silica gel column chromatography (heptane/ethyl acetate=1/2→ethyl acetate/methanol=19/1→9/1) to afford 112.3 g of the title compound as a pale yellow oil (quantitative).

$^1$H NMR (400 MHz, CDCl$_3$) δ 1.46 (s, 9H), 1.95 (m, 1H), 2.09 (m, 1H), 2.23-2.32 (m, 2H), 3.32 (s, 3H), 3.33 (s, 3H), 4.22 (m, 1H), 4.37 (s, 1H), 5.07 (d, J=12.0 Hz, 1H), 5.13 (d, J=12.0 Hz, 1H), 5.75 (br d, J=8.0 Hz, 1H), 7.30-7.36 (m, 5H); MS m/z 412 (M+H).

Step 3: (S)-1-Benzyl 2-tert-butyl 5-oxopiperidine-1,2-dicarboxylate (S)-tert-Butyl 2-(benzyloxycarbonylamino)-5-oxo-6-dimethyl sulfoxonium hexanoate (24.8 g) was dissolved in 1,2-dichloroethane (774 mL), and, after deaeration, di-μ-chlorobis-[(η-cycloocta-1,5-diene)]diiridium (I) (388.5 mg) was added under an argon atmosphere, followed by raising the temperature and allowing to react at +70° C. for 2 hours. The solvent of the reaction mixture was distilled off under reduced pressure, and the resulting residue was subjected to silica gel column chromatography (hexane/ethyl acetate=2/1) to afford 14.55 g of the title compound as a red oil (yield 76%).

$^1$H NMR (400 MHz, CDCl$_3$) δ 1.38 (s, 4.5H), 1.47 (s, 4.5H), 2.12-2.48 (m, 4H), 3.93 (d, J=19.0 Hz, 0.5H), 4.00 (d, J=18.8 Hz, 0.5H), 4.37 (d, J=18.8 Hz, 0.5H), 4.46 (d, J=19.0 Hz, 0.5H), 4.62 (dd, J=7.3, 6.6 Hz, 0.5H), 4.77 (dd, J=6.6, 5.9 Hz, 0.5H), 5.10-5.23 (m, 2H), 7.34-7.35 (m, 5H); MS m/z 334 (M+H).

Step 4: (2S,5S)-1-Benzyl 2-tert-butyl 5-hydroxypiperidine-1,2-dicarboxylate (1)

A solution of (S)-1-benzyl 2-tert butyl 5-oxopiperidine-1,2-dicarboxylate (14.55 g) in ethanol (437 mL) was ice-cooled, and sodium borohydride (1.65 g) was added, followed by allowing to react under ice cooling for 20 minutes. Saturated aqueous ammonium chloride solution was added dropwise to the reaction mixture until effervescence was quenched, and the generated salt was dissolved with the addition of water. The organic solvent of the mixture was distilled off under reduced pressure, and the aqueous layer of the residue was extracted with ethyl acetate. The organic layer was washed with saturated brine, followed by drying over anhydrous magnesium sulfate, and the solvent was distilled off under reduced pressure. The resulting residue was subjected to silica gel column chromatography (hexane/ethyl acetate=3/1→2/1) to afford 13.35 g of the title compound as a colorless oil (yield 91%). Enantiomeric excess 98.8% ee (CHIRALPAK AD-H, 4.6×150 mm, UV 210 nm, hexane/ethanol=4/1, flow rate 1 mL/min., retention time 9.1 min.).

[α]$^{20}_D$ −29.7° (c 1.3, CHCl$_3$), according to Non-Patent Document [Tetrahedron Asymmetry 2006, 17(17), 2479-2486. Jung, J C.; Avery, M A. "Diastereoselective synthesis of (2S,5S)- and (2S,5R)-N-benzyloxycarbonyl-5-hydroxyipecolic acids from trans-4-hydroxy-L-proline"] −27.9° (c 2.0, CHCl$_3$); $^1$H NMR (400 MHz, CDCl$_3$) δ 1.42 (s, 4.5H), 1.46 (s, 4.5H), 1.66-1.75 (m, 2H), 1.96-2.00 (m, 2H), 2.24-2.30 (m, 1H), 2.74-2.80 (m, 0.5H), 2.84-2.90 (m, 0.5H), 3.64 (br s, 1H), 4.15-4.20 (m, 0.5H), 4.23-4.27 (m, 0.5H), 4.65 (d, J=5.4 Hz, 0.5H), 4.78 (d, J=4.6 Hz, 0.5H), 5.07 (d, J=12.5 Hz, 1H), 5.21 (d, J=12.5 Hz, 1H), 7.26-7.37 (m, 5H); MS m/z 334 (M+H).

Sequential Synthesis of (2S,5S)-1-Benzyl 2-tert-butyl 5-hydroxypiperidine-1,2-dicarboxylate (1)

(S)-tert-Butyl 2-(benzyloxycarbonylamino)-5-oxo-6-dimethyl sulfoxonium hexanoate (112.3 g, 272 mmol) was dissolved in 1,2-dichloroethane (3.4 L), and, after deaeration, di-t-chlorobis-[(η-cycloocta-1,5-diene)]diiridium (I) (1.83 g) was added under an argon atmosphere, followed by raising the temperature to +70° C. within 1.75 hours and allowing to react for 1 hour. After cooling to room temperature, the solvent of the reaction mixture was distilled off under reduced pressure, and the resulting residue was dissolved in ethanol (1.1 L). The mixture was ice-cooled, and sodium borohydride (5.14 g) was added within 10 minutes, followed by allowing to react under ice cooling for 20 minutes. Saturated aqueous ammonium chloride solution (265 mL) was added dropwise to the reaction mixture until effervescence was quenched, and the generated salt was dissolved with the addition of water (250 mL). The organic solvent of the mixture was distilled off under reduced pressure, and the aqueous layer of the residue was extracted with ethyl acetate (0.9 L×3 times). The solvent was distilled off under reduced pressure, and the resulting residue was subjected to silica gel column chromatography (heptane/ethyl acetate=3/1→2/1) to afford 66.82 g of the title compound as a colorless oil (yield 73%). Instrumental data were consistent with those of Step 4 of Reference Example 1.

Reference Example 2

Tetrahydro-2H-pyran-4-carbohydrazide

A solution of methyl tetrahydro-2H-pyran-4-carboxylate (1.44 g, 10.0 mmol) in methanol (50 mL) was stirred at 50° C. To the reaction mixture, hydrazine.monohydrate (0.675 g) was added, followed by stirring at the same temperature for 2 hours, after completion of the reaction, the reaction mixture was concentrated and diluted with methylene chloride, the solution was then washed with saturated sodium bicarbonate aqueous solution and saturated brine, and the organic layer was dried over magnesium sulfate and the solvent was distilled off under reduced pressure to afford 952 mg of the title compound (yield 66.1%).

$^1$H NMR (400 MHz, CD$_3$OD) δ 1.59-1.83 (m, 4H), 2.37-2.60 (m, 1H), 3.38-3.47 (m, 2H), 3.87-3.96 (m, 2H); MS m/z 145 [M+H]$^+$.

Reference Example 3

Benzyl 2-(furan-2-carbonyl)hydrazinecarboxylate

Benzyl hydrazinecarboxylate (1.66 g, 10.0 mmol) was dissolved in tetrahydrofuran (20 mL) and water (20 mL) and added sodium hydrogen carbonate (1.68 g) thereto. Under ice cooling, furan-2-carbonyl chloride (1.30 g, 10 mmol) was gradually added, followed by stirring for 1 hour. After completion of the reaction, to the reaction solution was added 300 ml of ethyl acetate, followed by washing with saturated ammonium chloride solution and saturated brine. The organic layer was dried over magnesium sulfate, the solvent was distilled off under reduced pressure, and 5 ml of ethyl acetate was dissolved in the resulting residue, followed by gradually adding hexane (100 ml) to afford 2.30 g of the title compound as a solid (yield 88.4%).

$^1$H NMR (400 MHz, CDCl$_3$) δ 5.18 (s, 2H), 6.51 (m, 1H), 6.91 (br s, 1H), 7.17 (m, 1H), 7.33 (m, 5H), 7.47 (m, 1H), 8.17 (br s, 1H); MS m/z 261 [M+H]$^+$.

Reference Example 4

(R)-tert-Butyl 2-(2-((benzyloxy)carbonyl) hydrazinecarbonyl)-5-oxopyrrolidine-1-carboxylate A solution of (R)-1-(tert-butoxycarbonyl)-5-oxopyrrolidine-2-carboxylic acid (1.146 g, 5.00 mmol) in dehydrated methylene chloride (25 mL) was cooled to 0° C. under an argon atmosphere and gradually added dropwise isobutyl chloroformate (0.682 g) so that the temperature does not exceed 0° C. Then, triethylamine (0.505 g) was gradually added so that the temperature does not exceed 0° C., followed by stirring 30 minutes, thereby a mixed acid anhydride was prepared in the reaction system. To this reaction mixture was gradually added benzyl hydrazinecarboxylate (0.830 g), after the addition, followed by raising the temperature to room temperature and stirring for 1 hour. This reaction mixture was washed with 0.5M hydrochloric acid and saturated brine, the organic layer was dried over magnesium sulfate and then distilled off under reduced pressure. The resulting residue was subjected to silica gel column chromatography (hexane/ethyl acetate=4/1→0/1→ethyl acetate/methanol=30/1) to afford 1.53 g of the title compound (yield 80.1%).

$^1$H NMR (400 MHz, CDCl$_3$) δ 1.45 (s, 9H), 2.20 (m, 2H), 2.45 (m, 1H), 2.63 (m, 1H), 4.59 (br s, 1H), 5.16 (m, 2H), 6.84 (br s, 1H), 7.33 (m, 5H), 8.17 (br s, 1H); MS m/z 378 [M+H]$^+$.

Reference Example 5

(S)-tert-Butyl 2-(2-((benzyloxy)carbonyl)hydrazinecarbonyl)pyrrolidine-1-carboxylate (S)-1-(tert-butoxycarbonyl)pyrrolidine-2-carboxylic acid (1.076 g, 5.00 mmol) was stirred under an argon atmosphere at room temperature with dehydrated methylene chloride (16 mL). Then, N-ethyl-N'-(3-dimethylaminopropyl)carbodiimide hydrochloride (EDC, 1.15 g), 1-hydroxybenzotriazole.monohydrate (HOBt.H$_2$O, 0.918 g), and triethylamine (1.01 g) were added, followed by stirring for 10 minutes. Benzyl hydrazinecarboxylate (1.66 g) was added, followed by stirring for 18 hours. After completion of the reaction, the reaction solution was washed with 0.5M hydrochloric acid and saturated brine, then the organic layer was dried over magnesium sulfate, the solvent was distilled off under reduced pressure, after that, the resulting residue was subjected to silica gel column chromatography (hexane/ethyl acetate=4/1→0/1→ethyl acetate/methanol=30/1) to afford 1.48 g of the title compound (yield 81.6%).

$^1$H NMR (400 MHz, CDCl$_3$) δ 1.45 (s, 9H), 1.64 (m, 1H), 1.87-2.16 (m, 2H), 2.38 (m, 1H), 3.31-3.45 (m, 2H), 4.32 (m, 1H), 5.14-5.19 (m, 2H), 6.68 (br s, 1H), 7.34-7.40 (m, 5H), 8.76 (br s, 1H); MS m/z 364 [M+H]$^+$.

Reference Example 6

(S)-tert-Butyl 2-(2-((benzyloxy)carbonyl)hydrazinecarbonyl)-5-oxopyrrolidine-1-carboxylate (S)-tert-Butyl 2-(2-((benzyloxy)carbonyl)hydrazinecarbonyl)pyrrolidine-1-carboxylate (1.089 g, 3.00 mmol) described in Reference Example 5 was dissolved in methanol (15 mL), 10% palladium-carbon (50% water content, 200 mg) was added, followed by stirring at room temperature for 1 hour under hydrogen atmosphere. The catalyst of the reaction mixture was filtered through Celite and the solvent was concentrated under reduced pressure to afford 595.5 mg of the title compound (yield 86.6%).

$^1$H NMR (400 MHz, CD$_3$OD) δ 1.41-1.45 (m, 9H), 1.80-1.99 (m, 3H), 2.15-2.22 (m, 1H), 2.26-3.50 (m, 2H), 4.08-4.15 (m, 1H); MS m/z 230 [M+H]$^+$.

Reference Example 7 tert-Butyl (2-((1,3-dioxoisoindolin-2-yl)oxy)ethyl)carbamate tert-Butyl (2-hydroxyethyl)carbamate (1.61 g, 10.0 mmol) was stirred under an argon atmosphere at room temperature with dehydrated tetrahydrofuran (50 mL). Then, triphenylphosphine (2.75 g) and N-hydroxyphthalimide (Pht-OH, 1.71 g) were added. After the reaction mixture was under ice cooling, diethyl azodicarboxylate (DEAD, 1.82 g) was added dropwise gradually, followed by stirring at room temperature for 24 hours. After completion of the reaction, the residue resulting from distilling off the solvent under reduced pressure was subjected to silica gel column chromatography (hexane/ethyl acetate=4/1→1/1) to afford 2.61 g of the title compound (yield 85.2%).

$^1$H NMR (400 MHz, CDCl$_3$) δ 1.45 (s, 9H), 3.40-3.44 (m, 2H), 4.22-4.24 (m, 2H), 5.62 (br s, 1H), 7.73-7.85 (m, 4H); MS m/z 307 [M+H]$^+$.

Reference Example 8 tert-Butyl (2-((1,3-dioxoisoindolin-2-yl)oxy)ethyl)carbamate tert-Butyl (2-bromoethyl)carbamate (5.00 g, 23.5 mmol) was stirred under an argon atmosphere at room temperature with acetonitrile (74 mL). Then, N-hydroxyphthalimide (Pht-OH, 3.83 g) and triethylamine (5.64 g) were added, followed by stirring the reaction mixture at 70° C. for 24 hours. After completion of the reaction, the reaction solution was concentrated, followed by diluting with ethyl acetate and washing with 0.5M hydrochloric acid and saturated sodium bicarbonate aqueous solution, and the organic layer was dried over magnesium sulfate, to the residue resulting from distilling off the solvent under reduced pressure was added ethyl acetate (10 ml), followed by adding hexane, thereby 4.72 g of the title compound was afforded (yield 65.7%). The instrumental data were consistent with those of the compound of Reference Example 7.

Reference Example 9 tert-Butyl 2-(aminooxy)ethylcarbamate

To a solution of tert-butyl (2-((1,3-dioxoisoindolin-2-yl)oxy)ethyl)carbamate (1.83 g, 6.00 mmol) described in Reference Example 7 in methylene chloride (11 mL) was gradually added 9.8M methylamine methanol solution (1.83 mL), followed by stirring for 2 hours. The reaction solution was filtered and the filtrate was distilled off under reduced pressure, followed by extracting with 0.5M hydrochloric acid (24 mL). To the resulting aqueous layer were added methylene chloride and 1M sodium hydroxide (18 mL), thereby the target was extracted with ethylene chloride. The resulting organic layer was dried over magnesium sulfate and the solvent was distilled off under reduced pressure. 1.038 g of the title compound was afforded as the crude product (yield 98%).

$^1$H NMR (400 MHz, CDCl$_3$) δ 1.45 (m, 9H), 3.35-3.36 (m, 2H), 3.70-3.72 (m, 2H), 4.91 (br s, 1H), 5.47 (br s, 2H); MS m/z 177 [M+H]$^+$.

Reference Example 10

Benzyl (2-((1,3-dioxoisoindolin-2-yl)oxy)ethyl)carbamate

Benzyl (2-hydroxyethyl)carbamate (5.857 g, 30.0 mmol) was stirred under an argon atmosphere at room temperature with dehydrated tetrahydrofuran (150 mL). Then, triphenylphosphine (7.90 g) and N-hydroxyphthalimide (Pht-OH, 4.89 g) were added. After the reaction mixture was under ice cooling, 2.2M diethyl azodicarboxylate toluene solution (13.7 mL) was added dropwise gradually, followed by stirring overnight at room temperature. After completion of the reaction, the residue resulting from distilling off the solvent under reduced pressure was subjected to silica gel column chromatography (hexane/ethyl acetate=1/1) to afford 9.36 g of the title compound (yield 92%).

$^1$H NMR (400 MHz, CDCl$_3$) δ 3.50-3.54 (m, 2H), 4.26-4.34 (m, 2H), 5.14 (br s, 2H), 5.98 (br s, 1H), 7.18-7.40 (m, 5H), 7.75-8.06 (m, 4H); MS m/z 358 [M+H]$^+$.

Reference Example 11

Benzyl 2-(aminooxy)ethylcarbamate

To a solution of benzyl (2-((1,3-dioxoisoindolin-2-yl)oxy)ethyl)carbamate (9.36 g, 27.50 mmol) described in Reference Example 10 in methylene chloride (51 mL) was gradually added 9.8M methylamine methanol solution (8.50 mL), followed by stirring for 2 hours. The reaction solution was distilled off under reduced pressure, and methylene chloride (50 mL) and water (80 mL) were added, followed by adjusting to pH 1 with 5M hydrochloric acid, aqueous layer separation, and further washing with methylene chloride (50 mL). To the resulting aqueous layer was added methylene chloride (50 mL), followed by adjusting to pH 1 with 5M sodium hydroxide, organic layer separation, and further extracting the aqueous layer with methylene chloride (50 mL) twice. The combined organic layers were washed with 50% potassium carbonate aqueous solution, followed by drying over anhydrous potassium carbonate, and distilling off the solvent under reduced pressure. The resulting residue was subjected to silica gel column chromatography (ethyl acetate) to afford 5.61 g of the title compound (yield 97%).

$^1$H NMR (400 MHz, CDCl$_3$) δ 3.42-3.46 (m, 2H), 3.72-3.74 (m, 2H), 5.10 (s, 2H), 5.15 (br s, 1H), 7.29-7.39 (m, 5H); MS m/z 211 [M+H]$^+$.

Reference Example 12

2-(2-((Triisopropylsilyl)oxy)ethoxy)isoindoline-1,3-dione

Step 1

2-(2-Hydroxyethoxy)isoindoline-1,3-dione

To a solution of N-hydroxyphthalimide (2.20 g, 13.5 mmol) and sodium acetate (3.30 g) in dimethylsulfoxide (40 mL) was added 2-bromoethanol (2.88 mL) under an argon atmosphere at room temperature. The reaction mixture was stirred at 70° C. for 5 hours, followed by cooling to room temperature, adding water (40 mL), and extracting with methylene chloride. The resulting organic layer was washed with water, 2.5M hydrochloric acid, and saturated brine. The washed organic layer was dried over magnesium sulfate, the residue resulting from distilling off the solvent under reduced pressure was recrystallized with ethanol and water to afford 1.86 g of the title compound (yield 66%).

$^1$H NMR (400 MHz, CD$_3$OD) δ 3.84 (t, J=4.6 Hz, 2H), 4.26 (t, J=4.6 Hz, 2H), 7.89-7.80 (m, 4H); MS m/z 208 [M+H]$^+$.

Step 2

2-(2-((Triisopropylsilyl)oxy)ethoxy)isoindoline-1,3-dione

To a solution of 2-(2-hydroxyethoxy)isoindoline-1,3-dione (622 mg, 3.00 mmol) in dehydrated methylene chloride (6 mL), imidazole (306 mg) and chlorotriisopropylsilane (TIPSCl, 963 L) were added under an argon atmosphere at room temperature. After the reaction mixture was stirred at room temperature overnight, 2M hydrochloric acid was added to stop the reaction, followed by distilling off methylene chloride under reduced pressure. The resulting aqueous layer was extracted with ethyl acetate, followed by washing the organic layer with saturated brine and then drying over magnesium sulfate. The resulting residue was subjected to silica gel column chromatography (hexane/ethyl acetate=9/1→2/1) to afford 1.04 g of the title compound (yield 95%).

$^1$H NMR (400 MHz, CDCl$_3$) δ 0.93-1.06 (m, 21H), 4.09 (t, J=4.8 Hz, 2H), 4.33 (t, J=4.8 Hz, 2H), 7.70-7.76 (m, 2H), 7.80-7.86 (m, 2H); MS m/z 364 [M+H]$^+$.

Reference Example 13

(R)-tert-Butyl 3-(aminooxy)pyrrolidine-1-carboxylate

To (R)-tert-butyl 3-((1,3-dioxoisoindolin-2-yl)oxy)pyrrolidine-1-carboxylate (2.73 g, 8.21 mmol) prepared following a procedure analogous to Reference Example 7 from (R)-tert-butyl 3-hydroxypyrrolidine-1-carboxylate in methanol (43 mL) was gradually added hydrazine.monohydrate (1.54 g), followed by stirring for 2 hours. The reaction solution was filtered, and the residue resulting from distilling off the filtrate under reduced pressure was subjected to silica gel column chromatography (hexane/ethyl acetate=4/1→0/1) to afford 1.30 g of the title compound (yield 78.3%).

$^1$H NMR (400 MHz, CDCl$_3$) δ 1.45 (m, 9H), 1.86-1.88 (m, 1H), 2.01-2.06 (m, 1H), 3.26-3.60 (m, 4H), 4.42 (br s, 1H); MS m/z 203 [M+H]$^+$.

Reference Example 14 tert-Butyl 4-(2-((1,3-dioxoisoindolin-2-yl)oxy)acetyl)-1,4-diazepine-1-carboxylate tert-Butyl 1,4-diazepine-1-carboxylate (2.00 g, 10.0 mmol) was stirred under an argon atmosphere under ice cooling with dehydrated tetrahydrofuran (50 mL). After triethylamine (1.01 g) was added, chloroacetyl chloride (1.01 g) was gradually added. After completion of the reaction, N-hydroxyphthalimide (1.95 g) and triethylamine (2.22 g) were added. The reaction mixture was stirred at 60° C. for 22 hours. After completion of the reaction, the reaction solution was concentrated, followed by diluting with ethyl acetate, washing with 8% citric acid and saturated sodium bicarbonate aqueous solution, drying the organic layer over magnesium sulfate. The residue resulting from distilling off the solvent under reduced pressure was subjected to silica gel column chromatography (hexane/ethyl acetate=4/1→0/1) to afford 3.74 g of the title compound (yield 93.0%).

$^1$H NMR (400 MHz, CDCl$_3$) δ 1.45 (m, 9H), 1.85-1.99 (m, 2H), 3.37-4.11 (m, 8H), 4.84 (br s, 2H), 7.71-7.84 (m, 4H); MS m/z 404 [M+H]$^+$.

Reference Example 15 tert-Butyl 4-(2-(aminooxy)acetyl)-1,4-diazepine-1-carboxylate

To tert-butyl 4-(2-((1,3-dioxoisoindolin-2-yl)oxy)acetyl)-1,4-diazepine-1-carboxylate (2.14 g, 5.30 mmol) described in Reference Example 14 in methanol (16 mL) was gradually added 9.8M methylamine methanol solution (1.62 mL), followed by stirring for 2 hours. The residue resulting from the distilling off the reaction solution under reduced pressure was dissolved in ethyl acetate (50 ml), followed by extracting with 0.25M hydrochloric acid (20 mL). To the resulting aqueous layer were added methylene chloride and 0.3M sodium hydroxide (40 mL) and the target was extracted with methylene chloride. The resulting organic layer was dried over magnesium sulfate and the solvent was distilled off under reduced pressure. 1.298 g of the title compound was afforded as the crude product (yield 89.6%).

$^1$H NMR (400 MHz, CDCl$_3$) δ 1.45 (m, 9H), 1.85-1.99 (m, 2H), 3.36-3.63 (m, 8H), 4.37 (m, 2H), 5.92 (br s, 2H); MS m/z 274 [M+H]$^+$.

Reference Example 16 tert-Butyl 2-(aminooxy)ethyl(methyl)carbamate

The title compound was prepared from tert-butyl 2-hydroxyethyl(methyl)carbamate, following a procedure analogous to Reference Example 7 and Reference Example 13.

$^1$H NMR (400 MHz, CDCl$_3$) δ 1.46 (s, 9H), 2.88 (br s, 3H), 3.36-3.53 (m, 2H), 3.75 (t, J=6.2 Hz, 2H), 5.30-5.75 (m, 2H); MS m/z 191 [M+H]$^+$.

Reference Example 17 tert-Butyl (2-(aminooxy)ethyl) (isopropyl)carbamate

The title compound was prepared from tert-butyl 2-hydroxyethyl(isopropyl)carbamate, following a procedure analogous to Reference Example 7 and Reference Example 15.

$^1$H NMR (400 MHz, CDCl$_3$) δ 1.15 (d, J=6.4 Hz, 6H), 1.47 (s, 9H), 3.22-3.44 (m, 2H), 3.72 (t, J=6.4 Hz, 2H), 3.82-4.45 (m, 1H), 5.30-5.71 (m, 2H); MS m/z 219 [M+H]$^+$.

Reference Example 18

2-(Aminooxy)-N,N-dimethylethanamine dihydrochloride

The title compound was prepared according to *J. Med. Chem.*, 2000, 43 (15), pp 2332-2349.

$^1$H NMR (400 MHz, CDCl$_3$) δ 2.80 (s, 6H), 3.43 (t, J=4.6 Hz, 2H), 4.44 (d, J=4.6 Hz, 2H), 11.2 (br s, 2H); MS m/z 105 [M−2HCl+H]$^+$.

Reference Example 19

(S)-tert-Butyl (1-(aminooxy)propan-2-yl)carbamate

The title compound was prepared from (S)-tert-butyl 1-hydroxypropan-2-ylcarbamate, following a procedure analogous to Reference Example 7 and Reference Example 15.

$^1$H NMR (400 MHz, CDCl$_3$) δ 1.12 (d, J=6.8 Hz, 3H), 1.45 (s, 9H), 3.43-3.54 (m, 1H), 3.64 (dd, J=11.2, 4.0 Hz, 1H), 4.00 (br s, 1H), 4.64 (br s, 1H), 5.57 (br s, 1H), 6.64 (br s, 1H); MS m/z 191 [M+H]$^+$.

Reference Example 20 tert-Butyl 3-(aminooxy)propylcarbamate

The title compound was prepared from tert-butyl 3-hydroxypropylcarbamate, following a procedure analogous to Reference Example 7 and Reference Example 13.

$^1$H NMR (400 MHz, CDCl$_3$) δ 1.44 (s, 9H), 1.68-1.82 (m, 2H), 3.14-3.27 (m, 2H), 3.73 (t, J=6.0 Hz, 2H), 4.77 (br s, 1H), 5.40 (br s, 2H); MS m/z 191 [M+H]$^+$.

Reference Example 21

(S)-tert-Butyl 2-((aminooxy)methyl)azetidine-1-carboxylate

The title compound was prepared from (S)-tert-butyl 2-(hydroxymethyl)azetidine-1-carboxylate, following a procedure analogous to Reference Example 7 and Reference Example 15.

$^1$H NMR (400 MHz, CDCl$_3$) δ 1.45 (s, 9H), 1.97-2.11 (m, 1H), 2.19-2.30 (m, 1H), 3.78-3.93 (m, 4H), 4.42 (br s, 1H), 5.62 (br s, 1H); MS m/z 203 [M+H]$^+$.

Reference Example 22

(R)-tert-Butyl 2-(aminooxymethyl)pyrrolidine-1-carboxylate

The title compound was prepared from (R)-tert-butyl 2-(hydroxymethyl)pyrrolidine-1-carboxylate, following a procedure analogous to Reference Example 7 and Reference Example 13.

$^1$H NMR (400 MHz, CDCl$_3$) δ 1.47 (s, 9H), 1.68-1.97 (m, 4H) 3.33 (br s, 2H), 3.56 (br s, 1H), 3.61-3.82 (m, 1H), 3.88-4.26 (m, 1H), 5.37-5.74 (m, 2H); MS m/z 217 [M+H]$^+$.

Reference Example 23

(S)-tert-Butyl 2-((aminooxy)methyl)piperidine-1-carboxylate

The title compound was prepared from (S)-tert-butyl 2-(hydroxymethyl)piperidine-1-carboxylate, following a procedure analogous to Reference Example 7 and Reference Example 15.

$^1$H NMR (400 MHz, CDCl$_3$) δ 1.32-1.76 (m, 6H), 1.47 (s, 9H), 2.71-2.84 (m, 1H), 3.56 (dd, J=11.2, 5.2 Hz, 1H), 3.86-4.04 (m, 2H), 4.59 (br s, 1H), 5.64 (br s, 2H); MS m/z 231 [M+H]$^+$.

Reference Example 24

(S)-tert-Butyl 3-(aminooxy)pyrrolidine-1-carboxylate (S)-tert-Butyl 3-((1,3-dioxoisoindolin-2-yl)oxy)pyrrolidine-1-carboxylate (2.91 g, 8.77 mmol) prepared from (R)-tert-butyl 3-hydroxypyrrolidine-1-carboxylate following a procedure analogous to Reference Example 7 was gradually added to methanol (43 mL) and hydrazine.monohydrate (1.54 g), followed by stirring for 3 hours. The reaction solution was filtered and the residue resulting from distilling off the filtrate under reduced pressure was subjected to silica gel column chromatography (hexane/ethyl acetate=4/1→0/1) to afford 1.75 g of the title compound (yield 98.7%).

$^1$H NMR (400 MHz, CDCl$_3$) δ 1.42 (m, 9H), 1.86 (m, 1H), 2.01-2.06 (m, 1H), 3.28-3.60 (m, 4H), 4.23 (br s, 1H); MS m/z 203 [M+H]$^+$.

Reference Example 25 tert-Butyl 3-((aminooxy)methyl)azetidine-1-carboxylate

The title compound was prepared from tert-butyl 3-(hydroxymethyl)azetidine-1-carboxylate, following a procedure analogous to Reference Example 7 and Reference Example 15.

$^1$H NMR (400 MHz, CDCl$_3$) δ 1.43 (s, 9H), 2.68-2.90 (m, 1H), 3.57-3.88 (m, 4H), 3.88-4.09 (m, 2H), 5.43 (br s, 2H); MS m/z 203 [M+H]$^+$.

Example 1

(2S,5S)-tert-Butyl 5-hydroxypiperidine-2-carboxylate (2)

To a solution of (2S,5S)-1-benzyl 2-tert-butyl 5-hydroxypiperidine-1,2-dicarboxylate (67.2 g) described in Reference Example 1 in ethanol (900 mL) was added 10% palladium-carbon (water content approximately 50%, 10.1 g), followed by vigorously stirring under an hydrogen atmosphere at room temperature overnight. The catalyst of the mixture was filtered through Celite, followed by concentrating the filtrate, thereby 39.3 g of the title compound was afforded as the colorless solid (yield 97%). Enantiomeric excess 99% ee or more (CHIRALPAK AD-H, 4.6×150 mm, UV 210 nm, diethylamine/hexane/ethanol=0.1/80/20, flow rate 1 mL/min., retention time 6.3 min.).

[α]$^{20}_D$ −28.7° (c 1.01, CHCl$_3$); $^1$H NMR (400 MHz, CDCl$_3$) δ 1.47 (s, 9H), 1.63 (m, 1H), 1.79-1.84 (m, 3H), 2.82 (dd, J=12.2, 2.2 Hz, 1H), 3.02 (ddd, J=12.2, 3.7, 1.7 Hz, 1H), 3.21 (m, 1H), 3.80 (m, 1H); MS m/z 202 [M+H]$^+$.

Example 2

(2S,5S)-tert-Butyl 5-hydroxy-1-(2,2,2-trifluoroacetyl)piperidine-2-carboxylate (3)

A solution of (2S,5S)-tert-butyl 5-hydroxypiperidine-2-carboxylate (39.14 g, 194 mmol) in dehydrated tetrahydrofuran (450 mL) was cooled to a temperature between −3 and −5° C. under an argon atmosphere, followed by adding triethylamine (78.7 g) and adding dropwise trifluoroacetic anhydride (81.5 g) over 30 minutes. The reaction mixture was allowed to react at a temperature between −3 and −5° C. for 1 hour, followed by adding water (90 mL), raising the temperature to room temperature, and stirring for 1 hour. To the reaction mixture was added water (740 mL), followed by extracting with ethyl acetate (450 mL×three times) and washing the combined organic layers with 5% citric acid aqueous solution (450 mL), 6.5% sodium bicarbonate aqueous solution (450 mL) and water (450 mL) sequentially. The residue resulting from distilling off the solvent under reduced pressure was subjected to silica gel column chromatography (hexane/ethyl acetate=2/1) to afford 50.06 g of the title compound as a pale yellow solid (yield 87%). Enantiomeric excess 99% ee or more (CHIRALPAK AD-H, 4.6×150 mm, UV 210 nm, hexane/ethanol=4/1, flow rate 1 mL/min, retention time 4.2 min).

[α]$^{20}_D$ −54.10 (c 0.73, CHCl$_3$); $^1$H NMR (400 MHz, CDCl$_3$) δ observed as a mixture of 2 rotamers (7:3). 1.26-1.43 (m, 1H), 1.46 (s, 2.7H), 1.47 (s, 6.3H), 1.68-1.77 (m, 1H), 1.81 (d, J=4.8 Hz, 0.3H), 1.89 (d, J=5.2 Hz, 0.7H), 2.05-2.08 (m, 1H), 2.36-2.42 (m, 1H), 2.77 (dd, J=12.2, 12.0 Hz, 0.3H), 3.12 (dd, J=13.2, 10.7 Hz, 0.7H), 3.68-3.77 (m, 1H), 4.00 (m, 1H), 4.52-4.60 (m, 0.6H), 5.07 (d, J=5.9 Hz, 0.7H); MS m/z 298 [M+H]$^+$.

Example 3

(2S,5R)-tert-Butyl 5-(benzyloxyamino)-1-(2,2,2-trifluoroacetyl)piperidine-2-carboxylate (IV)

A solution of (2S,5S)-tert-butyl 5-hydroxy-1-(2,2,2-trifluoroacetyl)piperidine-2-carboxylate (10.22 g, 34.38 mmol) in dehydrated acetonitrile (113 mL) was cooled to a temperature between −30 and −40° C. under an argon atmosphere, followed by adding 2,6-lutidine (4.4 mL), then adding dropwise trifluoromethanesulfonic anhydride (5.92 mL) over 10 minutes, and further reacting at −30° C. for 15 minutes. To this reaction mixture was added benzyloxyamine (8.46 g) (washed with acetonitrile (5 mL)), followed by raising the temperature to 0° C. within 30 minutes, further adding 2,6-lutidine (4.4 mL), and allowing to react at a temperature between 0 and 5° C. for 3.5 days. This reaction mixture was concentrated under reduced pressure, the resulting residue was diluted with ethyl acetate (200 mL), followed by washing with water (200 mL), 10% citric acid aqueous solution (200 mL×three times), 6.5% sodium bicarbonate aqueous solution (100 mL), and saturated brine (100 mL) sequentially. Each aqueous layer was back-extracted with ethyl acetate (100 mL), the organic layers were combined and dried over anhydrous magnesium sulfate, and the solvent was distilled off under reduced pressure. The resulting residue was subjected to silica gel column chromatography (hexane/ethyl acetate=4/1) to afford 11.69 g of the title compound as a colorless oil (yield 85%). Enantiomeric excess 99.0% ee (CHIRALPAK AD-H, 4.6×150 mm, UV 210 nm, hexane/ethanol=9/1, flow rate 1 mL/min., retention time 4.5 min.).

[α]$^{20}_D$ −45.6° (c 0.73, CHCl$_3$); $^1$H NMR (400 MHz, CDCl$_3$) δ observed as a mixture of 2 rotamers (7:3). 1.46 (s, 2.7H), 1.48 (s, 6.3H), 1.62-1.65 (m, 2H), 1.93-2.05 (m, 2H), 3.13 (m, 0.3H), 3.24-3.29 (m, 1H), 3.46 (m, 0.7H), 4.12 (m, 0.3H), 4.58-4.77 (m, 2.7H), 5.06 (m, 0.7H), 5.38 (m, 1H), 7.30-7.36 (m, 5H); MS m/z 403 [M+H]$^+$.

Example 4

(2S,5R)-tert-Butyl 5-(benzyloxyamino)piperidine-2-carboxylate (4a)

To a solution of (2S,5R)-tert-butyl 5-(benzyloxyamino)-1-(2,2,2-trifluoroacetyl)piperidine-2-carboxylate (6.91 g, 17.17 mmol) in 1,4-dioxane (34 mL) was added water (9.2 mL), followed by adding dropwise 2.5M sodium hydroxide (13.7 mL) under ice-cooling, and allowing to react at the same temperature for 0.5 hours. To the reaction mixture was added acetic acid (approximately 1 mL), followed by concentrating under reduced pressure, and the resulting concentrated residue was extracted with ethyl acetate (58 mL, 29 mL). Each organic layer was washed with 50% potassium carbonate aqueous solution, and the combined organic layers were dehydrated over anhydrous sodium sulfate to distill off the solvent under reduced pressure. The resulting residue was subjected to silica gel column chromatography (hexane/ethyl acetate=4/1→0/1→ethyl acetate/methanol=19/1) to afford 4.74 g of the title compound as a colorless oil (yield 90%). Enantiomeric excess 98.9% ee (CHIRALPAK AD-H, 4.6×150 mm, UV 210 nm, diethylamine/hexane/ethanol=0.1/80/20, flow rate 1 mL/min., retention time 5.5 min.).

$[\alpha]^{20}_D$ −2.8° (c 0.73, CHCl$_3$); $^1$H NMR (400 MHz, CDCl$_3$) δ 1.28 (m, 1H, 1.42-1.46 (m, 10H), 1.92 (m, 1H), 2.04 (ddd, J=12.9, 7.3, 4.0 Hz, 1H), 2.43 (dd, J=12.0, 9.8 Hz, 1H), 2.98 (m, 1H), 3.16 (dd, J=11.0, 3.2 Hz, 1H), 3.57 (ddd, J=12.0, 4.2, 2.0 Hz, 1H), 4.68 (s, 2H), 7.29-7.35 (m, 5H); MS m/z 307 [M+H]$^+$.

Example 5

Sequential Synthesis of (2S,5R)-tert-Butyl 5-(benzyloxyamino)piperidine-2-carboxylate (4a)

A solution of (2S,5S)-tert-butyl 5-hydroxy-1-(2,2,2-trifluoroacetyl)piperidine-2-carboxylate (47.9 g, 161 mmol) in dehydrated acetonitrile (318 mL) was cooled to a temperature between −30 and −40° C. under an argon atmosphere, followed by adding 2,6-lutidine (20.5 mL), then adding dropwise trifluoromethanesulfonic anhydride (28.4 mL) over 40 minutes, and further allowing to react at −30° C. for 15 minutes. To this reaction mixture was added benzyloxyamine (39.7 g) (washed with acetonitrile (11 mL)) within 8 minutes, followed by raising the temperature to 0° C. within 30 minutes, further adding 2,6-lutidine (20.5 mL), and allowing to react at a temperature between 0 and 5° C. for 2 days. This reaction mixture was concentrated under reduced pressure, the resulting residue was diluted with ethyl acetate (960 mL), and washing with water (960 mL), 10% citric acid aqueous solution (960 mL×three times), 6.5% sodium bicarbonate aqueous solution (480 mL) and saturated brine (480 mL) sequentially. Each aqueous layer was back-extracted with ethyl acetate (960 mL), the organic layers were combined, and the solvent was distilled off under reduced pressure. The resulting residue was dissolved in 1,4-dioxane solution (320 mL) and water (86 mL), followed by adding dropwise 2.5M sodium hydroxide (128 mL) under ice-cooling, and allowing to react at the same temperature for 0.5 hours. To the reaction mixture was added acetic acid (approximately 9.3 mL), followed by concentrating under reduced pressure, the resulting concentrated residue was extracted with ethyl acetate (580 mL, 290 mL). Each organic layer was washed with 50% potassium carbonate aqueous solution (580 mL), followed by combining the organic layers and the solvent was distilled off under reduced pressure. The resulting residue was subjected to silica gel column chromatography (hexane/ethyl acetate=4/1→0/1→ethyl acetate/methanol=100/1→19/1) to afford 36.58 g of the title compound as a colorless oil (yield 74%). Instrumental data were consistent with those of Example 4.

Example 6

(2S,5R)-tert-Butyl 6-(benzyloxy)-7-oxo-1,6-diazabicyclo[3.2.1]octane-2-carboxylate (5a)

To a solution of (2S,5R)-tert-butyl 5-(benzyloxyamino)piperidine-2-carboxylate (4.14 g, 13.51 mmol) in dehydrated acetonitrile (615 mL) was added triethylamine (4.9 mL) under an argon atmosphere at 0° C., followed by adding dropwise diphosgene (1.18 mL) for 5 minutes, and stirring at the same temperature for 10 minutes. To this solution was added 4-dimethylaminopyridine (182 mg), followed by raising the temperature to room temperature and allowing to react for 3 hours. The reaction mixture was concentrated under reduced pressure to the volume of one tenth thereof, the resulting concentrated solution was diluted with ethyl acetate, followed by washing with water, 5% citric acid aqueous solution, 6.5% sodium bicarbonate aqueous solution, and saturated brine sequentially, then drying over anhydrous magnesium sulfate, and distilling off the solvent under reduced pressure. The resulting residue was subjected to silica gel column chromatography (hexane/ethyl acetate=2/1) to afford 3.09 g of the title compound (yield 69%). The resulting solid was recrystallized from ethyl acetate-hexane, the generated precipitate was filtered off. The wet crystal was washed with hexane, followed by drying at room temperature under reduced pressure, and the title compound was afforded as a colorless crystalline powder. Enantiomeric excess 99.4% ee (CHIRALPAK AD-H, 4.6×150 mm, hexane/ethanol=2/1, UV 210 nm, flow rate 1 mL/min., retention time 8.0 min.).

Mp 83°; $[\alpha]^{20}_D$ +5.9° (c 0.61, CHCl$_3$); $^1$H NMR (400 MHz, CDCl$_3$) δ 1.48 (s, 9H), 1.62 (m, 1H), 2.00-2.10 (m, 3H), 2.98 (d, J=11.7 Hz, 1H), 3.03 (m, 1H), 3.30 (m, 1H), 4.01 (m, 1H), 4.90 (d, J=11.5 Hz, 1H), 5.06 (d, J=11.5 Hz, 1H), 7.35-7.42 (m, 5H); MS m/z 333 [M+H]$^+$.

In powder X-ray diffraction diagram, the crystal of the title compound demonstrated characteristic peak patterns as shown in the following Table 1. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 1

Powder X-ray Diffraction of Compound (5a)

| 2θ (CuKα) | Peak Position Lattice spacing (d) Å | Relative Intensity I/I0 |
|---|---|---|
| 7.64 | 11.56 | 13 |
| 8.06 | 10.96 | 67 |
| 13.50 | 6.55 | 46 |
| 14.74 | 6.00 | 15 |
| 15.30 | 5.79 | 11 |
| 15.92 | 5.56 | 44 |
| 16.18 | 5.47 | 58 |
| 16.86 | 5.25 | 64 |
| 18.10 | 4.90 | 46 |
| 20.38 | 4.35 | 18 |
| 20.96 | 4.23 | 100 |
| 23.04 | 3.86 | 10 |

Example 7

(2S,5R)-tert-Butyl 6-(benzyloxy)-7-oxo-1,6-diazabicyclo[3.2.1]octane-2-carboxylate (5a): Reaction by Phosgene Gas To a solution of (2S,5R)-tert-butyl 5-(benzyloxyamino)piperidine-2-carboxylate (3.0 g, 9.791 mmol) in dehydrated acetonitrile (150 mL), under an argon atmosphere, at room temperature, were added triethylamine (3.82 mL) and 4-dimethylaminopyridine (120 mg), and phosgene gas (generated by adding diphosgene (1.548 g) dropwise on the activated carbon (1 g) warmed to 60° C. within 1.5 hours) was introduced by means of an argon stream, followed by stirring overnight. Excess phosgene was decomposed with concentrated ammonia water (0.6 mL), and the solvent of the reaction mixture was concentrated under reduced pressure. The residue was diluted with ethyl acetate (50 mL), washed sequentially with water (50 mL), 5% citric acid aqueous solution (50 mL), 6.5% sodium bicarbonate aqueous solution (25 mL), and saturated brine, then dried over anhydrous magnesium sulfate, and the solvent was distilled off under reduced pressure. The resulting residue was subjected to silica gel column chromatography (hexane/ethyl acetate=2/1) to afford 2.25 g of the title compound (yield 69%). The resulting solid was recrystallized from ethyl acetate-hexane, the generated precipitate was filtered off. The wet crystal was washed with hexane and subsequently dried under reduced pressure at room temperature to afford the title compound as a colorless crystalline powder. Instrumental data were consistent with those of the title compound of Example 6.

Example 8

(2S,5R)-6-(Benzyloxy)-7-oxo-1,6-diazabicyclo[3.2.1]octane-2-carboxylic acid cyclohexylamine salt (6a)

To a solution of (2S,5R)-tert-butyl 6-(benzyloxy)-7-oxo-1,6-diazabicyclo[3.2.1]octane-2-carboxylate (270 mg, 0.842 mmol) in methylene chloride (2 mL) was added trifluoroacetic acid (2 mL) under an argon atmosphere at 0° C., and the temperature was raised to room temperature, followed by allowing to react for 4 hours. The reaction mixture was concentrated, and the resulting residue was diluted with ethyl acetate, washed with water and saturated brine sequentially, dried over anhydrous magnesium sulfate, and the solvent was distilled off under reduced pressure. The resulting residue was dissolved in ethyl acetate (2.5 mL), and then a solution of cyclohexylamine (149 mg) in diethyl ether was added at room temperature, followed by stirring at 0° C. for 1 hour. The generated precipitate was filtered off, and the filter cake was washed with diethyl ether, followed by drying at room temperature under reduced pressure, and 270 mg of the title compound was afforded as a colorless crystalline powder (yield 86%).

Mp 175°; $[\alpha]^{20}_D$ –36.8° (c 0.50, H$_2$O); $^1$H NMR (400 MHz, dimethylsulfoxide-d6) δ 1.00-1.30 (m, 5H), 1.53-1.95 (m, 8H), 2.04-2.09 (m, 1H), 2.76 (d, J=11.6 Hz, 1H), 2.80-2.93 (m, 1H), 3.19 (d, J=11.2 Hz, 1H), 3.33 (br s, 2H), 3.40 (d, J=7.2 Hz, 1H), 3.51 (br s, 1H), 4.87 (d, J=11.6 Hz, 1H), 4.93 (d, J=11.6 Hz, 1H), 7.30-7.45 (m, 5H), 8.04 (br s, 1H); MS m/z 100, 277 [M-C$_6$H$_{13}$N+H]$^+$.

In powder X-ray diffraction diagram, the crystal of the title compound demonstrated characteristic peak patterns as shown in the following Table 2. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 2

Powder X-ray Diffraction of Compound (6a)

| 2θ (Cukα) | Lattice spacing (d) Å | Relative Intensity I/IO |
|---|---|---|
| 8.88 | 9.95 | 46 |
| 10.46 | 8.45 | 9 |
| 14.14 | 6.26 | 14 |
| 15.08 | 5.87 | 17 |
| 16.04 | 5.52 | 100 |
| 16.98 | 5.22 | 71 |
| 17.38 | 5.10 | 17 |
| 17.88 | 4.96 | 26 |
| 18.74 | 4.73 | 57 |
| 19.52 | 4.54 | 22 |
| 21.36 | 4.16 | 13 |
| 22.60 | 3.93 | 68 |
| 25.08 | 3.55 | 12 |

Example 9

(2S,5R)-6-(Benzyloxy)-7-oxo-1,6-diazabicyclo[3.2.1]octane-2-carboxylic acid (6b)

Cyclohexylamine salt (230 mg) of (2S,5R)-6-(benzyloxy)-7-oxo-1,6-diazabicyclo[3.2.1]octane-2-carboxylic acid was dissolved in saturated aqueous sodium dihydrogen phosphate solution, followed by extraction 4 times with ethyl acetate, and the combined organic layers were washed with saturated brine, and subsequently dried over anhydrous magnesium sulfate. The solvent was distilled off under reduced pressure, and dried under vacuum, to afford 161 mg of the title compound as a colorless foamy solid (yield 87%). Enantiomeric excess 99.9% ee or more (CHIRALPAK AD-H, 4.6×150 mm, trifluoroacetic acid/hexane/ethanol=0.1/80/20, UV 210 nm, flow rate 1 mL/min., retention time 10.5 min.).

$[\alpha]^{20}_D$ +11.5° (c 0.56, CHCl$_3$); $^1$H NMR (400 MHz, CDCl$_3$) δ 1.67 (m, 1H), 2.04-2.26 (m, 3H), 2.85 (d, J=12.0 Hz, 1H), 3.13 (m, 1H), 3.35 (m, 1H), 4.12 (m, 1H), 4.91 (d, J=11.3 Hz, 1H), 5.06 (d, J=11.3 Hz, 1H), 7.37-7.44 (m, 5H); MS m/z 277 [M+H]$^+$.

Example 10

(2S,5R)-6-(Benzyloxy)-7-oxo-1,6-diazabicyclo[3.2.1]octane-2-carboxylic acid (6b); treatment with diluted hydrochloric acid followed by crystallization (2S,5R)-6-(Benzyloxy)-7-oxo-1,6-diazabicyclo[3.2.1]octane-2-carboxylic acid cyclohexylamine salt (3.75 g, 10.0 mmol) was dissolved in water (50 ml). Ethyl acetate (100 mL) and 1M hydrochloric acid (20 mL) were added. The mixture was stirred, followed by extracting with ethyl acetate (100 mL each time) three times. The organic layer was dried over anhydrous magnesium sulfate, the solvent was concentrated to 10 mL under reduced pressure. 120 mL of hexane was gradually added while stirring under ice-cooling and the resulting precipitate was filtered off. The generated precipitate was filtered off. After the wet crystal was washed with hexane, and dried at room temperature under reduced pressure to afford 2.44 g of the title compound as a colorless crystalline powder. Mp 116° C.; the other instrumental data were consistent with those of the title compound of Example 9.

In powder X-ray diffraction diagram, the crystal of the title compound demonstrated characteristic peak patterns as shown in the following Table 3. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 3

Powder X-ray diffraction of compound (6b)

| Peak position | | |
|---|---|---|
| 2 θ (Cuka) | Lattice spacing (d) Å | Relative intensity I/IO |
| 10.80 | 8.19 | 10 |
| 12.38 | 7.14 | 14 |
| 13.32 | 6.64 | 11 |
| 14.06 | 6.29 | 81 |
| 15.82 | 5.60 | 33 |
| 17.02 | 5.21 | 92 |
| 18.04 | 4.91 | 12 |
| 19.28 | 4.60 | 37 |
| 21.06 | 4.21 | 100 |
| 24.08 | 3.69 | 42 |
| 25.80 | 3.45 | 16 |
| 28.52 | 3.13 | 33 |

Example 11

Dihydrochloride of (2S,5R)-5-(benzyloxyamino) piperidine-2-carboxylic acid (IV-a1)

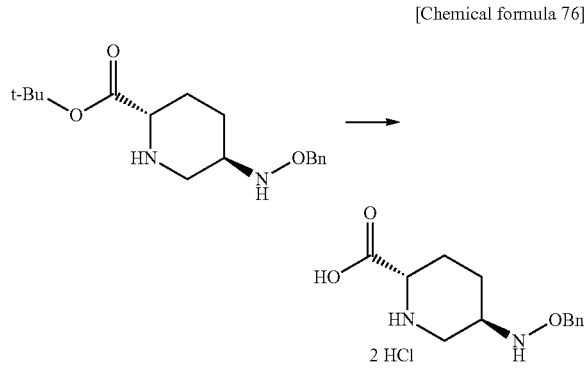

[Chemical formula 76]

To 5M hydrochloric acid (500 mL) was added (2S,5R)-tert-butyl 5-(benzyloxyamino)piperidine-2-carboxylate (46.69 g), followed by stirring at 65° C. for 2 hours. The reaction solution was cooled to room temperature, the residue resulting from concentrating the solvent under reduced pressure was dissolved in water (500 mL), followed by adding activated carbon (2.7 g) and stirring for 30 minutes. The activated carbon was removed by filtration, the filtrate was concentrated to dryness, followed by drying under vacuum overnight, and thereby 49.3 g of the title compound was afforded as a pale yellow solid (quantitative).

$^1$H NMR (400 MHz, D$_2$O) δ 1.39-1.49 (m, 1H), 1.59-1.70 (m, 1H), 1.88-1.95 (m, 1H), 2.20-2.28 (m, 1H), 2.78 (t, J=11.8 Hz, 1H), 3.19-3.28 (m, 1H), 3.48-3.52 (m, 1H), 3.68-3.72 (m, 1H), 3.57 (s, 3H), 3.70 (dd, J=3.4, 12.6 Hz), 4.68 (s, 2H), 7.26-7.32 (m, 5H); MS m/z 251 [M−2HCl+H]$^+$.

Example 12

Dihydrochloride of (2S,5R)-methyl 5-(benzyloxyamino)piperidine-2-carboxylate (4b)

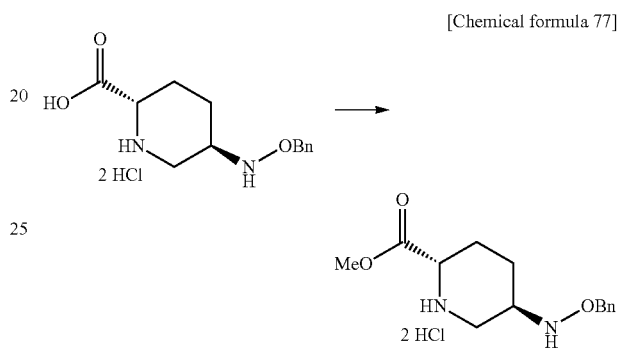

[Chemical formula 77]

To 2M hydrogen chloride methanol (7 mL) was added (2S,5R)-5-(benzyloxyamino)piperidine-2-carboxylic acid dihydrochloride (176 mg), followed by refluxing for 3 hours, the reaction solution was concentrated under reduced pressure, dried under vacuum overnight to afford the title compound as a pale yellow solid (quantitative).

$^1$H NMR (400 MHz, D$_2$O) δ 1.40-1.51 (m, 1H), 1.61-1.72 (m, 1H), 1.90-1.94 (m, 1H), 2.25-2.30 (m, 1H), 2.80 (t, J=11.2 Hz, 1H), 3.19-3.27 (m, 1H), 3.51-3.55 (m, 1H), 3.66 (s, 3H), 3.87-3.91 (m, 1H), 4.68 (s, 2H), 7.27 (s, 5H); MS m/z 265 [M−2HCl+H]$^+$.

Example 13

(2S,5R)-Methyl 5-(benzyloxyamino)piperidine-2-carboxylate (4b)

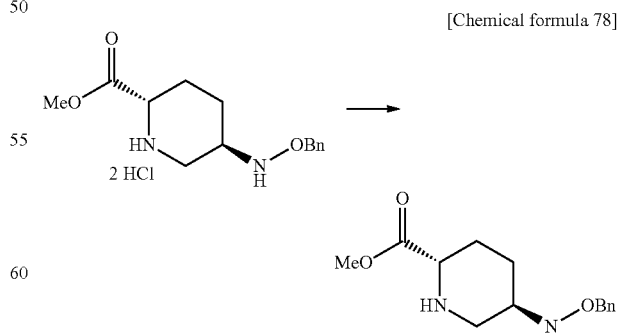

[Chemical formula 78]

To (2S,5R)-methyl 5-(benzyloxyamino)piperidine-2-carboxylate, dihydrochloride (1.319 g) were added ethyl acetate (20 mL) and 50% potassium carbonate aqueous solution (20 mL) for liquid separation and the aqueous layer was extracted with ethyl acetate (15 mL) three times. The organic layer was washed with saturated brine, dried over anhydrous sodium sulfate, and filtered, subsequently concentrated under reduced pressure, and dried under vacuum overnight to afford 975 mg of the title compound (yield 94%).

$^1$H NMR (400 MHz, CDCl$_3$) δ 1.25-1.35 (m, 1H), 1.49-1.59 (m, 1H), 1.89-2.11 (m, 2H), 2.45 (t, J=11.7 Hz, 1H), 2.96-3.03 (m, 1H), 3.28-3.92 (m, 2H), 3.72 (s, 3H), 4.68 (s, 2H), 7.26-7.35 (m, 5H); MS m/z 265 [M+H]$^+$.

Example 14

Direct Synthesis of dihydrochloride of (2S,5R)-methyl 5-(benzyloxyamino)piperidine-2-carboxylate (4b)

[Chemical formula 79]

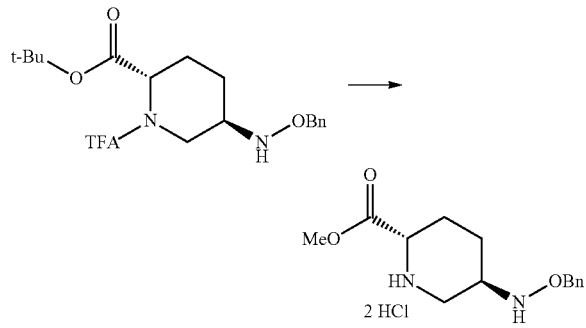

The crude material (507 mg, 1.26 mmol) of (2S,5R)-tert-butyl 5-(benzyloxyamino)-1-(2,2,2-trifluoroacetyl)piperidine-2-carboxylate described in Example 3 was dissolved in 2M hydrogen chloride methanol solution (10.3 mL), followed by refluxing for 33 hours. The reaction mixture was concentrated under reduced pressure to the volume of approximately 3.6 mL, and ethyl acetate (10.3 mL) was added to the concentrated solution to allow precipitating. The resulting precipitate was collected by suction filtration, the filter cake was washed with a small amount of ethyl acetate, followed by through-flow drying, and thereby 290 mg of the title compound was afforded as a white powder (yield 68%). The instrumental data were consistent with those of Example 12.

Example 15

(2S,5R)-Methyl 6-(benzyloxy)-7-oxo-1,6-diazabicyclo[3.2.1]octane-2-carboxylate (5b)

[Chemical formula 80]

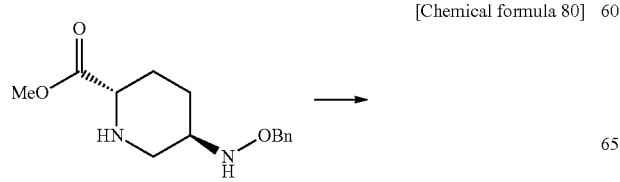

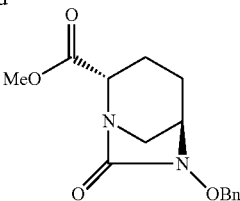

To (2S,5R)-methyl 5-(benzyloxyamino)piperidine-2-carboxylate (1.154 g, 4.37 mmol) was added dehydrated acetonitrile (198 mL), followed by ice-cooling. Triethylamine (1.60 mL) and diphosgene (0.389 mL) were sequentially added dropwise at 5° C. or less, followed by stirring at 2° C. for 20 minutes. Then, to the reaction solution was added 4-dimethylaminopyridine (70.0 mg), followed by stirring at room temperature for 10 hours. The reaction solution was concentrated under reduced pressure, followed by substituting and concentrating with ethyl acetate three times, and the solution was concentrated to 30 mL. Ethyl acetate (20 mL) and water (40 mL) were added thereto, followed by liquid separation, and the separated aqueous layer was extracted with ethyl acetate (30 mL) twice. The combined organic layers were washed with 5% citric acid aqueous solution (40 mL), 6.5% sodium bicarbonate aqueous solution (30 mL), and 5% brine (30 mL), and dried over anhydrous sodium sulfate, followed by filtration and concentration under reduced pressure. 1.16 g of the resulting residue was diluted with ethyl acetate (5.5 mL), and n-hexane (11 mL) was added, and a seed crystal was inoculated for crystallization. Further, n-hexane (49 mL) was added, followed by stirring at 0° C. for 1 hour. Subsequently, crystals were filtered, washed with n-hexane (60 mL), and then dried under vacuum to afford 882.3 mg of the title compound as colorless crystalline powder (yield 71%).

Mp 86°; [α]$^{20}_D$ +5.3° (c 1.10, CHCl$_3$); $^1$H NMR (400 MHz, CDCl$_3$) δ 1.65-1.70 (m, 1H), 2.03-2.12 (m, 3H), 2.90 (d, J=12.0 Hz, 1H), 3.07 (m, 1H), 3.79 (s, 3H), 4.12 (dd, J=4.6, 4.4 Hz, 1H), 4.91 (d, J=11.2 Hz, 1H), 5.06 (d, J=11.2 Hz, 1H), 7.35-7.44 (m, 5H); MS m/z 291 [M+H]$^+$.

In powder X-ray diffraction diagram, the crystal of the title compound demonstrated characteristic peak patterns as shown in the following Table 4. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 4

Powder X-ray Diffraction of Compound (5b)

| Peak Position | | |
|---|---|---|
| 2 θ (Cuka) | Lattice spacing (d) Å | Relative Intensity I/IO |
| 8.50 | 10.39 | 92 |
| 15.10 | 5.86 | 9 |
| 15.56 | 5.69 | 66 |
| 16.60 | 5.34 | 11 |
| 18.42 | 4.81 | 28 |
| 19.98 | 4.44 | 100 |
| 22.30 | 3.98 | 9 |
| 23.50 | 3.78 | 66 |
| 28.64 | 3.11 | 13 |
| 29.44 | 3.03 | 19 |

TABLE 4-continued

Powder X-ray Diffraction of Compound (5b)

| 2 θ (Cuka) | Lattice spacing (d) Å | Relative Intensity I/IO |
|---|---|---|
| 30.52 | 2.93 | 13 |
| 32.28 | 2.77 | 11 |

Example 16

(2S,5R)-6-(Benzyloxy)-7-oxo-1,6-diazabicyclo[3.2.1]octane-2-carboxylic acid (6b): Synthesis from (5b)

To (2S,5R)-methyl 6-(benzyloxy)-7-oxo-1,6-diazabicyclo[3.2.1]octane-2-carboxylate (809.0 mg, 2.79 mmol) were added tetrahydrofuran (8 mL) and water (3.6 mL), then 0.5M lithium hydroxide aqueous solution (6.41 mL) was added dropwise at 4.9° C. or less over 10 minutes. The reaction solution was stirred at 2° C. for 2 hours, followed by adding water (30 mL) and washing with ethyl acetate (25 mL). To the separated aqueous layer was added ethyl acetate (15 mL), the aqueous layer was adjusted to pH 4.0 with 1M hydrochloric acid aqueous solution, and extracted with ethyl acetate twice (ethyl acetate: total volume of 65 mL). The separated aqueous layer was adjusted to pH3.4 with 1M hydrochloric acid aqueous solution, and extracted with ethyl acetate once, subsequently the aqueous layer was adjusted to pH 2.4 and extracted with ethyl acetate twice. The resulting extraction liquid from a total of five extractions with ethyl acetate (175 mL) was washed with saturated brine (40 mL), dried over anhydrous sodium sulfate, filtrated, and then concentrated under reduced pressure. 759.1 mg of the resulting residue was diluted with ethyl acetate (5 mL), and n-hexane (3 mL) was added, and a seed crystal was inoculated for crystallization. Further, ethyl acetate/n-hexane (5/3) solution (8 mL) was added and stirred, subsequently n-hexane (20 mL) was added and stirred at 4° C. for 14 hours. The crystals were filtered, followed by washing with n-hexane (55 mL), subsequently drying under vacuum to afford 633.6 mg of the title compound as a colorless crystalline powder (yield 82%). The instrumental data of this were consistent with those of the compound of Example 9.

Example 17

(2S,5R)-7-Oxo-6-(sulfooxy)-1,6-diazabicyclo[3.2.1]octane-2-carbohydrazide

Step 1 tert-Butyl 2-{[(2S,5R)-6-benzyloxy-7-oxo-1,6-diazabicyclo[3.2.1]oct-2-yl]carbonyl}hydrazinecarboxylate To a solution of the carboxylic acid (6b, 371 mg, 1.34 mmol) of Example 9 or 16 in tetrahydrofuran (7 mL) were added triethylamine (0.227 mL) and isobutyl chloroformate (218 μl) under ice-cooling, followed by stirring at 0° C. for 15 minutes. To the reaction solution was added t-butyl carbazate (245 mg) at 0° C., followed by stirring at room temperature for 1.5 hours, and then concentrating under reduced pressure. The resulting residue was purified by silica gel column chromatography (hexane/ethyl acetate=1/1-0/1) to afford 583 mg of the title compound (yield 98%). $[\alpha]_D^{20}$ +54.30 (c 0.56, CHCl$_3$); $^1$H NMR (400 MHz, CDCl$_3$) δ 1.47 (s, 9H), 1.56-1.67 (m, 1H), 1.90-2.05 (m, 2H), 2.34-2.41 (m, 1H), 3.04-3.17 (m, 2H), 3.26-3.31 (m, 1H), 4.00 (d, J=7.6 Hz, 1H), 4.91 (d, J=11.2 Hz, 1H), 5.06 (d, J=11.2 Hz, 1H), 6.31 (br s, 1H), 7.34-7.46 (m, 5H), 8.14 (d, J=2.8 Hz, 1H); MS m/z 391 [M+H]$^+$.

Step 2 tert-Butyl 2-{[(2S,5R)-6-hydroxy-7-oxo-1,6-diazabicyclo[3.2.1]oct-2-yl]carbonyl}hydrazinecarboxylate The compound (573 mg, 1.47 mmol) of the above Step 1 was dissolved in methanol (10 mL), and 10% palladium-carbon (50% water content, 126 mg) was added, followed by stirring under hydrogen atmosphere at room temperature for 55 minutes. The catalyst of the reaction mixture was filtered through Celite, the solvent was concentrated under reduced pressure to afford 423 mg of the title compound (yield 96%).
$^1$H NMR (400 MHz, CD$_3$OD) δ 1.48 (s, 9H), 1.70-1.82 (m, 1H), 1.86-1.98 (m, 1H), 2.01-2.12 (m, 1H), 2.27 (br dd, J=14.6, 6.6 Hz, 1H), 3.11-3.25 (m, 2H), 3.70 (br s, 1H), 3.91 (br d, J=7.2 Hz, 1H); MS m/z 301 [M+H]$^+$.

Step 3

(2S,5R)-7-Oxo-6-(sulfooxy)-1,6-diazabicyclo[3.2.1]octane-2-carbohydrazide

To a solution of the compound (421 mg, 1.40 mmol) of the above Step 2 in pyridine (10 mL) was added sulfur trioxide-pyridine complex (1.01 g), followed by agitating at room temperature overnight. To the reaction solution was added methylene chloride, after filtration, followed by concentrating under reduced pressure, and adjusting to pH 8 with half-saturated sodium bicarbonate aqueous solution. The aqueous layer was washed with methylene chloride. Subsequently, to the aqueous layer were added tetrabutylammonium hydrogen sulfate (564 mg) and methylene chloride, followed by agitating for 15 minutes. The aqueous layer was extracted with methylene chloride, subsequently the resulting organic layer was dried over anhydrous sodium sulfate, after filtration, followed by concentrating under reduced pressure to afford 841 mg of tetrabutylammonium tert-butyl 2-{[(2S,5R)-7-oxo-6-(sulfooxy)-1,6-diazabicyclo[3.2.1]oct-2-yl]carbonyl}hydrazinecarboxylate.
$^1$H NMR (400 MHz, CDCl$_3$) δ 1.01 (t, J=7.4 Hz, 12H), 1.40-1.53 (m, 8H), 1.49 (s, 9H), 1.60-1.75 (m, 9H), 1.84-1.98 (m, 1H), 2.15-2.24 (m, 1H), 2.35-2.44 (m, 1H), 3.06-3.18 (m, 1H), 3.24-3.36 (m, 8H), 3.39 (br d, J=11.6 Hz, 1H), 3.97 (br d, J=7.2 Hz, 1H), 4.36 (br s, 1H), 6.31 (br s, 1H), 8.59-8.67 (m, 1H); MS m/z 381 [M−Bu$_4$N+2H]$^+$.

All the amount of the above tetrabutylammonium salt was dissolved in methylene chloride (15 mL), followed by adding trifluoroacetic acid (5 mL) and stirring at room temperature for 1 hour. Subsequently, the reaction solution was concentrated under reduced pressure, the resulting residue was washed with diethyl ether and dried. The resulting crude product was adjusted to pH 8 with sodium bicarbonate aqueous solution and subjected to octadecyl silica gel column chromatography to afford 227 mg of the title compound (2 steps, yield 58%). $[\alpha]_D^{20}$ −52.9° (c 0.15, H$_2$O); $^1$H NMR (400 MHz, D$_2$O) δ 1.63-1.73 (m, 1H), 1.76-1.87 (m, 1H), 1.90-1.99 (m, 1H), 2.00-2.09 (m, 1H), 2.97 (d, J=12.2 Hz, 1H), 3.17 (br d, J=12.2 Hz, 1H), 3.92 (d, J=7.2 Hz, 1H), 4.04-4.08 (m, 1H); MS m/z 281 [M+H]⁺.

Example 18

Sodium tert-butyl 1-methyl-2-{[(2SR,5RS)-7-oxo-6-(sulfooxy)-1,6-diazabicyclo[3.2.1]oct-2-yl]carbonyl}hydrazinecarboxylate Step 1 tert-Butyl 2-{[(2SR, 5RS)-6-benzyloxy-7-oxo-1,6-diazabicyclo[3.2.1]oct-2-yl]carbonyl}-1-methylhydrazinecarboxylate To a solution of (2SR,5RS)-6-(benzyloxy)-7-oxo-1,6-diazabicyclo[3.2.1]octane-2-carboxylic acid (400 mg, 1.45 mmol) and tert-butyl 1-methylhydrazinecarboxylate (232 mg) in tetrahydrofuran (14 mL) were added triethylamine (972 µL) and 2-chloro-1-methylpyridin-1-ium iodide (554 mg), followed by stirring at room temperature overnight. To the reaction solution was added saturated sodium bicarbonate aqueous solution, followed by extracting with chloroform. The organic layer was dried over sodium sulfate, and then concentrated. The resulting crude product was purified by silica gel column chromatography to afford 458 mg of the title compound (yield 78%).
¹H NMR (400 MHz, CDCl₃) δ 1.29-1.40 (m, 10H), 1.53-1.60 (m, 2H), 2.24-2.30 (m, 1H), 2.96-3.24 (m, 6H), 3.87 (d, J=1.7, 1H), 4.83 (d, J=2.8, 1H), 4.97 (d, J=2.8, 1H), 7.26-7.36 (m, 5H).

Step 2 tert-Butyl 2-{[(2SR, 5RS)-6-hydroxy-7-oxo-1,6-diazabicyclo[3.2.1]oct-2-yl]carbonyl}-1-methylhydrazinecarboxylate To a solution of the compound (485 mg, 1.20 mmol) of the above Step 1 in methanol (14 mL) was added 50% palladium-carbon (50% water content, 50 mg), followed by stirring under hydrogen atmosphere at room temperature for 2 hours. The catalyst in the reaction mixture was filtered off through PTFE membrane, followed by concentrating under reduced pressure. The resulting crude product was purified by silica gel column chromatography to afford 359 mg of the title compound (yield 95%). MS m/z 315 [M+H]⁺.

Step 3

Sodium tert-butyl 1-methyl-2-{[(2SR,5RS)-7-oxo-6-(sulfooxy)-1,6-diazabicyclo[3.2.1]oct-2-yl]carbonyl}hydrazinecarboxylate To a solution of all the amount of the compound of the above Step 2 in methylene chloride (10.0 mL) were added 2,6-lutidine (842 µL) and sulfur trioxide-pyridine complex (273 mg), followed by agitating at room temperature overnight. To the reaction solution was added chloroform, followed by liquid separation with water. The resulting pyridinium tert-butyl 2-{[(2SR,5RS)-7-oxo-6-(sulfooxy)-1,6-diazabicyclo[3.2.1]oct-2-yl]carbonyl}-1-methylhydrazinecarboxylate obtained in the aqueous layer was neutralized with saturated sodium bicarbonate aqueous solution, and purified by octadecyl silica gel column chromatography to afford 114 mg of the title compound (yield 23%).
¹H NMR (400 MHz, D₂O) δ 1.47 (s, 9H), 1.84 (m, 1H), 1.96-2.04 (m, 1H), 2.11-2.15 (m, 1H), 2.23-2.28 (m, 1H), 3.11 (s, 3H), 3.18 (d, J=3.0, 1H), 3.41 (d, J=2.7, 1H), 4.15 (d, J=1.9, 1H), 4.25 (br s, 1H); MS m/z 393 [M−Na]⁻.

Example 19

(2SR,5RS)-N'-Methyl-7-oxo-6-(sulfooxy)-1,6-diazabicyclo[3.2.1]octane-2-carbohydrazide Sodium tert-butyl 1-methyl-2-{[(2SR,5RS)-7-oxo-6-(sulfooxy)-1,6-diazabicyclo[3.2.1]oct-2-yl]carbonyl}hydrazinecarboxylate (100 mg, 0.24 mmol) of Example 18 was deprotected with trifluoroacetic acid, and purified by octadecyl silica gel column chromatography to afford 41 mg of the title compound (yield 58%).
¹H NMR (400 MHz, D₂O) δ 1.63-1.71 (m, 1H), 1.74-1.84 (m, 1H), 1.90-1.96 (m, 1H), 2.00-2.06 (m, 1H), 3.40 (s, 3H), 2.95 (d, J=3.0, 1H), 3.15 (d, J=3.0, 1H), 3.89 (d, J=1.6, 1H), 4.04 (br s, 1H), MS m/z 293 [M−H]⁻

Example 20

Sodium (2SR,5RS)-N',N'-dimethyl-7-oxo-6-(sulfooxy)-1,6-diazabicyclo[3.2.1]octane-2-carbohydrazide Step 1

(2SR,5RS)-6-Benzyloxy-N',N'-dimethyl-7-oxo-1,6-diazabicyclo[3.2.1]octane-2-carbohydrazide Following a procedure analogous to Example 18, from (2SR,5RS)-6-(benzyloxy)-7-oxo-1,6-diazabicyclo[3.2.1]octane-2-carboxylic acid (200 mg, 0.72 mmol) and 1,1-dimethylhydrazine (48 mg), 150 mg of the title compound was afforded (yield 65%).
¹H NMR (400 MHz, CDCl₃) δ 1.53 (m, 1H), 1.75-1.88 (m, 2H), 2.21-2.27 (m, 1H), 2.46 (s, 6H), 2.61 (d, J=2.6, 1H), 2.89 (d, J=2.6, 1H), 3.19-3.21 (m, 1H), 3.75 (d, J=1.9, 1H), 4.78 (d, J=2.9, 1H), 4.92 (d, J=2.9, 1H), 7.16-7.31 (m, 5H).

Step 2

(2SR,5RS)-N',N'-dimethyl-6-hydroxy-7-oxo-1,6-diazabicyclo[3.2.1]octane-2-carbohydrazide Following a procedure analogous to Example 17, from all the amount of the compound of the above Step 1, 101 mg of the title compound was afforded (yield 94%). MS m/z 229 [M+H]⁺.

Step 3

Sodium (2SR,5RS)-N',N'-dimethyl-7-oxo-6-(sulfooxy)-1,6-diazabicyclo[3.2.1]octane-2-carbohydrazide Following a procedure analogous to Example 18, pyridinium (2SR,5RS)-N',N'-dimethyl-7-oxo-6-(sulfooxy)-1,6-diazabicyclo[3.2.1]octane-2-carbohydrazide obtained from all the amount of the compound of the above Step 2 was neutralized with saturated sodium bicarbonate aqueous solution, and purified by octadecyl silica gel column chromatography to afford 65 mg of the title compound (yield 44%).

$^1$H NMR (400 MHz, D$_2$O) δ 1.80-1.98 (m, 2H), 2.07-2.20 (m, 2H), 2.59 (s, 6H), 3.11 (d, J=3.0, 1H), 3.33 (d, J=3.0, 1H), 4.01 (d, J=1.3, 1H), 4.22 (br s, 1H); MS m/z 307 [M−Na]$^-$.

Example 21

Sodium (2S,5R)-N'-acetyl-7-oxo-6-(sulfooxy)-1,6-diazabicyclo[3.2.1]octane-2-carbohydrazide Step 1

(2S,5R)-N'-acetyl-6-benzyloxy-7-oxo-1,6-diazabicyclo[3.2.1]octane-2-carbohydrazide To a solution of the carboxylic acid (6b, 2.37 g, 8.57 mmol) of Example 9 or 16 in tetrahydrofuran (50 mL) were added triethylamine (1.39 mL) and isobutyl chloroformate (1.32 mL) under ice-cooling, followed by agitating at 0° C. for 20 minutes. To the reaction solution was added acetohydrazide (807 mg) at 0° C., stirred at room temperature for 40 minutes and concentrated under reduced pressure. The resulting residue was purified by silica gel column chromatography (hexane/ethyl acetate=9/1) to afford 2.61 g of the title compound (yield 92%).

[α]$_D^{20}$ +92.3° (c 0.65, CHCl$_3$); $^1$H NMR (400 MHz, CDCl$_3$) δ 1.57-1.70 (m, 1H), 1.90-2.15 (m, 2H), 2.06 (s, 3H), 2.30-2.39 (m, 1H), 3.08 (br d, J=12.0 Hz, 1H), 3.13 (d, J=12.0 Hz, 1H), 3.31-3.37 (m, 1H), 4.02 (d, J=7.6 Hz, 1H), 4.92 (d, J=11.4 Hz, 1H), 5.06 (d, J=11.4 Hz, 1H), 7.33-7.50 (m, 5H), 7.72 (br s, 1H), 8.55 (br s, 1H); MS m/z 333 [M+H]$^+$.

Step 2

(2S,5R)-N'-Acetyl-6-hydroxy-7-oxo-1,6-diazabicyclo[3.2.1]octane-2-carbohydrazide The compound (2.48 g, 7.46 mmol) of the above Step 1 was dissolved in methanol (50 mL), followed by adding 10% palladium-carbon (50% water content, 313 mg), and stirring under hydrogen atmosphere at room temperature for 40 minutes. The catalyst of the reaction mixture was filtered through Celite and the solvent was concentrated under reduced pressure to afford 1.88 g of the title compound (quantitative).

[α]D$^{20}$ −30.5° (c 0.59, MeOH); $^1$H NMR (400 MHz, CD$_3$OD) δ 1.70-1.79 (m, 1H), 1.87-2.11 (m, 2H), 2.00 (s, 3H), 2.27 (br dd, J=15.0, 6.6 Hz, 1H), 3.15 (br d, J=12.0 Hz, 1H), 3.24 (d, J=12.0 Hz, 1H), 3.67-3.73 (m, 1H), 3.95 (d, J=7.2 Hz, 1H); MS m/z 243 [M+H]$^+$.

Step 3

Sodium (2S,5R)-N'-acetyl-7-oxo-6-(sulfooxy)-1,6-diazabicyclo[3.2.1]octane-2-carbohydrazide To a solution of the compound (1.87 g, 7.71 mmol) of the above Step 2 in pyridine (35 mL) was added sulfur trioxide-pyridine complex (5.51 g), followed by agitating at room temperature overnight. To the reaction solution was added methylene chloride, and filtrated, followed by concentrating under reduced pressure. To the resulting residue was added toluene, followed by azeotropy and concentration to dryness. The mixture was added to saturated phosphoric acid dihydrogen sodium aqueous solution (200 mL), followed by washing with ethyl acetate. Subsequently, tetrabutylammonium hydrogen sulfate (3.17 g) and ethyl acetate were added, followed by stirring for 10 minutes and then layer separation. The organic layer was dried over anhydrous sodium sulfate, followed by filtration and concentration under reduced pressure. The resulting residue was purified by silica gel column chromatography (methylene chloride/acetone/triethylamine=49/49/2) to afford 3.27 g of tetrabutylammonium (2S,5R)-N'-acetyl-7-oxo-6-(sulfooxy)-1,6-diazabicyclo[3.2.1]octane-2-carbohydrazide.

$^1$H NMR (400 MHz, CDCl$_3$) δ 1.01 (t, J=7.3 Hz, 12H), 1.45 (sex, J=7.3 Hz, 8H), 1.60-1.82 (m, 9H), 1.86-1.98 (m, 1H), 2.08 (s, 3H), 2.13-2.24 (m, 1H), 2.35 (br dd, J=15.2, 6.8 Hz, 1H), 3.17 (d, J=12.0 Hz, 1H), 3.23-3.40 (m, 8H), 3.37 (br d, J=12.0 Hz, 1H), 4.00 (d, J=7.6 Hz, 1H), 4.34 (br s, 1H), 7.92 (br s, 1H), 8.62 (br s, 1H); MS m/z 323 [M−Bu$_4$N+ 2H]$^+$.

The above tetrabutylammonium salt was reacted with DOWEX (Na type), and then subjected to octadecyl silica gel column chromatography (water) to afford 1.73 g of the title compound (yield 65%).

[α]$_D^{21}$ −44.9° (c 0.55, H$_2$O); $^1$H NMR (400 MHz, D$_2$O) δ 1.64-1.75 (m, 1H), 1.75-1.91 (m, 1H), 1.91-2.02 (m, 1H), 1.95 (s, 3H), 2.05-2.14 (m, 1H), 3.09 (d, J=12.6 Hz, 1H), 3.23 (br d, J=12.6 Hz, 1H), 4.05 (br d, J=7.2 Hz, 1H), 4.09 (br dd, J=5.8, 3.0 Hz, 1H); MS m/z 323 [M−Na+2H]$^+$; Na content 8.2%.

Example 22

Sodium (2S,5R)-7-oxo-N'-propanoyl-6-(sulfooxy)-1,6-diazabicyclo[3.2.1]octane-2-carbohydrazide Step 1

(2S,5R)-6-Benzyloxy-7-oxo-N'-propanoyl-1,6-diazabicyclo[3.2.1]octane-2-carbohydrazide To a solution of the carboxylic acid of Example 9 or 16 (6b, 354 mg, 1.28 mmol) in tetrahydrofuran (10 mL) were added triethylamine (0.216 mL) and isobutyl chloroformate (208 µl) under ice-cooling, followed by agitating at 0° C. for 15 minutes. To the reaction solution were added a solution of propionohydrazide (161 mg, prepared following a procedure analogous to Reference Example 3 and Reference Example 6) in tetrahydrofuran (3 mL) at 0° C., followed by stirring at room temperature for 1 hour, and then concentrating under reduced pressure. The resulting residue was purified by silica gel column chromatography (hexane/ethyl acetate=1/1-0/1) to afford 425 mg of the title compound (yield 96%).

[α]$_D^{21}$ +95.6° (c 0.46, CHCl$_3$); $^1$H NMR (400 MHz, CDCl$_3$) δ 1.20 (t, J=7.6 Hz, 3H), 1.56-1.66 (m, 1H), 1.91-2.05 (m, 2H), 2.25-2.40 (m, 3H), 3.09 (br d, J=12.0 Hz, 1H), 3.17 (d, J=12.0 Hz, 1H), 3.29-3.34 (m, 1H), 4.02 (d, J=7.6 Hz, 1H), 4.92 (d, J=11.4 Hz, 1H), 5.06 (d, J=11.4 Hz, 1H), 7.33-7.46 (m, 5H), 7.58 (br d, J=3.0 Hz, 1H), 8.50 (br d, J=3.0 Hz, 1H); MS m/z 347 [M+H]$^+$.

Step 2

(2S,5R)-6-Hydroxy-7-oxo-N'-propanoyl-1,6-diazabicyclo[3.2.1]octane-2-carbohydrazide The compound (417 mg, 1.20 mmol) of the above Step 1 was dissolved in methanol (10 mL), 10% palladium-carbon (50% water content, 110 mg) was added, followed by stirring under hydrogen atmosphere at room temperature for 50 minutes. The catalyst of the reaction mixture was filtered through Celite and the solvent was concentrated under reduced pressure to afford 297 mg of the title compound (yield 96%).

$^1$H NMR (400 MHz, CD$_3$OD) δ 1.17 (t, J=7.6 Hz, 3H), 1.69-1.79 (m, 1H), 1.88-1.99 (m, 1H), 2.02-2.11 (m, 1H), 2.24-2.32 (m, 1H), 2.28 (q, J=7.6 Hz, 2H), 3.16 (br d, J=11.6 Hz, 1H), 3.26 (d, J=11.6 Hz, 1H), 3.68-3.72 (m, 1H), 3.95 (d, J=7.6 Hz, 1H); MS m/z 257 [M+H]$^+$.

Step 3

Sodium (2S,5R)-7-oxo-N'-propanoyl-6-(sulfooxy)-1,6-diazabicyclo[3.2.1]octane-2-carbohydrazide To a solution of the compound (296 mg, 1.15 mmol) of the above Step 2 in pyridine (7.5 mL), sulfur trioxide-pyridine complex (843 mg) was added, followed by agitating at room temperature overnight. To the reaction solution was added methylene chloride, followed by filtering and concentrating under reduced pressure. To the residue was added toluene, followed by azeotropy. Thereby, pyridinium (2S,5R)-7-oxo-N'-propanoyl-6-(sulfooxy)-1,6-diazabicyclo[3.2.1]octane-2-carbohydrazide was afforded, followed by neutralizing with half-saturated sodium bicarbonate aqueous solution and then purifying octadecyl silica gel column chromatography to afford 357 mg of the title compound (yield 86%).

$[\alpha]_D^{21}$ −46.7° (c 0.28, H$_2$O); $^1$H NMR (400 MHz, D$_2$O) δ 1.02 (t, J=7.6 Hz, 3H), 1.64-1.76 (m, 1H), 1.78-1.90 (m, 1H), 1.93-2.02 (m, 1H), 2.10 (br dd, J=15.6, 7.2 Hz, 1H), 2.22 (q, J=7.6 Hz, 2H), 3.10 (d, J=12.0 Hz, 1H), 3.23 (br d, J=12.0 Hz, 1H), 4.04 (d, J=7.2 Hz, 1H), 4.07-4.12 (m, 1H); MS m/z 337 [M−Na+2H]$^+$.

Example 23

Sodium (2S,5R)-N'-(2-methylpropanoyl)-7-oxo-6-(sulfooxy)-1,6-diazabicyclo[3.2.1]octane-2-carbohydrazide Step 1

(2S,5R)-6-Benzyloxy-N'-(2-methylpropanoyl)-7-oxo-1,6-diazabicyclo[3.2.1]octane-2-carbohydrazide Following a procedure analogous to Example 17, from the carboxylic acid (6b, 363 mg, 1.31 mmol) of Example 9 or 16 and isobutyrohydrazide (190 mg), 440 mg of the title compound was afforded (yield 93%).

$[\alpha]_D^{20}$ +86.6° (c 0.50, CHCl$_3$); $^1$H NMR (400 MHz, CDCl$_3$) δ 1.21 (d, J=6.8 Hz, 3H), 1.23 (d, J=6.8 Hz, 3H), 1.55-1.63 (m, 1H), 1.91-2.07 (m, 2H), 2.30-2.38 (m, 1H), 2.48 (sep, J=6.8 Hz, 1H), 3.09 (br d, J=12.0 Hz, 1H), 3.18 (d, J=12.0 Hz, 1H), 3.28-3.32 (m, 1H), 4.02 (br d, J=7.6 Hz, 1H), 4.92 (d, J=11.4 Hz, 1H), 5.06 (d, J=11.4 Hz, 1H), 7.34-7.53 (m, 6H), 8.47 (br d, J=3.6 Hz, 1H); MS m/z 361 [M+H]$^+$.

Step 2

(2S,5R)-6-Hydroxy-N'-(2-methylpropanoyl)-7-oxo-1,6-diazabicyclo[3.2.1]octane-2-carbohydrazide Following a procedure analogous to Example 17, from the compound (426 mg, 1.18 mmol) of the above Step 1, 308 mg of the title compound was afforded (yield 97%).

$^1$H NMR (400 MHz, CD$_3$OD) δ 1.16 (d, J=7.0 Hz, 3H), 1.17 (d, J=7.0 Hz, 3H), 1.70-1.79 (m, 1H), 1.87-1.99 (m, 1H), 2.02-2.12 (m, 1H), 2.27 (br dd, J=15.0, 7.0 Hz, 1H), 2.53 (sep, J=7.0 Hz, 1H), 3.16 (br d, J=12.0 Hz, 1H), 3.27 (d, J=12.0 Hz, 1H), 3.67-3.73 (m, 1H), 3.94 (br d, J=7.6 Hz, 1H); MS m/z 271 [M+H]$^+$.

Step 3

Sodium (2S,5R)-N'-(2-methylpropanoyl)-7-oxo-6-(sulfooxy)-1,6-diazabicyclo[3.2.1]octane-2-carbohydrazide Following a procedure analogous to Example 22, from the compound (303 mg, 1.12 mmol) of the above Step 2, pyridinium (2S,5R)-N'-(2-methylpropanoyl)-7-oxo-6-(sulfooxy)-1,6-diazabicyclo[3.2.1]octane-2-carbohydrazide was afforded, and neutralized with saturated sodium bicarbonate aqueous solution, followed by purifying by octadecyl silica gel column chromatography, and 261 mg of the title compound was afforded (yield 62%).

$[\alpha]_D^{20}$ −40.3° (c 0.94, H$_2$O); $^1$H NMR (400 MHz, D$_2$O) δ 1.01 (d, J=6.8 Hz, 6H), 1.62-1.73 (m, 1H), 1.76-1.88 (m, 1H), 1.91-2.00 (m, 1H), 2.08 (br dd, J=15.6, 6.8 Hz, 1H), 2.46 (sep, J=6.8 Hz, 1H), 3.09 (d, J=12.4 Hz, 1H), 3.21 (br d, J=12.4 Hz, 1H), 4.03 (d, J=7.6 Hz, 1H), 4.06-4.10 (m, 1H); MS m/z 351 [M−Na+2H]$^+$.

Example 24

Sodium (2S,5R)-N'-(2,2-dimethylpropanoyl)-7-oxo-6-(sulfooxy)-1,6-diazabicyclo[3.2.1]octane-2-carbohydrazide Step 1

(2S,5R)-6-Benzyloxy-N'-(2,2-dimethylpropanoyl)-7-oxo-1,6-diazabicyclo[3.2.1]octane-2-carbohydrazide Following a procedure analogous to Example 18, from the carboxylic acid (6b, 400 mg, 1.44 mmol) of Example 9 or 16 and pivalic acid hydrazide (185 mg, 1.59 mmol), 506 mg of the title compound was afforded (yield 93%).

$^1$H NMR (400 MHz, CDCl$_3$) δ 1.14 (s, 9H), 1.49-1.54 (m, 1H), 1.77-1.88 (m, 2H), 2.14-2.19 (m, 1H), 2.93 (d, J=2.9, 1H), 3.11 (d, J=2.9, 1H), 3.18 (br s, 1H), 3.85 (d, J=1.8, 1H), 4.78 (d, J=2.8, 1H), 4.92 (d, J=2.8, 1H), 7.18-7.31 (m, 5H), 8.51 (s, 1H), 5.52 (s, 1H); MS m/z 375 [M+H]$^+$.

Step 2

(2S,5R)-N'-(2,2-Dimethylpropanoyl)-6-hydroxy-7-oxo-1,6-diazabicyclo[3.2.1]octane-2-carbohydrazide Following a procedure analogous to Example 17, from all the amount of the compound of the above Step 1, the title compound was afforded (quantitative).

Step 3

Sodium (2S,5R)-N'-(2,2-dimethylpropanoyl)-7-oxo-6-(sulfooxy)-1,6-diazabicyclo[3.2.1]octane-2-carbohydrazide Following a procedure analogous to Example 18, from all the amount of the compound of the above Step 2, and purification by octadecyl silica gel column chromatography, 404 mg of the title compound was afforded (yield 77%).

$^1$H NMR (400 MHz, D$_2$O) δ 1.09 (s, 3H), 1.10 (s, 3H), 1.11 (d, J=0.2, 3H), 1.67-1.73 (m, 1H), 1.74-1.88 (m, 1H), 1.95-1.99 (m, 1H), 2.08-2.14 (m, 1H), 3.14 (d, J=3.1, 1H), 3.22 (d, J=3.2, 1H), 3.70 (d, J=0.6, 1H), 4.04 (d, J=1.9, 1H), 4.10 (d, J=0.7, 1H); MS m/z 365 [M−Na+2H]$^+$, 363 [M−Na]$^−$.

Example 25

Sodium (2SR,5RS)-N'-acetyl-N'-methyl-7-oxo-6-(sulfooxy)-1,6-diazabicyclo[3.2.1]octane-2-carbohydrazide Step 1

(2SR,5RS)-N'-Acetyl-6-benzyloxy-N'-methyl-7-oxo-1,6-diazabicyclo[3.2.1]octane-2-carbohydrazide Following a procedure analogous to Example 17, from (2SR,5RS)-6-(benzyloxy)-7-oxo-1,6-diazabicyclo[3.2.1]octane-2-carboxylic acid (148 mg, 0.536 mmol) and N-methylacetohydrazide (64.0 mg, prepared from methylhydrazine and acetic anhydride), 221 mg of the title compound was afforded (yield 88%).

$^1$H NMR (400 MHz, CDCl$_3$) δ 1.59-1.73 (m, 1H), 1.88-2.10 (m, 2H), 2.02 (s, 1.8H), 2.17 (s, 1.2H), 2.31-2.39 (m, 1H), 2.69 (d, J=11.6 Hz, 0.6H), 3.07 (br d, J=11.6 Hz, 0.4H), 3.11-3.38 (m, 2H), 3.13 (s, 1.8H), 3.30 (s, 1.2H), 4.01 (d, J=7.2 Hz, 1H), 4.92 (d, J=11.6 Hz, 1H), 5.06 (d, J=11.6 Hz, 0.4H), 5.07 (d, J=11.2 Hz, 0.6H), 7.31-7.53 (m, 5H), 8.49 (br s, 0.4H), 8.58 (br s, 0.6H); MS m/z 347 [M+H]$^+$.

Step 2

(2SR,5RS)-N'-Acetyl-6-hydroxy-N'-methyl-7-oxo-1,6-diazabicyclo[3.2.1]octane-2-carbohydrazide Following a procedure analogous to Example 17, from the compound (216 mg, 0.624 mmol) of the above Step 1, 156 mg of the title compound was afforded (yield 98%).

$^1$H NMR (400 MHz, CD$_3$OD) δ 1.74-1.83 (m, 1H), 1.89-2.04 (m, 1H), 2.01 (s, 2.5H), 2.06-2.14 (m, 1H), 2.17 (s, 0.5H), 2.22-2.32 (m, 1H), 2.96 (d, J=11.6 Hz, 0.8H), 3.06-3.24 (m, 1.2H), 3.11 (s, 2.5H), 3.28 (s, 0.5H), 3.68-3.74 (m, 1H), 3.96 (br d, J=7.6 Hz, 1H); MS m/z 257 [M+H]$^+$.

Step 3

Sodium (2SR,5RS)-N'-acetyl-N'-methyl-7-oxo-6-(sulfooxy)-1,6-diazabicyclo[3.2.1]octane-2-carbohydrazide Following a procedure analogous to Example 22, the compound (150 mg, 0.585 mmol) of the above Step 2, pyridinium (2SR,5RS)-N'-acetyl-N'-methyl-7-oxo-6-(sulfooxy)-1,6-diazabicyclo[3.2.1]octane-2-carbohydrazide was afforded, neutralized with saturated sodium bicarbonate aqueous solution, and then purified by DIAION HP21 (MITSUBISHI CHEMICAL) column chromatography, 148 mg of the title compound was afforded (yield 71%).

$^1$H NMR (400 MHz, D$_2$O) δ 1.67-1.80 (m, 1H), 1.80-2.04 (m, 2H), 1.93 (s, 2.4H), 2.05-2.16 (m, 1H), 2.09 (s, 0.6H), 2.98 (d, J=12.0 Hz, 0.8H), 3.00 (s, 2.4H), 3.11 (d, J=12.0 Hz, 0.2H), 3.18 (s, 0.6H), 3.20 (br d, J=12.0 Hz, 0.2H), 3.28 (br d, J=12.0 Hz, 0.8H), 4.01-4.15 (m, 2H); MS m/z 337 [M−Na+2H]$^+$.

Example 26

(2SR,5RS)-N'-(Aminoacetyl)-7-oxo-6-(sulfooxy)-1,6-diazabicyclo[3.2.1]octane-2-carbohydrazide Step 1 tert-Butyl[2-(2-{[(2SR,5RS)-6-benzyloxy-7-oxo-1,6-diazabicyclo[3.2.1]oct-2-yl]carbonyl}hydrazinyl)-2-oxoethyl]carbamate To a solution of (2SR,5RS)-6-(benzyloxy)-7-oxo-1,6-diazabicyclo[3.2.1]octane-2-carboxylic acid (153 mg, 0.554 mmol) in tetrahydrofuran (3 mL) were added triethylamine (0.232 mL) and isobutyl chloroformate (89.1 μl) under ice-cooling, followed by agitating at 0° C. for 45 minutes. To the reaction solution was added a solution of tert-butyl 2-hydrazinyl-2-oxoethylcarbamate (129 mg, prepared following a procedure analogous to Reference Example 5 and Reference Example 6) in tetrahydrofuran (3 mL) at 0° C., followed by stirring at room temperature for 2.5 hours and concentrating under reduced pressure. The resulting residue was purified by silica gel column chromatography (hexane/ethyl acetate=7/3-0/10) to afford 179 mg of the title compound (yield 72%).

$^1$H NMR (400 MHz, CDCl$_3$) δ 1.45 (s, 9H), 1.57-1.70 (m, 1H), 1.91-2.06 (m, 2H), 2.28-2.38 (m, 1H), 3.07 (br d, J=12.0 Hz, 1H), 3.12 (d, J=12.0 Hz, 1H), 3.29-3.34 (m, 1H), 3.88 (dd, J=16.3, 6.1 Hz, 1H), 3.92 (dd, J=16.3, 6.1 Hz, 1H), 4.02 (br d, J=7.2 Hz, 1H), 4.91 (d, J=11.2 Hz, 1H), 5.05 (d, J=11.2 Hz, 1H), 5.24 (br t, J=6.1 Hz, 1H), 7.34-7.46 (m, 5H), 8.42 (br s, 1H), 8.53 (br s, 1H); MS m/z 448 [M+H]$^+$.

Step 2 tert-Butyl[2-(2-{[(2SR,5RS)-6-hydroxy-7-oxo-1,6-diazabicyclo[3.2.1]oct-2-yl]carbonyl}hydrazinyl)-2-oxoethyl]carbamate The compound (176 mg, 0.394 mmol) of the above Step 1 was dissolved in methanol (4 mL), followed by adding 10% palladium-carbon (50% water content, 42.4 mg), and stirring under hydrogen atmosphere at room temperature for 40 minutes. The catalyst of the reaction mixture was filtered through Celite, the solvent was concentrated under reduced pressure to afford 140 mg of the title compound (quantitative).

$^1$H NMR (400 MHz, CD$_3$OD) δ 1.45 (s, 9H), 1.69-1.79 (m, 1H), 1.87-2.00 (m, 1H), 2.01-2.11 (m, 1H), 2.27 (br dd, J=15.0, 6.6 Hz, 1H), 3.16 (br d, J=12.0 Hz, 1H), 3.24 (d, J=12.0 Hz, 1H), 3.67-3.73 (m, 1H), 3.81 (s, 2H), 3.95 (br d, J=7.2 Hz, 1H); MS m/z 358 [M+H]$^+$.

Step 3

(2SR,5RS)-N'-(Aminoacetyl)-7-oxo-6-(sulfooxy)-1,6-diazabicyclo[3.2.1]octane-2-carbohydrazide To a solution of the compound (137 mg, 0.382 mmol) of the above Step 2 in pyridine (4 mL) was added sulfur trioxide-pyridine complex (276 mg), followed by agitating at room temperature overnight. To the reaction solution was added methylene chloride, followed by filtration and concentration under reduced pressure. To the resulting residue was added toluene, followed by azeotropy. Thereby 405 mg of pyridinium tert-butyl[2-(2-{[(2SR,5RS)-7-oxo-6-(sulfooxy)-1,6-diazabicyclo[3.2.1]oct-2-yl]carbonyl}hydrazinyl)-2-oxoethyl]carbamate was afforded. MS m/z 438 [M−C$_5$H$_5$N+H]$^+$.

All the amount of the pyridinium salt was dissolved in methylene chloride (5 mL), and trifluoroacetic acid (1.7 mL) was added, followed by agitating at room temperature for 3.5 hours. The reaction solution was concentrated under reduced pressure. The resulting residue was washed with diethyl ether, and adjusted to pH 7 with sodium bicarbonate aqueous solution and lyophilized. The resulting crude product was purified by SEPABEADS SP207 (MITSUBISHI CHEMICAL) (acetonitrile/water=0/100-10/90). After lyophilisation, 42.6 mg of the title compound was afforded (2 steps, yield 33%).

$^1$H NMR (400 MHz, D$_2$O) δ 1.63-1.74 (m, 1H), 1.78-1.89 (m, 1H), 1.92-2.02 (m, 1H), 2.05-2.14 (m, 1H), 3.08 (d, J=12.4 Hz, 1H), 3.23 (br d, J=12.4 Hz, 1H), 4.06 (br d, J=6.4 Hz, 1H), 4.07-4.12 (m, 1H); MS m/z 338 [M+H]$^+$.

Example 27

(2S,5R)-N'-(3-Aminopropanoyl)-7-oxo-6-(sulfooxy)-1,6-diazabicyclo[3.2.1]octane-2-carbohydrazide Step 1 tert-Butyl[3-(2-{[(2S,5R)-6-benzyloxy-7-oxo-1,6-diazabicyclo[3.2.1]oct-2-yl]carbonyl}hydrazinyl)-3-oxopropyl]carbamate To a solution of the carboxylic acid (6b, 390 mg, 1.41 mmol) of Example 9 or 16 in methylene chloride (14.1 mL) were added triethylamine (393 μl), N-ethyl-N'-(3-dimethylaminopropyl)carbodiimide hydrochloride (406 mg), 1-hydroxybenzotriazole.monohydrate (324.6 mg), and tert-butyl (3-hydrazinyl-3-oxopropyl)carbamate (430.8 mg, prepared following a procedure analogous to Reference Example 2), followed by agitating at room temperature overnight. The reaction solution was concentrated under reduced pressure and the resulting residue was purified by silica gel column chromatography (ethyl acetate) to afford 347.3 mg of the title compound (yield 53.3%).

$^1$H NMR (400 MHz, CD$_3$OD) δ 1.32 (s, 9H), 1.55-1.63 (m, 1H), 1.75-1.91 (m, 2H), 2.11-2.17 (m, 1H), 2.31-2.34 (t, J=6.4 Hz, 2H), 2.92-2.95 (br d, J=11.6 Hz, 1H), 3.09-3.12 (d, J=11.6 Hz, 1H), 3.20-3.26 (t, J=6.4 Hz, 2H), 3.47 (br s, 1H), 3.86-3.88 (d, J=7.6 Hz, 1H), 4.82-4.85 (d, J=11.2 Hz, 1H), 4.89-4.92 (d, J=11.2 Hz, 1H), 7.27-7.31 (m, 3H), 7.35-7.38 (m, 2H); MS m/z 462 [M+H]$^+$.

Step 2 tert-Butyl[3-(2-{[(2S,5R)-6-hydroxy-7-oxo-1,6-diazabicyclo[3.2.1]oct-2-yl]carbonyl}hydrazinyl)-3-oxopropyl]carbamate All amount of the compound of the above Step 1 was dissolved in methanol (7.5 mL), followed by adding 10% palladium-carbon (50% water content, 69 mg) and stirring under hydrogen atmosphere at room temperature for 1 hour. The catalyst of the reaction mixture was filtered through Celite and the solvent was concentrated under reduced pressure to afford the title compound (quantitative).

Step 3

(2S,5R)-N'-(3-Aminopropanoyl)-7-oxo-6-(sulfooxy)-1,6-diazabicyclo[3.2.1]octane-2-carbohydrazide To a solution of all the amount of the compound of the above Step 2 in pyridine (7.5 mL) was added sulfur trioxide-pyridine complex (598.4 mg), followed by agitating at room temperature overnight. To the reaction solution was added methylene chloride, followed by filtration and concentration under reduced pressure. To the resulting residue was added toluene, followed by azeotropy. Thereby pyridinium tert-butyl[3-(2-{[(2S,5R)-7-oxo-6-(sulfooxy)-1,6-diazabicyclo[3.2.1]oct-2-yl]carbonyl}hydrazinyl)-3-oxopropyl]carbamate (quantitative) was afforded. MS m/z 450 [M−C$_5$H$_5$N−H]$^−$.

All the amount of the above pyridine salt was deprotected with trifluoroacetic acid, and purified by octadecyl silica gel column chromatography to afford 191 mg of the title compound (yield 72.3%).

$^1$H NMR (400 MHz, D$_2$O) δ 1.62-1.70 (m, 1H), 1.76-1.86 (m, 1H), 1.92-1.95 (m, 1H), 2.04-2.09 (m, 1H), 2.60-2.63 (t, J=6.8 Hz, 2H), 3.04-3.07 (d, J=12.0 Hz, 1H), 3.13-3.16 (t, J=6.8 Hz, 2H), 3.18-3.22 (d, J=11.6 Hz, 1H), 4.02-4.03 (d, J=7.2 Hz, 1H), 4.06 (br s, 1H); MS m/z 352 [M+H]$^+$.

Example 28

(2S,5R)-N'-[(4-Aminophenyl)acetyl]-7-oxo-6-(sulfooxy)-1,6-diazabicyclo[3.2.1]octane-2-carbohydrazide Step 1 tert-Butyl {4-[2-(2-{[(2S,5R)-6-benzyloxy-7-oxo-1,6-diazabicyclo[3.2.1]oct-2-yl]carbonyl}hydrazinyl)-2-oxoethyl]phenyl}carbamate Following a procedure analogous to Example 27, from the carboxylic acid (6b, 390 mg, 1.41 mmol) of Example 9 or 16 and tert-butyl (4-(2-hydrazinyl-2-oxoethyl)phenyl)carbamate (682.6 mg, prepared following a procedure analogous to Reference Example 5 and Reference Example 6), 550.8 mg of the title compound was afforded (yield 74.6%).

$^1$H NMR (400 MHz, CDCl$_3$) δ 1.45 (s, 9H), 1.56-1.64 (m, 1H), 1.86-1.97 (m, 2H), 2.27-2.33 (m, 1H), 3.03-3.06 (br d, J=11.6 Hz, 1H), 3.12-3.15 (d, J=11.6 Hz, 1H), 3.27 (br s, 1H), 3.75 (s, 2H), 3.96-3.98 (d, J=6.8 Hz, 1H), 4.87-4.89 (d, J=11.2 Hz, 1H), 5.01-5.04 (d, J=11.6 Hz, 1H), 6.47 (s, 1H), 7.21-7.24 (br d, J=10.8 Hz, 2H), 7.32-7.49 (m, 7H), 8.47 (br s, 1H); MS m/z 524 [M+H]$^+$.

Step 2 tert-Butyl {4-[2-(2-{[(2S,5R)-6-hydroxy-7-oxo-1,6-diazabicyclo[3.2.1]oct-2-yl]carbonyl}hydrazinyl)-2-oxoethyl]phenyl}carbamate Following a procedure analogous to Example 17, from all the amount of the compound of the above Step 1, 425 mg of the title compound was afforded (yield 93.2%). MS m/z 434 [M+H]$^+$.

Step 3

(2S,5R)-N'-[(4-Aminophenyl)acetyl]-7-oxo-6-(sulfooxy)-1,6-diazabicyclo[3.2.1]octane-2-carbohydrazide Following a procedure analogous to Example 17, from all the amount of the compound of the above Step 2, tetrabutylammonium tert-butyl {4-[2-(2-{[(2S,5R)-7-oxo-6-(sulfooxy)-1,6-diazabicyclo[3.2.1]oct-2-yl]carbonyl}hydrazinyl)-2-oxoethyl]phenyl}carbamate was afforded (quantitative). MS m/z 512 [M–Bu$_4$N]$^-$.

All the amount of the tetrabutylammonium salt was deprotected with trifluoroacetic acid, and purified by octadecyl silica gel column chromatography to afford 226 mg of the title compound (yield 55.8%).

$^1$H NMR (400 MHz, D$_2$O) δ 1.61-1.69 (m, 1H), 1.74-1.84 (m, 1H), 1.90-1.94 (m, 1H), 2.03-2.08 (m, 1H), 3.03-3.06 (d, J=12.0 Hz, 1H), 3.16-3.19 (d, J=12.0 Hz, 1H), 3.43 (br s, 2H), 3.99-4.01 (d, J=7.6 Hz, 1H), 4.05 (br s, 1H), 6.67-6.69 (d, J=8.4 Hz, 1H), 7.00-7.02 (d, J=8.4 Hz, 1H); MS m/z 412 [M–H]$^-$.

Example 29

Sodium (2S,5R)-N'-(methoxyacetyl)-7-oxo-6-(sulfooxy)-1,6-diazabicyclo[3.2.1]octane-2-carbohydrazide

Step 1

(2S,5R)-6-Benzyloxy-N'-(methoxyacetyl)-7-oxo-1,6-diazabicyclo[3.2.1]octane-2-carbohydrazide Following a procedure analogous to Example 27, from the carboxylic acid (6b, 390 mg, 1.41 mmol) of Example 9 or 16 and 2-methoxyacetohydrazide (220.7 mg), 397.1 mg of the title compound was afforded (yield 77.7%).

$^1$H NMR (400 MHz, CDCl$_3$) δ 1.50-1.59 (m, 1H), 1.85-1.94 (m, 2H), 2.26-2.33 (m, 1H), 3.01-3.04 (br d, J=12.4 Hz, 1H), 3.06-3.09 (d, J=12.0 Hz, 1H), 3.24 (s, 1H), 3.39 (s, 3H), 3.97-4.00 (m, 3H), 4.83-4.86 (d, J=11.6 Hz, 1H), 4.97-5.00 (d, J=11.6 Hz, 1H), 7.27-7.37 (m, 5H), 8.22 (m, 1H), 8.44 (m, 1H); MS m/z 363 [M+H]$^+$.

Step 2

(2S,5R)-6-Hydroxy-N'-(methoxyacetyl)-7-oxo-1,6-diazabicyclo[3.2.1]octane-2-carbohydrazide Following a procedure analogous to Example 17, from all the amount of the compound of the above Step 1, the title compound was afforded (quantitative). MS m/z 273 [M+H]$^+$.

Step 3

Sodium (2S,5R)-N'-(methoxyacetyl)-7-oxo-6-(sulfooxy)-1,6-diazabicyclo[3.2.1]octane-2-carbohydrazide Following a procedure analogous to Example 22, from all the amount of the compound of the above Step 2, pyridinium (2S,5R)-N'-(methoxyacetyl)-7-oxo-6-(sulfooxy)-1,6-diazabicyclo[3.2.1]octane-2-carbohydrazide was afforded, and neutralized with saturated sodium bicarbonate aqueous solution. After purification by SEPABEADS SP207 (MITSUBISHI CHEMICAL) column chromatography, 134.4 mg of the title compound was afforded (yield 32.7%).

$^1$H NMR (400 MHz, D$_2$O) δ 1.65-1.73 (m, 1H), 1.77-1.87 (m, 1H), 1.93-1.96 (m, 1H), 2.05-2.11 (m, 1H), 3.06-3.09 (br d, J=12.0 Hz, 1H), 3.19-3.22 (d, J=12.8 Hz, 1H), 3.31 (s, 3H), 3.97-4.04 (m, 3H), 4.07 (s, 1H); MS m/z 353 [M–Na+2H]$^+$.

Example 30

Sodium (2SR,5RS)-N'-benzoyl-7-oxo-6-(sulfooxy)-1,6-diazabicyclo[3.2.1]octane-2-carbohydrazide

Step 1

(2SR,5RS)-N'-Benzoyl-6-benzyloxy-7-oxo-1,6-diazabicyclo[3.2.1]octane-2-carbohydrazide To a solution of (2SR,5RS)-6-(benzyloxy)-7-oxo-1,6-diazabicyclo[3.2.1]octane-2-carboxylic acid (100.0 mg, 0.36 mmol) and benzohydrazide (54.2 mg) in tetrahydrofuran (4 mL) were added triethylamine (231 μL) and 2-chloro-1-methylpyridine-1-ium iodide (138.7 mg), followed by stirring at room temperature overnight. To the reaction solution was added saturated sodium bicarbonate aqueous solution, followed by extracting with chloroform. The organic layer was dried over sodium sulfate and then concentrated. The resulting crude product was purified by silica gel column chromatography to afford 123.0 mg of the title compound (yield 86%). MS m/z 395 [M+H]$^+$.

Step 2

(2SR,5RS)-N'-Benzoyl-6-hydroxy-7-oxo-1,6-diazabicyclo[3.2.1]octane-2-carbohydrazide To a solution of all the amount of the compound of the above Step 1 in methanol (3 mL) was added 50% palladium-carbon (50% water content, 20 mg), followed by stirring under hydrogen atmosphere at room temperature for 1 h. The catalyst in the reaction mixture was filtered off through PTFE membrane, followed by concentrating under reduced pressure. The resulting crude product was purified by silica gel column chromatography to afford 30 mg of the title compound (yield 32%)

$^1$H NMR (400 MHz, CD$_3$OD) δ 1.76-1.80 (m, 1H), 1.94-2.00 (m, 1H), 2.29-2.31 (m, 1H), 3.20-3.38 (m, 1H), 3.73 (br s, 1H), 4.02 (d, J=1.9, 1H), 7.47-7.90 (m, 1H); m/z 305 [M+H]$^+$.

Step 3

Sodium (2SR,5RS)-N'-benzoyl-7-oxo-6-(sulfooxy)-1,6-diazabicyclo[3.2.1]octane-2-carbohydrazide To a solution of all the amount of the compound of the above Step 2 in methylene chloride (2.0 mL) were added 2,6-lutidine (145 μL) and sulfur trioxide-pyridine complex (63 mg), followed by agitating at room temperature overnight. To the reaction solution was added chloroform, followed by liquid separation with water. The aqueous layer was concentrated to 1 mL under reduced pressure, followed by purification by octadecyl silica gel column chromatography. The resulting pyridinium (2SR,5RS)-N'-benzoyl-7-oxo-6-(sulfooxy)-1,6-diazabicyclo[3.2.1]octane-2-carbohydrazide was salt-exchanged with Dowex-Na type to afford 4 mg of the title compound (yield 37%).

¹H NMR (400 MHz, D₂O) δ 1.73-1.75 (m, 1H), 1.82-1.95 (m, 1H), 2.10-2.15 (m, 1H), 3.16 (d, J=3.2, 1H), 3.26 (d, J=3.0, 1H), 4.09 (m, 2H), 7.39-7.54 (m, 5H); MS m/z 385 [M−Na+2H]⁺.

Example 31

(2S,5R)-N'-(4-Aminobenzoyl)-7-oxo-6-(sulfooxy)-1,6-diazabicyclo[3.2.1]octane-2-carbohydrazide Step 1 tert-Butyl {4-[(2-{[(2S,5R)-6-benzyloxy-7-oxo-1,6-diazabicyclo[3.2.1]oct-2-yl]carbonyl}hydrazinyl)carbonyl]phenyl}carbamate Following a procedure analogous to Example 27, from the carboxylic acid (6b, 390 mg, 1.41 mmol) of Example 9 or 16 and tert-butyl (4-(hydrazinecarbonyl)phenyl)carbamate (653 mg, prepared following procedures analogous to Reference Example 5 and Reference Example 6), 689.5 mg of the title compound was afforded (yield 96.0%).

¹H NMR (400 MHz, CD₃OD) δ 1.52 (s, 9H), 1.68-1.75 (m, 1H), 1.89-2.00 (m, 2H), 2.24-2.30 (m, 1H), 3.07-3.10 (d, J=10.8 Hz, 1H), 3.30 (m, 1H), 3.58 (br s, 1H), 4.02-4.04 (d, J=7.6 Hz, 1H), 4.93-4.59 (d, J=11.6 Hz, 1H), 5.00-5.03 (d, J=11.6 Hz, 1H), 7.33-7.41 (m, 3H), 7.46-7.48 (m, 2H), 7.51 (d, J=8.8 Hz, 2H), 7.80 (d, J=8.8 Hz, 2H); MS m/z 510 [M+H]⁺.

Step 2 tert-Butyl {4-[(2-{[(2S,5R)-6-hydroxy-7-oxo-1,6-diazabicyclo[3.2.1]oct-2-yl]carbonyl}hydrazinyl)carbonyl]phenyl}carbamate Following a procedure analogous to Example 17, from all the amount of the compound of the above Step 1, the title compound was afforded (quantitative). MS m/z 420 [M+H]⁺

Step 3

(2S,5R)-N'-(4-Aminobenzoyl)-7-oxo-6-(sulfooxy)-1,6-diazabicyclo[3.2.1]octane-2-carbohydrazide Following a procedure analogous to Example 17, from all the amount of the compound of the above Step 2, tetrabutylammonium tert-butyl {4-[(2-{[(2S,5R)-7-oxo-6-(sulfooxy)-1,6-diazabicyclo[3.2.1]oct-2-yl]carbonyl}hydrazinyl)carbonyl]phenyl}carbamate was afforded (quantitative). MS m/z 498 [M−Bu₄N]⁻.

All the amount of the above tetrabutylammonium salt was deprotected with trifluoroacetic acid and purified by octadecyl silica gel column chromatography to afford 127.4 mg of the title compound (yield 23.6%).

¹H NMR (400 MHz, D₂O) δ 1.65-1.73 (m, 1H), 1.78-1.88 (m, 1H), 1.93-1.97 (m, 1H), 2.08-2.13 (m, 1H), 3.14-3.17 (d, J=12.0 Hz, 1H), 3.26-3.26 (d, J=12.0 Hz, 1H), 4.07 (m, 2H), 6.69-6.71 (d, J=8.4 Hz, 2H), 7.52-7.54 (d, J=8.4 Hz, 2H); MS m/z 400 [M+H]⁺.

Example 32

(2SR,5RS)-N'-(4-(Aminomethyl)benzoyl)-7-oxo-6-(sulfooxy)-1,6-diazabicyclo[3.2.1]octane-2-carbohydrazide Step 1 tert-Butyl {4-[(2-{[(2SR,5RS)-6-benzyloxy-7-oxo-1,6-diazabicyclo[3.2.1]oct-2-yl]carbonyl}hydrazinyl)carbonyl]benzyl}carbamate Following a procedure analogous to Example 27, from (2SR,5RS)-6-(benzyloxy)-7-oxo-1,6-diazabicyclo[3.2.1]octane-2-carboxylic acid (200 mg, 0.724 mmol) and tert-butyl 4-(hydrazinecarbonyl)benzylcarbamate (226 mg, prepared following procedures analogous to Reference Example 5 and Reference Example 6), 288.7 mg of the title compound was afforded (yield 76.1%).

¹H NMR (400 MHz, CDCl₃) δ 1.49 (s, 9H), 1.62 (m, 1H), 1.95-2.05 (m, 2H), 2.34-2.39 (m, 1H), 3.14 (br d, J=11.6 Hz, 1H), 3.20 (d, J=11.6 Hz, 1H), 3.34 (s, 1H), 4.07 (d, J=6.8 Hz, 1H), 4.36 (br d, J=5.6 Hz, 2H), 4.92 (d, J=11.6 Hz, 1H), 5.06 (d, J=11.4 Hz, 1H), 7.34-7.52 (m, 7H), 7.83 (d, J=8.4 Hz, 2H); MS m/z 524 [M+H]⁺.

Step 2 tert-Butyl {4-[(2-{[(2SR,5RS)-6-hydroxy-7-oxo-1,6-diazabicyclo[3.2.1]oct-2-yl]carbonyl}hydrazinyl)carbonyl]benzyl}carbamate Following a procedure analogous to Example 17, from all the amount of the compound of the above Step 1, 216.1 mg of the title compound was afforded (yield 90.4%).

¹H NMR (400 MHz, CD₃OD) δ 1.45 (s, 9H), 1.74-1.82 (m, 1H), 1.91-2.03 (m, 1H), 2.09-2.20 (m, 1H), 2.29-2.34 (m, 1H), 3.20-3.30 (m, 2H), 3.74 (s, 1H), 4.02 (d, J=7.6 Hz, 1H), 4.29 (br s, 2H), 7.39 (d, J=8.0 Hz, 2H), 7.86 (d, J=8.0 Hz, 2H);

Step 3

(2SR,5RS)-N'-(4-(Aminomethyl)benzoyl)-7-oxo-6-(sulfooxy)-1,6-diazabicyclo[3.2.1]octane-2-carbohydrazide Following a procedure analogous to Example 26, from all the amount of the compound of the above Step 2, pyridinium tert-butyl {4-[(2-{[(2SR,5RS)-7-oxo-6-(sulfooxy)-1,6-diazabicyclo[3.2.1]oct-2-yl]carbonyl}hydrazinyl)carbonyl]benzyl}carbamate was afforded (quantitative).

¹H NMR (400 MHz, D₂O) δ 1.29 (s, 9H), 1.74-1.76 (m, 1H), 1.81-1.89 (m, 1H), 1.96-1.91 (m, 1H), 2.11-2.15 (m, 1H), 3.18 (d, J=12.8 Hz, 1H), 3.27 (d, J=12.8 Hz, 1H), 3.59 (s, 1H), 4.12 (d, J=4.4 Hz, 1H), 4.19 (br s, 2H), 7.32 (d, J=7.6 Hz, 2H), 7.68 (d, J=7.6 Hz, 2H), 7.91-8.63 (m, 5H):

All the amount of the pyridine salt was deprotected with trifluoroacetic acid, and purified by DIAION HP21 (MITSUBISHI CHEMICAL) to afford 100.3 mg of the title compound (yield 48.7%).

¹H NMR (400 MHz, D₂O) δ 1.80-1.88 (m, 1H), 1.94-2.00 (m, 1H), 2.08 (m, 1H), 2.24-2.28 (m, 1H), 3.30 (d, J=12.4 Hz, 1H), 3.40 (d, J=12.0 Hz, 1H), 4.20-4.24 (m, 4H), 7.62 (d, J=8.0 Hz, 2H), 7.93 (d, J=8.0 Hz, 2H); MS m/z 414 [M+H]⁺

Example 33

Sodium (2SR,5RS)-7-oxo-N-(2-oxopyrrolidin-1-yl)-6-(sulfooxy)-1,6-diazabicyclo[3.2.1]octane-2-carboxamide

Step 1

(2SR,5RS)-6-Benzyloxy-7-oxo-N-(2-oxopyrrolidin-1-yl)-1,6-diazabicyclo[3.2.1]octane-2-carboxamide Following a procedure analogous to Example 17, from (2SR,5RS)-6-(benzyloxy)-7-oxo-1,6-diazabicyclo[3.2.1]octane-2-carboxylic acid (164 mg, 0.594 mmol) and 1-aminopyrrolidin-2-one hydrochloride (101 mg), 128 mg of the title compound was afforded (yield 60%).
$^1$H NMR (400 MHz, CDCl$_3$) δ 1.57-1.70 (m, 1H), 1.88-2.22 (m, 4H), 2.30-2.52 (m, 3H), 3.09 (br d, J=12.0 Hz, 1H), 3.22 (d, J=12.0 Hz, 1H), 3.30-3.35 (m, 1H), 3.46 (ddd, J=8.5, 8.5, 4.8 Hz, 1H), 3.73 (q, J=7.7 Hz, 1H), 4.02 (br d, J=7.6 Hz, 1H), 4.92 (d, J=11.2 Hz, 1H), 5.06 (d, J=11.2 Hz, 1H), 7.35-7.46 (m, 5H), 8.34 (br s, 1H); MS m/z 359 [M+H]$^+$.

Step 2

(2SR,5RS)-6-Hydroxy-7-oxo-N-(2-oxopyrrolidin-1-yl)-1,6-diazabicyclo[3.2.1]octane-2-carboxamide Following a procedure analogous to Example 17, from the compound (126 mg, 0.352 mmol) of the above Step 1, the title compound was afforded (quantitative).
$^1$H NMR (400 MHz, CD$_3$OD) δ 1.70-1.80 (m, 1H), 1.88-2.00 (m, 1H), 2.02-2.19 (m, 3H), 2.27 (br dd, J=15.0, 7.0 Hz, 1H), 2.40-2.47 (m, 2H), 3.16 (br d, J=11.6 Hz, 1H), 3.21 (d, J=11.6 Hz, 1H), 3.52-3.65 (m, 2H), 3.68-3.73 (m, 1H), 3.96 (d, J=7.6 Hz, 1H); MS m/z 269 [M+H]$^+$

Step 3

Sodium (2SR,5RS)-7-oxo-N-(2-oxopyrrolidin-1-yl)-6-(sulfooxy)-1,6-diazabicyclo[3.2.1]octane-2-carboxamide To a solution of all the amount of the compound of the above Step 2 in pyridine (3.5 mL) was added sulfur trioxide-pyridine complex (248 mg), followed by agitating at room temperature overnight. To the reaction solution was added methylene chloride, followed by filtration and concentration under reduced pressure. To the resulting residue was added toluene, followed by azeotropy. Thereby, 178 mg of pyridinium (2SR,5RS)-7-oxo-N-(2-oxopyrrolidin-1-yl)-6-(sulfooxy)-1,6-diazabicyclo[3.2.1]octane-2-carboxamide was afforded. MS m/z 349 [M–C$_5$H$_5$NH]$^+$.

All the amount of the above pyridinium salt was added to water and saturated sodium bicarbonate aqueous solution and adjusted to pH 7, followed by lyophilisation. The resulting crude product was purified by DIAION HP21 (MITSUBISHI CHEMICAL) (acetonitrile/water=100/0-90/10), followed by lyophilisation, and 103 mg of the title compound was afforded (2 steps, yield 79%).
$^1$H NMR (400 MHz, D$_2$O) δ 1.65-1.74 (m, 1H), 1.77-1.89 (m, 1H), 1.92-2.14 (m, 2H), 2.03 (qui, J=7.6 Hz, 2H), 2.38 (t, J=7.6 Hz, 2H), 3.06 (d, J=12.0 Hz, 1H), 3.23 (br d, J=12.0 Hz, 1H), 3.49 (t, J=7.6 Hz, 2H), 4.05 (br d, J=6.8 Hz, 1H), 4.08 (br dd, J=5.8, 3.0 Hz, 1H); MS m/z 349 [M–Na+2H]$^+$.

Example 34

Sodium (2S,5R)-7-oxo-6-(sulfooxy)-N'-(tetrahydro-2H-pyran-4-ylcarbonyl)-1,6-diazabicyclo[3.2.1]octane-2-carbohydrazide

Step 1

(2S,5R)-6-Benzyloxy-7-oxo-N'-(tetrahydro-2H-pyran-4-ylcarbonyl)-1,6-diazabicyclo[3.2.1]octane-2-carbohydrazide Following a procedure analogous to Example 27, from the carboxylic acid (6b, 390 mg, 1.41 mmol) of Example 9 or 16 and tetrahydro-2H-pyran-4-carbohydrazide (952 mg) described in Reference Example 2, 309.8 mg of the title compound was afforded (yield 54.5%).
$^1$H NMR (400 MHz, CD$_3$OD) δ 1.69-2.00 (m, 7H), 2.20-2.25 (m, 1H), 2.49-2.57 (m, 1H), 3.02 (br d, J=12.0 Hz, 1H), 3.20 (d, J=12.0 Hz, 1H), 3.41-3.47 (m, 2H), 3.56 (s, 1H), 3.94-3.97 (m, 3H), 4.91-4.94 (d, J=11.2 Hz, 1H), 4.98-5.01 (d, J=11.2 Hz, 1H), 7.34-7.47 (m, 5H); MS m/z 403 [M+H]$^+$.

Step 2

(2S,5R)-6-Hydroxy-7-oxo-N'-(tetrahydro-2H-pyran-4-ylcarbonyl)-1,6-diazabicyclo[3.2.1]octane-2-carbohydrazide Following a procedure analogous to Example 17, from all the amount of the compound of the above Step 1, the title compound was afforded (quantitative). MS m/z 313 [M+H]$^+$.

Step 3

Sodium (2S,5R)-7-oxo-6-(sulfooxy)-N'-(tetrahydro-2H-pyran-4-ylcarbonyl)-1,6-diazabicyclo[3.2.1]octane-2-carbohydrazide Following a procedure analogous to Example 22, from all the amount of the compound of the above Step 2, pyridinium (2S,5R)-7-oxo-6-(sulfooxy)-N'-(tetrahydro-2H-pyran-4-ylcarbonyl)-1,6-diazabicyclo[3.2.1]octane-2-carbohydrazide was afforded, and neutralized with saturated sodium bicarbonate aqueous solution, and then purified by SEPABEADS SP207 (MITSUBISHI CHEMICAL) column chromatography to afford 198.9 mg of the title compound (yield 62.4%).
$^1$H NMR (400 MHz, D$_2$O) δ 1.57-1.66 (m, 5H), 1.76-1.86 (m, 1H), 1.93 (m, 1H), 2.05-2.09 (m, 1H), 2.52-2.56 (m, 1H), 3.07-3.10 (br d, J=12.0 Hz, 1H), 3.20-3.23 (d, J=12.0 Hz, 1H), 3.36-3.41 (m, 2H), 3.86-3.89 (d, J=10.0 Hz, 2H), 4.02-4.04 (J=7.6 Hz, 1H), 4.07 (s, 1H); MS m/z 393 [M–Na+2H]$^+$.

Example 35

(2S,5R)-7-Oxo-N'-(piperidine-4-ylcarbonyl)-6-(sulfooxy)-1,6-diazabicyclo[3.2.1]octane-2-carbohydrazide

Step 1 tert-Butyl 4-[(2-{[(2S,5R)-6-benzyloxy-7-oxo-1,6-diazabicyclo[3.2.1]oct-2-yl]carbonyl}hydrazinyl)carbonyl]piperidine-1-carboxylate Following a procedure analogous to Example 27, from the carboxylic acid (6b, 390 mg, 1.41 mmol) of Example 9 or 16 and tert-butyl 4-(hydrazinecarbonyl)piperidine-1-carboxylate (642 mg, prepared following a procedure analogous to Reference Example 5 and Reference Example 6), 552.7 mg of the title compound was afforded (yield 78.1%).

$^1$H NMR (400 MHz, CDCl$_3$) δ 1.42 (s, 9H), 1.60-1.71 (m, 3H), 1.77-1.92 (m, 2H), 1.96-2.02 (m, 2H), 2.28-2.36 (m, 2H), 2.72-2.78 (dd, J=12 Hz, 2H), 3.06-3.09 (br d, J=12.0 Hz, 1H), 3.14-3.17 (d, J=11.6 Hz, 1H), 3.28 (br s, 1H), 4.00-4.01 (d, J=7.2 Hz, 1H), 4.07-4.12 (dd, J=14.4 Hz, 2H), 4.87-4.90 (d, 11.2 Hz, 1H), 5.02-5.04 (d, J=11.6 Hz, 1H), 7.23-7.41 (m, 5H), 7.57 (br s, 1H), 8.58 (br s, 1H); MS m/z 502 [M+H]$^+$.

Step 2 tert-Butyl 4-[(2-{[(2S,5R)-6-hydroxy-7-oxo-1,6-diazabicyclo[3.2.1]oct-2-yl]carbonyl}hydrazinyl) carbonyl]piperidine-1-carboxylate Following a procedure analogous to Example 17, from all the amount of the compound of the above Step 1, 423.8 mg of the title compound was afforded (yield 93.6%). MS m/z 412 [M+H]$^+$.

Step 3

(2S,5R)-7-Oxo-N'-(piperidine-4-ylcarbonyl)-6-(sulfooxy)-1,6-diazabicyclo[3.2.1]octane-2-carbohydrazide Following a procedure analogous to Example 26, from all the amount of the compound of the above Step 2, pyridinium tert-butyl 4-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate was afforded (quantitative). MS m/z 492 [M−C$_5$H$_5$NH]$^+$.

All the amount of the pyridine salt was deprotected with trifluoroacetic acid and purified by octadecyl silica gel column chromatography to afford 150 mg of the title compound (yield 37.2%).

$^1$H NMR (400 MHz, D$_2$O) δ 1.62-2.10 (m, 8H), 2.57-2.63 (m, 1H), 2.91-2.96 (dd, J=11.6, 12.8 Hz, 2H), 3.05-3.08 (d, J=12.4 Hz, 1H), 3.19-3.22 (d, J=12.0 Hz, 1H), 3.33-3.36 (d, J=13.2 Hz, 2H), 4.01-4.03 (d, J=7.6 Hz, 1H), 4.07 (br s, 1H); MS m/z 392 [M+H]$^+$.

Example 36

(2S,5R)-7-Oxo-N'-[(2S)-piperidine-2-ylcarbonyl]-6-(sulfooxy)-1,6-diazabicyclo[3.2.1]octane-2-carbohydrazide Step 1 tert-Butyl (2S)-2-[(2-{[(2S,5R)-6-benzyloxy-7-oxo-1,6-diazabicyclo[3.2.1]oct-2-yl] carbonyl}hydrazinyl)carbonyl]piperidine-1-carboxylate Following a procedure analogous to Example 27, from the carboxylic acid (6b, 390 mg, 1.41 mmol) of Example 9 or 16 and (S)-tert-butyl 2-(hydrazinecarbonyl)piperidine-1-carboxylate (634 mg, prepared following a procedure analogous to Reference Example 5 and Reference Example 6), 567 mg of the title compound was afforded (yield 80%).

$^1$H NMR (400 MHz, CDCl$_3$) δ 1.35-1.72 (m, 6H), 1.49 (s, 9H), 1.90-2.10 (m, 2H), 2.16-2.40 (m, 2H), 2.98-3.37 (m, 5H), 3.96-4.08 (m, 2H), 4.85 (br s, 1H), 4.92 (d, J=11.2 Hz, 1H), 5.06 (d, J=11.2 Hz, 1H), 7.33-7.47 (m, 5H), 8.30 (br s, 1H); MS m/z 502 [M+H]$^+$.

Step 2 tert-Butyl (2S)-2-[(2-{[(2S,5R)-6-hydroxy-7-oxo-1,6-diazabicyclo[3.2.1]oct-2-yl]carbonyl}hydrazinyl) carbonyl]piperidine-1-carboxylate Following a procedure analogous to Example 17, from all the amount of the compound of the above Step 1, the title compound was afforded (quantitative). MS m/z 410 [M−H]$^-$.

Step 3

(2S,5R)-7-Oxo-N'-[(2S)-piperidine-2-ylcarbonyl]-6-(sulfooxy)-1,6-diazabicyclo[3.2.1]octane-2-carbohydrazide To a solution of all the amount of the compound of the above Step 2 in pyridine (11.3 mL) was added sulfur trioxide-pyridine complex (899 mg), followed by agitating at room temperature overnight. To the reaction solution was added pyridine, followed by filtration and then concentration under reduced pressure. To the resulting residue was added toluene, followed by azeotropy and concentration to dryness. A saturated sodium dihydrogen phosphate aqueous solution (15 mL) was added, the aqueous layer was washed with ethyl acetate, and subsequently tetrabutylammonium hydrogen sulfate (421 mg) and ethyl acetate (30 mL) were added, followed by agitating 10 minutes. The aqueous layer was extracted with ethyl acetate, then the resulting organic layer was dried over anhydrous sodium sulfate, filtrated, and concentrated under reduced pressure to afford tetrabutylammonium tert-butyl (2S)-2-[(2-{[(2S,5R)-7-oxo-6-(sulfooxy)-1,6-diazabicyclo[3.2.1]oct-2-yl] carbonyl}hydrazinyl)carbonyl]piperidine-1-carboxylate (quantitative).

$^1$H NMR (400 MHz, CDCl$_3$) δ 1.01 (t, J=7.4 Hz, 12H), 1.30-1.75 (m, 23H), 1.44 (s, 9H), 1.84-1.98 (m, 2H), 2.13-2.42 (m, 2H), 2.97-3.12 (m, 1H), 3.20-3.46 (m, 10H), 3.80-4.15 (m, 2H), 4.36 (br s, 1H), 4.86 (br s, 1H), 8.43 (br s, 1H); MS m/z 490 [M−Bu$_4$N]$^-$.

All the amount of the above tetrabutylammonium salt was dissolved in methylene chloride (5.7 mL), and trifluoroacetic acid (5.7 mL) was added under ice-cooling, followed by agitating at 0° C. for 30 minutes. The reaction solution was concentrated under reduced pressure and the resulting residue was washed with diethyl ether, followed by adjusting to pH 7 with sodium bicarbonate aqueous solution, purifying by octadecyl silica gel column chromatography (water), and lyophilizing. Thereby, 104 mg of the title compound was afforded (3 steps, yield 23%).

$^1$H NMR (400 MHz, D$_2$O) δ 1.42-2.17 (m, 10H), 2.83-2.97 (m, 1H), 3.06 (d, J=12.0 Hz, 1H), 3.23 (br d, J=12.0 Hz, 1H), 3.34 (br d, J=12.0 Hz, 1H), 3.81 (dd, J=12.0, 3.0 Hz, 1H), 3.99-4.13 (m, 2H); MS m/z 392 [M+H]$^+$.

Example 37

(2S,5R)-7-Oxo-N'-[(2R)-piperidine-2-ylcarbonyl]-6-(sulfooxy)-1,6-diazabicyclo[3.2.1]octane-2-carbohydrazide

Step 1 tert-butyl (2R)-2-[(2-{[(2S,5R)-6-Benzyloxy-7-oxo-1,6-diazabicyclo[3.2.1]oct-2-yl]carbonyl}hydrazinyl)carbonyl]piperidine-1-carboxylate Following a procedure analogous to Example 27, from the carboxylic acid (6b, 390 mg, 1.41 mmol) of Example 9 or 16 and (R)-tert-butyl 2-(hydrazinecarbonyl)piperidine-1-carboxylate (630 mg, prepared following a procedure analogous to Reference Example; Hydrogen addition), 648 mg of the title compound was afforded (yield 92%).

$^1$H NMR (400 MHz, CDCl$_3$) δ 1.35-1.72 (m, 6H), 1.49 (s, 9H), 1.90-2.06 (m, 2H), 2.15-2.40 (m, 2H), 2.80-3.32 (m, 5H), 3.94-4.07 (m, 2H), 4.86 (br s, 1H), 4.92 (d, J=11.4 Hz, 1H), 5.06 (d, J=11.4 Hz, 1H), 7.34-7.45 (m, 5H), 8.40 (br s, 1H); MS m/z 502 [M+H]$^+$.

Step 2 tert-Butyl (2R)-2-[(2-{[(2S,5R)-6-hydroxy-7-oxo-1,6-diazabicyclo[3.2.1]oct-2-yl]carbonyl}hydrazinyl)carbonyl]piperidine-1-carboxylate Following a procedure analogous to Example 17, from all the amount of the compound of the above Step 1, the title compound was afforded (quantitative).

$^1$H NMR (400 MHz, CD$_3$OD) δ 1.35-1.60 (m, 2H), 1.46 (s, 9H), 1.60-1.82 (m, 4H), 1.87-2.15 (m, 2H), 2.17-2.34 (m, 2H), 3.10-3.20 (m, 2H), 3.24-3.36 (m, 2H), 3.67-3.73 (m, 1H), 3.91-4.05 (m, 2H); MS m/z 412 [M+H]$^+$.

Step 3

(2S,5R)-7-Oxo-N'-[(2R)-piperidine-2-ylcarbonyl]-6-(sulfooxy)-1,6-diazabicyclo[3.2.1]octane-2-carbohydrazide Following a procedure analogous to Example 17, from all the amount of the compound of the above Step 2, tetrabutylammonium tert-butyl (2R)-2-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate was afforded (quantitative). MS m/z 490 [M–Bu$_4$N]$^-$.

All the amount of the above tetrabutylammonium salt was deprotected with trifluoroacetic acid, and purified by octadecyl silica gel column chromatography to afford 158.8 mg of the title compound (3 steps, yield 31%).

$^1$H NMR (400 MHz, D$_2$O) δ 1.42-1.88 (m, 7H), 1.91-2.01 (m, 1H), 2.03-2.17 (m, 2H), 2.88-2.98 (m, 1H), 3.05 (d, J=12.0 Hz, 1H), 3.22 (br d, J=12.0 Hz, 1H), 3.35 (br d, J=12.8 Hz, 1H), 3.89 (dd, J=12.0, 3.2 Hz, 1H), 3.99-4.13 (m, 2H); MS m/z 392 [M+H]$^+$.

Example 38

(2S,5R)-7-Oxo-N'-[(2S)-pyrrolidin-2-ylcarbonyl]-6-(sulfooxy)-1,6-diazabicyclo[3.2.1]octane-2-carbohydrazide

Step 1 tert-Butyl (2S)-2-[(2-{[(2S,5R)-6-benzyloxy-7-oxo-1,6-diazabicyclo[3.2.1]oct-2-yl]carbonyl}hydrazinyl)carbonyl]pyrrolidine-1-carboxylate Following a procedure analogous to Example 27, from the carboxylic acid (6b, 390 mg, 1.41 mmol) of Example 9 or 16 and (S)-tert-butyl 2-(hydrazinecarbonyl)pyrrolidine-1-carboxylate (573 mg) described in Reference Example 6, 555 mg of the title compound was afforded (yield 80.1%).

$^1$H NMR (400 MHz, CD$_3$OD) δ 1.41 (s, 9H), 1.70-1.73 (m, 1H), 1.86-2.09 (m, 5H), 2.13-2.28 (m, 2H), 3.01-3.04 (br d, J=11.6 Hz, 1H), 3.15-3.21 (t, J=11.6 Hz, 1H), 3.31-3.40 (m, 1H), 3.48-3.56 (m, 2H), 3.94-3.96 (d, J=7.2 Hz, 1H), 4.23-4.26 (d, J=7.2 Hz, 1H), 4.91-4.94 (d, J=11.6 Hz, 1H), 4.98-5.01 (d, J=11.6 Hz, 1H), 7.34-7.40 (m, 3H), 7.45-7.47 (m, 2H); MS m/z 488 [M+H]$^+$.

Step 2 tert-Butyl (2S)-2-[(2-{[(2S,5R)-6-hydroxy-7-oxo-1,6-diazabicyclo[3.2.1]oct-2-yl]carbonyl}hydrazinyl)carbonyl]pyrrolidine-1-carboxylate Following a procedure analogous to Example 17, from all the amount of the compound of the above Step 1, the title compound was afforded (quantitative).

$^1$H NMR (400 MHz, CD$_3$OD) δ 1.41 (s, 9H), 1.70-1.75 (m, 1H), 1.82-2.04 (m, 5H), 2.18-2.27 (m, 2H), 3.09-3.21 (m, 2H), 3.32-3.37 (m, 1H), 3.46-3.51 (m, 1H), 3.65 (br s, 1H), 3.89-3.91 (d, J 7.6 Hz, 1H), 4.20-4.23 (m, 1H); MS m/z 398 [M+H]$^+$.

Step 3

(2S,5R)-7-Oxo-N'-[(2S)-pyrrolidin-2-ylcarbonyl]-6-(sulfooxy)-1,6-diazabicyclo[3.2.1]octane-2-carbohydrazide Following a procedure analogous to Example 17, from all the amount of the compound of the above Step 2, 782.1 mg of tetrabutylammonium tert-butyl (2S)-2-[(2-{[(2S,5R)-7-oxo-6-(sulfooxy)-1,6-diazabicyclo[3.2.1]oct-2-yl]carbonyl}hydrazinyl)carbonyl]pyrrolidine-1-carboxylate was afforded (yield 96.3%). MS m/z 476 [M–Bu$_4$N]$^-$.

All the amount of the tetrabutylammonium salt was deprotected with trifluoroacetic acid, and purified by octadecyl silica gel column chromatography to afford 143.8 mg of the title compound (yield 35.2%).

$^1$H NMR (400 MHz, D$_2$O) δ 1.66-1.85 (m, 6H), 2.04-2.16 (m, 2H), 2.99-3.30 (m, 4H), 3.87-4.18 (m, 3H); MS m/z 378 [M+H]$^+$.

Example 39

(2S,5R)-7-Oxo-N'-[(2R)-pyrrolidin-2-ylcarbonyl]-6-(sulfooxy)-1,6-diazabicyclo[3.2.1]octane-2-carbohydrazide

Step 1 tert-butyl (2R)-2-[(2-{[(2S,5R)-6-Benzyloxy-7-oxo-1,6-diazabicyclo[3.2.1]oct-2-yl]carbonyl}hydrazinyl)carbonyl]pyrrolidine-1-carboxylate Following a procedure analogous to Example 27, from the carboxylic acid (6b, 390 mg, 1.41 mmol) of Example 9 or 16 and (R)-tert-butyl 2-(hydrazinecarbonyl)pyrrolidine-1-carboxylate (573 mg, prepared following procedures analogous to Reference Example 5 and Reference Example 6), 624.3 mg of the title compound was afforded (yield 90.8%).

$^1$H NMR (400 MHz, CDCl$_3$) δ 1.40 (s, 9H), 1.52-1.57 (m, 1H), 1.81-1.97 (m, 5H), 2.25-2.56 (m, 2H), 3.01-3.07 (m, 2H), 3.17 (br s, 1H), 3.17-3.42 (m, 2H), 3.94-3.96 (d, J=7.2 Hz, 1H), 4.30 (m, 1H), 4.82-4.85 (d, J=11.2 Hz, 1H), 4.97-5.00 (d, J=11.2 Hz, 1H), 7.27-7.37 (m, 5H), 8.37 (br s, 1H), 8.94 (br s, 1H); MS m/z 488 [M+H]$^+$.

Step 2 tert-Butyl (2R)-2-[(2-{[(2S,5R)-6-hydroxy-7-oxo-1,6-diazabicyclo[3.2.1]oct-2-yl]carbonyl}hydrazinyl)carbonyl]pyrrolidine-1-carboxylate Following a procedure analogous to Example 17, from all the amount of the compound of the above Step 1, the title compound was afforded (quantitative).

$^1$H NMR (400 MHz, CDCl$_3$) δ 1.40 (s, 9H), 1.52-1.57 (m, 1H), 1.81-1.97 (m, 5H), 2.25-2.56 (m, 2H), 3.01-3.07 (m, 2H), 3.17 (br s, 1H), 3.17-3.42 (m, 2H), 3.94-3.96 (d, J=7.2 Hz, 1H), 4.30 (m, 1H), 4.82-4.85 (d, J=11.2 Hz, 1H), 4.97-5.00 (d, J=11.2 Hz, 1H), 7.27-7.37 (m, 5H), 8.37 (br s, 1H), 8.94 (br s, 1H); MS m/z 398 [M+H]$^+$.

Step 3

(2S,5R)-7-Oxo-N'-[(2R)-pyrrolidin-2-ylcarbonyl]-6-(sulfooxy)-1,6-diazabicyclo[3.2.1]octane-2-carbohydrazide Following a procedure analogous to Example 17, from all the amount of the compound of the above Step 2, tetrabutylammonium tert-butyl (2R)-2-[(2-{[(2S,5R)-7-oxo-6-(sulfooxy)-1,6-diazabicyclo[3.2.1]oct-2-yl]carbonyl}hydrazinyl)carbonyl]pyrrolidine-1-carboxylate (quantitative) was afforded. Subsequently, all the amount of the tetrabutylammonium salt was deprotected with trifluoroacetic acid, and purified by octadecyl silica gel column chromatography to afford 132.5 mg of the title compound (yield 27.4%).

$^1$H NMR (400 MHz, D$_2$O) δ 1.68-1.71 (m, 1H), 1.76-1.88 (m, 4H), 1.92 (m, 1H), 2.04-2.18 (m, 2H), 2.99-3.02 (d, J=12.0 Hz, 1H), 3.04-3.21 (m, 3H), 3.92-4.00 (m, 2H), 4.06 (br s, 1H); MS m/z 378 [M+H]$^+$.

Example 40

(2S,5R)-N'-{[(2S,4R)-4-Cyclopropylmethylpiperidine-2-yl]carbonyl}-7-oxo-6-(sulfooxy)-1,6-diazabicyclo[3.2.1]octane-2-carbohydrazide

Step 1 tert-Butyl (2S,4R)-2-[2-{[(2S,5R)-6-benzyloxy-7-oxo-1,6-diazabicyclo[3.2.1]oct-2-yl]carbonyl}hydrazinyl)carbonyl]-4-cyclopropylmethylpiperidine-1-carboxylate Following a procedure analogous to Example 27, from the carboxylic acid (6b, 390 mg, 1.41 mmol) of Example 9 or 16 and (2S,4R)-tert-butyl 4-(cyclopropylmethyl)-2-(hydrazinecarbonyl)piperidine-1-carboxylate (595 mg, prepared following procedures analogous to Reference Example 5 and Reference Example 6), 707.6 mg of the title compound was afforded (yield 90.3%).

$^1$H NMR (400 MHz, CDCl$_3$) δ 0.01 (m, 2H), 0.40-0.42 (m, 2H), 0.66 (m, 1H), 1.18-1.68 (m, 8H), 1.46 (s, 9H), 1.82-2.17 (m, 2H), 2.30-2.34 (m, 1H), 3.10-3.18 (m, 2H), 3.29-3.33 (m, 2H), 3.65 (m, 1H), 4.01-4.02 (d, J=7.2 Hz, 1H), 4.40-4.44 (m, 1H), 4.89-4.92 (d, J=11.6 Hz, 1H), 5.04-5.07 (d, J=11.2 Hz, 1H), 7.26-7.44 (m, 5H), 8.02 (br s, 1H), 8.39 (br s, 1H); MS m/z 556 [M+H]$^+$.

Step 2 tert-Butyl (2S,4R)-4-cyclopropylmethyl-2-[(2-{[(2S,5R)-6-hydroxy-7-oxo-1,6-diazabicyclo[3.2.1]oct-2-yl]carbonyl}hydrazinyl)carbonyl]piperidine-1-carboxylate Following a procedure analogous to Example 17, from all the amount of the compound of the above Step 1, the title compound was afforded (quantitative).

$^1$H NMR (400 MHz, CD$_3$OD) δ 0.01 (m, 2H), 0.38 (m, 2H), 0.67 (m, 1H), 1.21-1.24 (m, 2H), 1.42 (s, 9H), 1.70-1.94 (m, 6H), 2.06-2.10 (m, 2H), 2.19-2.25 (m, 1H), 3.10-3.26 (m, 4H), 3.66 (m, 1H), 3.90-3.92 (d, J=7.2 Hz, 1H), 4.25 (m, 1H); MS m/z 466 [M+H]$^+$.

Step 3

(2S,5R)-N'-{[(2S,4R)-4-Cyclopropylmethylpiperidine-2-yl]carbonyl}-7-oxo-6-(sulfooxy)-1,6-diazabicyclo[3.2.1]octane-2-carbohydrazide Following a procedure analogous to Example 17, from all the amount of the compound of the above Step 2, 993.5 mg of tetrabutylammonium tert-butyl (2S,4R)-4-cyclopropylmethyl-2-[(2-{[(2S,5R)-7-oxo-6-(sulfooxy)-1,6-diazabicyclo[3.2.1]oct-2-yl]carbonyl}hydrazinyl)carbonyl]piperidine-1-carboxylate was afforded (yield 98.9%). MS m/z 544 [M−Bu$_4$N]$^-$.

All the amount of the tetrabutylammonium salt was deprotected with trifluoroacetic acid, and purified by octadecyl silica gel column chromatography to afford 221.9 mg of the title compound (yield 39.5%).

$^1$H NMR (400 MHz, D$_2$O) δ 0.01 (m, 2H), 0.37-0.42 (m, 2H), 0.66-0.70 (m, 1H), 1.18-1.22 (m, 2H), 1.31-1.41 (m, 1H), 1.42-1.52 (dd, J=13.2 Hz, 1H), 1.73-2.06 (m, 5H), 2.15-2.20 (m, 1H), 2.32-2.35 (m, 1H), 3.01-3.05 (td, J=2.8, 13.2 Hz, 1H), 3.13-3.16 (d, J=12.0 Hz, 1H), 3.30-3.33 (d,

J=12.4 Hz, 1H), 3.46-3.49 (d, J=13.2 Hz, 1H), 3.98-4.02 (dd, 2.8, 12.8 Hz, 1H), 4.12-4.14 (d, 8.8 Hz, 1H), 4.18 (br s, 1H); MS m/z 446 [M+H]$^+$.

Example 41

Sodium (2S,5R)-7-oxo-N'-{[(2S)-5-oxopyrrolidin-2-yl]carbonyl}-6-(sulfooxy)-1,6-diazabicyclo[3.2.1]octane-2-carbohydrazide

Step 1 tert-Butyl (2S)-2-[(2-{[(2S,5R)-6-benzyloxy-7-oxo-1,6-diazabicyclo[3.2.1]oct-2-yl]carbonyl}hydrazinyl)carbonyl]-5-oxopyrrolidine-1-carboxylate Following a procedure analogous to Example 27, from the carboxylic acid (6b, 390 mg, 1.41 mmol) of Example 9 or 16 and (S)-tert-butyl 2-(hydrazinecarbonyl)-5-oxopyrrolidine-1-carboxylate (730 mg, prepared following procedures analogous to Reference Example 5 and Reference Example 6), 643.5 mg of the title compound was afforded (yield 90.9%).

$^1$H NMR (400 MHz, CDCl$_3$) δ 1.50 (s, 9H), 1.57-1.66 (m, 1H), 1.89-2.02 (m, 2H), 2.21-2.31 (m, 3H), 2.42-2.49 (m, 1H), 2.72-2.81 (m, 1H), 3.06 (m, 2H), 3.29 (br s, 1H), 4.01-4.02 (d, J=6.8 Hz, 1H), 4.59-4.62 (m, 1H), 4.87-4.90 (d, J=11.6 Hz, 1H), 5.02-5.05 (d, J=11.2 Hz, 1H), 7.34-7.41 (m, 5H), 8.25 (br s, 1H), 8.52 (br s, 1H); MS m/z 502 [M+H]$^+$.

Step 2 tert-Butyl (2S)-2-[(2-{[(2S,5R)-6-hydroxy-7-oxo-1,6-diazabicyclo[3.2.1]oct-2-yl]carbonyl}hydrazinyl)carbonyl]-5-oxopyrrolidine-1-carboxylate Following a procedure analogous to Example 17, from all the amount of the compound of the above Step 1, the title compound was afforded (quantitative).

$^1$H NMR (400 MHz, CD$_3$OD) δ 1.45 (s, 9H), 1.76 (m, 1H), 1.88-1.99 (m, 1H), 2.05-2.19 (m, 2H), 2.22-2.26 (m, 1H), 2.34-2.50 (m, 2H), 2.58-2.68 (m, 1H), 3.12-3.16 (br d, J=12.4 Hz, 1H), 3.20-3.37 (d, J=12.0 Hz, 1H), 3.70 (br s, 1H), 3.94-3.96 (d, J=7.6 Hz, 1H), 4.66-4.69 (d, J=9.2 Hz, 1H); MS m/z 412 [M+H]$^+$.

Step 3

Sodium (2S,5R)-7-oxo-N'-{[(2S)-5-oxopyrrolidin-2-yl]carbonyl}-6-(sulfooxy)-1,6-diazabicyclo[3.2.1]octane-2-carbohydrazide Following a procedure analogous to Example 17, from all the amount of the compound of the above Step 2, tetrabutylammonium tert-butyl (2S)-2-[(2-{[(2S,5R)-7-oxo-6-(sulfooxy)-1,6-diazabicyclo[3.2.1]oct-2-yl]carbonyl}hydrazinyl)carbonyl]-5-oxopyrrolidine-1-carboxylate was afforded (quantitative). All the amount of the tetrabutylammonium salt was deprotected with trifluoroacetic acid, and neutralized with saturated sodium bicarbonate aqueous solution, then purified by octadecyl silica gel column chromatography to afford 292.6 mg of the title compound (yield 55.9%).

$^1$H NMR (400 MHz, D$_2$O) δ 1.63-1.70 (m, 1H), 1.76-1.86 (m, 1H), 1.92-2.10 (m, 3H), 2.23-2.49 (m, 3H), 3.06-3.09 (d, J=12.0 Hz, 1H), 3.19-3.22 (d, J=12.0 Hz, 1H), 4.02-4.04 (d, J=11.2 Hz, 1H), 4.07 (br s, 1H), 4.27-4.30 (dd, J=5.2, 8.8 Hz, 1H); MS m/z 392 [M−Na+2H]$^+$.

Example 42

Sodium (2S,5R)-7-oxo-N'-{[(2R)-5-oxopyrrolidin-2-yl]carbonyl}-6-(sulfooxy)-1,6-diazabicyclo[3.2.1]octane-2-carbohydrazide

Step 1 tert-Butyl (2R)-2-[(2-{[(2S,5R)-6-benzyloxy-7-oxo-1,6-diazabicyclo[3.2.1]oct-2-yl]carbonyl}hydrazinyl)carbonyl]-5-oxopyrrolidine-1-carboxylate Following a procedure analogous to Example 27, the carboxylic acid (6b, 390 mg, 1.41 mmol) of Example 9 or 16 and (R)-tert-butyl 2-(hydrazinecarbonyl)-5-oxopyrrolidine-1-carboxylate (730 mg, prepared following a procedure analogous to Reference Example 6 from the compound described in Reference Example 4), 431.2 mg of the title compound was afforded (yield 60.9%).

$^1$H NMR (400 MHz, CDCl$_3$) δ 1.44 (s, 9H), 1.56 (m, 1H), 1.81-1.91 (m, 2H), 2.14-2.28 (m, 3H), 2.34-2.44 (m, 1H), 2.64-2.73 (m, 1H), 3.00-3.17 (m, 2H), 3.20 (s, 1H), 3.92-3.94 (d, J=7.2 Hz, 1H), 4.51-4.53 (d, J=5.6 Hz, 1H), 4.82-4.85 (d, J=11.2 Hz, 1H), 4.96-4.99 (d, J=11.6 Hz, 1H), 7.29-7.36 (m, 5H), 8.13 (br s, 1H), 8.43 (br s, 1H); MS m/z 502 [M+H]$^+$.

Step 2 tert-Butyl (2R)-2-[(2-{[(2S,5R)-6-hydroxy-7-oxo-1,6-diazabicyclo[3.2.1]oct-2-yl]carbonyl}hydrazinyl)carbonyl]-5-oxopyrrolidine-1-carboxylate Following a procedure analogous to Example 17, from all the amount of the compound of the above Step 1, the title compound was afforded (quantitative). MS m/z 412 [M+H]$^+$.

Step 3

Sodium (2S,5R)-7-oxo-N'-{[(2R)-5-oxopyrrolidin-2-yl]carbonyl}-6-(sulfooxy)-1,6-diazabicyclo[3.2.1]octane-2-carbohydrazide Following a procedure analogous to Example 17, from all the amount of the compound of the above Step 2, tetrabutylammonium tert-butyl (2R)-2-[(2-{[(2S,5R)-7-oxo-6-(sulfooxy)-1,6-diazabicyclo[3.2.1]oct-2-yl]carbonyl}hydrazinyl)carbonyl]-5-oxopyrrolidine-1-carboxylate was afforded (quantitative). MS m/z 490 [M−Bu$_4$N]$^-$.

All the amount of the tetrabutylammonium salt was deprotected with trifluoroacetic acid, and neutralized with saturated sodium bicarbonate aqueous solution, and then purified by octadecyl silica gel column chromatography to afford 179.5 mg of the title compound (yield 50.5%).

$^1$H NMR (400 MHz, D$_2$O) δ 1.67-1.71 (m, 1H), 1.78-1.86 (m, 1H), 1.92-2.16 (m, 3H), 2.26-2.45 (m, 3H), 3.04-3.07 (d, J=12.4 Hz, 1H), 3.19-3.22 (br d, J=12.0 Hz, 1H), 4.01-4.03 (d, J=8.4 Hz, 1H), 4.06 (br s, 1H), 4.22-4.28 (dd, J=4.8, 8.8 Hz, 1H); MS m/z 392 [M−Na+2H]$^+$.

Example 43

Sodium (2S,5R)-N'-(furan-2-ylcarbonyl)-7-oxo-6-(sulfooxy)-1,6-diazabicyclo[3.2.1]octane-2-carbohydrazide Step 1

(2S,5R)-6-Benzyloxy-N'-(furan-2-ylcarbonyl)-7-oxo-1,6-diazabicyclo[3.2.1]octane-2-carbohydrazide Following a procedure analogous to Example 27, from the carboxylic acid (6b, 552 mg, 2.00 mmol) of Example 9 or 16 and furan-2-carbohydrazide (390 mg, prepared following a procedure analogous to Reference Example 6 from the compound described in Reference Example 3), 291.8 mg of the title compound was afforded (yield 37.9%).

$^1$H NMR (400 MHz, CDCl$_3$) δ 1.57-1.65 (m, 1H), 1.89-2.02 (m, 2H), 2.33-2.38 (m, 1H), 3.10-3.13 (d, J=11.6 Hz, 1H), 3.21-3.24 (d, J=12.0 Hz, 1H), 3.31 (s, 1H), 4.07-4.12 (m, 1H), 4.89-4.92 (d, J=11.2 Hz, 1H), 5.03-5.06 (d, J=11.2 Hz, 1H), 6.50-6.52 (dd, J=1.6, 3.2 Hz, 1H), 7.17 (d, J=3.2 Hz, 1H), 7.32-7.43 (m, 5H), 7.47 (d, J=1.6 Hz, 1H), 8.41 (m, 1H), 8.62 (m, 1H); MS m/z 385 [M+H]$^+$

Step 2

(2S,5R)-N'-(Furan-2-ylcarbonyl)-6-hydroxy-7-oxo-1,6-diazabicyclo[3.2.1]octane-2-carbohydrazide Following a procedure analogous to Example 17, from all the amount of the compound of the above Step 1, the title compound was afforded (quantitative). MS m/z 295 [M+H]$^+$.

Step 3

Sodium (2S,5R)-N'-(furan-2-ylcarbonyl)-7-oxo-6-(sulfooxy)-1,6-diazabicyclo[3.2.1]octane-2-carbohydrazide Following a procedure analogous to Example 22, from all the amount of the compound of the above Step 2, pyridinium (2S,5R)-N'-(furan-2-ylcarbonyl)-7-oxo-6-(sulfooxy)-1,6-diazabicyclo[3.2.1]octane-2-carbohydrazide was afforded, and neutralized with saturated sodium bicarbonate aqueous solution, and then purified by octadecyl silica gel column chromatography to afford 54.8 mg of the title compound (yield 18.2%).

$^1$H NMR (400 MHz, D$_2$O) δ 1.66-1.74 (m, 1H), 1.80-1.97 (m, 2H), 2.08-2.17 (m, 1H), 3.11-3.14 (d, J=12.0 Hz, 1H), 3.23-3.26 (d, J=12.4 Hz, 1H), 4.09 (m, 2H), 6.51 (d, J=3.6 Hz, 1H), 7.13 (d, J=3.6 Hz, 1H), 7.58 (s, 1H); MS m/z 375 [M−Na+2H]$^+$.

Example 44

Sodium (2S,5R)-N'-(1,3-oxazol-4-ylcarbonyl)-7-oxo-6-(sulfooxy)-1,6-diazabicyclo[3.2.1]octane-2-carbohydrazide Step 1

(2S,5R)-6-Benzyloxy-N'-(1,3-oxazol-4-ylcarbonyl)-7-oxo-1,6-diazabicyclo[3.2.1]octane-2-carbohydrazide Following a procedure analogous to Example 27, from the carboxylic acid (6b, 390 mg, 1.41 mmol) of Example 9 or 16 and oxazol-4-carbohydrazide (613 mg, prepared following a procedure analogous to Reference Example 2), 335.2 mg of the title compound was afforded (yield 61.7%).

$^1$H NMR (400 MHz, CDCl$_3$) δ 1.63-1.65 (m, 1H), 1.80-2.00 (m, 2H), 2.29-2.37 (m, 1H), 3.08-3.11 (br d, J=13.2 Hz, 1H), 3.15-3.18 (d, J=12.0 Hz, 1H), 3.30 (br s, 1H), 4.07-4.08 (d, J=7.2 Hz, 1H), 4.87-4.91 (d, J=11.2 Hz, 1H), 5.02-5.06 (d, J=11.2 Hz, 1H), 7.34-7.42 (m, 5H), 7.88 (s, 1H), 8.25 (s, 1H), 8.61 (br s, 1H), 8.73 (br s, 1H); MS m/z 386 [M+H]$^+$.

Step 2

(2S,5R)-6-Hydroxy-N'-(1,3-oxazol-4-ylcarbonyl)-7-oxo-1,6-diazabicyclo[3.2.1]octane-2-carbohydrazide Following a procedure analogous to Example 17, from all the amount of the compound of the above Step 1, the title compound was afforded (quantitative). MS m/z 296 [M+H]$^+$.

Step 3

Sodium (2S,5R)-N'-(1,3-oxazol-4-ylcarbonyl)-7-oxo-6-(sulfooxy)-1,6-diazabicyclo[3.2.1]octane-2-carbohydrazide Following a procedure analogous to Example 22, from all the amount of the compound of the above Step 2, pyridinium (2S,5R)-N'-(1,3-oxazol-4-ylcarbonyl)-7-oxo-6-(sulfooxy)-1,6-diazabicyclo[3.2.1]octane-2-carbohydrazide was afforded, and neutralized with saturated sodium bicarbonate aqueous solution, and then purified by octadecyl silica gel column chromatography to afford 195 mg of the title compound (yield 56.5%).

$^1$H NMR (400 MHz, D$_2$O) δ 1.70-1.73 (m, 1H), 1.75-1.88 (m, 1H), 1.93-1.97 (m, 1H), 2.06-2.14 (m, 1H), 3.09-3.12 (d, J=12.0 Hz, 1H), 3.18-3.24 (br d, J=12.8 Hz, 1H), 4.04-4.06 (d, J=7.6 Hz, 1H), 4.08-4.09 (m, 1H), 8.05 (s, 1H), 8.27 (s, 1H); MS m/z 376 [M−Na+2H]$^+$.

Example 45

Sodium (2S,5R)-7-oxo-N'-(pyridine-3-ylcarbonyl)-6-(sulfooxy)-1,6-diazabicyclo[3.2.1]octane-2-carbohydrazide Step 1

(2S,5R)-6-Benzyloxy-7-oxo-N'-(pyridine-3-ylcarbonyl)-1,6-diazabicyclo[3.2.1]octane-2-carbohydrazide A solution of the carboxylic acid (6b, 390 mg, 1.41 mmol) of Example 9 or 16 in dehydrated methylene chloride (14.1 mL) was cooled to 0° C. under an argon atmosphere, and isobutyl chloroformate (231.1 mg) was gradually added so that the temperature does not exceed 0° C. Then, triethylamine (185 mg) was gradually added so that the temperature does not exceed 0° C. followed by stirring for 30 minutes, thereby a mixed acid anhydride in the reaction system was prepared. To this reaction mixture was gradually added nicotinic acid hydrazide (580 mg). After the addition, the temperature was raised to room temperature, followed by stirring for 1 hour. This reaction mixture was washed with 0.5M hydrochloric acid and saturated brine, and the organic layer was dried over magnesium sulfate, and then distilled off under reduced pressure. The resulting residue was subjected to silica gel column chromatography (hexane/ethyl acetate=4/1-0/1, ethyl acetate/methanol=30/1) to afford 439.5 mg of the title compound as a colorless oil (yield 78.8%).

$^1$H NMR (400 MHz, CD$_3$OD) δ 1.68-1.75 (m, 1H), 1.88-2.02 (m, 2H), 2.25-2.30 (m, 1H), 3.08-3.11 (d, J=12.4 Hz, 1H), 3.28-3.33 (m, 1H), 3.60 (br s, 1H), 4.03-4.08 (d, J=12.0 Hz, 1H), 4.90 (d, J=11.2 Hz, 1H), 5.00 (d, J=11.2 Hz, 1H), 7.33-7.41 (m, 3H), 7.45-7.48 (m, 2H), 7.54-7.58 (dd, J=5.0, 8.0 Hz, 1H), 8.26-8.29 (dd, J=2.0, 8.0 Hz, 1H), 8.71-8.72 (dd, J=1.2, 4.8 Hz, 1H), 9.00-9.01 (dd, J=0.8, 2.0 Hz, 1H); MS m/z 396 [M+H]$^+$.

Step 2

(2S,5R)-6-Hydroxy-7-oxo-N'-(pyridine-3-ylcarbonyl)-1,6-diazabicyclo[3.2.1]octane-2-carbohydrazide All the amount of the compound of the above Step 1 was dissolved in methanol (11 mL), and 10% palladium-carbon (50% water content, 80 mg) was added, followed by stirring under hydrogen atmosphere at room temperature for 1 hour. The catalyst of the reaction mixture was filtered through Celite, and the solvent was concentrated under reduced pressure to afford 319.7 mg of the title compound (yield 94.3%). MS m/z 306 [M+H]$^+$.

Step 3

Sodium (2S,5R)-7-oxo-N'-(pyridine-3-ylcarbonyl)-6-(sulfooxy)-1,6-diazabicyclo[3.2.1]octane-2-carbohydrazide To a solution of all the amount of the compound of the above Step 2 in pyridine (10.0 mL) was added sulfur trioxide-pyridine complex (796 mg), followed by agitating at room temperature overnight. To the reaction solution was added methylene chloride, followed by filtration and concentration under reduced pressure. To the resulting residue was added toluene, followed by azeotropy. Thereby, pyridinium (2S,5R)-7-oxo-N'-(pyridine-3-ylcarbonyl)-6-(sulfooxy)-1,6-diazabicyclo[3.2.1]octane-2-carbohydrazide was afforded, and neutralized with saturated sodium bicarbonate aqueous solution, and then purified by octadecyl silica gel column chromatography to afford 193.1 mg of the title compound (yield 45.6%).

$^1$H NMR (400 MHz, D$_2$O) δ 1.67-1.75 (m, 1H), 1.80-1.90 (m, 1H), 1.95-1.99 (m, 1H), 2.06-2.16 (m, 1H), 3.14-3.18 (d, J=12.4 Hz, 1H), 3.25-3.28 (br d, J=12.0 Hz, 1H), 4.10 (m, 2H), 7.46-7.49 (dd, J=5.2, 8.0 Hz, 1H), 8.12-8.14 (d, J=8.0 Hz, 1H), 8.58-8.60 (d, J=5.2 Hz, 1H), 8.81 (s, 1H); MS m/z 386 [M−Na+2H]$^+$

Example 46

Sodium (2S,5R)-7-oxo-N'-(pyridine-4-ylcarbonyl)-6-(sulfooxy)-1,6-diazabicyclo[3.2.1]octane-2-carbohydrazide Step 1

(2S,5R)-6-Benzyloxy-7-oxo-N'-(pyridine-4-ylcarbonyl)-1,6-diazabicyclo[3.2.1]octane-2-carbohydrazide Following a procedure analogous to Example 27, from the carboxylic acid (6b, 390 mg, 1.41 mmol) of Example 9 or 16 and isonicotinic acid hydrazide (580.1 mg, commercially available), the title compound was afforded (quantitative).

$^1$H NMR (500 MHz, CDCl$_3$) δ 1.60 (m, 1H), 1.97-2.04 (m, 2H), 2.34-2.36 (m, 1H), 3.15 (m, 2H), 3.35 (br s, 1H), 4.08-4.12 (m, 1H), 4.92-4.94 (d, J=11.0 Hz, 1H), 5.06-5.08 (d, J=11.0 Hz, 1H), 7.26-7.46 (m, 5H), 7.67-7.68 (m, 2H), 8.78-8.79 (m, 2H); MS m/z 396 [M+H]$^+$.

Step 2

(2S,5R)-6-Hydroxy-7-oxo-N'-(pyridine-4-ylcarbonyl)-1,6-diazabicyclo[3.2.1]octane-2-carbohydrazide Following a procedure analogous to Example 17, from all the amount of the compound of the above Step 1, the title compound was afforded (quantitative).

$^1$H NMR (400 MHz, CD$_3$OD) δ 1.69-1.77 (m, 1H), 1.86-1.97 (m, 1H), 2.02-2.11 (m, 1H), 2.19-2.31 (m, 1H), 3.16-3.36 (m, 2H), 3.68 (br s, 1H), 3.97-3.99 (d, J=6.8 Hz, 1H), 7.79-7.80 (d, J=6.0 Hz, 2H), 8.65-8.65 (d, J=6.4 Hz, 2H); MS m/z 306 [M+H]$^+$.

Step 3

Sodium (2S,5R)-7-oxo-N'-(pyridine-4-ylcarbonyl)-6-(sulfooxy)-1,6-diazabicyclo[3.2.1]octane-2-carbohydrazide Following a procedure analogous to Example 26, from all the amount of the compound of the above Step 2, pyridinium (2S,5R)-7-oxo-N'-(pyridine-4-ylcarbonyl)-6-(sulfooxy)-1,6-diazabicyclo[3.2.1]octane-2-carbohydrazide was afforded, and neutralized with saturated sodium bicarbonate aqueous solution, then purified by octadecyl silica gel column chromatography to afford 255.9 mg of the title compound (yield 44.5%).

$^1$H NMR (400 MHz, D$_2$O) δ 1.65-1.73 (m, 1H), 1.78-1.86 (m, 1H), 1.93-197 (m, 1H), 2.04-2.14 (m, 1H), 3.12-3.15 (d, J=12.0 Hz, 1H), 3.23-3.26 (d, J=6.8 Hz, 1H), 4.08-4.10 (m, 2H), 7.72-7.73 (d, J=4.4 Hz, 2H), 8.60-8.61 (d, J=5.2 Hz, 2H); MS m/z 386 [M−Na+2H]$^+$.

Example 47

Sodium N,N-dimethyl2-{[(2S,5R)-7-oxo-6-(sulfooxy)-1,6-diazabicyclo[3.2.1]oct-2-yl]carbonyl}hydrazinecarboxamide Step 1

2-{[(2S,5R)-6-Benzyloxy-7-oxo-1,6-diazabicyclo[3.2.1]oct-2-yl]carbonyl}-N,N-dimethylhydrazinecarboxamide Following a procedure analogous to Example 45, from the carboxylic acid (6b, 400 mg, 1.44 mmol) of Example 9 or 16 and N,N-dimethylhydrazinecarboxamide (491 mg, prepared following procedures analogous to Reference Example 3 and Reference Example 6), 385.2 mg of the title compound was afforded (yield 73.6%).

$^1$H NMR (400 MHz, CDCl$_3$) δ 1.61 (m, 1H), 1.90-2.02 (m, 2H), 2.32-2.37 (m, 1H), 2.95 (s, 6H), 3.05-3.08 (d, J=12.8 Hz, 1H), 3.25 (br s, 1H), 3.29-3.32 (d, J=12.0 Hz, 1H), 3.99-4.01 (d, J=6.8 Hz, 1H), 4.87-4.90 (d, J=11.2 Hz,

1H), 5.02-5.05 (d, J=11.2 Hz, 1H), 6.39 (br s, 1H), 7.34-7.41 (m, 5H), 8.24 (br s, 1H); MS m/z 361 [M+H]$^+$.

Step 2

2-{[(2S,5R)-6-Hydroxy-7-oxo-1,6-diazabicyclo[3.2.1]oct-2-yl]carbonyl}-N,N-dimethylhydrazinecarboxamide Following a procedure analogous to Example 17, from all the amount of the compound of the above Step 1, the title compound was afforded (quantitative). MS m/z 272 [M+H]$^+$.

Step 3

Sodium N,N-dimethyl2-{[(2S,5R)-7-oxo-6-(sulfooxy)-1,6-diazabicyclo[3.2.1]oct-2-yl]carbonyl}hydrazinecarboxamide Following a procedure analogous to Example 22, from all the amount of the compound of the above Step 2, pyridinium 2-{[(2S,5R)-7-oxo-6-(sulfooxy)-1,6-diazabicyclo[3.2.1]oct-2-yl]carbonyl}-N,N-dimethylhydrazinecarboxamide was afforded, and neutralized with saturated sodium bicarbonate aqueous solution, then purified by octadecyl silica gel column chromatography to afford 305.2 mg of the title compound (yield 77.1%).
$^1$H NMR (400 MHz, D$_2$O) δ 1.64-1.72 (m, 1H), 1.76-1.87 (m, 1H), 1.93-1.98 (m, 1H), 2.07-2.12 (m, 1H), 2.81 (s, 6H), 3.11-3.14 (d, J=12.4 Hz, 1H), 3.20-3.23 (d, J=12.4 Hz, 1H), 4.01-4.03 (d, J=11.2 Hz, 1H), 4.08-4.09 (m, 1H); MS m/z 352 [M−Na+2H]$^+$.

Example 48

Sodium N,N-diethyl2-{[(2S,5R)-7-oxo-6-(sulfooxy)-1,6-diazabicyclo[3.2.1]oct-2-yl]carbonyl}hydrazinecarboxamide Step 1

2-{[(2S,5R)-6-Benzyloxy-7-oxo-1,6-diazabicyclo[3.2.1]oct-2-yl]carbonyl}-N,N-diethylhydrazinecarboxamide Following a procedure analogous to Example 27, from the carboxylic acid (6b, 390 mg, 1.41 mmol) of Example 9 or 16 and N,N-diethylhydrazine carboxamide (656 mg, prepared following procedures analogous to Reference Example 3 and Reference Example 6), 108.6 mg of the title compound was afforded (yield 19.7%).
$^1$H NMR (400 MHz, CDCl$_3$) δ 1.16-1.19 (t, J=7.2 Hz, 6H), 1.55-1.62 (m, 1H), 1.89-2.05 (m, 2H), 2.24-2.36 (m, 1H), 3.06-3.09 (br d, J=12.4 Hz, 1H), 3.18-3.38 (m, 6H), 4.00-4.02 (br d, J=7.6 Hz, 1H), 4.87-4.90 (d, J=11.2 Hz, 1H), 5.04-5.06 (d, J=11.2 Hz, 1H), 6.36 (br s, 1H), 7.24-7.40 (m, 5H), 8.32 (br s, 1H); MS m/z 390 [M+H]$^+$.

Step 2

N,N-Diethyl 2-{[(2S,5R)-6-hydroxy-7-oxo-1,6-diazabicyclo[3.2.1]oct-2-yl]carbonyl}hydrazinecarboxamide Following a procedure analogous to Example 17, from all the amount of the compound of the above Step 1, the title compound was afforded (quantitative). MS m/z 300 [M+H]$^+$.

Step 3

Sodium N,N-diethyl 2-{[(2S,5R)-7-oxo-6-(sulfooxy)-1,6-diazabicyclo[3.2.1]oct-2-yl]carbonyl}hydrazinecarboxamide Following a procedure analogous to Example 22, from all the amount of the compound of the above Step 2, pyridinium N,N-diethyl 2-{[(2S,5R)-7-oxo-6-(sulfooxy)-1,6-diazabicyclo[3.2.1]oct-2-yl]carbonyl}hydrazinecarboxamide was afforded, and neutralized with saturated sodium bicarbonate aqueous solution, and then purified by octadecyl silica gel column chromatography to afford 63.0 mg of the title compound (yield 56.4%).
$^1$H NMR (400 MHz, D$_2$O) δ 0.97-1.01 (t, J=7.2 Hz, 6H), 1.62-1.68 (m, 1H), 1.70-1.85 (m, 1H), 1.92-1.96 (m, 1H), 2.05-2.11 (m, 1H), 3.09-3.22 (m, 6H), 3.99-4.01 (d, J=7.8 Hz, 1H), 4.06 (br s, 1H); MS m/z 380 [M−Na+2H]$^+$.

Example 49

Sodium 2-{[(2SR,5RS)-7-oxo-6-(sulfooxy)-1,6-diazabicyclo[3.2.1]oct-2-yl]carbonyl}-N-phenylhydrazinecarboxamide Step 1

2-{[(2SR,5RS)-6-Benzyloxy-7-oxo-1,6-diazabicyclo[3.2.1]oct-2-yl]carbonyl}-N-phenylhydrazinecarboxamide Following a procedure analogous to Example 30, from (2SR,5RS)-6-(benzyloxy)-7-oxo-1,6-diazabicyclo[3.2.1]octane-2-carboxylic acid (100 mg, 0.36 mmol) and N-phenylhydrazinecarboxamide (60 mg), 134 mg of the title compound was afforded (yield 94%). MS m/z 410 [M+H]$^+$.

Step 2

2-{[(2SR,5RS)-6-Hydroxy-7-oxo-1,6-diazabicyclo[3.2.1]oct-2-yl]carbonyl}-N-phenylhydrazinecarboxamide Following a procedure analogous to Example 17, from all the amount of the compound of the above Step 1, 35 mg of the title compound was afforded (yield 33%).
$^1$H NMR (400 MHz, CD$_3$OD) δ 1.76-1.82 (m, H), 1.91-1.98 (m, H), 2.04-2.08 (m, 1H), 2.25-2.31 (m, 1H), 3.17 (d, J=3.0, 1H), 3.25 (d, J=3.0, 1H), 3.70 (br. s, 1H), 4.00 (d, J=1.8, 1H), 7.00 (dd, J=2.1, 2.2, 1H), 7.23-7.28 (m, 1H), 7.39-7.42 (m, 1H); m/z 320 [M+H]$^+$.

Step 3

Sodium 2-{[(2SR,5RS)-7-oxo-6-(sulfooxy)-1,6-diazabicyclo[3.2.1]oct-2-yl]carbonyl}-N-phenylhydrazinecarboxamide Following a procedure analogous to Example 30, pyridinium 2-{[(2SR,5RS)-7-oxo-6-(sulfooxy)-1,6-diazabicyclo[3.2.1]oct-2-yl]carbonyl}-N-phenylhydrazine carboxamide obtained from the compound (30 mg, 0.10 mmol) of the above Step 2 was neutralized with saturated sodium bicarbonate aqueous solution, and purified by octadecyl silica gel column chromatography to afford 19 mg of the title compound (yield 43%).

¹H NMR (400 MHz, D₂O) δ 1.65-1.73 (m, 1H), 1.78-1.88 (m, 1H), 1.93-1.97 (m, 1H), 2.06-2.12 (m, 1H), 3.08 (d, J=3.0, 1H), 3.22 (d, J=3.2, 1H), 4.06 (m, 2H), 7.18-7.27 (m, 5H); MS m/z 400 [M−Na+2H]⁺.

Example 50

Sodium (2S,5R)-N'-(morpholin-4-ylcarbonyl)-7-oxo-6-(sulfooxy)-1,6-diazabicyclo[3.2.1]octane-2-carbohydrazide Step 1

(2S,5R)-6-Benzyloxy-N'-(morpholin-4-ylcarbonyl)-7-oxo-1,6-diazabicyclo[3.2.1]octane-2-carbohydrazide Following a procedure analogous to Example 27, from the carboxylic acid (6b, 390 mg, 1.41 mmol) of Example 9 or 16 and morpholine-4-carbohydrazide (584.3 mg, prepared following procedures analogous to Reference Example 3 and Reference Example 6), 323 mg of the title compound was afforded (yield 56.8%).

¹H NMR (400 MHz, CDCl₃) δ 1.58-1.65 (m, 1H), 1.91-2.02 (m, 2H), 2.32-2.37 (m, 1H), 3.06-3.09 (d, J=11.6 Hz, 1H), 3.24-3.27 (m, 1H), 3.36-3.46 (m, 4H), 3.63-3.69 (m, 4H), 4.00-4.02 (br d, J=7.6 Hz, 1H), 4.88-4.90 (d, J=11.2 Hz, 1H), 5.02-5.05 (d, J=11.2 Hz, 1H), 6.52 (br s, 1H), 7.34-7.42 (m, 5H), 8.30 (br s, 1H); MS m/z 404 [M+H]⁺.

Step 2

(2S,5R)-6-Hydroxy-N'-(morpholin-4-ylcarbonyl)-7-oxo-1,6-diazabicyclo[3.2.1]octane-2-carbohydrazide Following a procedure analogous to Example 17, from all the amount of the compound of the above Step 1, the title compound was afforded (quantitative). MS m/z 314 [M+H]⁺.

Step 3

Sodium (2S,5R)-N'-(morpholin-4-ylcarbonyl)-7-oxo-6-(sulfooxy)-1,6-diazabicyclo[3.2.1]octane-2-carbohydrazide Following a procedure analogous to Example 22, from all the amount of the compound of the above Step 2, pyridinium (2S,5R)-N'-(morpholin-4-ylcarbonyl)-7-oxo-6-(sulfooxy)-1,6-diazabicyclo[3.2.1]octane-2-carbohydrazide was afforded, and neutralized with saturated sodium bicarbonate aqueous solution, and then purified by octadecyl silica gel column chromatography to afford 152 mg of the title compound (yield 45.7%).

¹H NMR (400 MHz, D₂O) δ 1.65-1.72 (m, 1H), 1.78-1.88 (m, 1H), 1.94-1.98 (m, 1H), 2.07-2.13 (m, 1H), 3.10-3.13 (d, J=12.0 Hz, 1H), 3.21-3.24 (d, J=12.0 Hz, 1H), 3.32-3.35 (m, 4H), 3.61-3.63 (m, 4H), 4.02-4.04 (d, J=7.6 Hz, 1H), 4.08 (br s, 1H); MS m/z 394 [M−Na+2H]⁺.

Example 51

Sodium methyl 2-{[(2S,5R)-7-oxo-6-(sulfooxy)-1,6-diazabicyclo[3.2.1]oct-2-yl]carbonyl}hydrazinecarboxylate Step 1

Methyl 2-{[(2S,5R)-6-benzyloxy-7-oxo-1,6-diazabicyclo[3.2.1]oct-2-yl]carbonyl}hydrazinecarboxylate Following a procedure analogous to Example 17, from the carboxylic acid (6b, 1.30 g, 4.71 mmol) of Example 9 or 16 and methyl carbazate (538 mg), 1.64 g of the title compound was afforded (quantitative).

[α]_D²⁰ +53.2° (c 0.60, CHCl₃); ¹H NMR (400 MHz, CDCl₃) δ 1.56-1.68 (m, 1H), 1.90-2.08 (m, 2H), 2.30-2.40 (m, 1H), 3.02-3.20 (m, 2H), 3.30 (br s, 1H), 3.76 (br s, 3H), 4.01 (d, J=7.2 Hz, 1H), 4.91 (d, J=11.4 Hz, 1H), 5.06 (d, J=11.4 Hz, 1H), 6.59 (br s, 1H), 7.33-7.46 (m, 5H), 8.23 (br d, J=2.4 Hz, 1H); MS m/z 349 [M+H]⁺.

Step 2

Methyl 2-{[(2S,5R)-6-hydroxy-7-oxo-1,6-diazabicyclo[3.2.1]oct-2-yl]carbonyl}hydrazinecarboxylate Following a procedure analogous to Example 17, from the compound (2.11 g, 6.06 mmol) of the above Step 1, 1.22 g of the title compound was afforded (yield 78%).

[α]_D²⁰ −34.8° (c 0.57, MeOH); ¹H NMR (400 MHz, CD₃OD) δ 1.70-1.79 (m, 1H), 1.87-1.98 (m, 1H), 2.02-2.12 (m, 1H), 2.26 (br dd, J=14.6, 6.6 Hz, 1H), 3.12-3.25 (m, 2H), 3.67-3.75 (m, 1H), 3.72 (s, 3H), 3.92 (br d, J=7.6 Hz, 1H); MS m/z 259 [M+H]⁺.

Step 3

Sodium methyl 2-{[(2S,5R)-7-oxo-6-(sulfooxy)-1,6-diazabicyclo[3.2.1]oct-2-yl]carbonyl}hydrazinecarboxylate To a solution of the compound (1.21 g, 4.70 mmol) of the above Step 2 in pyridine (30 mL) was added sulfur trioxide-pyridine complex (3.39 g), followed by agitating at room temperature overnight. To the reaction solution was added methylene chloride, followed by filtration and concentration under reduced pressure. To the resulting residue was added toluene, followed by azeotropy and concentration to dryness. A saturated sodium dihydrogen phosphate aqueous solution (100 mL) was added, the aqueous layer was washed with ethyl acetate, followed by adding tetrabutylammonium hydrogen sulfate (1.93 g) and ethyl acetate (10 mL), and agitating for 10 minutes. The aqueous layer was extracted with ethyl acetate. Subsequently, the resulting organic layer was dried over anhydrous sodium sulfate, filtrated, and concentrated under reduced pressure. The resulting residue was purified by silica gel column chromatography (methylene chloride/acetone/triethylamine=49/49/2) to afford 2.09 g of tetrabutylammonium methyl 2-{[(2S,5R)-7-oxo-6-(sulfooxy)-1,6-diazabicyclo[3.2.1]oct-2-yl]carbonyl}hydrazinecarboxylate.

¹H NMR (400 MHz, CDCl₃) δ 1.01 (t, J=7.4 Hz, 12H), 1.45 (sex, J=7.4 Hz, 8H), 1.60-1.75 (m, 9H), 1.86-1.98 (m, 1H), 2.15-2.24 (m, 1H), 2.37 (br dd, J=15.0, 7.0 Hz, 1H), 3.05-3.20 (m, 1H), 3.25-3.34 (m, 8H), 3.38 (br d, J=11.6 Hz, 1H), 3.78 (s, 3H), 3.99 (d, J=7.6 Hz, 1H), 4.35 (br s, 1H), 6.55 (br s, 1H), 8.28 (br s, 1H); MS m/z 339 [M−Bu$_4$N+ 2H]$^+$.

After all the amount of the tetrabutylammonium salt was treated with DOWEX (Na type), the resulting crude product was purified by SP207 (acetonitrile/water=0/100-5/95) and lyophilized to afford 880 mg of the title compound (yield 52%).

$[\alpha]_D^{21}$ −37.6° (c 0.36, H$_2$O); $^1$H NMR (400 MHz, D$_2$O) δ 1.62-1.73 (m, 1H), 1.76-1.88 (m, 1H), 1.92-2.00 (m, 1H), 2.08 (br dd, J=15.6, 6.8 Hz, 1H), 3.04 (br d, J=12.0 Hz, 1H), 3.21 (br d, J=12.0 Hz, 1H), 3.61 (s, 3H), 4.02 (br d, J=7.6 Hz, 1H), 4.04-4.10 (m, 1H); MS m/z 339 [M−Na+2H]$^+$; Na content 7.9%.

Example 52

Sodium ethyl 2-{[(2S,5R)-7-oxo-6-(sulfooxy)-1,6-diazabicyclo[3.2.1]oct-2-yl]carbonyl}hydrazinecarboxylate Step 1

Ethyl 2-{[(2S,5R)-6-benzyloxy-7-oxo-1,6-diazabicyclo[3.2.1]oct-2-yl]carbonyl}hydrazinecarboxylate Following a procedure analogous to Example 17, from the carboxylic acid (6b, 352 mg, 1.27 mmol) of Example 9 or 16 and ethyl carbazate (184 mg), 388 mg of the title compound was afforded (yield 84%).

$[\alpha]_D^{20}$ +53.40 (c 0.64, CHCl$_3$); $^1$H NMR (400 MHz, CDCl$_3$) δ 1.28 (t, J=7.2 Hz, 3H), 1.55-1.66 (m, 1H), 1.90-2.05 (m, 2H), 2.31-2.40 (m, 1H), 3.03-3.17 (m, 2H), 3.27-3.32 (m, 1H), 4.01 (d, J=7.2 Hz, 1H), 4.20 (q, J=7.2 Hz, 2H), 4.92 (d, J=11.2 Hz, 1H), 5.06 (d, J=11.2 Hz, 1H), 6.47 (br s, 1H), 7.35-7.46 (m, 5H), 8.19 (br s, 1H); MS m/z 363 [M+H]$^+$.

Step 2

Ethyl 2-{[(2S,5R)-6-hydroxy-7-oxo-1,6-diazabicyclo[3.2.1]oct-2-yl]carbonyl}hydrazinecarboxylate Following a procedure analogous to Example 17, from the compound (369 mg, 1.02 mmol) of the above Step 1, the title compound was afforded (quantitative).

$[\alpha]_D^{20}$ −29.9° (c 0.62, MeOH); $^1$H NMR (400 MHz, CD$_3$OD) δ 1.27 (br t, J=7.2 Hz, 3H), 1.68-1.82 (m, 1H), 1.87-1.99 (m, 1H), 2.01-2.15 (m, 1H), 2.27 (br dd, J=15.0, 6.6 Hz, 1H), 3.11-3.25 (m, 2H), 3.70 (br s, 1H), 3.92 (br d, J=7.2 Hz, 1H), 4.16 (q, J=7.2 Hz, 2H); MS m/z 273 [M+H]$^+$.

Step 3

Sodium ethyl 2-{[(2S,5R)-7-oxo-6-(sulfooxy)-1,6-diazabicyclo[3.2.1]oct-2-yl]carbonyl}hydrazinecarboxylate Following a procedure analogous to Example 22, from all the amount of the compound of the above Step 2, pyridinium ethyl 2-{[(2S,5R)-7-oxo-6-(sulfooxy)-1,6-diazabicyclo[3.2.1]oct-2-yl]carbonyl}hydrazinecarboxylate was afforded, and neutralized with saturated sodium bicarbonate aqueous solution, and then purified by DIAION HP21 (MITSUBISHI CHEMICAL) column chromatography to afford 108 mg of the title compound (2 steps, yield 29%).

$[\alpha]_D^{21}$ −34.5° (c 0.52, H$_2$O); $^1$H NMR (400 MHz, D$_2$O) δ 1.11 (br t, J=7.2 Hz, 3H), 1.61-1.72 (m, 1H), 1.75-1.88 (m, 1H), 1.90-2.00 (m, 1H), 2.08 (br dd, J=15.2, 7.2 Hz, 1H), 3.03 (br d, J=12.0 Hz, 1H), 3.21 (br d, J=12.0 Hz, 1H), 4.05 (br d, J=7.6 Hz, 1H), 4.04 (q, J=7.2 Hz, 2H), 4.07 (br s, 1H); MS m/z 353 [M−Na+2H]$^+$.

Example 53

Sodium tert-butyl 2-{[(2SR,5RS)-7-oxo-6-(sulfooxy)-1,6-diazabicyclo[3.2.1]oct-2-yl]carbonyl}hydrazinecarboxylate Step 1 tert-Butyl 2-{[(2SR, 5RS)-6-benzyloxy-7-oxo-1,6-diazabicyclo[3.2.1]oct-2-yl]carbonyl}hydrazinecarboxylate Following a procedure analogous to Example 18, from (2SR,5RS)-6-(benzyloxy)-7-oxo-1,6-diazabicyclo[3.2.1]octane-2-carboxylic acid (280 mg, 1.01 mmol) and tert-butyl hydrazinecarboxylate (147 mg), 299 mg of the title compound was afforded (yield 68%).

$^1$H NMR (400 MHz, CDCl$_3$) δ 1.33 (s, 9H), 1.49-1.55 (m, 1H), 1.74-1.91 (m, 2H), 2.18-2.23 (m, 1H), 2.96 (m, 2H), 3.18 (br s, 1H), 3.78 (d, J=1.9, 1H), 4.78 (d, J=2.8, 1H), 4.93 (d, J=2.8, 1H), 6.69 (s, 1H), 7.19-7.32 (m, 5H), 8.31 (s, 1H), MS m/z 391 [M+H]$^+$.

Step 2 tert-Butyl 2-{[(2SR,5RS)-6-hydroxy-7-oxo-1,6-diazabicyclo[3.2.1]oct-2-yl]carbonyl}hydrazinecarboxylate Following a procedure analogous to Example 17, from the compound (310 mg, 0.79 mmol) of the above Step 1, 200 mg of the title compound was afforded (yield 84%). MS m/z 301 [M+H]$^+$.

Step 3

Sodium tert-butyl 2-{[(2SR,5RS)-7-oxo-6-(sulfooxy)-1,6-diazabicyclo[3.2.1]oct-2-yl]carbonyl}hydrazinecarboxylate Following a procedure analogous to Example 18, pyridinium tert-butyl 2-{[(2SR,5RS)-7-oxo-6-(sulfooxy)-1,6-diazabicyclo[3.2.1]oct-2-yl]carbonyl}hydrazinecarboxylate obtained from the compound (118 mg, 0.39 mmol) of the above Step 2 was neutralized with saturated sodium bicarbonate aqueous solution, and then purified by octadecyl silica gel column chromatography to afford 73 mg of the title compound (yield 46%).

$^1$H NMR (400 MHz, D$_2$O) δ 1.47 (s, 9H), 1.84-1.88 (m, 1H), 1.93-2.03 (m, 1H), 2.10-2.14 (m, 1H), 2.22-2.28 (m, 1H), 3.20 (d, J=3.0, 1H), 3.38 (d, J=3.1, 1H), 4.16 (d, J=1.7, 1H), 4.24 (br s, 1H); MS m/z 379 [M−Na]$^-$.

Example 54

Sodium (2S,5R)-N'-(methylsulfonyl)-7-oxo-6-(sulfooxy)-1,6-diazabicyclo[3.2.1]octane-2-carbohydrazide

Step 1

(2S,5R)-6-Benzyloxy-N'-(methylsulfonyl)-7-oxo-1,6-diazabicyclo[3.2.1]octane-2-carbohydrazide Following a procedure analogous to Example 17, from the carboxylic acid (6b, 345 mg, 1.25 mmol) of Example 9 or 16 and methanesulfonyl hydrazide (193 mg), 359 mg of the title compound was afforded (yield 78%).

$[\alpha]_D^{20}$ +22.8° (c 0.55, $CHCl_3$); $^1$H NMR (400 MHz, $CDCl_3$) δ 1.54-1.66 (m, 1H), 1.96-2.09 (m, 2H), 2.26-2.36 (m, 1H), 2.74 (d, J=12.0 Hz, 1H), 3.02 (s, 3H), 3.11 (br d, J=12.0 Hz, 1H), 3.31-3.34 (m, 1H), 4.08 (d, J=7.6 Hz, 1H), 4.91 (d, J=11.4 Hz, 1H), 5.06 (d, J=11.4 Hz, 1H), 6.78 (br s, 1H), 7.35-7.48 (m, 5H), 8.71 (br s, 1H); MS m/z 369 $[M+H]^+$.

Step 2

(2S,5R)-6-Hydroxy-N'-(methylsulfonyl)-7-oxo-1,6-diazabicyclo[3.2.1]octane-2-carbohydrazide Following a procedure analogous to Example 17, from the compound (347 mg, 0.943 mmol) of the above Step 1, 259 mg of the title compound was afforded (quantitative).

$^1$H NMR (400 MHz, $CD_3OD$) δ 1.71-1.84 (m, 1H), 1.88-2.01 (m, 1H), 2.02-2.15 (m, 1H), 2.20-2.30 (m, 1H), 2.98-3.09 (m, 1H), 3.01 (s, 3H), 3.15 (br d, J=10.4 Hz, 1H), 3.67-3.75 (m, 1H), 3.93 (br d, J=7.6 Hz, 1H); MS m/z 279 $[M+H]^+$.

Step 3

Sodium (2S,5R)-N'-(methylsulfonyl)-7-oxo-6-(sulfooxy)-1,6-diazabicyclo[3.2.1]octane-2-carbohydrazide Following a procedure analogous to Example 22, from the compound (253 mg, 0.909 mmol) of the above Step 2, pyridinium (2S,5R)-N'-(methylsulfonyl)-7-oxo-6-(sulfooxy)-1,6-diazabicyclo[3.2.1]octane-2-carbohydrazide was afforded, and neutralized with saturated sodium bicarbonate aqueous solution, and then purified by octadecyl silica gel column chromatography to afford 65.9 mg of the title compound (yield 19%).

$[\alpha]_D^{20}$ −44.1° (c 0.10, $H_2O$); $^1$H NMR (400 MHz, $D_2O$) δ 1.63-1.72 (m, 1H), 1.75-1.88 (m, 1H), 1.90-2.00 (m, 1H), 2.07 (br dd, J=15.4, 7.0 Hz, 1H), 2.94 (d, J=12.0 Hz, 1H), 2.99 (s, 3H), 3.20 (br d, J=12.0 Hz, 1H), 4.01 (d, J=7.2 Hz, 1H), 4.03-4.09 (m, 1H); MS m/z 359 $[M−Na+2H]^+$.

Example 55

Sodium (2SR,5RS)-N-(morpholin-4-yl)-7-oxo-6-(sulfooxy)-1,6-diazabicyclo[3.2.1]octane-2-carboxamide

Step 1

(2SR,5RS)-6-Benzyloxy-N-(morpholin-4-yl)-7-oxo-1,6-diazabicyclo[3.2.1]octane-2-carboxamide To a solution of (2SR,5RS)-6-(benzyloxy)-7-oxo-1,6-diazabicyclo[3.2.1]octane-2-carboxylic acid (142 mg, 0.513 mmol) in methylene chloride (3.5 mL) were added triethylamine (226 μl), N-ethyl-N'-(3-dimethylaminopropyl)carbodiimide hydrochloride (125 mg), 1-hydroxybenzotriazole.monohydrate (100 mg), and morpholin-4-amine (62.7 μl), followed by agitating at room temperature overnight. The reaction solution was concentrated under reduced pressure, and the resulting residue was purified by silica gel column chromatography (ethyl acetate) to afford 149 mg of the title compound (yield 80%).

$^1$H NMR (400 MHz, $CDCl_3$) δ 1.57-1.66 (m, 1H), 1.86-2.06 (m, 2H), 2.37 (br dd, J=14.2, 6.8 Hz, 1H), 2.72 (d, J=11.8 Hz, 1H), 2.74-2.88 (m, 4H), 3.01 (br d, J=11.8 Hz, 1H), 3.28-3.33 (m, 1H), 3.81 (t, J=4.6 Hz, 4H), 3.90 (br d, J=7.6 Hz, 1H), 4.91 (d, J=11.4 Hz, 1H), 5.06 (d, J=11.4 Hz, 1H), 7.32-7.48 (m, 6H); MS m/z 361 $[M+H]^+$.

Step 2

(2SR,5RS)-6-Hydroxy-N-(morpholin-4-yl)-7-oxo-1,6-diazabicyclo[3.2.1]octane-2-carboxamide Following a procedure analogous to Example 17, from the compound (170 mg, 0.471 mmol) of the above Step 1, the title compound was afforded (quantitative).

$^1$H NMR (400 MHz, $CD_3OD$) δ 1.74-1.84 (m, 1H), 1.85-1.97 (m, 1H), 2.02-2.11 (m, 1H), 2.21 (br dd, J=14.8, 7.2 Hz, 1H), 2.81 (br t, J=4.4 Hz, 4H), 3.01 (d, J=11.6 Hz, 1H), 3.12 (br d, J=11.6 Hz, 1H), 3.69 (br s, 1H), 3.76 (br t, J=4.4 Hz, 4H), 3.81 (br d, J=7.6 Hz, 1H); MS m/z 271 $[M+H]^+$.

Step 3

Sodium (2SR,5RS)-N-(morpholin-4-yl)-7-oxo-6-(sulfooxy)-1,6-diazabicyclo[3.2.1]octane-2-carboxamide Following a procedure analogous to Example 22, from all the amount of the compound of the above Step 2, pyridinium (2SR,5RS)-N-(morpholin-4-yl)-7-oxo-6-(sulfooxy)-1,6-diazabicyclo[3.2.1]octane-2-carboxamide was afforded, and neutralized with saturated sodium bicarbonate aqueous solution, and then purified by SEPABEADS SP207 (MITSUBISHI CHEMICAL) column chromatography to afford 104 mg of the title compound (2 steps, yield 63%).

$^1$H NMR (400 MHz, $D_2O$) δ 1.65-1.85 (m, 2H), 1.90-1.99 (m, 1H), 2.00-2.08 (m, 1H), 2.68-2.80 (m, 4H), 3.97 (d, J=12.0 Hz, 1H), 3.18 (br d, J=12.0 Hz, 1H), 3.70 (br t, J=4.6 Hz, 4H), 3.89 (br d, J=7.0 Hz, 1H), 4.07 (br dd, J=5.6, 2.8 Hz, 1H); MS m/z 351 $[M−Na+2H]^+$.

Example 56

Sodium (2S,5R)-N-methoxy-7-oxo-6-(sulfooxy)-1,6-diazabicyclo[3.2.1]octane-2-carboxamide

Step 1

(2S,5R)-6-Benzyloxy-N-methoxy-7-oxo-1,6-diazabicyclo[3.2.1]octane-2-carboxamide To a solution of the carboxylic acid (6b, 965 mg, 3.49 mmol) of Example 9 or 16 in tetrahydrofuran (20 mL) were added triethylamine (1.95 mL), N-ethyl-N'-(3-dimethylaminopropyl)carbodiimide hydrochloride (802 mg), 1-hydroxybenzotriazole.monohydrate (658 mg), and O-methyl-hydroxylamine hydrochloride (363 mg), followed by agitating to room temperature overnight. The reaction solution was concentrated under reduced pressure, and the resulting residue was purified by silica gel column chromatography (hexane/ethyl acetate=9/1-0/10) to afford 773 mg of the title compound (yield 72%).

$[\alpha]_D^{20}$ −19.8° (c 0.60, CHCl$_3$); $^1$H NMR (400 MHz, CDCl$_3$) δ 1.60-1.71 (m, 1H), 1.88-2.07 (m, 2H), 2.32 (br dd J=14.2, 7.4 Hz, 1H), 2.80 (d, J=11.6 Hz, 1H), 3.00 (br d, J=11.6 Hz, 1H), 3.30-3.35 (m, 1H), 3.78 (s, 3H), 3.94 (d, J=7.6 Hz, 1H), 4.90 (d, J=11.6 Hz, 1H), 5.05 (d, J=11.6 Hz, 1H), 7.34-7.46 (m, 5H), 9.22 (br s, 1H); MS m/z 306 [M+H]$^+$.

Step 2

(2S,5R)-6-Hydroxy-N-methoxy-7-oxo-1,6-diazabicyclo[3.2.1]octane-2-carboxamide

Following a procedure analogous to Example 17, from the compound (770 mg, 2.52 mmol) of the above Step 1, 486 mg of the title compound was afforded (yield 90%).

$[\alpha]_D^{20}$ −76.8° (c 0.34, MeOH); $^1$H NMR (400 MHz, CD$_3$OD) δ 1.74-1.84 (m, 1H), 1.86-1.98 (m, 1H), 2.03-2.13 (m, 1H), 2.20 (br dd J=15.0, 7.0 Hz, 1H), 3.05 (d, J=11.8 Hz, 1H), 3.12 (br d, J=11.8 Hz, 1H), 3.66-3.74 (m, 1H), 3.71 (s, 3H), 3.82 (br d, J=7.6 Hz, 1H); MS m/z 216 [M+H]$^+$.

Step 3

Sodium (2S,5R)-N-methoxy-7-oxo-6-(sulfooxy)-1,6-diazabicyclo[3.2.1]octane-2-carboxamide Following a procedure analogous to Example 17, from the compound (483 mg, 2.24 mmol) of the above Step 2, 963 mg of tetrabutylammonium (2S,5R)-N-methoxy-7-oxo-6-(sulfooxy)-1,6-diazabicyclo[3.2.1]octane-2-carboxamide was afforded.

$^1$H NMR (400 MHz, CDCl$_3$) δ 0.93 (t, J=7.4 Hz, 12H), 1.37 (sex, J=7.4 Hz, 8H), 1.53-1.72 (m, 9H), 1.77-1.90 (m, 1H), 2.05-2.15 (m, 1H), 2.27 (br dd, J=14.8, 6.4 Hz, 1H), 2.84 (d, J=11.6 Hz, 1H), 3.14-3.31 (m, 9H), 3.73 (s, 3H), 3.87 (br d, J=7.6 Hz, 1H), 4.25 (br s, 1H), 9.32 (br s, 1H); MS m/z 296 [M−Na+2H]$^+$.

All the amount of the tetrabutylammonium salt was subjected to ion exchange by DOWEX (Na type), and then purified by octadecyl silica gel column chromatography to afford 401 mg of the title compound (yield 56%).

$[\alpha]D^{20}$ −49.0° (c 0.85, H$_2$O); $^1$H NMR (400 MHz, D$_2$O) δ 1.66-1.87 (m, 2H), 1.91-2.07 (m, 2H), 3.02 (d, J=12.0 Hz, 1H), 3.18 (br d, J=12.0 Hz, 1H), 3.62 (s, 3H), 3.92 (dd, J=8.0, 2.4 Hz, 1H), 4.07 (dd, J=6.0, 2.8 Hz, 1H); MS m/z 296 [M+H]$^+$; Na content 10.9%.

Example 57

Sodium (2SR,5RS)-N-ethoxy-7-oxo-6-(sulfooxy)-1,6-diazabicyclo[3.2.1]octane-2-carboxamide Step 1

(2SR,5RS)-6-Benzyloxy-N-ethoxy-7-oxo-1,6-diazabicyclo[3.2.1]octane-2-carboxamide Following a procedure analogous to Example 27, from (2SR,5RS)-6-(benzyloxy)-7-oxo-1,6-diazabicyclo[3.2.1]octane-2-carboxylic acid (150 mg, 0.58 mmol) and O-ethylhydroxylamine hydrochloride (85 mg), 95 mg of the title compound was afforded (yield 39%). MS m/z 320 [M+H]+.

Step 2

(2SR,5RS)-N-Ethoxy 6-hydroxy-7-oxo-1,6-diazabicyclo[3.2.1]octane-2-carboxamide

Following a procedure analogous to Example 17, from all the amount of the compound of the above Step 1, 88 mg of the title compound was afforded (yield 96%).

Step 3

Sodium (2SR,5RS)-N-ethoxy-7-oxo-6-(sulfooxy)-1,6-diazabicyclo[3.2.1]octane-2-carboxamide Following a procedure analogous to Example 18, from all the amount of the compound of the above Step 2, pyridinium (2SR,5RS)-N-ethoxy-7-oxo-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 30 mg of the title compound (yield 24%).

$^1$H NMR (400 MHz, D$_2$O) δ 1.09 (t, J=1.7, 3H), 1.66-1.86 (m, 2H), 1.91-2.02 (m, 2H), 3.00 (d, J=3.0, 1H), 3.17 (d, J=2.9, 1H), 3.84 (q, J=1.7, 2H), 3.92 (d, J=1.7, 1H), 4.06 (m, 1H); MS m/z 308 [M−Na]$^-$.

Example 58

Sodium (2S,5R)-N-(cyclobutylmethoxy)-7-oxo-6-(sulfooxy)-1,6-diazabicyclo[3.2.1]octane-2-carboxamide Step 1

(2S,5R)-6-Benzyloxy-N-(cyclobutylmethoxy)-7-oxo-1,6-diazabicyclo[3.2.1]octane-2-carboxamide Following a procedure analogous to Example 45, from the carboxylic acid (6b, 379 mg, 1.37 mmol) of Example 9 or 16 and O-(cyclobutylmethyl)hydroxylamine (274 mg, prepared following a procedure analogous to Reference Example 7 and Reference Example 15), 359.4 mg of the title compound was afforded (yield 73%).

$^1$H NMR (400 MHz, CDCl$_3$) δ 1.55-2.15 (m, 9H), 2.28-2.39 (m, 1H), 2.59-2.72 (m, 1H), 2.77 (d, J=11.6 Hz, 1H), 3.00 (br d, J=11.6 Hz, 1H), 3.26-3.34 (m, 1H), 3.83-3.89 (m, 1H), 3.90-3.97 (m, 2H), 4.90 (d, J=11.4 Hz, 1H), 5.05 (d, J=11.4 Hz, 1H), 7.34-7.46 (m, 5H), 8.98 (s, 1H); MS m/z 360 [M+H]$^+$.

Step 2

(2S,5R)-N-(Cyclobutylmethoxy)-6-hydroxy-7-oxo-1,6-diazabicyclo[3.2.1]octane-2-carboxamide Following a procedure analogous to Example 17, from all the amount of the compound of the above Step 1, the title compound was afforded (quantitative). MS m/z 270 [M+H]$^+$.

Step 3

Sodium (2S,5R)-N-(cyclobutylmethoxy)-7-oxo-6-(sulfooxy)-1,6-diazabicyclo[3.2.1]octane-2-carboxamide Following a procedure analogous to Example 18, from all the amount of the compound of the above Step 2, pyridinium (2S,5R)-N-(cyclobutylmethoxy)-7-oxo-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 157.8 mg of the title compound (2 steps, yield 42%).

$^1$H NMR (400 MHz, D$_2$O) δ 1.55-1.86 (m, 6H), 1.88-2.07 (m, 4H), 2.46-2.57 (m, 1H), 3.00 (d, J=12.0 Hz, 1H), 3.18 (br d, J=12.0 Hz, 1H), 3.79 (d, J=7.2 Hz, 2H), 3.87-3.94 (m, 1H), 4.05-4.10 (m, 1H); MS m/z 350 [M−Na+2H]$^+$.

Example 59

(2S,5R)-N-(2-Aminoethoxy)-7-oxo-6-(sulfooxy)-1,6-diazabicyclo[3.2.1]octane-2-carboxamide (II-059)

[Chemical formula 81]

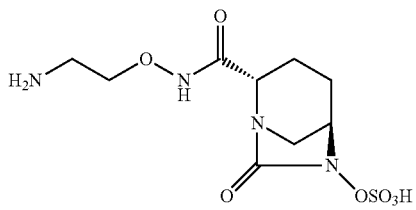

Step 1 tert-Butyl {2-[({[(2S,5R)-6-benzyloxy-7-oxo-1,6-diazabicyclo[3.2.1]oct-2-yl]carbonyl}amino)oxy]ethyl}carbamate

[Chemical formula 82]

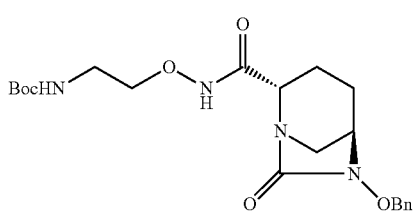

To a solution of the carboxylic acid (6b, 1.34 g, 4.87 mmol) of Example 9 or 16 in methylene chloride (35 mL) were added triethylamine (2.71 mL), N-ethyl-N'-(3-dimethylaminopropyl)carbodiimide hydrochloride (1.41 g), 1-hydroxybenzotriazole.monohydrate (1.15 g), and tert-butyl 2-(aminooxy)ethylcarbamate (1.12 g) described in Reference Example 9, followed by agitating at room temperature overnight. To the residue resulting from concentrating the reaction solution under reduced pressure was added water, followed by extracting with ethyl acetate. The resulting organic layer was washed with 0.1M hydrochloric acid, saturated sodium bicarbonate aqueous solution, and a saturated sodium chloride aqueous solution, dried over anhydrous sodium sulfate, filtrated, and concentrated. The resulting residue was purified by silica gel column chromatography (hexane/ethyl acetate=8/2-0/10) to afford 1.77 g of the title compound (yield 84%).

[α]$_D^{20}$ −0.08° (c 0.29, CHCl$_3$); $^1$H NMR (400 MHz, CDCl$_3$) δ 1.44 (s, 9H), 1.56-1.70 (m, 1H), 1.90-2.09 (m, 2H), 2.25-2.38 (m, 1H), 2.76 (d, J=11.6 Hz, 1H), 3.03 (br d, J=11.6 Hz, 1H), 3.24-3.47 (m, 3H), 3.84-4.01 (m, 3H), 4.90 (d, J=11.6 Hz, 1H), 5.05 (d, J=11.6 Hz, 1H), 5.44 (br s, 1H), 7.34-7.48 (m, 5H), 9.37 (br s, 1H); MS m/z 435 [M+H]$^+$; enantiomeric excess 99.9% ee or more (CHIRALPAK AD-H, 4.6×150 mm, hexane/ethanol=2/1, UV 210 nm, flow rate 1 mL/min., retention time 4.95 min. (2R,5S), 6.70 min. (2S,5R).

Step 2 tert-Butyl {2-[({[(2S,5R)-6-hydroxy-7-oxo-1,6-diazabicyclo[3.2.1]oct-2-yl]carbonyl}amino)oxy]ethyl}carbamate

[Chemical formula 83]

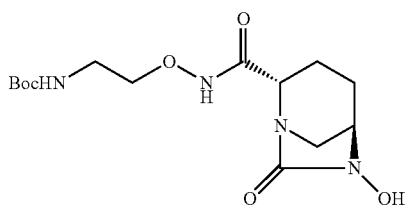

To a solution of the compound (3.91 g, 9.01 mmol) of the above Step 1 in methanol (80 mL) was added 10% palladium carbon catalyst (50% water content, 803 mg), followed by agitating under hydrogen atmosphere for 45 minutes. The reaction solution was filtered through Celite and concentrated under reduced pressure to afford 3.11 g of the title compound (quantitative).

$^1$H NMR (400 MHz, CD$_3$OD) δ 1.44 (s, 9H), 1.73-1.83 (m, 1H), 1.86-1.99 (m, 1H), 2.01-2.12 (m, 1H), 2.22 (br dd, J=15.0, 7.0 Hz, 1H), 3.03 (d, J=12.0 Hz, 1H), 3.12 (br d, J=12.0 Hz, 1H), 3.25-3.35 (m, 2H), 3.68-3.71 (m, 1H), 3.82-3.91 (m, 3H); MS m/z 345 [M+H]$^+$.

Step 3

(2S,5R)-N-(2-Aminoethoxy)-7-oxo-6-(sulfooxy)-1,6-diazabicyclo[3.2.1]octane-2-carboxamide To a solution of the compound (3.09 g, 8.97 mmol) of the above Step 2 in methylene chloride (80 mL) were added 2,6-lutidine (3.20 mL) and sulfur trioxide-pyridine complex (3.58 g), followed by agitating at room temperature overnight. The reaction solution was poured into half-saturated sodium bicarbonate aqueous solution, and the aqueous layer was washed with chloroform. To the aqueous layer were added tetrabutylammonium hydrogen sulfate (3.47 g) and chloroform (30 mL), followed by agitating for 10 minutes. The aqueous layer was extracted with chloroform, and the resulting organic layer was dried over anhydrous sodium sulfate, filtrated, and concentrated under reduced pressure to afford 5.46 g of tetrabutylammonium tert-butyl {2-[({[(2S, 5R)-7-oxo-6-(sulfooxy)-1,6-diazabicyclo[3.2.1]oct-2-yl]carbonyl}amino)oxy]ethyl}carbamate (yield 91%).

¹H NMR (400 MHz, CDCl₃) δ 1.01 (t, J=7.4 Hz, 12H), 1.37-1.54 (m, 8H), 1.45 (s, 9H), 1.57-1.80 (m, 9H), 1.85-1.98 (m, 1H), 2.14-2.24 (m, 1H), 2.30-2.39 (m, 1H), 2.83 (d, J=11.6 Hz, 1H), 3.20-3.50 (m, 11H), 3.85-3.99 (m, 3H), 4.33-4.38 (m, 1H), 5.51 (br s, 1H), 9.44 (br s, 1H); MS m/z 425 [M−Bu₄N+2H]⁺.

To a solution of the tetrabutylammonium salt (5.20 g, 7.82 mmol) in methylene chloride (25 mL) was added trifluoroacetic acid (25 mL) under ice-cooling, followed by agitating at 0° C. for 1 hour. The reaction solution was concentrated under reduced pressure. The resulting residue was washed with diethyl ether, and adjusted to pH 7 with a sodium bicarbonate aqueous solution, and then purified by octadecyl silica gel column chromatography (water), and then lyophilized to afford 1.44 g of the title compound (yield 57%).

[α]D²⁴ −63.5° (c 0.83, H₂O); ¹H NMR (400 MHz, D₂O) δ 1.66-1.76 (m, 1H), 1.76-1.88 (m, 1H), 1.91-2.00 (m, 1H), 2.00-2.08 (m, 1H), 3.02 (d, J=12.0 Hz, 1H), 3.15 (t, J=5.0 Hz, 2H), 3.18 (br d, J=12.0 Hz, 1H), 3.95 (dd, J=7.8, 2.2 Hz, 1H), 4.04 (t, J=5.0 Hz, 2H), 4.07 (dd, J=6.4, 3.2 Hz, 1H); MS m/z 325 [M+H]⁺.

Example 60

Sodium tert-butyl {2-[({[(2S,5R)-7-oxo-6-(sulfooxy)-1,6-diazabicyclo[3.2.1]oct-2-yl]carbonyl}amino)oxy]ethyl}carbamate (II-060)

[Chemical formula 84]

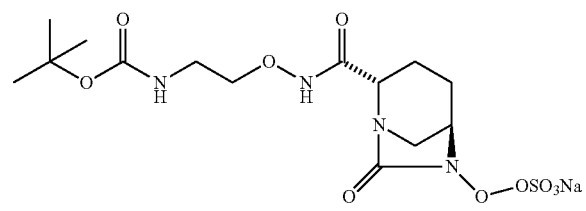

From the compound (1.700 g, 4.938 mmol) of Step 2 of Example 59, pyridinium tert-butyl {2-[({[(2S,5R)-7-oxo-6-(sulfooxy)-1,6-diazabicyclo[3.2.1]oct-2-yl]carbonyl}amino)oxy]ethyl}carbamate was afforded, and neutralized with saturated sodium bicarbonate aqueous solution, and then purified by octadecyl silica gel column chromatography to afford 926.7 mg of the title compound (yield 43.6%).

¹H NMR (400 MHz, D₂O) δ 1.28 (s, 9H), 1.68-1.83 (m, 2H), 1.92-2.07 (m, 2H), 3.00-3.03 (d, J=12.8 Hz, 1H), 3.16-3.22 (m, 3H), 3.81-3.84 (d, J=4.8 Hz, 2H), 3.90-3.92 (d, J=6.4 Hz, 1H), 4.06-4.07 (br s, 1H); MS m/z 423 [M−Na]⁻.

Example 61

(2S,5R)-N-[2-(Methylamino)ethoxy]-7-oxo-6-(sulfooxy)-1,6-diazabicyclo[3.2.1]octane-2-carboxamide (II-061)

[Chemical formula 85]

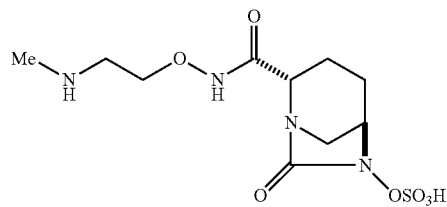

Step 1 tert-Butyl{2-[({[(2S,5R)-6-benzyloxy-7-oxo-1,6-diazabicyclo[3.2.1]oct-2-yl]carbonyl}amino)oxy]ethyl}methylcarbamate

[Chemical formula 86]

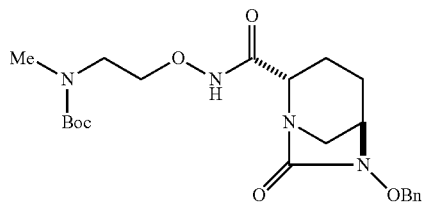

Following a procedure analogous to Example 27, from the carboxylic acid (6b, 390 mg, 1.41 mmol) of Example 9 or 16 and tert-butyl (2-(aminooxy)ethyl)(methyl)carbamate (436 mg) described in Reference Example 16, 347.8 mg of the title compound was afforded (yield 55%).

¹H NMR (400 MHz, CDCl₃) δ 1.46 (s, 9H), 1.58-1.70 (m, 1H), 1.88-2.07 (m, 2H), 2.25-2.36 (m, 1H), 2.70-3.08 (m, 2H), 2.88 (s, 3H), 3.23-3.41 (m, 2H), 3.51-3.68 (m, 1H), 3.83-4.10 (m, 3H), 4.90 (d, J=11.4 Hz, 1H), 5.06 (d, J=11.4 Hz, 1H), 7.32-7.47 (m, 5H), 10.11 (br s, 1H); MS m/z 449 [M+H]⁺.

Step 2 tert-butyl {2-[({[(2S,5R)-6-Hydroxy-7-oxo-1,6-diazabicyclo[3.2.1]oct-2-yl]carbonyl}amino)oxy]ethyl}methylcarbamate

[Chemical formula 87]

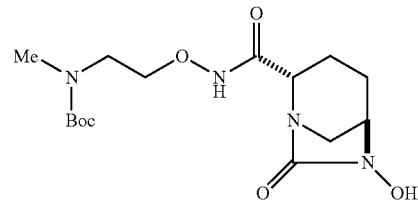

Following a procedure analogous to Example 17, from all the amount of the compound of the above Step 1, the title compound was afforded (quantitative).

$^1$H NMR (400 MHz, CD$_3$OD) δ 1.46 (s, 9H), 1.73-1.83 (m, 1H), 1.86-2.00 (m, 1H), 2.01-2.13 (m, 1H), 2.14-2.28 (m, 1H), 2.93 (s, 3H), 3.04 (d, J=10.8 Hz, 1H), 3.08-3.18 (m, 1H), 3.43-3.55 (m, 2H), 3.65-3.72 (m, 1H), 3.79-3.88 (m, 1H), 3.92-4.05 (m, 2H); MS m/z 359 [M+H]$^+$.

Step 3

(2S,5R)-N-[2-(Methylamino)ethoxy]-7-oxo-6-(sulfooxy)-1,6-diazabicyclo[3.2.1]octane-2-carboxamide Following a procedure analogous to Example 59, from all the amount of the compound of the above Step 2, tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}methylcarbamate was afforded (quantitative).

$^1$H NMR (400 MHz, CDCl$_3$) δ 1.01 (t, J=7.2 Hz, 12H), 1.36-1.53 (m, 8H), 1.47 (s, 9H), 1.57-1.77 (m, 9H), 1.83-1.98 (m, 1H), 2.13-2.25 (m, 1H), 2.28-2.40 (m, 1H), 2.82-2.96 (m, 4H), 3.22-3.42 (m, 11H), 3.60-4.08 (m, 3H), 4.34 (br s, 1H), 10.15 (br s, 1H); MS m/z 437 [M−Bu$_4$N]$^−$.

All the amount of the above tetrabutylammonium salt was deprotected with trifluoroacetic acid, and purified by octadecyl silica gel column chromatography to afford 149.4 mg of the title compound (3 steps, yield 57%).

$^1$H NMR (500 MHz, D$_2$O) δ 1.73-1.97 (m, 2H), 1.98-2.07 (m, 1H), 2.08-2.18 (m, 1H), 2.74 (s, 3H), 3.09 (d, J=12.0 Hz, 1H), 3.21-3.32 (m, 3H), 4.04 (dd, J=7.5, 2.0 Hz, 1H), 4.10-4.23 (m, 3H); MS m/z 337 [M−H]$^−$.

Example 62

(2S,5R)-N-[2-(Ethylamino)ethoxy]-7-oxo-6-(sulfooxy)-1,6-diazabicyclo[3.2.1]octane-2-carboxamide Step 1 tert-Butyl{2-[({[(2S,5R)-6-benzyloxy-7-oxo-1,6-diazabicyclo[3.2.1]oct-2-yl]carbonyl}amino)oxy]ethyl}ethylcarbamate Following a procedure analogous to Example 45, from the carboxylic acid (6b, 414 mg, 1.50 mmol) of Example 9 or 16 and tert-butyl (2-(aminooxy)ethyl) (ethyl)carbamate (744 mg, prepared following procedures analogous to Reference Example 7 and Reference Example 15), 541.6 mg of the title compound was afforded (yield 78%).

$^1$H NMR (400 MHz, CDCl$_3$) δ 1.11 (t, J=7.2 Hz, 3H), 1.46 (s, 9H), 1.58-1.74 (m, 1H), 1.89-2.08 (m, 2H), 2.24-2.38 (m, 1H), 2.72-2.91 (m, 1H), 2.92-3.11 (m, 1H), 3.12-3.42 (m, 4H), 3.43-3.66 (m, 1H), 3.85-4.05 (m, 3H), 4.90 (d, J=11.4 Hz, 1H), 5.06 (d, J=11.4 Hz, 1H), 7.33-7.47 (m, 5H), 10.18 (br s, 1H); MS m/z 463 [M+H]$^+$.

Step 2 tert-Butyl ethyl{2-[({[(2S,5R)-6-hydroxy-7-oxo-1,6-diazabicyclo[3.2.1]oct-2-yl]carbonyl}amino)oxy]ethyl}carbamate Following a procedure analogous to Example 17, from all the amount of the compound of the above Step 1, the title compound was afforded (quantitative).

$^1$H NMR (400 MHz, CD$_3$OD) δ 1.22 (t, J=7.0 Hz, 3H), 1.46 (s, 9H), 1.73-1.84 (m, 1H), 1.86-1.98 (m, 1H), 2.02-2.12 (m, 1H), 2.14-2.27 (m, 1H), 3.04 (d, J=11.6 Hz, 1H), 3.09-3.18 (m, 1H), 3.25-3.37 (m, 2H), 3.43-3.54 (m, 2H), 3.66-3.72 (m, 1H), 3.79-3.88 (m, 1H), 3.89-4.03 (m, 2H); MS m/z 373 [M+H]$^+$.

Step 3

(2S,5R)-N-[2-(Ethylamino)ethoxy]-7-oxo-6-(sulfooxy)-1,6-diazabicyclo[3.2.1]octane-2-carboxamide Following a procedure analogous to Example 59, from all the amount of the compound of the above Step 2, tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}ethylcarbamate was afforded (quantitative). MS m/z 451 [M−Bu$_4$N]$^−$.

All the amount of the above tetrabutylammonium salt was deprotected with trifluoroacetic acid and purified by octadecyl silica gel column chromatography to afford 166.6 mg of the title compound (3 steps, yield 40%).

$^1$H NMR (500 MHz, D$_2$O) δ 1.25 (t, J=7.3 Hz, 3H), 1.73-1.83 (m, 1H), 1.84-1.95 (m, 1H), 1.97-2.15 (m, 2H), 3.05-3.13 (m, 3H), 3.22-3.29 (m, 3H), 3.99-4.04 (m, 1H), 4.10-4.17 (m, 3H); MS m/z 353 [M+H]$^+$.

Example 63

(2S,5R)-7-Oxo-N-[2-(propylamino)ethoxy]-6-(sulfooxy)-1,6-diazabicyclo[3.2.1]octane-2-carboxamide Step 1 tert-Butyl {2-[({[(2S,5R)-6-benzyloxy-7-oxo-1,6-diazabicyclo[3.2.1]oct-2-yl]carbonyl}amino)oxy]ethyl}propylcarbamate Following a procedure analogous to Example 45, from the carboxylic acid (6b, 414 mg, 1.50 mmol) of Example 9 or 16 and tert-butyl (2-(aminooxy)ethyl)(propyl)carbamate (801 mg, prepared following procedures analogous to Reference Example 7 and Reference Example 15), 552.2 mg of the title compound was afforded (yield 77%).

$^1$H NMR (400 MHz, CDCl$_3$) δ 0.87 (t, J=7.2 Hz, 3H), 1.45 (s, 9H), 1.53 (sext, J=7.2 Hz, 2H), 1.58-1.73 (m, 1H), 1.87-2.07 (m, 2H), 2.23-2.36 (m, 1H), 2.83 (d, J=11.2 Hz, 1H), 2.96-3.40 (m, 5H), 3.44-3.64 (m, 1H), 3.83-4.07 (m, 3H), 4.90 (d, J=11.4 Hz, 1H), 5.06 (d, J=11.4 Hz, 1H), 7.32-7.48 (m, 5H), 10.20 (br s, 1H); MS m/z 477 [M+H]$^+$.

Step 2 tert-Butyl {2-[({[(2S,5R)-6-hydroxy-7-oxo-1,6-diazabicyclo[3.2.1]oct-2-yl]carbonyl}amino)oxy]ethyl}propylcarbamate Following a procedure analogous to Example 17, from all the amount of the compound of the above Step 1, 436.7 mg of the title compound was afforded (yield 97%).

$^1$H NMR (400 MHz, CD$_3$OD) δ 0.89 (t, J=7.5 Hz, 3H), 1.40-1.61 (m, 2H), 1.46 (s, 9H), 1.66-2.00 (m, 2H), 2.02-2.28 (m, 2H), 3.04 (d, J=11.6 Hz, 1H), 3.09-3.19 (m, 1H), 3.24 (t, J=7.2 Hz, 2H), 3.42-3.56 (m, 2H), 3.62-3.74 (m, 1H), 3.79-4.05 (m, 3H); MS m/z 387 [M+H]$^+$.

Step 3

(2S,5R)-7-Oxo-N-[2-(propylamino)ethoxy]-6-(sulfooxy)-1,6-diazabicyclo[3.2.1]octane-2-carboxamide Following a procedure analogous to Example 59, from all the amount of the compound of the above Step 2, tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}propylcarbamate was afforded (quantitative). MS m/z 465 [M−Bu$_4$N]$^-$.

All the amount of the above tetrabutylammonium salt was deprotected with trifluoroacetic acid, and purified by octadecyl silica gel column chromatography to afford 226.9 mg of the title compound (3 steps, yield 53%).

$^1$H NMR (500 MHz, D$_2$O) δ 0.92 (t, J=7.5 Hz, 3H), 1.66 (sext, J=7.5 Hz, 2H), 1.74-1.82 (m, 1H), 1.83-1.94 (m, 1H), 1.97-2.13 (m, 2H), 3.00 (t, J=7.5 Hz, 2H), 3.11 (d, J=12.0 Hz, 1H), 3.21-3.29 (m, 3H), 3.96-4.03 (m, 1H), 4.09-4.17 (m, 3H); MS m/z 367 [M+H]$^+$.

Example 64

(2S,5R)-7-Oxo-N-[2-(propan-2-ylamino)ethoxy]-6-(sulfooxy)-1,6-diazabicyclo[3.2.1]octane-2-carboxamide (II-064)

[Chemical formula 88]

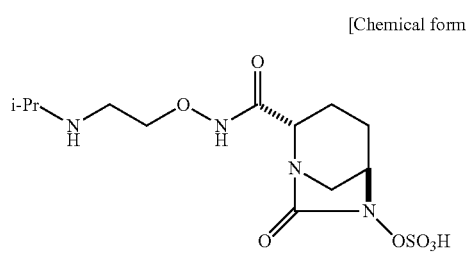

Step 1 tert-Butyl {2-[({[(2S,5R)-6-benzyloxy-7-oxo-1,6-diazabicyclo[3.2.1]oct-2-yl]carbonyl}amino)oxy]ethyl}propan-2-ylcarbamate

[Chemical formula 89]

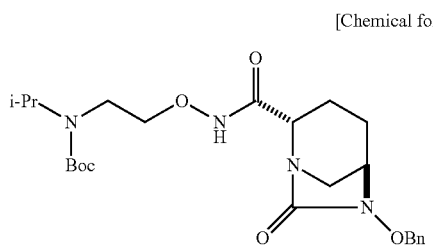

Following a procedure analogous to Example 45, from the carboxylic acid (6b, 414 mg, 1.50 mmol) of Example 9 or 16 and tert-butyl (2-(aminooxy)ethyl)(isopropyl)carbamate (596 mg) described in Reference Example 17, 578.4 mg of the title compound was afforded (yield 81%).

$^1$H NMR (400 MHz, CDCl$_3$) δ 1.15 (d, J=6.8 Hz, 6H), 1.46 (s, 9H), 1.55-1.70 (m, 1H), 1.89-2.07 (m, 2H), 2.25-2.37 (m, 1H), 2.73-2.90 (m, 1H), 2.98-3.08 (m, 1H), 3.22-3.38 (m, 2H), 3.40-3.60 (m, 1H), 3.83-4.06 (m, 4H), 4.90 (d, J=11.2 Hz, 1H), 5.06 (d, J=11.2 Hz, 1H), 7.35-7.46 (m, 5H), 10.29 (br s, 1H); MS m/z 477 [M+H]$^+$.

Step 2 tert-Butyl {2-[({[(2S,5R)-6-hydroxy-7-oxo-1,6-diazabicyclo[3.2.1]oct-2-yl]carbonyl}amino)oxy]ethyl}propan-2-ylcarbamate

[Chemical formula 90]

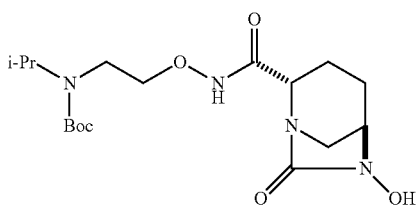

Following a procedure analogous to Example 17, from all the amount of the compound of the above Step 1, the title compound was afforded (quantitative).

$^1$H NMR (400 MHz, CD$_3$OD) δ 1.09-1.23 (m, 6H), 1.46 (s, 9H), 1.73-2.27 (m, 4H), 3.06 (d, J=11.6 Hz, 1H), 3.08-3.50 (m, 4H), 3.64-3.73 (m, 1H), 3.79-3.98 (m, 3H); MS m/z 387 [M+H]$^+$.

Step 3

(2S,5R)-7-Oxo-N-[2-(propan-2-ylamino)ethoxy]-6-(sulfooxy)-1,6-diazabicyclo[3.2.1]octane-2-carboxamide Following a procedure analogous to Example 59, from all the amount of the compound of the above Step 2, tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}propan-2-ylcarbamate was afforded (quantitative).

$^1$H NMR (400 MHz, CDCl$_3$) δ 1.01 (d, J=7.4 Hz, 12H), 1.10-1.20 (m, 6H), 1.33-1.77 (m, 17H), 1.46 (s, 9H), 1.84-1.97 (m, 1H), 2.12-2.25 (m, 1H), 2.28-2.40 (m, 1H), 2.79-2.95 (m, 1H), 3.17-3.45 (m, 9H), 3.50-3.67 (m, 1H), 3.80-4.07 (m, 5H), 4.34 (br s, 1H), 10.36 (br s, 1H); MS m/z 465 [M−Bu$_4$N]$^-$.

All the amount of the above tetrabutylammonium salt was deprotected with trifluoroacetic acid, and purified by octadecyl silica gel column chromatography to afford 252.1 mg of the title compound (3 steps, yield 57%).

$^1$H NMR (500 MHz, D$_2$O) δ 1.28 (d, J=6.5 Hz, 6H), 1.74-1.83 (m, 1H), 1.85-1.96 (m, 1H), 1.98-2.14 (m, 2H), 3.11 (d, J=12.5 Hz, 1H), 3.22-3.30 (m, 3H), 3.40 (quint, J=6.5 Hz, 1H), 4.01 (br d, J=5.5 Hz, 1H), 4.09-4.18 (m, 3H); MS m/z 367 [M+H]$^+$.

Example 65

(2S,5R)-N-[2-(Dimethylamino)ethoxy]-7-oxo-6-(sulfooxy)-1,6-diazabicyclo[3.2.1]octane-2-carboxamide

[Chemical formula 91]

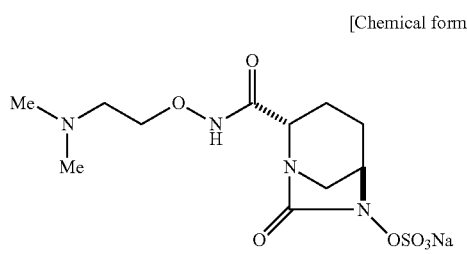

Step 1

(2S,5R)-6-Benzyloxy-N-[2-(dimethylamino)ethoxy]-7-oxo-1,6-diazabicyclo[3.2.1]octane-2-carboxamide

[Chemical formula 92]

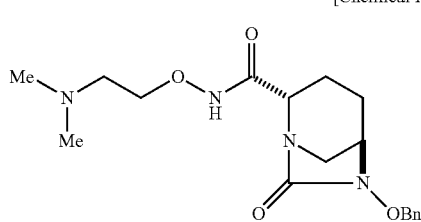

A solution of the carboxylic acid (6b, 553 mg, 2.00 mmol) of Example 9 or 16 in dehydrated methylene chloride (10 mL) was cooled to 0° C. under an argon atmosphere, followed by adding dropwise isobutyl chloroformate (289 µL, 2.20 mmol). Then, triethylamine (293 µL) was added, followed by stirring for 30 minutes. Thereby, a mixed acid anhydride was prepared in the reaction system. To this reaction mixture were gradually added 2-(aminooxy)-N,N-dimethylethanamine dihydrochloride (591 mg) described in Reference Example 18 and triethylamine (930 µL) while washing with dehydrated methylene chloride (7.0 mL), followed by stirring at the same temperature for 1 hour. This reaction mixture was filtered though Kiriyama filter paper. Subsequently, the residue was washed with methanol and the filtrate was concentrated under reduced pressure. The resulting residue was dissolved in methylene chloride and water, and the organic layer extracted with methylene chloride was dried over magnesium sulfate, followed by distilling off under reduced pressure. The resulting residue was subjected to silica gel column chromatography (amino silica, chloroform/methanol=10/1) to afford 291.1 mg of the title compound as a colorless oil (yield 40%).

$^1$H NMR (400 MHz, CDCl$_3$) δ 1.45-1.85 (m, 4H), 2.29 (s, 6H), 2.60 (t, J=5.2 Hz, 2H), 2.81 (d, J=11.6 Hz, 1H), 2.97 (br d, J=11.6 Hz, 1H), 3.28-3.34 (m, 1H), 3.92-4.07 (m, 3H), 4.90 (d, J=11.6 Hz, 1H), 5.05 (d, J=11.6 Hz, 1H), 7.35-7.48 (m, 5H); MS m/z 363 [M+H]$^+$.

Step 2

(2S,5R)-N-[2-(Dimethylamino)ethoxy]-6-hydroxy-7-oxo-1,6-diazabicyclo[3.2.1]octane-2-carboxamide

[Chemical formula 93]

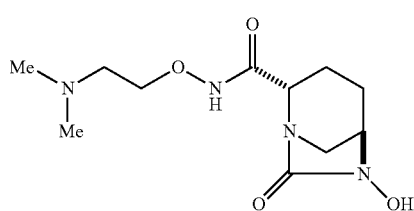

Following a procedure analogous to Example 17, from all the amount of the compound of the above Step 1, the title compound was afforded (quantitative).

$^1$H NMR (400 MHz, CDCl$_3$) δ 1.74-1.84 (m, 1H), 1.87-1.98 (m, 1H), 2.03-2.12 (m, 1H), 2.15-2.24 (m, 1H), 2.36 (s, 6H), 2.67-2.74 (m, 2H), 3.07 (br d, J=11.6 Hz, 1H), 3.12 (br d, J=11.6 Hz, 1H), 3.67-3.72 (m, 1H), 3.83 (br d, J=6.4 Hz, 1H), 3.96-4.06 (m, 2H); MS m/z 273 [M+H]$^+$.

Step 3

(2S,5R)-N-[2-(Dimethylamino)ethoxy]-7-oxo-6-(sulfooxy)-1,6-diazabicyclo[3.2.1]octane-2-carboxamide Following a procedure analogous to Example 18, from all the amount of the compound of the above Step 2, pyridinium (2S,5R)-N-[2-(dimethylamino)ethoxy]-7-oxo-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 130.7 mg of the title compound (2 steps, yield 43%).

$^1$H NMR (400 MHz, D$_2$O) δ 1.68-1.84 (m, 2H), 1.86-2.04 (m, 2H), 2.80 (s, 6H), 3.09-3.17 (m, 2H), 3.17-3.29 (m, 2H), 3.80-3.90 (m, 1H), 4.02-4.13 (m, 3H); MS m/z 353 [M+H]$^+$.

Example 66

(2S,5R)-N-{[(2S)-2-Aminopropyl]oxy}-7-oxo-6-(sulfooxy)-1,6-diazabicyclo[3.2.1]octane-2-carboxamide (II-066)

[Chemical formula 94]

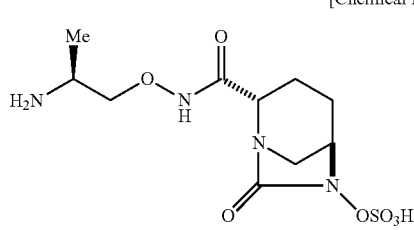

Step 1 tert-Butyl {(2S)-1-[({[(2S,5R)-6-benzyloxy-7-oxo-1,6-diazabicyclo[3.2.1]oct-2-yl]carbonyl}amino)oxy]propan-2-yl}carbamate

[Chemical formula 95]

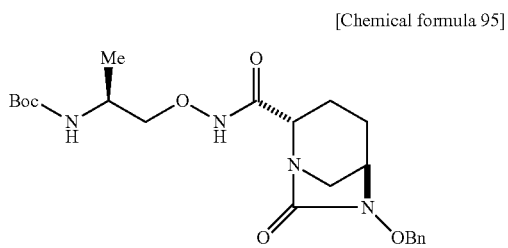 [SMILES: C[C@@H](CONC(=O)[C@@H]1CC[C@@H]2CN1C(=O)N2OCc1ccccc1)NC(=O)OC(C)(C)C]

Following a procedure analogous to Example 45, from the carboxylic acid (6b, 414 mg, 1.50 mmol) of Example 9 or 16 and (S)-tert-butyl (1-(aminooxy)propan-2-yl)carbamate (550 mg) described in Reference Example 19, 585.6 mg of the title compound was afforded (yield 87%).

$^1$H NMR (400 MHz, CDCl$_3$) δ 1.17 (d, J=6.4 Hz, 3H), 1.44 (s, 9H), 1.55-1.70 (m, 1H), 1.90-2.10 (m, 2H), 2.26-2.34 (m, 1H), 2.80 (d, J=12.0 Hz, 1H), 3.06 (br d, J=12.0 Hz, 1H), 3.27-3.34 (m, 1H), 3.64-3.74 (m, 1H), 3.86-3.98 (m, 3H), 4.81 (br d, J=7.6 Hz, 1H), 4.90 (d, J=11.6 Hz, 1H), 5.05 (d, J=11.6 Hz, 1H), 7.34-7.45 (m, 5H), 9.68 (br s, 1H); MS m/z 449 [M+H]$^+$.

Step 2 tert-Butyl {(2S)-1-[({[(2S,5R)-6-hydroxy-7-oxo-1,6-diazabicyclo[3.2.1]oct-2-yl]carbonyl}amino)oxy]propan-2-yl}carbamate

[Chemical formula 96]

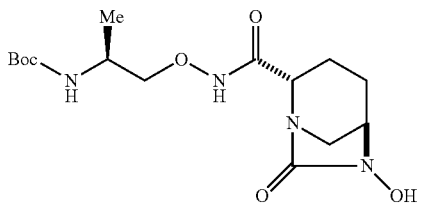

Following a procedure analogous to Example 17, from all the amount of the compound of the above Step 1, the title compound was afforded (quantitative).

$^1$H NMR (400 MHz, CD$_3$OD) δ 1.16 (d, J=6.4 Hz, 3H), 1.44 (s, 9H), 1.74-1.84 (m, 1H), 1.86-1.98 (m, 1H), 2.03-2.12 (m, 1H), 2.21 (br dd, J=15.2, 6.8 Hz, 1H), 3.06 (d, J=12.0 Hz, 1H), 3.14 (br d, J=12.0 Hz, 1H), 3.68-3.72 (m, 1H), 3.74-3.87 (m, 4H); MS m/z 359 [M+H]$^+$.

Step 3

(2S,5R)-N-{[(2S)-2-Aminopropyl]oxy}-7-oxo-6-(sulfooxy)-1,6-diazabicyclo[3.2.1]octane-2-carboxamide Following a procedure analogous to Example 59, from all the amount of the compound of the above Step 2, tetrabutylammonium tert-butyl {(2S)-1-[({[(2S,5R)-7-oxo-6-(sulfooxy)-1,6-diazabicyclo[3.2.1]oct-2-yl]carbonyl}amino)oxy]propan-2-yl}carbamate was afforded (quantitative). MS m/z 437 [M−Bu$_4$N]$^-$.

All the amount of the above tetrabutylammonium salt was deprotected with trifluoroacetic acid, and then purified by octadecyl silica gel column chromatography to afford 117.1 mg of the title compound (3 steps, yield 26%).

$^1$H NMR (400 MHz, D$_2$O) δ 1.17 (d, J=6.8 Hz, 3H), 1.66-1.89 (m, 2H), 1.91-2.08 (m, 2H), 3.02 (d, J=12.0 Hz, 1H), 3.18 (br d, J=12.0 Hz, 1H), 3.47-3.58 (m, 1H), 3.82 (dd, J=11.8, 9.4 Hz, 1H), 3.92-4.02 (m, 2H), 4.05-4.10 (m, 1H); MS m/z 339 [M+H]$^+$.

Example 67

(2S,5R)-N-{[(2R)-2-Aminopropyl]oxy}-7-oxo-6-(sulfooxy)-1,6-diazabicyclo[3.2.1]octane-2-carboxamide (II-067)

[Chemical formula 97]

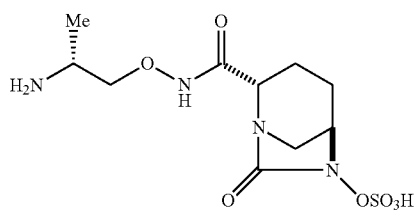

Step 1 tert-Butyl {(2R)-1-[({[(2S,5R)-6-benzyloxy-7-oxo-1,6-diazabicyclo[3.2.1]oct-2-yl]carbonyl}amino)oxy]propan-2-yl}carbamate

[Chemical formula 98]

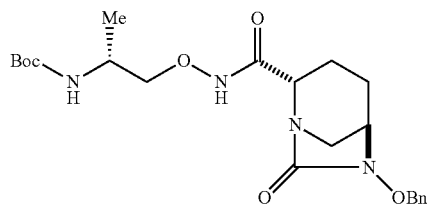

Following a procedure analogous to Example 45, from the carboxylic acid (6b, 414 mg, 1.50 mmol) of Example 9 or 16 and (R)-tert-butyl (1-(aminooxy)propan-2-yl)carbamate (569 mg, prepared following procedures analogous to Reference Example 7 and Reference Example 15), 625 mg of the title compound was afforded (yield 93%).

$^1$H NMR (400 MHz, CDCl$_3$) δ 1.14 (d, J=6.4 Hz, 3H), 1.43 (s, 9H), 1.53-1.70 (m, 1H), 1.90-2.06 (m, 2H), 2.28-2.36 (m, 1H), 2.79 (d, J=12.0 Hz, 1H), 3.02 (br d, J=12.0 Hz, 1H), 3.28-3.33 (m, 1H), 3.56-3.68 (m, 1H), 3.84 (dd, J=11.2, 3.6 Hz, 1H), 3.92-4.04 (m, 2H), 4.66 (br d, J=8.0 Hz, 1H), 4.91 (d, J=11.2 Hz, 1H), 5.06 (d, J=11.2 Hz, 1H), 7.35-7.45 (m, 5H), 9.94 (br s, 1H); MS m/z 449 [M+H]$^+$.

Step 2 tert-butyl {(2R)-1-[({[(2S,5R)-6-hydroxy-7-oxo-1,6-diazabicyclo[3.2.1]oct-2-yl]carbonyl}amino)oxy]propan-2-yl}carbamate

[Chemical formula 99]

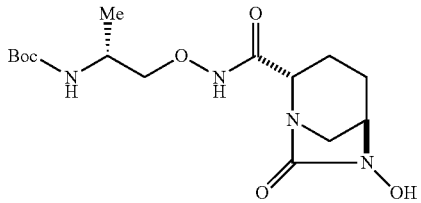

Following a procedure analogous to Example 17, from all the amount of the compound of the above Step 1, the title compound was afforded (quantitative).

$^1$H NMR (400 MHz, CD$_3$OD) δ 1.15 (d, J=6.4 Hz, 3H), 1.44 (s, 9H), 1.73-1.84 (m, 1H), 1.86-2.00 (m, 1H), 2.01-2.12 (m, 1H), 2.19-2.29 (m, 1H), 3.06 (d, J=11.6 Hz, 1H), 3.10-3.20 (m, 1H), 3.67-3.72 (m, 1H), 3.73-3.92 (m, 4H); MS m/z 359 [M+H]+.

Step 3

(2S,5R)-N-{[(2R)-2-Aminopropyl]oxy}-7-oxo-6-(sulfooxy)-1,6-diazabicyclo[3.2.1]octane-2-carboxamide Following a procedure analogous to Example 59, from all the amount of the compound of the above Step 2, tetrabutylammonium tert-butyl {(2R)-1-[({[(2S,5R)-7-oxo-6-(sulfooxy)-1,6-diazabicyclo[3.2.1]oct-2-yl]carbonyl}amino)oxy]propan-2-yl}carbamate was afforded (quantitative). MS m/z 437 [M−Bu$_4$N]$^-$.

All the amount of the above tetrabutylammonium salt was deprotected with trifluoroacetic acid and purified by octadecyl silica gel column chromatography to afford 212.6 mg of the title compound (3 steps, yield 45%).

$^1$H NMR (400 MHz, D$_2$O) δ 1.17 (d, J=6.8 Hz, 3H), 1.66-1.78 (m, 1H), 1.78-1.88 (m, 1H), 1.90-2.06 (m, 2H), 3.02 (d, J=12.0 Hz, 1H), 3.18 (br d, J=12.0 Hz, 1H), 3.48-3.58 (m, 1H), 3.83 (dd, J=11.8, 9.0 Hz, 1H), 3.94 (br d, J=7.2 Hz, 1H), 3.98 (dd, J=11.8, 3.4 Hz, 1H), 4.06-4.10 (m, 1H); MS m/z 339 [M+H]+.

Example 68

(2S,5R)-N-{[(2S)-1-Aminopropan-2-yl]oxy}-7-oxo-6-(sulfooxy)-1,6-diazabicyclo[3.2.1]octane-2-carboxamide

Step 1 tert-Butyl {(2S)-2-[({[(2S,5R)-6-benzyloxy-7-oxo-1,6-diazabicyclo[3.2.1]oct-2-yl]carbonyl}amino)oxy]propyl}carbamate Following a procedure analogous to Example 45, from the carboxylic acid (6b, 414 mg, 1.50 mmol) of Example 9 or 16 and (S)-tert-butyl (2-(aminooxy)propyl)carbamate (597 mg, prepared following procedures analogous to Reference Example 7 and Reference Example 15), 626.6 mg of the title compound was afforded (yield 93%).

$^1$H NMR (400 MHz, CDCl$_3$) δ 1.22 (d, J=6.4 Hz, 3H), 1.40-1.70 (m, 1H), 1.44 (s, 9H), 1.92-2.08 (m, 2H), 2.27-2.36 (m, 1H), 2.77 (d, J=11.6 Hz, 1H), 2.94-3.08 (m, 2H), 3.30-3.35 (m, 1H), 3.38-3.50 (m, 1H), 3.95-4.05 (m, 2H), 4.91 (d, J=11.4 Hz, 1H), 5.05 (d, J=11.4 Hz, 1H), 5.48-5.60 (m, 1H), 7.35-7.45 (m, 5H), 9.25 (br s, 1H); MS m/z 449 [M+H]+.

Step 2 tert-Butyl {(2S)-2-[({[(2S,5R)-6-hydroxy 7-oxo-1,6-diazabicyclo[3.2.1]oct-2-yl]carbonyl}amino)oxy]propyl}carbamate Following a procedure analogous to Example 17, from all the amount of the compound of the above Step 1, the title compound was afforded (quantitative).

$^1$H NMR (400 MHz, CD$_3$OD) δ 1.20 (d, J=6.4 Hz, 3H), 1.44 (s, 9H), 1.74-1.85 (m, 1H), 1.86-2.00 (m, 1H), 2.01-2.12 (m, 1H), 2.16-2.25 (m, 1H), 3.06 (d, J=11.6 Hz, 1H), 3.10-3.18 (m, 2H), 3.23-3.38 (m, 1H), 3.66-3.73 (m, 1H), 3.83-3.90 (m, 1H), 3.92-4.01 (m, 1H); MS m/z 359 [M+H]+.

Step 3

(2S,5R)-N-{[(2S)-1-Aminopropan-2-yl]oxy}-7-oxo-6-(sulfooxy)-1,6-diazabicyclo[3.2.1]octane-2-carboxamide Following a procedure analogous to Example 59, from all the amount of the compound of the above Step 2, tetrabutylammonium tert-butyl {(2S)-2-[({[(2S,5R)-7-oxo-6-(sulfooxy)-1,6-diazabicyclo[3.2.1]oct-2-yl]carbonyl}amino)oxy]propyl}carbamate was afforded (quantitative). MS m/z 437 [M−Bu$_4$N]$^-$.

All the amount of the above tetrabutylammonium salt was deprotected with trifluoroacetic acid, and then purified by octadecyl silica gel column chromatography to afford 175.0 mg of the title compound (3 steps, yield 37%).

$^1$H NMR (400 MHz, D$_2$O) δ 1.19 (d, J=6.4 Hz, 3H), 1.67-1.88 (m, 2H), 1.91-2.10 (m, 2H), 2.91-3.00 (m, 1H), 3.01-3.13 (m, 2H), 3.19 (br d, J=12.4 Hz, 1H), 3.95 (br d, J=7.2 Hz, 1H), 4.08 (br s, 1H), 4.11-4.20 (m, 1H); MS m/z 339 [M+H]+.

Example 69

(2S,5R)-N-(3-Aminopropoxy)-7-oxo-6-(sulfooxy)-1,6-diazabicyclo[3.2.1]octane-2-carboxamide (II-069)

[Chemical formula 100]

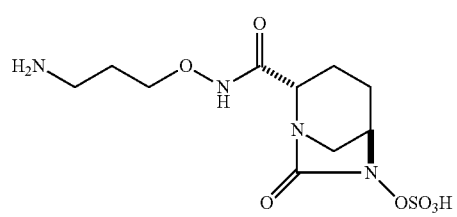

Step 1 tert-Butyl {3-[({[(2S,5R)-6-benzyloxy-7-oxo-1,6-diazabicyclo[3.2.1]oct-2-yl]carbonyl}amino)oxy]propyl}carbamate

[Chemical formula 101]

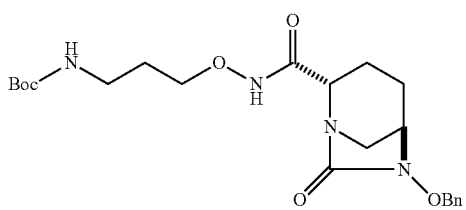

Following a procedure analogous to Example 27, from the carboxylic acid (6b, 390 mg, 1.41 mmol) of Example 9 or 16 and tert-butyl (3-(aminooxy)propyl)carbamate (730 mg) described in Reference Example 20, the title compound 398.1 mg was afford (yield 63%).

$^1$H NMR (400 MHz, CDCl$_3$) δ 1.44 (s, 9H), 1.50-1.67 (m, 1H), 1.75-1.86 (m, 2H), 1.88-2.07 (m, 2H), 2.28-2.37 (m, 2H), 2.77 (d, J=11.0 Hz, 1H), 3.01 (br d, J=11.0 Hz, 1H), 3.20-3.38 (m, 3H), 3.89-4.04 (m, 3H), 4.90 (d, J=11.4 Hz, 1H), 5.05 (d, J=11.4 Hz, 1H), 5.17 (br s, 1H), 7.36-7.45 (m, 5H), 9.21 (br s, 1H); MS m/z 449 [M+H]$^+$.

Step 2 tert-Butyl {3-[({[(2S,5R)-6-hydroxy-7-oxo-1,6-diazabicyclo[3.2.1]oct-2-yl]carbonyl}amino)oxy]propyl}carbamate

[Chemical formula 102]

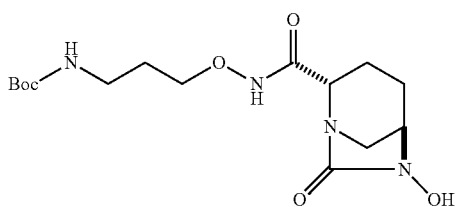

Following a procedure analogous to Example 17, from the compound (392.8 mg, 876 μmol) of the above Step 1, the title compound was afforded (quantitative).

$^1$H NMR (400 MHz, CD$_3$OD) δ 1.43 (s, 9H), 1.73-1.99 (m, 4H), 2.01-2.12 (m, 1H), 2.13-2.24 (m, 1H), 3.07 (d, J=11.6 Hz, 1H), 3.09-3.21 (m, 3H), 3.69 (br s, 1H), 3.80-3.96 (m, 3H); MS m/z 359 [M+H]$^+$.

Step 3

(2S,5R)-N-(3-Aminopropoxy)-7-oxo-6-(sulfooxy)-1,6-diazabicyclo[3.2.1]octane-2-carboxamide Following a procedure analogous to Example 59, from all the amount of the compound of the above Step 2, tetrabutylammonium tert-butyl {3-[({[(2S,5R)-7-oxo-6-(sulfooxy)-1,6-diazabicyclo[3.2.1]oct-2-yl]carbonyl}amino)oxy]propyl}carbamate was afforded (quantitative).

$^1$H NMR (400 MHz, CDCl$_3$) δ 1.01 (t, J=7.4 Hz, 12H), 1.33-1.53 (m, 8H), 1.47 (s, 9H), 1.55-1.96 (m, 12H), 2.14-2.23 (m, 1H), 2.31-2.41 (m, 1H), 2.85 (br d, J=11.2 Hz, 1H), 3.15-3.42 (m, 11H), 3.88-4.07 (m, 3H), 4.35 (br s, 1H), 5.27 (br s, 1H), 9.26 (br s, 1H); MS m/z 437 [M−Bu$_4$N]$^-$.

All the amount of the above tetrabutylammonium salt was deprotected with trifluoroacetic acid, and then purified by octadecyl silica gel column chromatography to afford 138.4 mg of the title compound (3 steps, yield 47%).

$^1$H NMR (400 MHz, D$_2$O) δ 1.67-2.05 (m, 6H), 3.00-3.19 (m, 4H), 3.82-3.94 (m, 3H), 4.05-4.10 (m, 1H); MS m/z 337 [M−H]$^-$.

Example 70

Sodium (2S,5R)-2-(1,2-oxazolidin-2-ylcarbonyl)-6-(sulfooxy)-1,6-diazabicyclo[3.2.1]octane-7-one

Step 1

(2S,5R)-6-Benzyloxy-2-(1,2-oxazolidin-2-ylcarbonyl)-1,6-diazabicyclo[3.2.1]octane-7-one Following a procedure analogous to Example 27, from the carboxylic acid (6b, 550 mg, 2.00 mmol) of Example 9 or 16 and 1,2-oxazolidine hydrochloride (328.6 mg, commercially available), 588 mg of the title compound was afforded (yield 88.7%).

$^1$H NMR (400 MHz, CDCl$_3$) δ 1.26-2.34 (m, 6H), 2.95 (m, 1H), 3.33 (m, 2H), 3.74 (m, 2H), 3.98-4.42 (m, 3H), 4.92 (m, 1H), 5.03-5.06 (m, 1H), 7.26-7.52 (m, 5H); MS m/z 332 [M+H]$^+$.

Step 2

(2S,5R)-6-Hydroxy 2-(1,2-oxazolidin-2-ylcarbonyl)-1,6-diazabicyclo[3.2.1]octane-7-one Following a procedure analogous to Example 17, from all the amount of the compound of the above Step 1, the title compound was afforded (quantitative). MS m/z 242 [M+H]$^+$.

Step 3

Sodium (2S,5R)-2-(1,2-oxazolidin-2-ylcarbonyl)-6-(sulfooxy)-1,6-diazabicyclo[3.2.1]octane-7-one Following a procedure analogous to Example 22, from all the amount of the compound of the above Step 2, pyridinium (2S,5R)-2-(1,2-oxazolidin-2-ylcarbonyl)-6-(sulfooxy)-1,6-diazabicyclo[3.2.1]octane-7-one was afforded, and neutralized with saturated sodium bicarbonate aqueous solution, and then purified by octadecyl silica gel column chromatography to afford 281.3 mg of the title compound (yield 46.9%).

$^1$H NMR (400 MHz, D$_2$O) δ 1.79-1.98 (m, 4H), 2.28-2.30 (m, 2H), 3.13-3.24 (m, 2H), 3.61-4.33 (m, 6H); MS m/z 322 [M−Na+2H]$^+$.

Example 71

Sodium (2S,5R)-2-(1,2-oxazinan-2-ylcarbonyl)-6-(sulfooxy)-1,6-diazabicyclo[3.2.1]octane-7-one

Step 1

(2S,5R)-6-benzyloxy-2-(1,2-oxazinan-2-ylcarbonyl)-1,6-diazabicyclo[3.2.1]octane-7-one Following a procedure analogous to Example 27, from the carboxylic acid (6b, 552 mg, 2.00 mmol) of Example 9 or 16 and 1,2-oxazinane (261 mg), 679 mg of the title compound was afforded (yield 98.3%).

$^1$H NMR (400 MHz, CDCl$_3$) δ 1.63-2.10 (m, 8H), 2.93-2.96 (br d, J=9.2 Hz, 1H), 3.28-3.31 (d, J=11.6 Hz, 1H), 3.34 (s, 1H), 3.61 (br s, 1H), 3.93-4.14 (m, 3H), 4.47 (br s, 1H), 4.89-4.92 (d, J=11.2 Hz, 1H), 5.03-5.06 (d, J=11.6 Hz, 1H), 7.23-7.52 (m, 5H); MS m/z 346 [M+H]$^+$.

Step 2

(2S,5R)-6-Hydroxy2-(1,2-oxazinan-2-ylcarbonyl)-1,6-diazabicyclo[3.2.1]octane-7-one Following a procedure analogous to Example 17, from all the amount of the compound of the above Step 1, the title compound was afforded (quantitative). MS m/z 256 [M+H]$^+$.

Step 3

Sodium (2S,5R)-2-(1,2-oxazinan-2-ylcarbonyl)-6-(sulfooxy)-1,6-diazabicyclo[3.2.1]octane-7-one Following a procedure analogous to Example 22, from all the amount of the compound of the above Step 2, pyridinium (2S,5R)-2-(1,2-oxazinan-2-ylcarbonyl)-6-(sulfooxy)-1,6-diazabicyclo[3.2.1]octane-7-one was afforded, and neutralized with saturated sodium bicarbonate aqueous solution, and then purified by octadecyl silica gel column chromatography to afford 297 mg of the title compound (yield 42.4%).

$^1$H NMR (400 MHz, D$_2$O) δ 1.64-1.97 (m, 8H), 2.99-3.16 (m, 1H), 3.21-3.24 (d, J=12.0 Hz, 1H), 3.54-4.37 (m, 6H); MS m/z 336 [M−Na+2H]$^+$.

Example 72

Sodium (2S,5R)-N-[2-(morpholin-4-yl)ethoxy]-7-oxo-6-(sulfooxy)-1,6-diazabicyclo[3.2.1]octane-2-carboxamide

Step 1

(2S,5R)-6-Benzyloxy-N-[2-(morpholin-4-yl)ethoxy]-7-oxo-1,6-diazabicyclo[3.2.1]octane-2-carboxamide Following a procedure analogous to Example 45, from the carboxylic acid (6b, 414 mg, 1.50 mmol) of Example 9 or 16 and O-(2-morpholinoethyl)hydroxylamine (306 mg, Huhu Technology), 629.6 mg of the title compound was afforded (quantitative).

$^1$H NMR (400 MHz, CDCl$_3$) δ 1.60-1.73 (m, 1H), 1.85-2.06 (m, 2H), 2.33 (br dd, J=14.4, 7.6 Hz, 1H), 2.46-2.60 (m, 4H), 2.62-2.74 (m, 2H), 2.80 (d, J=11.8 Hz, 1H), 2.98 (br d, J=11.8 Hz, 1H), 3.28-3.34 (m, 1H), 3.70-3.81 (m, 4H), 3.93 (br d, J=7.2 Hz, 1H), 3.97-4.11 (m, 2H), 4.90 (d, J=11.2 Hz, 1H), 5.06 (d, J=11.2 Hz, 1H), 7.35-7.45 (m, 5H), 9.93 (br s, 1H); MS m/z 405 [M+H]$^+$.

Step 2

(2S,5R)-6-Hydroxy-N-[2-(morpholin-4-yl)ethoxy]-7-oxo-1,6-diazabicyclo[3.2.1]octane-2-carboxamide Following a procedure analogous to Example 17, from all the amount of the compound of the above Step 1, 452.4 mg of the title compound was afforded (yield 96%).

$^1$H NMR (400 MHz, CD$_3$OD) δ 1.77-1.85 (m, 1H), 1.86-1.98 (m, 1H), 2.03-2.13 (m, 1H), 2.16-2.25 (m, 1H), 2.50-2.61 (m, 4H), 2.68 (t, J=5.4 Hz, 2H), 3.05 (d, J=11.6 Hz, 1H), 3.12 (br d, J=11.6 Hz, 1H), 3.67-3.74 (m, 5H), 3.84 (br d, J=7.2 Hz, 1H), 4.02-4.06 (m, 2H); MS m/z 315 [M+H]$^+$.

Step 3

Sodium (2S,5R)-N-[2-(morpholin-4-yl)ethoxy]-7-oxo-6-(sulfooxy)-1,6-diazabicyclo[3.2.1]octane-2-carboxamide Following a procedure analogous to Example 18, from all the amount of the compound of the above Step 2, pyridinium (2S,5R)-N-[2-(morpholin-4-yl)ethoxy]-7-oxo-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 30.9 mg of the title compound (4 steps, yield 21%).

$^1$H NMR (500 MHz, D$_2$O) δ 1.77-1.87 (m, 2H), 1.93-2.06 (m, 2H), 2.51-2.65 (m, 4H), 2.67 (t, J=5.5 Hz, 2H), 3.16 (br d, J=11.8 Hz, 1H), 3.24 (d, J=11.8 Hz, 1H), 3.66-3.76 (m, 4H), 3.85 (br d, J=5.0 Hz, 1H), 3.95 (t, J=5.5 Hz, 2H), 4.13 (br s, 1H); MS m/z 395 [M−Na+2H]$^+$.

Example 73

(2S,5R)-7-Oxo-N-[2-(piperazin-1-yl)ethoxy]-6-(sulfooxy)-1,6-diazabicyclo[3.2.1]octane-2-carboxamide

Step 1 tert-Butyl 4-{2-[({[(2S,5R)-6-benzyloxy-7-oxo-1,6-diazabicyclo[3.2.1]oct-2-yl]carbonyl}amino)oxy]ethyl}piperazine-1-carboxylate Following a procedure analogous to Example 27, from the carboxylic acid (6b, 552 mg, 2.00 mmol) of Example 9 or 16 and tert-butyl 4-(2-(aminooxy)ethyl)piperazine-1-carboxylate (735 mg, prepared following procedures analogous to Reference Example 7 and Reference Example 15), 476.5 mg of the title compound was afforded (yield 47.3%).

$^1$H NMR (400 MHz, CDCl$_3$) δ 1.45 (s, 9H), 1.64-2.06 (m, 3H), 2.30-2.35 (m, 1H), 2.58-2.66 (m, 4H), 2.68-2.69 (m, 2H), 2.77-2.80 (d, J=11.6 Hz, 1H), 2.96-2.99 (d, J=11.6 Hz, 1H), 3.31 (br s, 1H), 3.79-3.82 (m, 4H), 3.92-3.94 (d, J=8.0 Hz, 1H), 3.99-4.09 (m, 2H), 4.88-4.92 (d, J=11.2 Hz, 1H), 5.04-5.07 (d, J=11.6 Hz, 1H), 7.34-7.42 (m, 5H); MS m/z 504 [M+H]$^+$.

Step 2 tert-Butyl 4-{2-[({[(2S,5R)-6-hydroxy-7-oxo-1,6-diazabicyclo[3.2.1]oct-2-yl]carbonyl}amino)oxy]ethyl}piperazine-1-carboxylate Following a procedure analogous to Example 17, from all the amount of the compound of the above Step 1, the title compound was afforded (quantitative). MS m/z 414 [M+H]$^+$.

Step 3

(2S,5R)-7-Oxo-N-[2-(piperazin-1-yl)ethoxy]-6-(sulfooxy)-1,6-diazabicyclo[3.2.1]octane-2-carboxamide Following a procedure analogous to Example 59, from all the amount of the compound of the above Step 2, tetrabutylammonium tert-butyl 4-{2-[({[(2S,5R)-7-oxo-6-(sulfooxy)-1,6-diazabicyclo[3.2.1]oct-2-yl]carbonyl}amino)oxy]ethyl}piperazine-1-carboxylate was afforded (quantitative). MS m/z 492 [M–Bu$_4$N]$^-$.

All amount of the tetrabutylammonium salt was deprotected with trifluoroacetic acid, and then purified by octadecyl silica gel column chromatography to afford 12.3 mg of the title compound (yield 3.3%).

$^1$H NMR (400 MHz, D$_2$O) δ 1.74 (m, 2H), 1.76 (m, 2H), 2.65-2.69 (m, 6H), 2.96 (m, 4H), 2.98-2.99 (d, J=5.2 Hz, 1H), 3.17-3.20 (d, J=10.8 Hz, 1H), 3.86-3.89 (m, 3H), 4.04 (br s, 1H); MS m/z 394 [M+H]$^+$.

Example 74

(2S,5R)-7-Oxo-N-[2-(1,4-diazepan-1-yl)ethoxy]-6-(sulfooxy)-1,6-diazabicyclo[3.2.1]octane-2-carboxamide

Step 1 tert-butyl 4-{2-[({[(2S,5R)-6-Benzyloxy-7-oxo-1,6-diazabicyclo[3.2.1]oct-2-yl]carbonyl}amino)oxy]ethyl}-1,4-diazepine-1-carboxylate Following a procedure analogous to Example 17, from the carboxylic acid (6b, 548 mg, 1.98 mmol) of Example 9 or 16 and tert-butyl 4-(2-(aminooxy)ethyl)-1,4-diazepine-1-carboxylate (921 mg, prepared following procedures analogous to Reference Example 7 and Reference Example 15), 1.13 g of the title compound was afforded. MS m/z 518 [M+H]+.

Step 2 tert-Butyl 4-{2-[({[(2S,5R)-6-hydroxy-7-oxo-1,6-diazabicyclo[3.2.1]oct-2-yl]carbonyl}amino)oxy]ethyl}-1,4-diazepine-1-carboxylate Following a procedure analogous to Example 17, from all amount of the compound of the above Step 1, 910 mg of the title compound was afforded. MS m/z 428 [M+H]$^+$.

Step 3

(2S,5R)-7-Oxo-N-[2-(1,4-diazepan-1-yl)ethoxy]-6-(sulfooxy)-1,6-diazabicyclo[3.2.1]octane-2-carboxamide To a solution of all the amount of the compound of the above Step 2 in methylene chloride (20 mL) were added 2,6-lutidine (692 μl) and sulfur trioxide-pyridine complex (945 mg), followed by agitating at room temperature overnight. After completion of the reaction, this reaction mixture was filtered, and the filtrate was concentrated to afford 1.67 g of pyridinium tert-butyl 4-{2-[({[(2S,5R)-7-oxo-6-(sulfooxy)-1,6-diazabicyclo[3.2.1]oct-2-yl]carbonyl}amino)oxy]ethyl}-1,4-diazepine-1-carboxylate. MS m/z 506 [M-C$_5$H$_5$NH]$^-$.

The above pyridinium salt (1.00 g, 1.19 mmol) was dissolved in methylene chloride (2.0 mL), and to which was added trifluoroacetic acid (2.0 mL) under ice-cooling and agitated at 0° C. for 30 minutes. The reaction solution was concentrated under reduced pressure, and the resulting residue was washed with diethyl ether, and adjusted pH with sodium bicarbonate aqueous solution to pH 7, and then purified by octadecyl silica gel column chromatography (methanol/water=0/10-5/5). After lyophilisation, 111 mg of the title compound was afforded (4 steps, yield 23%).

$^1$H NMR (400 MHz, D$_2$O) δ 1.64-2.07 (m, 6H), 2.73-2.85 (m, 4H), 2.90-3.04 (m, 3H), 3.13-3.28 (m, 5H), 3.90-3.98 (m, 3H), 4.05-4.09 (m, 5H); MS m/z 408 [M+H]$^+$.

Example 75

(2S,5R)-N-[(2S)-Azetidin-2-ylmethoxy]-7-oxo-6-(sulfooxy)-1,6-diazabicyclo[3.2.1]octane-2-carboxamide (II-075)

[Chemical formula 103]

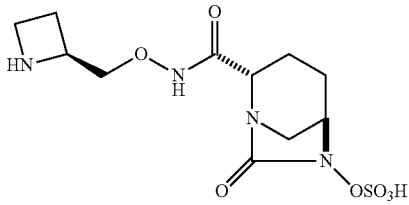

Step 1 tert-Butyl (2S)-2-{[({[(2S,5R)-6-benzyloxy-7-oxo-1,6-diazabicyclo[3.2.1]oct-2-yl]carbonyl}amino)oxy]methyl}azetidine-1-carboxylate

[Chemical formula 104]

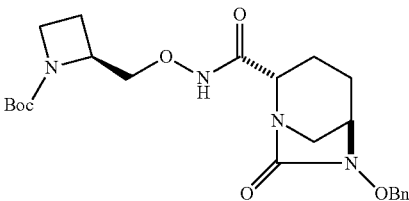

Following a procedure analogous to Example 45, from the carboxylic acid (6b, 553 mg, 2.00 mmol) of Example 9 or 16 and (S)-tert-butyl 2-((aminooxy)methyl)azetidine-1-carboxylate (578 mg) described in Reference Example 21, 760.1 mg of the title compound was afforded (yield 83%).

$^1$H NMR (400 MHz, CDCl$_3$) δ 1.46 (s, 9H), 1.56-1.70 (m, 1H), 1.88-2.07 (m, 3H), 2.23-2.34 (m, 2H), 2.84 (d, J=11.6

Hz, 1H), 3.02 (d, J=11.6 Hz, 1H), 3.28 (br s, 1H), 3.77-4.03 (m, 4H), 4.06-4.15 (m, 1H), 4.37-4.48 (m, 1H), 4.89 (d, J=11.6 Hz, 1H), 5.04 (d, J=11.6 Hz, 1H), 7.34-7.44 (m, 5H), 10.63 (br s, 1H); MS m/z 461 [M+H]⁺.

Step 2 tert-Butyl (2S)-2-{[({[(2S,5R)-6-hydroxy-7-oxo-1,6-diazabicyclo[3.2.1]oct-2-yl]carbonyl}amino)oxy]methyl}azetidine-1-carboxylate

[Chemical formula 105]

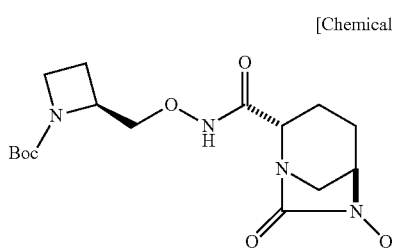

Following a procedure analogous to Example 17, from the compound (699 mg, 1.52 mmol) of the above Step 1, the title compound was afforded (quantitative).

¹H NMR (400 MHz, CD₃OD) δ 1.44 (s, 9H), 1.74-1.85 (m, 1H), 1.86-1.99 (m, 1H), 2.02-2.14 (m, 1H), 2.16-2.40 (m, 3H), 3.06 (d, J=11.6 Hz, 1H), 3.10-3.17 (m, 1H), 3.67-3.74 (m, 1H), 3.75-3.93 (m, 3H), 4.01 (dd, J=10.6, 10.6 Hz, 1H), 4.14 (dd, J=10.6, 10.6 Hz, 1H), 4.37-4.47 (m, 1H); MS m/z 371 [M+H]⁺.

Step 3

(2S,5R)-N-[(2S)-Azetidin-2-ylmethoxy]-7-oxo-6-(sulfooxy)-1,6-diazabicyclo[3.2.1]octane-2-carboxamide Following a procedure analogous to Example 59, from all amount of the compound of the above Step 2, tetrabutylammonium tert-butyl (2S)-2-{[({[(2S,5R)-7-oxo-6-(sulfooxy)-1,6-diazabicyclo[3.2.1]oct-2-yl]carbonyl}amino)oxy]methyl}azetidine-1-carboxylate was afforded (quantitative).

¹H NMR (400 MHz, CDCl₃) δ 1.01 (t, J=7.2 Hz, 12H), 1.30-2.10 (m, 19H), 1.46 (s, 9H), 2.12-2.39 (m, 3H), 2.89 (br d, J=12.0 Hz, 1H), 3.23-3.39 (m, 9H), 3.76-3.93 (m, 3H), 3.95-4.06 (m, 1H), 4.08-4.18 (m, 1H), 4.33 (br s, 1H), 4.37-4.50 (m, 1H); MS m/z 449 [M−Bu₄N]⁻.

All the amount of the above tetrabutylammonium salt was deprotected with trifluoroacetic acid, and then purified by octadecyl silica gel column chromatography, 172.3 mg of the title compound was afforded (3 steps, yield 32%).

¹H NMR (500 MHz, D₂O) δ 1.71-1.83 (m, 1H), 1.84-1.97 (m, 1H), 1.98-2.16 (m, 2H), 2.36-2.49 (m, 1H), 2.50-2.61 (m, 1H), 3.10 (d, J=12.0 Hz, 1H), 3.22-3.30 (m, 1H), 3.92-4.12 (m, 5H), 4.25-4.36 (m, 1H), 4.68-4.77 (m, 1H); MS m/z 351 [M+H]⁺.

Example 76

(2S,5R)-7-Oxo-N-[(2S)-pyrrolidin-2-ylmethoxy]-6-(sulfooxy)-1,6-diazabicyclo[3.2.1]octane-2-carboxamide Step 1 tert-Butyl (2S)-2-{[({[(2S,5R)-6-benzyloxy-7-oxo-1,6-diazabicyclo[3.2.1]oct-2-yl]carbonyl}amino)oxy]methyl}pyrrolidine-1-carboxylate Following a procedure analogous to Example 27, from the carboxylic acid (6b, 390 mg, 1.41 mmol) of Example 9 or 16 and (S)-tert-butyl 2-((aminooxy)methyl)pyrrolidine-1-carboxylate (649 mg, prepared following procedures analogous to Reference Example 7 and Reference Example 13), 477 mg of the title compound was afforded (yield 71%).

¹H NMR (400 MHz, CDCl₃) δ 1.46 (s, 9H), 1.62-1.77 (m, 1H), 1.70-2.07 (m, 6H), 2.21-2.37 (m, 1H), 2.88 (br d, J=12.4 Hz, 1H), 2.98-3.10 (m, 1H), 3.25-3.38 (m, 3H), 3.65-4.05 (m, 3H), 4.08-4.24 (m, 1H), 4.90 (d, J=11.6 Hz, 1H), 5.05 (d, J=11.6 Hz, 1H), 7.32-7.46 (m, 5H), 10.22 (s, 1H); MS m/z 475 [M+H]⁺.

Step 2 tert-Butyl (2S)-2-{[({[(2S,5R)-6-hydroxy-7-oxo-1,6-diazabicyclo[3.2.1]oct-2-yl]carbonyl}amino)oxy]methyl}pyrrolidine-1-carboxylate Following a procedure analogous to Example 17, from all the amount of the compound of the above Step 1, the title compound was afforded (quantitative).

¹H NMR (400 MHz, CD₃OD) δ 1.46 (s, 9H), 1.72-2.27 (m, 8H), 2.99-3.18 (m, 2H), 3.25-3.56 (m, 2H), 3.66-4.10 (m, 5H); MS m/z 385 [M+H]⁺.

Step 3

(2S,5R)-7-Oxo-N-[(2S)-pyrrolidin-2-ylmethoxy]-6-(sulfooxy)-1,6-diazabicyclo[3.2.1]octane-2-carboxamide Following a procedure analogous to Example 26, from all the amount of the compound of the above Step 2, 385.6 mg of pyridinium tert-butyl (2S)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate was afforded (71%).

¹H NMR (400 MHz, CDCl₃) δ 1.45 (s, 9H), 1.65-2.57 (m, 8H), 2.96-3.12 (m, 1H), 3.25-3.44 (m, 4H), 3.68-4.18 (m, 3H), 4.25 (br s, 1H), 7.92-8.00 (m, 2H), 8.45 (dd, J=7.6, 7.6 Hz, 1H), 8.98-9.07 (m, 1H), 10.61 (br s, 1H); MS m/z 463 [M−C₅H₅NH]⁻.

All the amount of the above pyridinium salt was deprotected with trifluoroacetic acid, and then purified by octadecyl silica gel column chromatography to afford 58.1 mg of the title compound (3 steps, yield 16%).

¹H NMR (400 MHz, D₂O) δ 1.78-2.12 (m, 8H), 3.04 (d, J=12.4 Hz, 1H), 3.18 (br d, J=12.4 Hz, 1H), 3.24 (t, J=7.2 Hz, 2H), 3.83 (ddd, J=8.2, 8.2, 3.4 Hz, 1H), 3.89-3.97 (m, 2H), 4.04-4.11 (m, 2H); MS m/z 365 [M+H]⁺.

Example 77

(2S,5R)-7-Oxo-N-[(2R)-pyrrolidin-2-ylmethoxy]-6-(sulfooxy)-1,6-diazabicyclo[3.2.1]octane-2-carboxamide (II-077)

[Chemical formula 106]

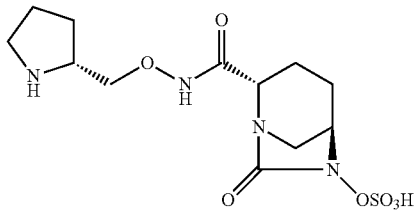

Step 1 tert-Butyl (2R)-2-{[({[(2S,5R)-6-benzyloxy-7-oxo-1,6-diazabicyclo[3.2.1]oct-2-yl]carbonyl}amino)oxy]methyl}pyrrolidine-1-carboxylate

[Chemical formula 107]

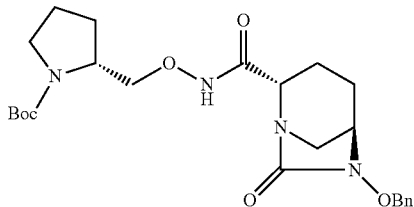

Following a procedure analogous to Example 27, from the carboxylic acid (6b, 390 mg, 1.41 mmol) of Example 9 or 16 and (R)-tert-butyl 2-((aminooxy)methyl)pyrrolidine-1-carboxylate (796 mg) described in Reference Example 22, 336 mg of the title compound was afforded (yield 50%).

¹H NMR (400 MHz, CDCl₃) δ 1.45 (s, 9H), 1.52-1.72 (m, 1H), 1.80-2.09 (m, 6H), 2.27-2.39 (m, 1H), 2.84 (br d, J=12.4 Hz, 1H), 2.96-3.08 (m, 1H), 3.28-3.44 (m, 3H), 3.60-3.86 (m, 2H), 3.89-4.06 (m, 1H), 4.14-4.29 (m, 1H), 4.90 (d, J=11.2 Hz, 1H), 5.06 (d, J=11.2 Hz, 1H), 7.32-7.47 (m, 5H), 10.56 (s, 1H); MS m/z 475 [M+H]⁺.

Step 2 tert-Butyl (2R)-2-{[({[(2S,5R)-6-hydroxy-7-oxo-1,6-diazabicyclo[3.2.1]oct-2-yl]carbonyl}amino)oxy]methyl}pyrrolidine-1-carboxylate

[Chemical formula 108]

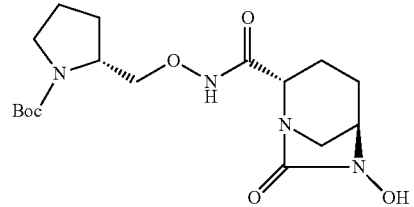

Following a procedure analogous to Example 17, from all the amount of the compound of the above Step 1, the title compound was afforded (quantitative).

¹H NMR (400 MHz, CD₃OD) δ 1.46 (s, 9H), 1.73-2.27 (m, 8H), 3.06 (d, J=11.6 Hz, 1H), 3.09-3.18 (m, 1H), 3.24-3.40 (m, 2H), 3.67-3.71 (m, 1H), 3.73-4.12 (m, 4H); MS m/z 385 [M+H]⁺.

Step 3

(2S,5R)-7-Oxo-N-[(2R)-pyrrolidin-2-ylmethoxy]-6-(sulfooxy)-1,6-diazabicyclo[3.2.1]octane-2-carboxamide Following a procedure analogous to Example 59, from all the amount of the compound of the above Step 2, tetrabutylammonium tert-butyl (2R)-2-{[({[(2S,5R)-7-oxo-6-(sulfooxy)-1,6-diazabicyclo[3.2.1]oct-2-yl]carbonyl}amino)oxy]methyl}pyrrolidine-1-carboxylate was afforded (quantitative).

¹H NMR (400 MHz, CDCl₃) δ 1.01 (t, J=7.4 Hz, 12H), 1.34-1.51 (m, 8H), 1.46 (s, 9H), 1.55-1.78 (m, 10H), 1.80-2.01 (m, 4H), 2.11-2.23 (m, 1H), 2.29-2.42 (m, 1H), 2.88 (br d, J=11.2 Hz, 1H), 3.21-3.43 (m, 10H), 3.60-3.86 (m, 2H), 3.88-4.07 (m, 2H), 4.16-4.28 (m, 1H), 4.34 (br s, 1H), 10.62 (br s, 1H); MS m/z 463 [M–Bu₄N+2H]⁺.

All the amount of the above tetrabutylammonium salt was deprotected with trifluoroacetic acid, and then purified by octadecyl silica gel column chromatography to afford 77.4 mg of the title compound (3 steps, yield 30%).

¹H NMR (500 MHz, D₂O) δ 1.66-2.18 (m, 8H), 3.14 (d, J=12.8 Hz, 1H), 3.23 (br d, J=12.8 Hz, 1H), 3.30 (t, J=7.3 Hz, 2H), 3.89 (ddd, J=8.2, 8.2, 3.4 Hz, 1H), 3.92-4.01 (m, 2H), 4.09-4.18 (m, 2H); MS m/z 365 [M+H]⁺.

Example 78

(2S,5R)-7-Oxo-N-[(2S)-piperidine-2-ylmethoxy]-6-(sulfooxy)-1,6-diazabicyclo[3.2.1]octane-2-carboxamide (II-078)

[Chemical formula 109]

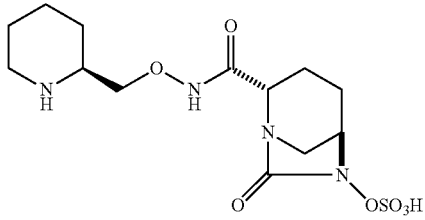

Step 1 tert-Butyl (2S)-2-{[({[(2S,5R)-6-benzyloxy-7-oxo-1,6-diazabicyclo[3.2.1]oct-2-yl]carbonyl}amino)oxy]methyl}piperidine-1-carboxylate

[Chemical formula 110]

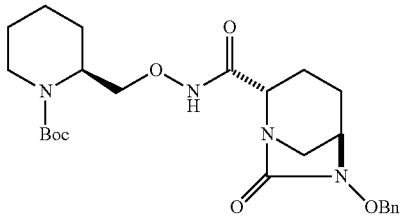

Following a procedure analogous to Example 45, from the carboxylic acid (6b, 276 mg, 1.00 mmol) of Example 9 or 16 and (S)-tert-butyl 2-((aminooxy)methyl)piperidine-1-carboxylate (300 mg) described in Reference Example 23, 353.3 mg of the title compound was afforded (yield 72%).

$^1$H NMR (400 MHz, CDCl$_3$) δ 1.30-1.75 (m, 7H), 1.46 (s, 9H), 1.90-2.10 (m, 2H), 2.22-2.34 (m, 1H), 2.72-2.90 (m, 1H), 2.85 (d, J=11.2 Hz, 1H), 3.09 (br d, J=11.2 Hz, 1H), 3.26-3.32 (m, 1H), 3.68-3.84 (m, 1H), 3.90-4.01 (m, 2H), 4.06-4.15 (m, 1H), 4.44-4.58 (m, 1H), 4.90 (d, J=11.4 Hz, 1H), 5.05 (d, J=11.4 Hz, 1H), 7.35-7.46 (m, 5H), 10.14 (br s, 1H); MS m/z 489 [M+H]$^+$.

Step 2 tert-Butyl (2S)-2-{[({[(2S,5R)-6-hydroxy-7-oxo-1,6-diazabicyclo[3.2.1]oct-2-yl]carbonyl}amino)oxy]methyl}piperidine-1-carboxylate

[Chemical formula 111]

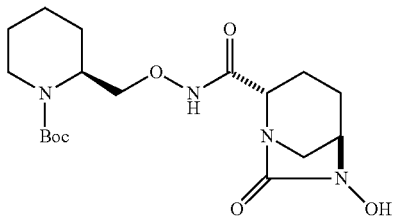

Following a procedure analogous to Example 17, from all the amount of the compound of the above Step 1, the title compound was afforded (quantitative).

$^1$H NMR (400 MHz, CD$_3$OD) δ 1.33-1.70 (m, 5H), 1.45 (s, 9H), 1.74-2.00 (m, 3H), 2.03-2.12 (m, 1H), 2.17-2.26 (m, 1H), 2.82-2.93 (m, 1H), 3.06 (d, J=12.0 Hz, 1H), 3.14 (br d, J=12.0 Hz, 1H), 3.68-3.92 (m, 1H), 3.84 (br d, J=6.8 Hz, 1H), 3.92-4.08 (m, 3H), 4.43-4.51 (m, 1H); MS m/z 399 [M+H]$^+$.

Step 3

(2S,5R)-7-Oxo-N-[(2S)-piperidine-2-ylmethoxy]-6-(sulfooxy)-1,6-diazabicyclo[3.2.1]octane-2-carboxamide Following a procedure analogous to Example 59, from all the amount of the compound of the above Step 2, tetrabutylammonium tert-butyl (2S)-2-{[({[(2S,5R)-7-oxo-6-(sulfooxy)-1,6-diazabicyclo[3.2.1]oct-2-yl]carbonyl}amino)oxy]methyl}piperidine-1-carboxylate was afforded (quantitative).

$^1$H NMR (400 MHz, CDCl$_3$) δ 1.01 (t, J=7.2 Hz, 12H), 1.14-1.79 (m, 23H), 1.45 (s, 9H), 1.84-2.00 (m, 1H), 2.12-2.23 (m, 1H), 2.24-2.38 (m, 1H), 2.72-2.83 (m, 1H), 2.92 (br d, J=12.8 Hz, 1H), 3.21-3.34 (m, 8H), 3.36-3.45 (m, 1H), 3.72-4.18 (m, 4H), 4.35 (br s, 1H), 4.45-4.56 (m, 1H); MS m/z 477 [M−Bu$_4$N]$^-$.

All the amount of the above tetrabutylammonium salt was deprotected with trifluoroacetic acid and purified by octadecyl silica gel column chromatography to afford 52.8 mg of the title compound (3 steps, yield 19%).

$^1$H NMR (400 MHz, D$_2$O) δ 1.31-1.60 (m, 3H), 1.68-1.89 (m, 5H), 1.92-2.10 (m, 2H), 2.82-2.91 (m, 1H), 3.05 (d, J=12.0 Hz, 1H), 3.18 (br d, J=12.0 Hz, 1H), 3.26-3.40 (m, 2H), 3.87 (dd, J=11.8, 9.0 Hz, 1H), 3.94 (br d, J=7.2 Hz, 1H), 3.97 (dd, J=11.8, 3.4 Hz, 1H), 4.07-4.12 (m, 1H); MS m/z 377 [M−H]$^-$.

Example 79

(2S,5R)-N-(Azetidin-3-yloxy)-7-oxo-6-(sulfooxy)-1,6-diazabicyclo[3.2.1]octane-2-carboxamide Step 1 tert-Butyl 3-[({[(2S,5R)-6-benzyloxy-7-oxo-1,6-diazabicyclo[3.2.1]oct-2-yl]carbonyl}amino)oxy]azetidine-1-carboxylate Following a procedure analogous to Example 27, from the carboxylic acid (6b, 413 mg, 1.50 mmol) of Example 9 or 16 and tert-butyl 3-(aminooxy)azetidine-1-carboxylate (375 mg, prepared following procedures analogous to Reference Example 7 and Reference Example 13), 558 mg of the title compound was afforded (yield 84%).

[α]$_D^{24}$ −17.0° (c 0.30, CHCl$_3$); $^1$H NMR (400 MHz, CDCl$_3$) δ 1.43 (s, 9H), 1.57-1.70 (m, 1H), 1.84-2.07 (m, 2H), 2.31 (br dd, J=14.6, 7.4 Hz, 1H), 2.41 (d, J=11.4 Hz, 1H), 3.01 (br d, J=11.4 Hz, 1H), 3.29-3.34 (m, 1H), 3.93-4.03 (m, 2H), 4.05-4.16 (m, 2H), 4.69-4.76 (m, 1H), 4.90 (d, J=11.6 Hz, 1H), 5.05 (d, J=11.6 Hz, 1H), 7.33-7.45 (m, 5H), 8.18 (br s, 1H); MS m/z 447 [M+H]$^+$.

Step 2 tert-Butyl 3-[({[(2S,5R)-6-hydroxy-7-oxo-1,6-diazabicyclo[3.2.1]oct-2-yl]carbonyl}amino)oxy]azetidine-1-carboxylate Following a procedure analogous to Example 17, from the compound (543 mg, 1.22 mmol) of the above Step 1, 428 mg of the title compound was afforded (99%).

$^1$H NMR (400 MHz, CD$_3$OD) δ 1.44 (s, 9H), 1.72-1.84 (m, 1H), 1.85-1.99 (m, 1H), 2.00-2.11 (m, 1H), 2.15-2.24 (m, 1H), 3.00 (d, J=11.6 Hz, 1H), 3.11 (br d, J=11.6 Hz, 1H), 3.69 (br s, 1H), 3.85 (br d, J=7.6 Hz, 1H), 3.88-4.00 (m, 2H), 4.03-4.17 (m, 2H), 4.67-4.76 (m, 1H); MS m/z 357 [M+H]$^+$.

Step 3

(2S,5R)-N-(Azetidin-3-yloxy)-7-oxo-6-(sulfooxy)-1,6-diazabicyclo[3.2.1]octane-2-carboxamide Following a procedure analogous to Example 59, from the compound (424 mg, 1.19 mmol) of the above Step 2, 739 mg of tetrabutylammonium tert-butyl 3-[({[(2S,5R)-7-oxo-6-(sulfooxy)-1,6-diazabicyclo[3.2.1]oct-2-yl]carbonyl}amino)oxy]azetidine-1-carboxylate was afforded (yield 91%).

$^1$H NMR (400 MHz, CDCl$_3$) δ 1.01 (t, J=7.4 Hz, 12H), 1.37-1.53 (m, 8H), 1.44 (s, 9H), 1.57-1.78 (m, 9H), 1.83-1.96 (m, 1H), 2.14-2.23 (m, 1H), 2.34 (br dd, J=15.0, 7.0 Hz, 1H), 2.79 (d, J=11.6 Hz, 1H), 3.23-3.40 (m, 9H), 3.93 (br d, J=7.6 Hz, 1H), 3.95-4.15 (m, 4H), 4.33-4.38 (m, 1H), 4.70-4.78 (m, 1H), 9.24 (br s, 1H); MS m/z 435 [M−Bu$_4$N]$^-$.

The tetrabutylammonium salt (720 mg, 1.06 mmol) was deprotected with trifluoroacetic acid, and then purified by octadecyl silica gel column chromatography to afford 144 mg of the title compound (yield 40%).

[α]$_D^{25}$ −69.2° (c 0.32, H$_2$O); $^1$H NMR (400 MHz, D$_2$O) δ 1.67-1.78 (m, 1H), 1.78-1.89 (m, 1H), 1.92-2.09 (m, 2H), 3.00 (d, J=12.2 Hz, 1H), 3.20 (br d, J=12.2 Hz, 1H), 3.97 (br d, J=7.2 Hz, 1H), 4.04-4.14 (m, 3H), 4.25-4.33 (m, 2H), 4.76-4.84 (m, 1H); MS m/z 337 [M+H]⁺.

Example 80

(2S,5R)-7-Oxo-N-[(3R)-pyrrolidin-3-yloxy]-6-(sulfooxy)-1,6-diazabicyclo[3.2.1]octane-2-carboxamide Step 1 tert-Butyl (3R)-3-[({[(2S,5R)-6-benzyloxy-7-oxo-1,6-diazabicyclo[3.2.1]oct-2-yl]carbonyl}amino)oxy]pyrrolidine-1-carboxylate Following a procedure analogous to Example 27, from the carboxylic acid (6b, 553 mg, 2.00 mmol) of Example 9 or 16 and (R)-tert-butyl 3-(aminooxy)pyrrolidine-1-carboxylate (606 mg) described in Reference Example 13, 904.6 mg of the title compound was afforded (yield 98.3%).

¹H NMR (400 MHz, CDCl₃) δ 1.46 (s, 9H), 1.61-1.68 (m, 1H), 1.83-2.09 (m, 3H), 2.13-2.19 (m, 1H), 2.28-2.34 (m, 1H), 2.75 (d, J=11.6 Hz, 1H), 3.03 (br d, J=11.6 Hz, 1H), 3.31-3.37 (m, 5H), 3.96 (d, J=6.8 Hz, 1H), 4.68 (br s, 1H), 4.90 (d, J=11.6 Hz, 1H), 5.05 (d, J=11.6 Hz, 1H), 7.26-7.43 (m, 5H), 9.06-9.20 (m, 1H); MS m/z 461 [M+H]⁺.

Step 2 tert-Butyl (3R)-3-[({[(2S,5R)-6-hydroxy-7-oxo-1,6-diazabicyclo[3.2.1]oct-2-yl]carbonyl}amino)oxy]pyrrolidine-1-carboxylate Following a procedure analogous to Example 17, from the compound (805 mg, 1.75 mmol) of the above Step 1, the title compound was afforded (quantitative).

¹H NMR (400 MHz, CD₃OD) δ 1.46 (s, 9H), 1.75-2.12 (m, 4H), 2.15-2.28 (m, 2H), 3.06 (d, J=11.6 Hz, 1H), 3.13 (br d, J=11.6 Hz, 1H), 3.25-3.50 (m, 2H), 3.60 (br d, J=12.8 Hz, 1H), 3.70 (br s, 1H), 3.87 (br d, J=7.2 Hz, 1H), 4.34-4.38 (m, 1H), 4.56-4.63 (m, 1H); MS m/z 371 [M+H]⁺.

Step 3

(2S,5R)-7-Oxo-N-[(3R)-pyrrolidin-3-yloxy]-6-(sulfooxy)-1,6-diazabicyclo[3.2.1]octane-2-carboxamide Following a procedure analogous to Example 59, from all the amount of the compound of the above Step 2, tetrabutylammonium tert-butyl (3R)-3-[({[(2S,5R)-2-oxo-6-(sulfooxy)-1,6-diazabicyclo[3.2.1]oct-2-yl]carbonyl}amino)oxy]pyrrolidine-1-carboxylate was afforded (quantitative). MS m/z 449 [M−Bu₄N]⁻.

All the amount of the above tetrabutylammonium salt was deprotected with trifluoroacetic acid, and then purified by octadecyl silica gel column chromatography to afford 204.7 mg of the title compound (3 steps, yield 33%).

¹H NMR (400 MHz, D₂O) δ 1.67-1.88 (m, 2H), 1.92-2.15 (m, 3H), 2.17-2.26 (m, 1H), 3.02 (d, J=12.0 Hz, 1H), 3.20 (br d, J=12.0 Hz, 1H), 3.27-3.44 (m, 3H), 3.48 (d, J=12.8 Hz, 1H), 3.96 (br d, J=7.2 Hz, 1H), 4.06-4.11 (m, 1H), 4.69-4.74 (m, 1H); MS m/z 349 [M−H]⁻.

Example 81

(2S,5R)-7-Oxo-N-[(3S)-pyrrolidin-3-yloxy]-6-(sulfooxy)-1,6-diazabicyclo[3.2.1]octane-2-carboxamide (II-081)

[Chemical formula 112]

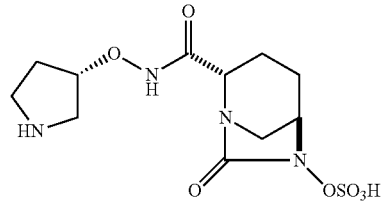

Step 1 tert-Butyl (3S)-3-[({[(2S,5R)-6-benzyloxy-7-oxo-1,6-diazabicyclo[3.2.1]oct-2-yl]carbonyl}amino)oxy]pyrrolidine-1-carboxylate

[Chemical formula 113]

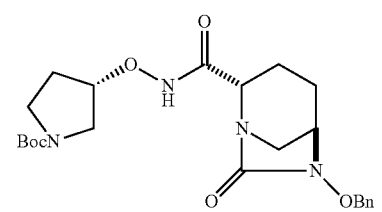

Following a procedure analogous to Example 27, from the carboxylic acid (6b, 553 mg, 2.00 mmol) of Example 9 or 16 and (S)-tert-butyl 3-(aminooxy)pyrrolidine-1-carboxylate (606 mg) described in Reference Example 24, 920.4 mg of the title compound was afforded (quantitative).

¹H NMR (400 MHz, CDCl₃) δ 1.46 (s, 9H), 1.61-1.68 (m, 1H), 1.89-2.09 (m, 3H), 2.15-2.19 (m, 1H), 2.28-2.34 (m, 1H), 2.75 (d, J=11.6 Hz, 1H), 2.95-3.06 (m, 1H), 3.31 (br s, 1H), 3.35-3.68 (m, 4H), 3.97 (d, J=7.6 Hz, 1H), 4.60 (br d, J=23.2 Hz, 1H), 4.90 (d, J=11.6 Hz, 1H), 5.05 (d, J=11.6 Hz, 1H), 7.26-7.43 (m, 5H), 9.08 (br d, J=23.2 Hz, 1H); MS m/z 461 [M+H]⁺.

Step 2 tert-Butyl (3S)-3-[({[(2S,5R)-6-hydroxy-7-oxo-1,6-diazabicyclo[3.2.1]oct-2-yl]carbonyl}amino)oxy]pyrrolidine-1-carboxylate

[Chemical formula 114]

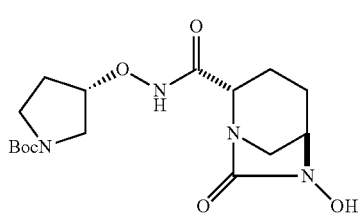

Following a procedure analogous to Example 17, from the compound (869 mg, 1.89 mmol) of the above Step 1, the title compound was afforded (quantitative).

¹H NMR (400 MHz, CD₃OD) δ 1.47 (s, 9H), 1.75-2.12 (m, 4H), 2.13-2.25 (m, 2H), 3.05 (d, J=12.0 Hz, 1H), 3.13 (br d, J=12.0 Hz, 1H), 3.25-3.50 (m, 2H), 3.61 (br d, J=13.2 Hz, 1H), 3.70 (br s, 1H), 3.86 (br d, J=7.2 Hz, 1H), 4.32-4.38 (m, 1H), 4.54-4.62 (m, 1H); MS m/z 371 [M+H]⁺.

Step 3

(2S,5R)-7-Oxo-N-[(3S)-pyrrolidin-3-yloxy]-6-(sulfooxy)-1,6-diazabicyclo[3.2.1]octane-2-carboxamide Following a procedure analogous to Example 59, from all the amount of the compound of the above Step 2, tetrabutylammonium tert-butyl (3S)-3-[({[(2S,5R)-7-oxo-6-(sulfooxy)-1,6-diazabicyclo[3.2.1]oct-2-yl]carbonyl}amino)oxy]pyrrolidine-1-carboxylate was afforded (quantitative). MS m/z 449 [M–Bu₄N]⁻.

All the amount of the above tetrabutylammonium salt was deprotected with trifluoroacetic acid, and then purified by octadecyl silica gel column chromatography to afford 170.7 mg of the title compound (3 steps, yield 26%).

¹H NMR (400 MHz, D₂O) δ 1.71-1.92 (m, 2H), 1.95-2.18 (m, 3H), 2.21-2.30 (m, 1H), 3.07 (d, J=12.2 Hz, 1H), 3.24 (br d, J=12.2 Hz, 1H), 3.31-3.45 (m, 3H), 3.51 (d, J=13.6 Hz, 1H), 3.99 (br d, J=6.0 Hz, 1H), 4.10-4.14 (m, 1H), 4.72-4.77 (m, 1H); MS m/z 349 [M–H]⁻.

Example 82

(2S,5R)-N-(Azetidin-3-ylmethoxy)-7-oxo-6-(sulfooxy)-1,6-diazabicyclo[3.2.1]octane-2-carboxamide
(II-082)

[Chemical formula 115]

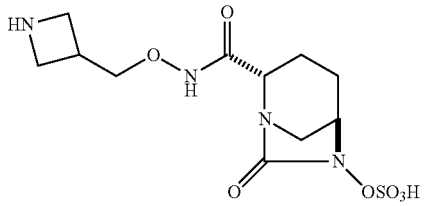

Step 1 tert-Butyl 3-{[({[(2S,5R)-6-benzyloxy-7-oxo-1,6-diazabicyclo[3.2.1]oct-2-yl]carbonyl}amino)oxy]methyl}azetidine-1-carboxylate

[Chemical formula 116]

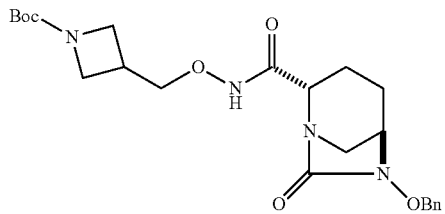

Following a procedure analogous to Example 45, from the carboxylic acid (6b, 553 mg, 2.00 mmol) of Example 9 or 16 and tert-butyl 3-((aminooxy)methyl)azetidine-1-carboxylate (564 mg) described in Reference Example 25, 699.7 mg of the title compound was afforded (yield 76%).

¹H NMR (400 MHz, CDCl₃) δ 1.43 (s, 9H), 1.54-1.70 (m, 1H), 1.87-2.06 (m, 2H), 2.27-2.35 (m, 1H), 2.75 (d, J=11.6 Hz, 1H), 2.80-2.90 (m, 1H), 3.01 (br d, J=11.6 Hz, 1H), 3.32 (br s, 1H), 3.68-3.76 (m, 2H), 3.94 (br d, J=7.6 Hz, 1H), 4.00-4.15 (m, 4H), 4.90 (d, J=11.8 Hz, 1H), 5.05 (d, J=11.8 Hz, 1H), 7.35-7.44 (m, 5H), 9.08 (br s, 1H); MS m/z 461 [M+H]⁺.

Step 2 tert-Butyl 3-{[({[(2S,5R)-6-hydroxy-7-oxo-1,6-diazabicyclo[3.2.1]oct-2-yl]carbonyl}amino)oxy]methyl}azetidine-1-carboxylate

[Chemical formula 117]

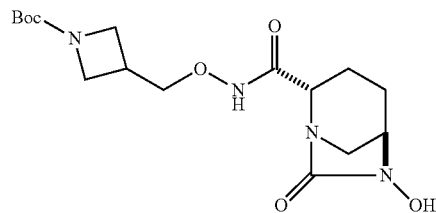

Following a procedure analogous to Example 17, from the compound (642 mg, 1.39 mmol) of the above Step 1, the title compound was afforded (quantitative).

¹H NMR (400 MHz, CD₃OD) δ 1.43 (s, 9H), 1.74-1.85 (m, 1H), 1.86-1.97 (m, 1H), 2.04-2.13 (m, 1H), 2.16-2.24 (m, 1H), 2.84-2.94 (m, 1H), 3.05 (d, J=11.6 Hz, 1H), 3.13 (br d, J=11.6 Hz, 1H), 3.68-3.82 (m, 3H), 3.83 (br d, J=6.8 Hz, 1H), 3.97-4.06 (m, 4H); MS m/z 371 [M+H]⁺.

Step 3

(2S,5R)-N-(Azetidin-3-ylmethoxy)-7-oxo-6-(sulfooxy)-1,6-diazabicyclo[3.2.1]octane-2-carboxamide Following a procedure analogous to Example 59, from all the amount of the compound of the above Step 2, tetrabutylammonium tert-butyl 3-{[({[(2S,5R)-7-oxo-6-(sulfooxy)-1,6-diazabicyclo[3.2.1]oct-2-yl]carbonyl}amino)oxy]methyl}azetidine-1-carboxylate was afforded (quantitative).

¹H NMR (400 MHz, CDCl₃) δ 1.01 (t, J=7.2 Hz, 12H), 1.37-1.51 (m, 8H), 1.46 (s, 9H), 1.54-1.75 (m, 9H), 1.82-1.97 (m, 1H), 2.13-2.25 (m, 1H), 2.29-2.40 (m, 1H), 2.77-2.95 (m, 2H), 3.24-3.40 (m, 9H), 3.64-4.16 (m, 7H), 4.36 (br s, 1H), 9.16 (br s, 1H); MS m/z 449 [M–Bu₄N]⁻.

All the amount of the above tetrabutylammonium salt was deprotected with trifluoroacetic acid, and then purified by octadecyl silica gel column chromatography to afford 164.7 mg of the title compound (3 steps, yield 34%).

¹H NMR (400 MHz, D₂O) δ 1.65-1.89 (m, 2H), 1.92-2.06 (m, 2H), 3.06 (d, J=12.4 Hz, 1H), 3.10-3.22 (m, 2H), 3.90-4.00 (m, 5H), 4.07-4.14 (m, 3H); MS m/z 351 [M+H]⁺.

Example 83

(2S,5R)-7-Oxo-N-[(3R)-piperidine-3-ylmethoxy]-6-(sulfooxy)-1,6-diazabicyclo[3.2.1]octane-2-carboxamide

Step 1 tert-Butyl (3R)-3-{[({[(2S,5R)-6-benzyloxy-7-oxo-1,6-diazabicyclo[3.2.1]oct-2-yl]carbonyl}amino)oxy]methyl}piperidine-1-carboxylate Following a procedure analogous to Example 27, from the carboxylic acid (6b, 390 mg, 1.41 mmol) of Example 9 or 16 and (R)-tert-butyl 3-((aminooxy)methyl)piperidine-1-carboxylate (527 mg, prepared following procedures analogous to Reference Example 7 and Reference Example 13), 333 mg of the title compound was afforded (yield 48%).

$^1$H NMR (400 MHz, CDCl$_3$) δ 1.15-2.10 (m, 8H), 1.45 (s, 9H), 2.25-2.40 (m, 1H), 2.70-3.08 (m, 4H), 3.27-3.37 (m, 1H), 3.65-4.00 (m, 5H), 4.90 (d, J=11.2 Hz, 1H), 5.05 (d, J=11.2 Hz, 1H), 7.34-7.46 (m, 5H), 9.22 (br s, 1H); MS m/z 489 [M+H]$^+$.

Step 2 tert-Butyl (3R)-3-{[({[(2S,5R)-6-hydroxy-7-oxo-1,6-diazabicyclo[3.2.1]oct-2-yl]carbonyl}amino)oxy]methyl}piperidine-1-carboxylate Following a procedure analogous to Example 17, from all the amount of the compound of the above Step 1, the title compound was afforded (quantitative).

$^1$H NMR (400 MHz, CD$_3$OD) δ 1.24-1.37 (m, 1H), 1.40-1.56 (m, 1H), 1.45 (s, 9H), 1.64-1.73 (m, 1H), 1.75-2.00 (m, 4H), 2.03-2.13 (m, 1H), 2.15-2.26 (m, 1H), 2.65-2.95 (m, 2H), 3.06 (d, J=12.0 Hz, 1H), 3.13 (br d, J=12.0 Hz, 1H), 3.67-3.91 (m, 5H), 4.01-4.08 (m, 1H); MS m/z 399 [M+H]$^+$.

Step 3

(2S,5R)-7-Oxo-N-[(3R)-piperidine-3-ylmethoxy]-6-(sulfooxy)-1,6-diazabicyclo[3.2.1]octane-2-carboxamide Following a procedure analogous to Example 59, from All the amount of the compound of the above Step 2, tetrabutylammonium tert-butyl (3R)-3-{[({[(2S,5R)-7-oxo-6-(sulfooxy)-1,6-diazabicyclo[3.2.1]oct-2-yl]carbonyl}amino)oxy]methyl}piperidine-1-carboxylate was afforded (quantitative).

$^1$H NMR (400 MHz, CDCl$_3$) δ 1.01 (dd, J=7.6, 6.8 Hz, 12H), 1.11-1.99 (m, 23H), 1.46 (s, 9H), 2.12-2.24 (m, 1H), 2.30-2.42 (m, 1H), 2.67-2.96 (m, 3H), 3.19-3.38 (m, 9H), 3.70-3.99 (m, 5H), 4.35 (br s, 1H), 9.16 (br s, 1H); MS m/z 477 [M−Bu$_4$N]$^-$.

All the amount of the above tetrabutylammonium salt was deprotected with trifluoroacetic acid, and then purified by octadecyl silica gel column chromatography to afford 106 mg of the title compound (3 steps, yield 41%).

$^1$H NMR (400 MHz, CDCl$_3$) δ 1.16-1.28 (m, 1H), 1.54-1.88 (m, 5H), 1.92-2.16 (m, 3H), 2.72 (t, J=12.2 Hz, 1H), 2.81 (ddd, J=12.8, 12.8, 3.5 Hz, 1H), 3.02 (d, J=12.0 Hz, 1H), 3.15-3.28 (m, 2H), 3.37-3.44 (m, 1H), 3.70 (dd, J=10.3, 7.6 Hz, 1H), 3.79 (dd, J=10.3, 5.0 Hz, 1H), 3.88-3.94 (m, 1H), 4.06-4.10 (m, 1H); MS m/z 377 [M−H]$^-$.

Example 84

(2S,5R)-7-Oxo-N-(piperidine-4-yloxy)-6-(sulfooxy)-1,6-diazabicyclo[3.2.1]octane-2-carboxamide

Step 1 tert-Butyl 4-[({[(2S,5R)-6-benzyloxy-7-oxo-1,6-diazabicyclo[3.2.1]oct-2-yl]carbonyl}amino)oxy]piperidine-1-carboxylate Following a procedure analogous to Example 27, from the carboxylic acid (6b, 552 mg, 2.00 mmol) of Example 9 or 16 and tert-butyl 4-(aminooxy)piperidine-1-carboxylate (1.08 g, prepared following procedures analogous to Reference Example 7 and Reference Example 13), 688.5 mg of the title compound was afforded (yield 72.5%).

$^1$H NMR (400 MHz, CDCl$_3$) δ 1.43 (s, 9H), 1.58-1.66 (m, 5H), 1.85-2.02 (m, 2H), 2.27 (m, 1H), 2.75-2.77 (br d, J=11.6 Hz, 1H), 2.99-3.02 (d, J=11.6 Hz, 1H), 3.07-3.13 (m, 2H), 3.29 (s, 1H), 3.71-3.77 (m, 2H), 3.94-3.96 (d, J=7.2 Hz, 1H), 3.98-4.08 (m, 1H), 4.86-4.90 (d, J=11.2 Hz, 1H), 5.01-5.05 (d, J=11.2 Hz, 1H), 7.34-7.41 (m, 5H), 9.02 (br s, 1H); MS m/z 475 [M+H]$^+$.

Step 2 tert-Butyl 4-[({[(2S,5R)-6-hydroxy-7-oxo-1,6-diazabicyclo[3.2.1]oct-2-yl]carbonyl}amino)oxy]piperidine-1-carboxylate Following a procedure analogous to Example 17, from all the amount of the compound of the above Step 1, the title compound was afforded (quantitative). MS m/z 385 [M+H]+.

Step 3

(2S,5R)-7-Oxo-N-(piperidine-4-yloxy)-6-(sulfooxy)-1,6-diazabicyclo[3.2.1]octane-2-carboxamide Following a procedure analogous to Example 17, from all the amount of the compound of the above Step 2, tetrabutylammonium tert-butyl 4-[({[(2S,5R)-7-oxo-6-(sulfooxy)-1,6-diazabicyclo[3.2.1]oct-2-yl]carbonyl}amino)oxy]piperidine-1-carboxylate was afforded (quantitative). MS m/z 463 [M−Bu$_4$N]$^-$.

All the amount of the tetrabutylammonium salt was deprotected with trifluoroacetic acid, and then purified by octadecyl silica gel column chromatography to afford 216.3 mg of the title compound (yield 40.9%).

$^1$H NMR (400 MHz, D$_2$O) δ 1.69-2.08 (m, 8H), 2.99-3.06 (m, 3H), 3.18-3.21 (d, J=12.0 Hz, 1H), 3.26-3.31 (m, 2H), 3.96-3.97 (d, J=3.2 Hz, 1H), 4.08-4.12 (m, 2H); MS m/z 365 [M+H]$^+$.

Example 85

(2S,5R)-7-Oxo-N-(piperidine-4-ylmethoxy)-6-(sulfooxy)-1,6-diazabicyclo[3.2.1]octane-2-carboxamide

Step 1 tert-Butyl 4-{[({[(2S,5R)-6-benzyloxy-7-oxo-1,6-diazabicyclo[3.2.1]oct-2-yl]carbonyl}amino)oxy]methyl}piperidine-1-carboxylate Following a procedure analogous to Example 27, from the carboxylic acid (6b, 390 mg, 1.41 mmol) of Example 9 or 16 and tert-butyl 4-((aminooxy)methyl)piperidine-1-carboxylate (749 mg, prepared following procedures analogous to Reference Example 7 and Reference Example 13), 360.3 mg of the title compound was afforded (yield 52%).

$^1$H NMR (400 MHz, CDCl$_3$) δ 1.12-1.30 (m, 2H), 1.45 (s, 9H), 1.55-1.69 (m, 1H), 1.70-1.79 (m, 2H), 1.80-2.07 (m, 3H), 2.27-2.38 (m, 1H), 2.60-2.80 (m, 2H), 2.76 (d, J=11.8 Hz, 1H), 3.01 (br d, J=11.8 Hz, 1H), 3.31 (br s, 1H), 3.68-3.83 (m, 2H), 3.94 (br d, J=7.2 Hz, 1H), 4.02-4.20 (m, 2H), 4.91 (d, J=11.4 Hz, 1H), 5.05 (d, J=11.4 Hz, 1H), 7.35-7.44 (m, 5H), 9.04 (br s, 1H); MS m/z 489 [M+H]$^+$.

Step 2 tert-Butyl 4-{[({[(2S,5R)-6-hydroxy-7-oxo-1,6-diazabicyclo[3.2.1]oct-2-yl]carbonyl}amino)oxy]methyl}piperidine-1-carboxylate Following a procedure analogous to Example 17, from all the amount of the compound of the above Step 1, the title compound was afforded (quantitative).

$^1$H NMR (400 MHz, CD$_3$OD) δ 1.11-1.23 (m, 2H), 1.45 (s, 9H), 1.74-1.97 (m, 5H), 2.02-2.11 (m, 1H), 2.15-2.23 (m, 1H), 2.66-2.88 (m, 2H), 3.06 (d, J=11.2 Hz, 1H), 3.09-3.16 (m, 1H), 3.67-3.76 (m, 3H), 3.82 (br d, J=6.8 Hz, 1H), 4.07 (br d, J=13.6 Hz, 2H); MS m/z 399 [M+H]$^+$.

Step 3

(2S,5R)-7-Oxo-N-(piperidine-4-ylmethoxy)-6-(sulfooxy)-1,6-diazabicyclo[3.2.1]octane-2-carboxamide Following a procedure analogous to Example 17, from all the amount of the compound of the above Step 2, 504 mg of tetrabutylammonium tert-butyl 4-{[({[(2S,5R)-7-oxo-6-(sulfooxy)-1,6-diazabicyclo[3.2.1]oct-2-yl]carbonyl}amino)oxy]methyl}piperidine-1-carboxylate was afforded (yield 95%).

$^1$H NMR (400 MHz, CDCl$_3$) δ 1.01 (t, J=7.2 Hz, 12H), 1.17-1.82 (m, 21H), 1.43 (s, 9H), 1.82-1.95 (m, 2H), 2.12-2.22 (m, 1H), 2.31-2.40 (m, 1H), 2.63-2.78 (m, 2H), 2.84 (d, J=12.0 Hz, 1H), 3.16-3.38 (m, 9H), 3.70-3.86 (m, 2H), 3.91 (br d, J=7.6 Hz, 1H), 4.00-4.19 (m, 2H), 4.34 (br s, 1H), 9.15 (br s, 1H); MS m/z 477 [M–Bu$_4$N]$^-$.

All the amount of the above tetrabutylammonium salt was deprotected with trifluoroacetic acid, and then purified by octadecyl silica gel column chromatography to afford 103 mg of the title compound (3 steps, yield 37%).

$^1$H NMR (400 MHz, D$_2$O) δ 1.30-1.46 (m, 2H), 1.68-2.11 (m, 7H), 2.85-2.95 (m, 2H), 3.03 (d, J=12.0 Hz, 1H), 3.19 (br d, J=12.0 Hz, 1H), 3.34 (br d, J=12.0 Hz, 2H), 3.73 (d, J=6.0 Hz, 2H), 3.93 (d, J=7.2 Hz, 1H), 4.06-4.14 (m, 1H); MS m/z 377 [M–H]$^-$.

Example 86

Sodium (2S,5R)-N-[2-(1H-Imidazol-1-yl)ethoxy]-7-oxo-6-(sulfooxy)-1,6-diazabicyclo[3.2.1]octane-2-carboxamide Step 1

(2S,5R)-6-benzyloxy-N-[2-(1H-Imidazol-1-yl)ethoxy]-7-oxo-1,6-diazabicyclo[3.2.1]octane-2-carboxamide Following a procedure analogous to Example 45, from the carboxylic acid (6b, 552 mg, 2.00 mmol) of Example 9 or 16 and O-(2-(1H-Imidazol-1-yl)ethyl)hydroxylamine (386 mg, prepared following procedures analogous to Reference Example 7 and Reference Example 13), 770 mg of the title compound was afforded (quantitative).

$^1$H NMR (400 MHz, CD$_3$OD) δ 1.70-1.71 (m, 1H), 1.81-1.96 (m, 2H), 2.09-2.14 (m, 1H), 2.90-2.93 (br d, J=11.6 Hz, 1H), 3.14 (m, 1H), 3.80-3.85 (m, 2H), 4.12 (m, 1H), 4.22-4.35 (m, 2H), 4.85-4.96 (dd, J=11.2 Hz, 2H), 7.05 (s, 1H), 7.22-7.41 (m, 6H), 8.05 (s, 1H); MS m/z 386 [M+H]$^+$.

Step 2

(2S,5R)-6-Hydroxy-N-[2-(1H-Imidazol-1-yl)ethoxy]-7-oxo-1,6-diazabicyclo[3.2.1]octane-2-carboxamide Following a procedure analogous to Example 17, from all the amount of the compound of the above Step 1, the title compound was afforded (quantitative). MS m/z 296 [M+H]$^+$.

Step 3

Sodium (2S,5R)-N-[2-(1H-Imidazol-1-yl)ethoxy]-7-oxo-6-(sulfooxy)-1,6-diazabicyclo[3.2.1]octane-2-carboxamide Following a procedure analogous to Example 18, from all the amount of the compound of the above Step 2, pyridinium (2S,5R)-N-[2-(1H-Imidazol-1-yl)ethoxy]-7-oxo-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford the title compound 63.6 mg (yield 8.00%).

$^1$H NMR (400 MHz, D$_2$O) δ 1.66-1.85 (m, 2H), 1.97-2.09 (m, 2H), 2.94-2.97 (d, J=12.0 Hz, 1H), 3.14-3.17 (d, J=11.6 Hz, 1H), 3.87-3.89 (d, J=7.2 Hz, 1H), 4.07 (s, 1H), 4.13-4.15 (m, 2H), 4.23-4.26 (m, 2H), 7.00 (s, 1H), 7.19 (s, 1H), 7.86 (s, 1H); MS m/z 376 [M–Na+2H]$^+$.

Example 87

Sodium (2S,5R)-7-oxo-N-[2-(1H-pyrrol-1-yl)ethoxy]-6-(sulfooxy)-1,6-diazabicyclo[3.2.1]octane-2-carboxamide Step 1

(2S,5R)-6-Benzyloxy-7-oxo-N-[2-(1H-pyrrol-1-yl)ethoxy]-1,6-diazabicyclo[3.2.1]octane-2-carboxamide Following a procedure analogous to Example 27, from the carboxylic acid (6b, 690 mg, 2.50 mmol) of Example 9 or 16 and O-(2-(1H-pyrrol-1-yl)ethyl)hydroxylamine (450.5 mg, prepared following procedures analogous to Reference Example 7 and Reference Example 15), 506 mg of the title compound was afforded (yield 52.6%).

$^1$H NMR (400 MHz, CDCl$_3$) δ 1.60-1.65 (m, 1H), 1.87-2.03 (m, 2H), 2.26-2.31 (m, 1H), 2.66-2.69 (d, J=11.6 Hz, 1H), 2.93-2.96 (br d, J=11.6 Hz, 1H), 3.29 (br s, 1H), 3.88-3.90 (d, J=7.6 Hz, 1H), 4.09-4.23 (m, 4H), 4.87-4.90 (d, J=11.6 Hz, 1H), 5.02-5.05 (d, J=11.6 Hz, 1H), 6.17 (s, 2H), 6.71 (s, 2H), 7.33-7.43 (m, 5H); MS m/z 385 [M+H]$^+$.

Step 2

(2S,5R)-6-Hydroxy-7-oxo-N-[2-(1H-pyrrol-1-yl)ethoxy]-1,6-diazabicyclo[3.2.1]octane-2-carboxamide Following a procedure analogous to Example 17, from all the amount of the compound of Example 17, the title compound was afforded (quantitative). MS m/z 295 [M+H]$^+$.

Step 3

Sodium (2S,5R)-7-oxo-N-[2-(1H-pyrrol-1-yl)ethoxy]-6-(sulfooxy)-1,6-diazabicyclo[3.2.1]octane-2-carboxamide Following a procedure analogous to Example 22, from all the amount of the compound of the above Step 2, pyridinium (2S,5R)-7-oxo-N-[2-(1H-pyrrol-1-yl)ethoxy]-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 153 mg of the title compound (yield 29.4%).

$^1$H NMR (400 MHz, D$_2$O) δ 1.64-1.83 (m, 2H), 1.91-2.08 (m, 2H), 2.91-2.94 (d, J=12.0 Hz, 1H), 3.13-3.16 (br d, J=12.0 Hz, 1H), 3.87-3.89 (d, J=11.6 Hz, 1H), 4.05-4.09 (m, 5H), 6.17 (s, 2H), 6.74 (s, 2H); MS m/z 375 [M−Na+2H]$^+$.

Example 88

Disodium 1-{2-[({[(2S,5R)-7-oxo-6-(sulfonateoxy)-1,6-diazabicyclo[3.2.1]oct-2-yl]carbonyl}amino)oxy]ethyl}-1H-Imidazol-2-sulfonate A fraction resulting from purification by octadecyl silica gel column chromatography in Example 86, Step 3 gave 71.6 mg of the title compound (yield 7.16%).

$^1$H NMR (400 MHz, D$_2$O) δ 1.66-1.73 (m, 1H), 1.76-1.86 (m, 1H), 1.92-2.08 (m, 2H), 2.96-2.99 (d, J=12.0 Hz, 1H), 3.17-3.20 (d, J=12.4 Hz, 1H), 3.92-3.94 (d, J=8.0 Hz, 1H), 4.07-4.08 (d, J=3.2 Hz, 1H), 4.22-4.24 (m, 2H), 4.41-4.44 (m, 2H), 7.53 (s, 1H), 7.61 (s, 1H); MS m/z 456 [M−2Na+3H]$^+$.

Example 89

Sodium (2S,5R)-N-[2-(dimethylamino)-2-oxoethoxy]-7-oxo-6-(sulfooxy)-1,6-diazabicyclo[3.2.1]octane-2-carboxamide

Step 1

(2S,5R)-6-Benzyloxy-N-[2-(dimethylamino)-2-oxoethoxy]-7-oxo-1,6-diazabicyclo[3.2.1]octane-2-carboxamide Following a procedure analogous to Example 45, from the carboxylic acid (6b, 428 mg, 1.55 mmol) of Example 9 or 16 and 2-(aminooxy)-N,N-dimethylacetamide (244 mg, Huhu Technology), 269.2 mg of the title compound was afforded (yield 46%).

$^1$H NMR (400 MHz, CDCl$_3$) δ 1.50-1.70 (m, 1H), 1.87-2.10 (m, 2H), 2.24-2.37 (m, 1H), 2.78 (d, J=12.0 Hz, 1H), 2.91 (s, 3H), 2.97 (s, 3H), 3.03 (br d, J=12.0 Hz, 1H), 3.26-3.32 (m, 1H), 3.90-3.96 (m, 1H), 4.50-4.67 (m, 2H), 4.90 (d, J=11.4 Hz, 1H), 5.04 (d, J=11.4 Hz, 1H), 7.35-7.45 (m, 5H), 10.04 (br s, 1H); MS m/z 377 [M+H]$^+$.

Step 2

(2S,5R)-N-[2-(Dimethylamino)-2-oxoethoxy]-6-hydroxy-7-oxo-1,6-diazabicyclo[3.2.1]octane-2-carboxamide Following a procedure analogous to Example 17, from all the amount of the compound of the above Step 1, the title compound was afforded (quantitative).

$^1$H NMR (400 MHz, CD$_3$OD) δ 1.73-1.84 (m, 1H), 1.85-1.99 (m, 1H), 2.02-2.12 (m, 1H), 2.16-2.26 (m, 1H), 2.95 (s, 3H), 3.02-3.15 (m, 2H), 3.05 (s, 3H), 3.67-3.73 (m, 1H), 3.85 (br d, J=7.2 Hz, 1H), 4.57-4.68 (m, 2H); MS m/z 287 [M+H]$^+$.

Step 3

Sodium (2S,5R)-N-[2-(dimethylamino)-2-oxoethoxy]-7-oxo-6-(sulfooxy)-1,6-diazabicyclo[3.2.1]octane-2-carboxamide Following a procedure analogous to Example 18, from all the amount of the compound of the above Step 2, pyridinium (2S,5R)-N-[2-(dimethylamino)-2-oxoethoxy]-7-oxo-6-(sulfooxy)-1,6-diazabicyclo[3.2.1]octane-2-carboxamide was afforded, and neutralized with saturated sodium bicarbonate aqueous solution, and then purified with octadecyl silica gel column chromatography to afford 180.0 mg of the title compound (2 steps, yield 65%).

$^1$H NMR (500 MHz, D$_2$O) δ 1.72-1.85 (m, 2H), 1.89-2.20 (m, 2H), 2.86 (s, 3H), 2.99 (s, 3H), 3.11 (br d, J=11.8 Hz, 1H), 3.28 (br d, J=11.8 Hz, 1H), 3.76-3.81 (m, 1H), 4.08-4.12 (m, 1H), 4.49 (s, 2H); MS m/z 367 [M−Na+2H]+.

Example 90

(2S,5R)-7-Oxo-N-[2-oxo-2-(piperazin-1-yl)ethoxy]-6-(sulfooxy)-1,6-diazabicyclo[3.2.1]octane-2-carboxamide

Step 1 tert-Butyl 4-{[({[(2S,5R)-6-benzyloxy-7-oxo-1,6-diazabicyclo[3.2.1]oct-2-yl]carbonyl}amino)oxy]acetyl}piperazine-1-carboxylate Following a procedure analogous to Example 27, from the carboxylic acid (6b, 552 mg, 2.00 mmol) of Example 9 or 16 and tert-butyl 4-(2-(aminooxy)acetyl)piperazine-1-carboxylate (686.2 mg, prepared following procedures analogous to Reference Example 14 and Reference Example 15), 499.8 mg of the title compound was afforded (yield 48.3%).

$^1$H NMR (400 MHz, CDCl$_3$) δ 1.43 (s, 9H), 1.67 (m, 1H), 1.90-2.04 (m, 2H), 2.26-2.31 (m, 1H), 2.75-2.78 (d, J=11.6 Hz, 1H), 3.01-3.04 (d, J=11.6 Hz, 1H), 3.33 (m, 3H), 3.45 (m, 4H), 3.58 (m, 2H), 3.92-3.94 (d, J=11.2 Hz, 1H), 4.53-4.56 (d, J=14.4 Hz, 1H), 4.60-4.63 (d, J=14.4 Hz, 1H), 4.88-4.92 (d, J=11.6 Hz, 1H), 5.02-5.07 (d, J=11.6 Hz, 1H), 7.26-7.43 (m, 5H); MS m/z 518 [M+H]+.

Step 2 tert-Butyl 4-{[({[(2S,5R)-6-hydroxy-7-oxo-1,6-diaz-abicyclo[3.2.1]oct-2-yl]carbonyl}amino)oxy]acetyl}piperazine-1-carboxylate Following a procedure analogous to Example 17, from all the amount of the compound of the above Step 1, the title compound was afforded (quantitative). MS m/z 428 [M+H]$^+$.

Step 3

(2S,5R)-7-Oxo-N-[2-oxo-2-(piperazin-1-yl)ethoxy]-6-(sulfooxy)-1,6-diazabicyclo[3.2.1]octane-2-carboxamide Following a procedure analogous to Example 17, from all the amount of the compound of the above Step 2, tetrabutylammonium tert-butyl 4-{[({[(2S,5R)-7-oxo-6-(sulfooxy)-1,6-diazabicyclo[3.2.1]oct-2-yl]carbonyl}amino)oxy]acetyl}piperazine-1-carboxylate was afforded (quantitative).

$^1$H NMR (400 MHz, CDCl$_3$) δ 1.00 (m, 12H), 1.40 (m, 8H), 1.43 (s, 9H), 1.62 (m, 8H), 1.84-1.94 (m, 1H), 2.08 (m, 1H), 2.16-2.20 (m, 1H), 2.29-2.34 (m, 1H), 2.81-2.84 (d, J=12.0 Hz, 1H), 3.35-3.37 (m, 3H), 3.45 (m, 4H), 3.54 (m, 2H), 3.89-3.92 (d, J=12.4 Hz, 1H), 4.09-4.14 (m, 8H), 4.31 (br s, 1H), 4.51-4.59 (d, J=14.4 Hz, 1H), 4.61-4.65 (d, J=14.4 Hz, 1H); MS m/z 508 [M–Bu$_4$N+H]$^+$.

All the amount of the above tetrabutylammonium salt was deprotected with trifluoroacetic acid and purified by octadecyl silica gel column chromatography to afford 149.8 mg of the title compound (yield 38.1%).

$^1$H NMR (400 MHz, D$_2$O) δ 1.17-1.89 (m, 2H), 1.96-2.12 (m, 2H), 3.05-3.08 (d, J=12.4 Hz, 1H), 3.19-3.26 (dt, J=5.2, 16.8 Hz, 4H), 3.22 (m, 1H), 3.68-3.75 (dt, J=5.2, 16.8 Hz, 4H), 3.94-3.96 (d, J=5.6 Hz, 1H), 4.11-4.12 (br s, 1H), 4.61-4.68 (m, 2H); MS m/z 408 [M+H]$^+$.

Example 91

Sodium (2S,5R)-N-[2-(morpholin-4-yl)-2-oxoethoxy]-7-oxo-6-(sulfooxy)-1,6-diazabicyclo[3.2.1]octane-2-carboxamide Step 1

(2S,5R)-6-Benzyloxy-N-[2-(morpholin-4-yl)-2-oxoethoxy]-7-oxo-1,6-diazabicyclo[3.2.1]octane-2-carboxamide Following a procedure analogous to Example 27, from the carboxylic acid (6b, 690 mg, 2.50 mmol) of Example 9 or 16 and 2-(aminooxy)-1-morpholinoethanone (641 mg, prepared following procedures analogous to Reference Example 14 and Reference Example 15), 941.9 mg of the title compound was afforded (yield 90.0%).

$^1$H NMR (400 MHz, CDCl$_3$) δ 1.61-1.66 (m, 1H), 1.91-2.04 (m, 2H), 2.21-2.31 (m, 1H), 2.77-2.79 (d, J=11.6 Hz, 1H), 2.96-2.97 (d, J=4.4 Hz, 1H), 3.01-3.04 (br d, J=11.2 Hz, 1H), 3.29-3.38 (m, 4H), 3.57-3.70 (m 4H), 3.92-3.94 (d, J=7.2 Hz, 1H), 4.52-4.66 (dd, J=11.6, 14.4 Hz, 2H), 4.87-4.91 (d, J=11.6 Hz, 1H), 5.02-5.05 (d, J=11.6 Hz, 1H), 7.36-7.47 (m, 5H); MS m/z 419 [M+H]$^+$.

Step 2

(2S,5R)-6-Hydroxy-N-[2-(morpholin-4-yl)-2-oxoethoxy]-7-oxo-1,6-diazabicyclo[3.2.1]octane-2-carboxamide Following a procedure analogous to Example 17, from all the amount of the compound of the above Step 1, the title compound was afforded (quantitative). MS m/z 329 [M+H]$^+$.

Step 3

Sodium (2S,5R)-N-[2-(morpholin-4-yl)-2-oxoethoxy]-7-oxo-6-(sulfooxy)-1,6-diazabicyclo[3.2.1]octane-2-carboxamide Following a procedure analogous to Example 22, from all the amount of the compound of the above Step 2, pyridinium (2S,5R)-N-[2-(morpholin-4-yl)-2-oxoethoxy]-7-oxo-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 152 mg of the title compound (yield 15.7%).

$^1$H NMR (400 MHz, D$_2$O) δ 1.67-1.85 (m, 2H), 1.92-2.04 (m, 2H), 3.00-3.03 (d, J=12.0 Hz, 1H), 3.15-3.18 (d, J=12.0 Hz, 1H), 3.37-3.47 (m, 4H), 3.60-3.62 (m, 4H), 3.90-3.92 (d, J=6.4 Hz, 1H), 4.6 (br s, 1H), 4.62-4.68 (m, 2H); MS m/z 409 [M–Na+2H]$^+$.

Example 92

(2S,5R)-N-[2-(1,4-Diazepan-1-yl)-2-oxoethoxy]-7-oxo-6-(sulfooxy)-1,6-diazabicyclo[3.2.1]octane-2-carboxamide Step 1 tert-Butyl 4-{[({[(2S,5R)-6-benzyloxy-7-oxo-1,6-diazabicyclo[3.2.1]oct-2-yl]carbonyl}amino)oxy]acetyl}-1,4-diazepine-1-carboxylate Following a procedure analogous to Example 27, from the carboxylic acid (6b, 690 mg, 2.50 mmol) of Example 9 or 16 and tert-butyl 4-(2-(aminooxy)acetyl)-1,4-diazepine-1-carboxylate (1.298 g) described in Reference Example 15, 517.6 mg of the title compound was afforded (yield 38.9%).

$^1$H NMR (400 MHz, CDCl$_3$) δ 1.44 (s, 9H), 1.58 (m, 1H), 1.83-1.96 (m, 3H), 2.27 (m, 1H), 2.75 (m, 1H), 2.99 (m, 1H), 3.30-3.80 (m, 9H), 3.90 (br s, 1H), 4.58 (m, 2H), 4.88 (m, 1H), 5.03 (m, 1H), 7.24-7.37 (m, 5H); MS m/z 532 [M+H]$^+$.

Step 2 tert-Butyl 4-{[({[(2S,5R)-6-hydroxy-7-oxo-1,6-diaz-abicyclo[3.2.1]oct-2-yl]carbonyl}amino)oxy]acetyl}-1,4-diazepine-1-carboxylate Following a procedure analogous to Example 17, from all the amount of the compound of the above Step 1, the title compound was afforded (quantitative). MS m/z 442 [M+H]$^+$.

Step 3

(2S,5R)-N-[2-(1,4-Diazepan-1-yl)-2-oxoethoxy]-7-oxo-6-(sulfooxy)-1,6-diazabicyclo[3.2.1]octane-2-carboxamide Following a procedure analogous to Example 17, from all the amount of the compound of the above Step 2, tetrabutylammonium tert-butyl 4-{[({[(2S,5R)-7-oxo-6-(sulfooxy)-1,6-diazabicyclo[3.2.1]oct-2-yl]carbonyl}amino)oxy]acetyl}-1,4-diazepine-1-carboxylate was afforded (quantitative). MS m/z 520 [M−Bu$_4$N]$^−$.

The above tetrabutylammonium salt (742.4 mg, 0.973 mmol) was deprotected with trifluoroacetic acid, and then purified by octadecyl silica gel column chromatography to afford 153.1 mg of the title compound (yield 37.3%).

$^1$H NMR (400 MHz, D$_2$O) δ 1.71-1.89 (m, 2H), 1.97-2.16 (m, 4H), 3.06-3.10 (d, J=12.0 Hz, 1H), 3.19-3.22 (d, J=12.4 Hz, 1H), 3.25-3.29 (m, 3H), 3.36-3.39 (m, 2H), 3.50-3.60 (m, 2H), 3.73-3.75 (m, 2H), 3.94-3.95 (d, J=7.2 Hz, 1H), 4.11 (s, 1H), 4.62-4.69 (m, 2H); MS m/z 422 [M+H]$^+$.

Example 93

Sodium (2S,5R)-7-oxo-N-[2-(2-oxopyrrolidin-1-yl)ethoxy]-6-(sulfooxy)-1,6-diazabicyclo[3.2.1]octane-2-carboxamide

Step 1

(2S,5R)-6-Benzyloxy-7-oxo-N-[2-(2-oxopyrrolidin-1-yl)ethoxy]-1,6-diazabicyclo[3.2.1]octane-2-carboxamide Following a procedure analogous to Example 27, from the carboxylic acid (6b, 550 mg, 2.00 mmol) of Example 9 or 16 and 1-(2-(aminooxy)ethyl)pyrrolidin-2-one (518.4 mg), 699.5 mg of the title compound was afforded (yield 86.9%).

$^1$H NMR (400 MHz, CDCl$_3$) δ 1.60-1.66 (m, 1H), 1.92-2.11 (m, 4H), 2.26-2.31 (m, 1H), 2.40-2.44 (m, 2H), 2.78-2.81 (br d, J=12.0 Hz, 1H), 3.06-3.09 (d, J=11.6 Hz, 1H), 3.27 (br s, 1H), 3.33-3.38 (m, 1H), 3.44-3.54 (m, 2H), 3.68-3.74 (m, 1H), 3.94-4.14 (m, 3H), 4.87-4.90 (d, J=11.2 Hz, 1H), 5.02-5.04 (d, J=11.2 Hz, 1H), 7.26-7.42 (m, 5H), 10.10 (br s, 1H); MS m/z 403 [M+H]$^+$.

Step 2

(2S,5R)-6-Hydroxy-7-oxo-N-[2-(2-oxopyrrolidin-1-yl)ethoxy]-1,6-diazabicyclo[3.2.1]octane-2-carboxamide Following a procedure analogous to Example 17, from all the amount of the compound of the above Step 1, the title compound was afforded (quantitative). MS m/z 313 [M+H]$^+$.

Step 3

Sodium (2S,5R)-7-oxo-N-[2-(2-oxopyrrolidin-1-yl)ethoxy]-6-(sulfooxy)-1,6-diazabicyclo[3.2.1]octane-2-carboxamide Following a procedure analogous to Example 22, from all the amount of the compound of the above Step 2, pyridinium (2S,5R)-7-oxo-N-[2-(2-oxopyrrolidin-1-yl)ethoxy]-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 460.6 mg of the title compound (yield 64.2%).

$^1$H NMR (400 MHz, D$_2$O) δ 1.67-1.73 (m, 1H), 1.79-1.87 (m, 1H), 1.90-2.06 (m, 4H), 2.30-2.34 (t, J=8.4 Hz, 1H), 3.01-3.08 (d, J=12.4 Hz, 1H), 3.19-3.22 (d, J=12.0 Hz, 1H), 3.38-3.50 (m, 4H), 3.93-3.99 (m, 3H), 4.09 (br s, 1H); MS m/z 393 [M−Na+2H]$^+$.

Example 94

Sodium (2S,5R)-7-oxo-N-[2-(2-oxoimidazolidin-1-yl)ethoxy]-6-(sulfooxy)-1,6-diazabicyclo[3.2.1]octane-2-carboxamide

Step 1

(2S,5R)-6-Benzyloxy-7-oxo-N-[2-(2-oxoimidazolidin-1-yl)ethoxy]-1,6-diazabicyclo[3.2.1]octane-2-carboxamide Following a procedure analogous to Example 45, from the carboxylic acid (6b, 390 mg, 1.41 mmol) of Example 9 or 16 and 1-(2-(aminooxy)ethyl)imidazolidin-2-one (512 mg, prepared following procedures analogous to Reference Example 7 and Reference Example 15), 347 mg of the title compound was afforded (yield 61%).

$^1$H NMR (400 MHz, CDCl$_3$) δ 1.50-1.68 (m, 1H), 1.91-2.06 (m, 2H), 2.24-2.35 (m, 1H), 2.80 (d, J=12.0 Hz, 1H), 3.06 (br d, J=12.0 Hz, 1H), 3.21-3.39 (m, 2H), 3.40-3.68 (m, 5H), 3.92-4.06 (m, 3H), 4.32 (br s, 1H), 4.89 (d, J=11.6 Hz, 1H), 5.04 (d, J=11.6 Hz, 1H), 7.33-7.44 (m, 5H), 10.10 (br s, 1H); MS m/z 404 [M+H]$^+$.

Step 2

(2S,5R)-6-Hydroxy-7-oxo-N-[2-(2-oxoimidazolidin-1-yl)ethoxy]-1,6-diazabicyclo[3.2.1]octane-2-carboxamide Following a procedure analogous to Example 17, all the amount of the compound of the above Step 1, the title compound was afforded (quantitative).

$^1$H NMR (400 MHz, CD$_3$OD) δ 1.74-1.84 (m, 1H), 1.87-2.13 (m, 2H), 2.16-2.27 (m, 1H), 3.04 (d, J=11.6 Hz, 1H), 3.11-3.18 (m, 1H), 3.27-3.49 (m, 4H), 3.58-3.66 (m, 2H), 3.67-3.73 (m, 1H), 3.85 (br d, J=7.6 Hz, 1H), 3.92-4.05 (m, 2H); MS m/z 314 [M+H]$^+$.

Step 3

Sodium (2S,5R)-7-oxo-N-[2-(2-oxoimidazolidin-1-yl)ethoxy]-6-(sulfooxy)-1,6-diazabicyclo[3.2.1]octane-2-carboxamide To a solution of all the amount of the compound of the above Step 2 in methylene chloride (8.6 mL) were added 2,6-lutidine (300 μl) and sulfur trioxide-pyridine complex (410 mg), followed by agitating at room temperature overnight. To the reaction solution was added methylene chloride, followed by filtration and concentration under reduced pressure. To the resulting 486.7 mg of pyridinium (2S,5R)-7-oxo-N-[2-(2-oxoimidazolidin-1-yl)ethoxy]-6-(sulfooxy)-1,6-diazabicyclo[3.2.1]octane-2-carboxamide was added sodium bicarbonate aqueous solution, followed by lyophilisation. Thereby, the crude product was afforded. The resulting crude product was purified by octadecyl silica gel column chromatography to afford 36.8 mg of the title compound (2 steps, yield 10%).

$^1$H NMR (400 MHz, D$_2$O) δ 1.59-2.08 (m, 4H), 3.02 (d, J=12.6 Hz, 1H), 3.18 (br d, J=12.6 Hz, 1H), 3.27-3.49 (m, 4H), 3.59-3.67 (m, 2H), 3.90-3.98 (m, 3H), 4.05-4.10 (m, 1H); MS m/z 394 [M−Na+2H]$^+$.

Example 95

Sodium (2S,5R)-N-(2-hydroxyethoxy)-7-oxo-6-(sulfooxy)-1,6-diazabicyclo[3.2.1]octane-2-carboxamide Step 1

(2S,5R)-6-Benzyloxy-7-oxo-N-(2-triisopropylsilyloxyethoxy)-1,6-diazabicyclo[3.2.1]octane-2-carboxamide Following a procedure analogous to Example 45, from the carboxylic acid (6b, 553 mg, 2.00 mmol) of Example 9 or 16 and O-(2-((triisopropylsilyl)oxy)ethyl)hydroxylamine (630 mg, prepared following a procedure analogous to Reference Example 15 from the compound of Reference Example 12), 695.0 mg of the title compound was afforded (yield 71%).

$^1$H NMR (400 MHz, CDCl$_3$) δ 1.00-1.20 (m, 21H), 1.57-1.70 (m, 1H), 1.88-2.10 (m, 2H), 2.28-2.37 (m, 1H), 2.78 (d, J=11.6 Hz, 1H), 2.98 (br d, J=11.6 Hz, 1H), 3.31 (br s, 1H), 3.87-4.08 (m, 5H), 4.90 (d, J=11.4 Hz, 1H), 5.05 (d, J=11.4 Hz, 1H), 7.35-7.45 (m, 5H), 9.38 (br s, 1H); MS m/z 492 [M+H]$^+$.

Step 2

(2S,5R)-6-Hydroxy-7-oxo-N-(2-triisopropylsilyloxyethoxy)-1,6-diazabicyclo[3.2.1]octane-2-carboxamide Following a procedure analogous to Example 17, from all the amount of the compound of the above Step 1, 530.7 mg of the title compound was afforded (yield 94%).

$^1$H NMR (400 MHz, CD$_3$OD) δ 1.00-1.20 (m, 21H), 1.74-1.85 (m, 1H), 1.86-1.99 (m, 1H), 2.01-2.13 (m, 1H), 2.15-2.25 (m, 1H), 3.06 (d, J=11.6 Hz, 1H), 3.12 (br d, J=11.6 Hz, 1H), 3.69 (br s, 1H), 3.82 (br d, J=7.2 Hz, 1H), 3.90-4.01 (m, 4H); MS m/z 402 [M+H]$^+$.

Step 3

Sodium (2S,5R)-N-(2-hydroxyethoxy)-7-oxo-6-(sulfooxy)-1,6-diazabicyclo[3.2.1]octane-2-carboxamide Following a procedure analogous to Example 59, from all the amount of the compound of the above Step 2, tetrabutylammonium (2S,5R)-7-oxo-6-(sulfooxy)-N-(2-triisopropylsilyloxyethoxy)-1,6-diazabicyclo[3.2.1]octane-2-carboxamide was afforded (quantitative).

$^1$H NMR (400 MHz, CDCl$_3$) δ 0.87-1.19 (m, 33H), 1.36-1.98 (m, 18H), 2.13-2.23 (m, 1H), 2.31-2.42 (m, 1H) 2.85 (br d, J=11.6 Hz, 1H), 3.21-3.38 (m, 9H), 3.83-4.17 (m, 5H), 4.35 (br s, 1H), 9.37 (br s, 1H); MS m/z 480 [M−Bu$_4$N]$^−$.

All the amount of the above tetrabutylammonium salt was deprotected with trifluoroacetic acid, and then purified by octadecyl silica gel column chromatography to afford 140.2 mg of the title compound (3 steps, yield 29%).

$^1$H NMR (400 MHz, D$_2$O) δ 1.65-1.88 (m, 2H), 1.91-2.08 (m, 2H), 3.04 (d, J=12.0 Hz, 1H), 3.18 (br d, J=12.0 Hz, 1H), 3.63-3.69 (m, 2H), 3.85-3.96 (m, 3H), 4.05-4.09 (m, 1H); MS m/z 324 [M−Na]$^−$.

Example 96

Sodium (2S,5R)-N-(2-methoxyethoxy)-7-oxo-6-(sulfooxy)-1,6-diazabicyclo[3.2.1]octane-2-carboxamide Step 1

(2S,5R)-6-Benzyloxy-N-(2-methoxyethoxy)-7-oxo-1,6-diazabicyclo[3.2.1]octane-2-carboxamide Following a procedure analogous to Example 45, from the carboxylic acid (6b, 414 mg, 1.50 mmol) of Example 9 or 16 and O-(2-methoxyethyl)hydroxylamine (190 mg, Huhu Technology), 386.7 mg of the title compound was afforded (yield 74%).

$^1$H NMR (400 MHz, CDCl$_3$) δ 1.57-1.72 (m, 1H), 1.88-2.10 (m, 2H), 2.29-2.37 (m, 1H), 2.78 (d, J=11.8 Hz, 1H), 2.99 (br d, J=11.8 Hz, 1H), 3.30 (br s, 1H), 3.39 (s, 3H), 3.63 (t, J=4.4 Hz, 2H), 3.95 (br d, J=7.6 Hz, 1H), 4.01-4.15 (m, 2H), 4.90 (d, J=11.4 Hz, 1H), 5.05 (d, J=11.4 Hz, 1H), 7.35-7.45 (m, 5H), 9.32 (br s, 1H); MS m/z 350 [M+H]$^+$.

Step 2

(2S,5R)-6-Hydroxy-N-(2-methoxyethoxy)-7-oxo-1,6-diazabicyclo[3.2.1]octane-2-carboxamide Following a procedure analogous to Example 17, from all the amount of the compound of the above Step 1, 272.4 mg of the title compound was afforded (yield 95%).

$^1$H NMR (400 MHz, CD$_3$OD) δ 1.74-1.85 (m, 1H), 1.86-1.98 (m, 1H), 2.02-2.12 (m, 1H), 2.16-2.25 (m, 1H), 3.08 (d, J=11.6 Hz, 1H), 3.12 (br d, J=11.6 Hz, 1H), 3.37 (s, 3H), 3.61-3.65 (m, 2H), 3.67-3.72 (m, 1H), 3.82 (br d, J=8.4 Hz, 1H), 3.99-4.03 (m, 2H); MS m/z 260 [M+H]$^+$.

Step 3

Sodium (2S,5R)-N-(2-methoxyethoxy)-7-oxo-6-(sulfooxy)-1,6-diazabicyclo[3.2.1]octane-2-carboxamide Following a procedure analogous to Example 18, from all the amount of the compound of the above Step 2, pyridinium (2S,5R)-N-(2-methoxyethoxy)-7-oxo-6-(sulfooxy)-1,6-diazabicyclo[3.2.1]octane-2-carboxamide was afforded, and neutralized with saturated sodium bicarbonate aqueous solution, and then purified by octadecyl silica gel column chromatography to afford 247.4 mg of the title compound (2 steps, yield 62%).

$^1$H NMR (500 MHz, D$_2$O) δ 1.69-1.78 (m, 1H), 1.78-1.88 (m, 1H), 1.93-2.01 (m, 1H), 2.01-2.09 (m, 1H), 3.06 (d, J=12.3 Hz, 1H), 3.20 (br d, J=12.3 Hz, 1H), 3.28 (s, 3H), 3.57-3.62 (m, 2H), 3.94 (br d, J=6.5 Hz, 1H), 3.94-3.99 (m, 2H), 4.08-4.13 (m, 1H); MS m/z 340 [M–Na+2H]$^+$.

Example 97

Sodium (2S,5R)-N-[2-(methylsulfonyl)ethoxy]-7-oxo-6-(sulfooxy)-1,6-diazabicyclo[3.2.1]octane-2-carboxamide

Step 1

(2S,5R)-6-Benzyloxy-N-[2-(methylsulfonyl)ethoxy]-7-oxo-1,6-diazabicyclo[3.2.1]octane-2-carboxamide Following a procedure analogous to Example 45, from the carboxylic acid (6b, 414 mg, 1.50 mmol) of Example 9 or 16 and O-(2-(methylsulfonyl)ethyl)hydroxylamine (279 mg, Huhu Technology), 293 mg of the title compound was afforded (yield 49%).

$^1$H NMR (400 MHz, CDCl$_3$) δ 1.44-1.70 (m, 1H), 1.90-2.10 (m, 2H), 2.24-2.36 (m, 1H), 2.74 (d, J=12.0 Hz, 1H), 3.04 (br d, J=12.0 Hz, 1H), 3.12 (s, 3H), 3.31-3.39 (m, 3H), 3.96 (br d, J=7.6 Hz, 1H), 4.38 (br t, J=5.4 Hz, 2H), 4.91 (d, J=11.4 Hz, 1H), 5.05 (d, J=11.4 Hz, 1H), 7.36-7.45 (m, 5H), 9.31 (br s, 1H); MS m/z 398 [M+H]$^+$.

Step 2

(2S,5R)-6-Hydroxy-N-[2-(methylsulfonyl)ethoxy]-7-oxo-1,6-diazabicyclo[3.2.1]octane-2-carboxamide Following a procedure analogous to Example 17, from all the amount of the compound of the above Step 1, the title compound was afforded (quantitative).

$^1$H NMR (400 MHz, CD$_3$OD) δ 1.77-1.86 (m, 1H), 1.87-1.99 (m, 1H), 2.03-2.13 (m, 1H), 2.17-2.26 (m, 1H), 3.04 (d, J=12.0 Hz, 1H), 3.07-3.18 (m, 4H), 3.46 (t, J=5.6 Hz, 2H), 3.68-3.74 (m, 1H), 3.86 (br d, J=6.4 Hz, 1H), 4.30 (t, J=5.6 Hz, 2H); MS m/z 308 [M+H]$^+$.

Step 3

Sodium (2S,5R)-N-[2-(methylsulfonyl)ethoxy]-7-oxo-6-(sulfooxy)-1,6-diazabicyclo[3.2.1]octane-2-carboxamide To a solution of a total amount of the compound of the above Step 2 in methylene chloride (7.4 mL) were added 2,6-lutidine (257 μl) and sulfur trioxide-pyridine complex (352 mg), followed by agitating at room temperature overnight. The resulting pyridinium (2S,5R)-N-[2-(methylsulfonyl)ethoxy]-7-oxo-6-(sulfooxy)-1,6-diazabicyclo[3.2.1]octane-2-carboxamide was neutralized by adding saturated sodium bicarbonate aqueous solution. The organic solvent was distilled off under reduced pressure, followed by lyophilization, thereby the crude product was afforded. The resulting crude product was purified by octadecyl silica gel column chromatography to afford 51.1 mg of the title compound (2 steps, yield 17%).

$^1$H NMR (400 MHz, D$_2$O) δ 1.65-1.86 (m, 2H), 1.90-2.06 (m, 2H), 3.00-3.10 (m, 1H), 3.05 (s, 3H), 3.06 (d, J=12.0 Hz, 1H), 3.15 (br d, J=12.0 Hz, 1H), 3.49 (br t, J=5.6 Hz, 2H), 3.86-3.93 (m, 1H), 4.05-4.09 (m, 1H), 4.22 (br t, J=5.6 Hz, 1H); MS m/z 388 [M–Na+2H]$^+$.

Example 98

(2S,5R)-5-(Benzyloxyamino)-1-(2,2,2-trifluoroacetyl)piperidine-2-carboxylic acid (IV-a2)

[Chemical formula 118]

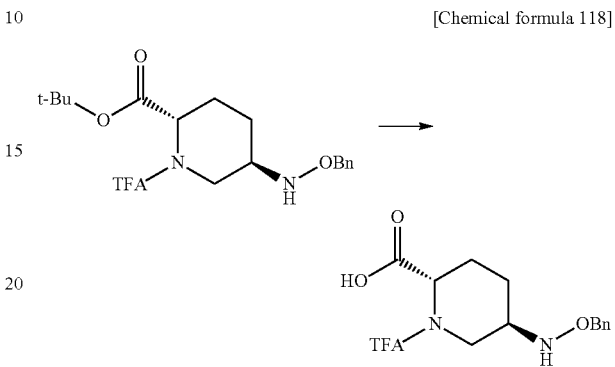

A solution of (2S,5R)-tert-Butyl 5-(benzyloxyamino)-1-(2,2,2-trifluoroacetyl)piperidine-2-carboxylate (1.50 g, 3.73 mmol) in methylene chloride (5.0 mL) was ice-cooled, and trifluoroacetic acid (5.0 mL) was added, and reacted at the same temperature for 30 min. and then at room temperature for 2 h. The reaction mixture was concentrated under reduced pressure, then water and 6.5% sodium bicarbonate aqueous solution was added to the residue. After pH was adjusted to ca. pH 8, aqueous layer was washed with ethyl acetate. To this aqueous layer was added 5% potassium hydrogen sulfate aqueous solution. After pH was adjusted to ca. pH 5.6, the aqueous layer was extracted with ethyl acetate. After the organic layer was washed with saturated brine, dehydrated over anhydrous magnesium sulfate, and the solvent was distilled off under reduced pressure to afford 0.913 g of the title compound (yield 71%).

$^1$H NMR (400 MHz, CDCl$_3$) δ observed as a mixture of 2 rotamers (approx. 6:4). 1.68-1.76 (m, 2H), 2.05-2.08 (m, 2H), 3.14 (d, J=14.4 Hz, 0.4H), 3.27 (m, 1H), 3.48 (m, 0.6H), 4.15 (m, 1H), 4.58-4.75 (m, 3H), 5.20 (m, 1H), 4.30-4.38 (m, 5H); MS m/z 347 [M+H]$^+$.

Example 99

(2S,5R)-5-((Benzyloxy)amino)-1-(tert-butoxycarbonyl)piperidine-2-carboxylic acid (IV-a3)

[Chemical formula 119]

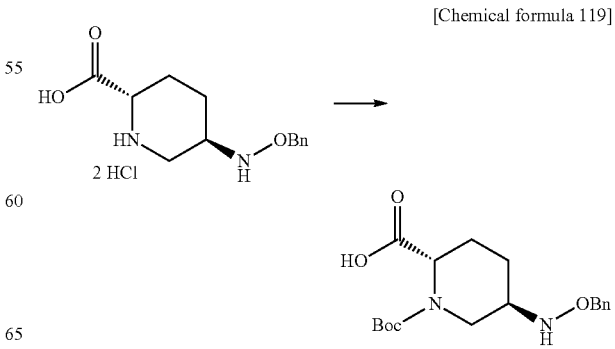

(2S,5R)-5-(Benzyloxyamino)piperidine-2-carboxylic acid, dihydrochloride (2.00 g, 6.19 mmol) described in Example 11 was added to 1,4-dioxane (10 mL) and water (15 mL), followed by addition of 5M sodium hydroxide aqueous solution (3.7 mL), and stirred under ice cooling. Further potassium carbonate (854 mg) and di-tert-butoxycarbonyl dicarbonate (1.69 g) were added to the mixture, and a temperature was elevated to room temperature, followed by stirring overnight. The resulting solution was concentrated, and the aqueous solution of which was adjusted to pH 3.3 with citric acid.monohydrate, and then extracted with ethyl acetate (20 mL) twice, and washed with saturated brine, dried over anhydrous sodium sulfate, and filtered. The solvent was concentrated under reduced pressure. The resulting residue was subjected to silica gel column chromatography (ethyl acetate) to afford 1.879 g of the title compound (yield 87%).

$^1$H NMR (400 MHz, CDCl$_3$) δ 1.46 (s, 9H), 1.50-1.72 (m, 2H), 1.98-2.10 (m, 2H), 3.12-3.19 (m, 2H), 4.13-4.20 (m, 1H), 4.76 (d, J=11.5 Hz, 1H), 4.70 (d, J=11.5 Hz, 1H), 4.85-4.92 (m, 1H), 7.26-7.35 (m, 5H); MS m/z 351 [M+H]$^+$.

Example 100

Sequential synthesis of (2S,5R)-5-((Benzyloxy)amino)-1-(tert-butoxycarbonyl)piperidine-2-carboxylic acid (IV-a3)

[Chemical formula 120]

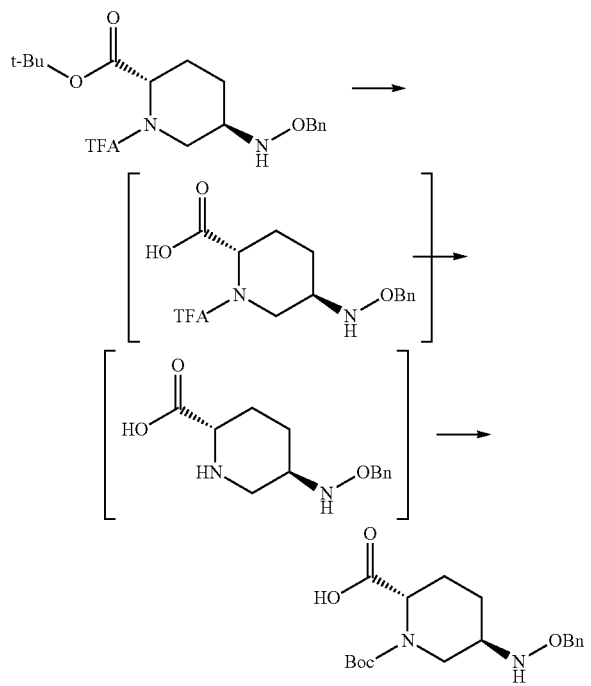

A solution of (2S,5R)-tert-Butyl 5-(benzyloxyamino)-1-(2,2,2-trifluoroacetyl)piperidine-2-carboxylate (66.8 g, 166.0 mmol) described in Example 3 in methylene chloride (135 mL) was ice-cooled, and to which was added trifluoroacetic acid (135 mL), followed by reacting at the same temperature for 30 min, and further at room temperature for 2 h., and then the reaction mixture was concentrated under reduced pressure. The residue was dissolved in ethyl acetate (500 mL), and washed with 25% monosodium citrate (200 mL) and saturated brine (200 mL), and dried over anhydrous magnesium sulfate, and then solvent was distilled off under reduced pressure. The residue was dissolved in 1,4-dioxane (133 mL), and to which was added 5M sodium hydroxide (133 mL) under ice cooling, followed by stirring for 1 h., and then the mixture was concentrated under reduced pressure. After the aqueous layer was washed with ether (200 mL), pH was adjusted to pH 10 by addition of 5M hydrochloric acid (55 mL), and to which were added potassium carbonate (23 g) and di-tert-butyl dicarbonate (44 g), followed by stirring overnight. The organic solvent of the mixture was concentrated under reduced pressure, and the concentrated mixture was washed with ether (200 mL). The aqueous layer was adjusted to pH 3.9 with citric acid, and extracted with ethyl acetate (500 mL, 250 mL). The organic layer was washed with saturated brine (250 mL), and dried over anhydrous sodium sulfate. The solvent was concentrated under reduced pressure to afford 48.02 g of the title compound (yield 83%). Instrumental data were consistent with those of Example 99.

Example 101

(2S,5R)-5-((Benzyloxy)amino)-1-(2-trimethylsilylethoxycarbonyl)piperidine-2-carboxylic acid (IV-a4)

[Chemical formula 121]

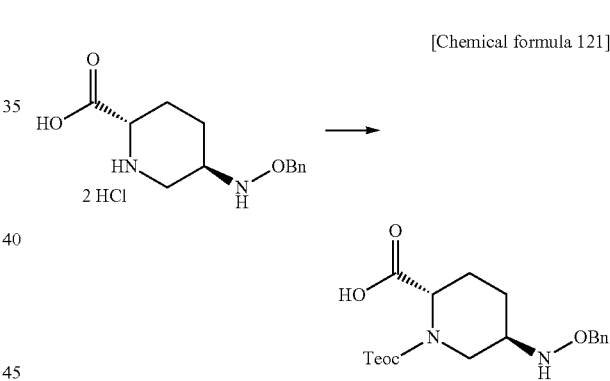

To (2S,5R)-5-(benzyloxyamino)piperidine-2-carboxylic acid, dihydrochloride (3.23 g, 10 mmol) described in Example 11 were added 1,4-dioxane (10 mL), water (15 mL) and 5M sodium hydroxide (6 mL), and stirred under ice cooling. Potassium carbonate (1.38 g), N-(trimethylsilylethyloxycarbonyloxy)succinimide (2.85 g) were added further to the mixture, and the temperature was elevated to room temperature, followed by stirring overnight. The mixture was adjusted to pH 4 with citric acid.monohydrate, and extracted with ethyl acetate (50 mL) twice. The organic layer was washed with water and saturated brine and concentrated under reduced pressure. The residue was subjected to silica gel column chromatography (ethyl acetate/hexane=1:1→1:0) to afford 3.41 g of the title compound (yield 86%).

$^1$H NMR (400 MHz, CDCl$_3$) δ 0.01 (s, 9H), 0.97 (t, J=8.3 Hz, 2H), 1.59-1.68 (m, 2H), 1.97-2.02 (m, 2H), 3.00-3.25 (m, 2H), 4.08-4.19 (m, 3H), 4.65 (d, J=11.3 Hz, 1H), 4.71 (d, J=11.3 Hz, 1H), 4.72-4.89 (m, 1H), 7.23-7.32 (m, 5H); MS m/z 395 [M+H]$^+$.

Example 102

(2S,5R)-N-(2-tert-Butoxycarbonylaminoethoxy)-5-(benzyloxyamino)-1-(2,2,2-trifluoroacetyl)piperidine-2-carboxamide (IV-b2-Boc-059)

[Chemical formula 122]

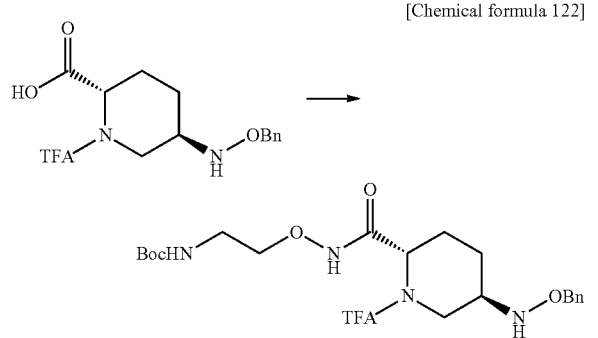

(2S,5R)-5-(Benzyloxyamino)-1-(2,2,2-trifluoroacetyl)piperidine-2-carboxylic acid (0.879 g, 2.54 mmol) described in Example 98 and tert-butyl 2-(aminooxy)ethylcarbamate (0.559 g) of Reference Example 9 were dissolved in N,N-dimethylformamide (11 mL), and to which was added 1-hydroxybenzotriazole.monohydrate (0.489 g), followed by ice-cooling. To this was added N-ethyl-N'-(3-dimethylaminopropyl)carbodiimide hydrochloride (0.613 g), and the temperature was elevated to room temperature, followed by reacting for 3 h. Water was added to the reacted mixture, and extracted with ethyl acetate. After the organic layer was washed with 10% citric acid aqueous solution, water, 6.5% sodium bicarbonate aqueous solution and saturated brine sequentially, and then the solvent was distilled off under reduced pressure. The resulting oil residue was purified by silica gel column chromatography (n-hexane/ethyl acetate=1/2) to afford 1.07 g of the title compound (yield 84%).

$^1$H NMR (400 MHz, CDCl$_3$) δ observed as a mixture of 2 rotamers (approx. 7:3). 1.26 (m, 0.3H), 1.44 (s, 9H), 1.70 (m, 0.7H), 1.81-2.12 (m, 3H), 3.10 (br. d, J=14.4 Hz, 0.3H), 3.30 (m, 3H), 3.54 (br. d, J=12.4 Hz, 0.7H), 3.87 (m, 2H), 4.15 (d, J=13.2 Hz, 0.7H), 4.58-4.79 (m, 2.6H), 4.90 (m, 0.7H), 4.97 (m, 0.3H), 5.11 (m, 0.7H), 5.33 (m, 1H), 7.26-7.38 (m, 5H), 9.75 (br. s, 0.7H), 10.48 (br. s, 0.3H); MS m/z 505 [M+H]$^+$.

Example 103

(2S,5R)-N-(2-tert-Butoxycarbonylaminoethoxy)-5-(benzyloxyamino)piperidine-2-carboxamide (IV-c-Boc-059)

[Chemical formula 123]

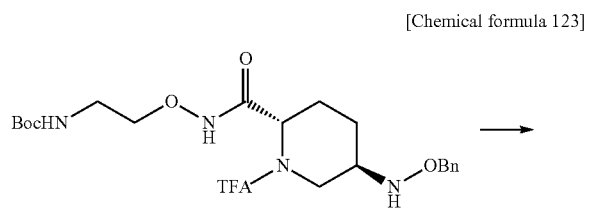

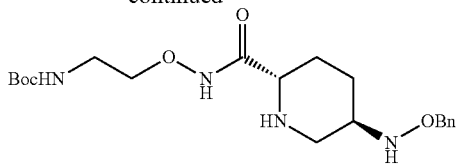

(2S,5R)-N-(2-tert-butoxycarbonylaminoethoxy)-5-(benzyloxyamino)-1-(2,2,2-trifluoroacetyl)piperidine-2-carboxamide (1.07 g, 2.06 mmol) was dissolved in 1,4-dioxane (4.2 mL), to which was added water (1.1 mL), and followed by ice cooling. To this was added 1M sodium hydroxide aqueous solution (6.3 mL), and followed by reaction at the same temperature for 2.5 h. pH was adjusted to ca. pH 7 by the addition of acetic acid to the reaction mixture. The organic solvent was distilled off under reduced pressure. The resulting aqueous solution was extracted with ethyl acetate. After the organic layer was washed with saturated brine, and dehydrated with anhydrous sodium sulfate, and the solvent was distilled off under reduced pressure. The resulting oil residue was purified by silica gel column chromatography (ethyl acetate/methanol=9/1) to afford 0.80 g of the title compound (yield 93%).

$^1$H NMR (400 MHz, CDCl$_3$) δ 1.36-1.44 (m, 10H), 1.74 (m, 1H), 1.95 (m, 1H), 2.10 (m, 1H), 2.68 (m, 1H), 3.14 (m, 1H), 3.33 (m, 2H), 3.42 (m, 1H), 3.50 (m, 1H), 3.88 (m, 2H), 4.66 (s, 2H), 5.49 (br. m, 1H), 7.29-7.37 (m, 5H); MS m/z 409 [M+H]$^+$.

Example 104

(2S,5R)-N-(2-tert-Butoxycarbonylaminoethoxy)-5-(benzyloxyamino)-1-[2-(trimethylsilyl)ethyloxycarbonyl]piperidine-2-carboxamide (IV-b4-059)

[Chemical formula 124]

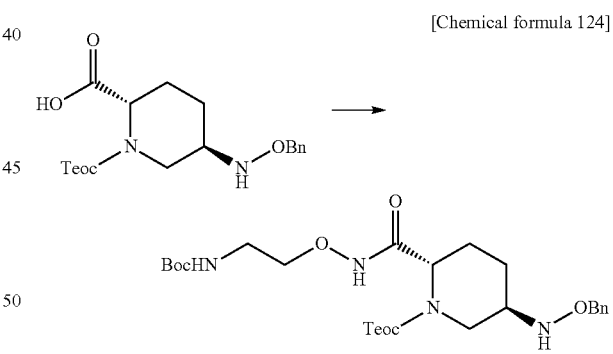

(2S,5R)-5-(Benzyloxyamino)-1-((2-(trimethylsilyl)ethoxy)carbonyl)piperidine-2-carboxylic acid (601 mg, 1.52 mmol) described in Example 101 and tert-butyl 2-(aminooxy)ethylcarbamate (303 mg, 1.72 mmol) of Reference Example 9 were dissolved in N,N-dimethylformamide (5.8 mL), to which was added 1-hydroxybenzotriazole.monohydrate (264 mg), followed by ice cooling. To this was added N-ethyl-N'-(3-dimethylaminopropyl)carbodiimide hydrochloride (330 mg), a temperature was elevated to room temperature, followed by reaction for 5 h. Water was added to the reaction mixture and extracted with ethyl acetate. After the organic layer was washed with 10% citric acid aqueous solution, water, 6.5% sodium bicarbonate aqueous solution and saturated brine sequentially, the organic layer was dehydrated over anhydrous magnesium sulfate, and then the solvent was distilled off under reduced pressure. The resulting oil residue was purified by silica gel column chromatography (n-hexane/ethyl acetate=1/2) to afford 450 mg of the title compound (yield 54%).

¹H NMR (400 MHz, CDCl₃) δ 0.01 (s, 9H), 0.98 (m, 2H), 1.42 (s, 9H), 1.58 (m, 1H), 1.84-1.96 (m, 3H), 3.04 (m, 1H), 3.18 (br. s, 1H), 3.28 (m, 1H), 3.35 (m, 1H), 3.85 (m, 2H), 4.16-4.35 (m, 3H), 4.63-4.75 (m, 3H), 5.32-5.70 (br. m, 2H), 4.26-4.33 (m, 5H), 9.44 (br. s, 1H); MS m/z 553 [M+H]⁺.

Example 105

Synthesis from tert-Butyl 2-((2S,5R)-5-(benzyloxyamino)piperidine-2-carboxamideoxy)ethylcarbamate (IV-c-Boc-059): (IV-b4-Boc-059)

[Chemical formula 125]

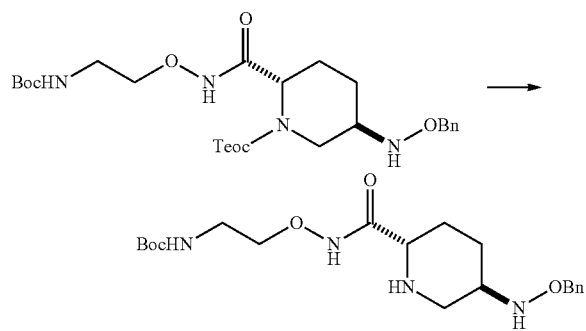

(2S,5R)-N-(2-tert-Butoxycarbonylaminoethoxy)-5-(benzyloxyamino)-1-[2-(trimethylsilyl)ethyloxycarbonyl]piperidine-2-carboxamide (417 mg, 0.754 mmol) was dissolved in tetrahydrofuran (5.5 mL), to which was added 1.0M fluorotetra-n-butylammonium tetrahydrofuran solution (1.9 mL), followed by reaction at 50° C. for 24 h. The reaction mixture was diluted with ethyl acetate, and washed with 6.5% sodium bicarbonate aqueous solution, water and saturated brine sequentially, after which time, the organic layer was dehydrated over anhydrous sodium sulfate, and the solvent was distilled off under reduced pressure. The resulting oil residue was purified by silica gel column chromatography (ethyl acetate→ethyl acetate/methanol=9/1) to afford 250 mg of the title compound (yield 81%). Instrumental data were consistent with those of Example 103.

Example 106

(2S,5R)-N-(2-Benzyloxycarbonylaminoethoxy)-5-(benzyloxyamino)-1-(tert-butoxycarbonyl)piperidine-2-carboxamide (IV-c-Cbz-059)

[Chemical formula 126]

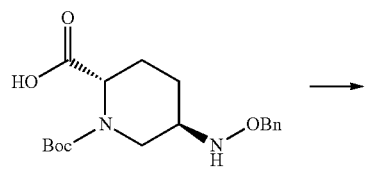

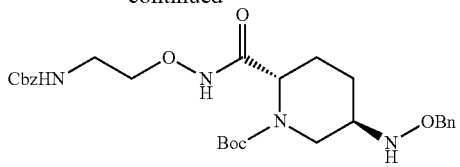

(2S,5R)-5-((Benzyloxy)amino)-1-(tert-butoxycarbonyl)piperidine-2-carboxylic acid (1.879 g, 5.362 mmol) described in Example 99 or 100, benzyl 2-(aminooxy)ethylcarbamate (1.41 g, 6.707 mmol) of Reference Example 11 and 1-hydroxybenzotriazole.monohydrate (220 mg) were dissolved in methylene chloride (20 mL), followed by stirring under ice cold. To this was added N-ethyl-N'-(3-dimethylaminopropyl)carbodiimide hydrochloride (1.29 g), and a temperature was elevated to room temperature, followed by stirring overnight. The mixture was diluted with methylene chloride (20 mL), and washed with water, 10% citric acid aqueous solution, saturated sodium bicarbonate aqueous solution, and saturated brine sequentially, and then dried over magnesium sulfate. The solvent was concentrated under reduced pressure to afford 2.91 g of the title compound (quantitative).

¹H NMR (400 MHz, CDCl₃) δ 1.46 (s, 9H), 1.50-1.93 (m, 4H), 3.40 (m, 2H), 3.89 (m, 2H), 4.15-4.21 (m, 1H), 4.61 (m, 1H), 4.69 (d, J=11.6 Hz, 1H), 4.76 (d, J=11.6 Hz, 1H), 5.11 (s, 2H), 5.86 (s, 1H), 7.27-7.36 (m, 5H), 9.28 (s, 1H); MS m/z 543 [M+H]⁺.

Example 107

(2S,5R)-N-(2-Benzyloxycarbonylaminoethoxy)-5-(benzyloxyamino)piperidine-2-carboxamide (IV-c-Cbz-059)

[Chemical formula 127]

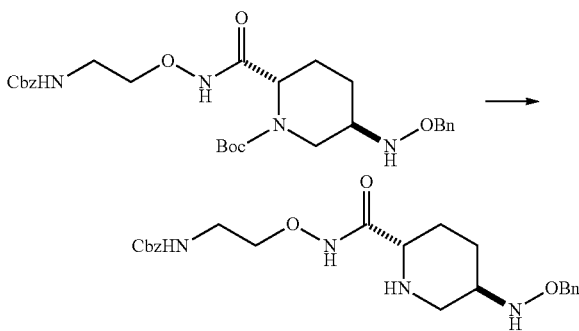

(2S,5R)-N-(2-Benzyloxycarbonylaminoethoxy)-5-(benzyloxyamino)-1-(tert-butoxycarbonyl)piperidine-2-carboxamide (2.91 g, 5.362 mmol) was dissolved in 1,4-dioxane (5 mL), to which was added under ice cooling 4M hydrochloric acid-dioxane solution (10 mL). After stirring for 2 h., the mixture was concentrated under reduced pressure, dissolved in water (30 mL), and washed with ether. The aqueous layer was ice-cooled, and pH was set to ca. pH 7 with 5M sodium hydroxide and acetic acid, and then extracted with ethyl acetate. The organic layer was washed with saturated brine, and dried over anhydrous sodium sulfate, and then the solvent was concentrated under reduced pressure. The residue was subjected to silica gel column chromatography (chloroform→chloroform/methanol=3:1) to afford 2.27 g of the title compound (yield 95%).

$^{1}$H NMR (400 MHz, CDCl$_{3}$) δ 1.22-1.34 (m, 1H), 1.50-1.58 (m, 1H), 1.89-1.92 (m, 1H), 1.92-2.06 (m, 1H), 2.43-2.48 (m, 1H), 2.95 (m, 1H), 3.23-3.27 (m, 1H), 3.40-3.42 (m, 2H), 3.71-3.73 (m, 2H), 3.89-3.92 (m, 2H), 4.66 (s, 2H), 5.11 (s, 2H), 5.91 (s, 1H), 7.26-7.52 (m, 10H); MS m/z 443 [M+H]$^{+}$.

Example 108

Benzyl {2-[({[(2S,5R)-6-benzyloxy-7-oxo-1,6-diazabicyclo[3.2.1]oct-2-yl]carbonyl}amino)oxy]ethyl}carbamate (IIa-Cbz-059)

[Chemical formula 128]

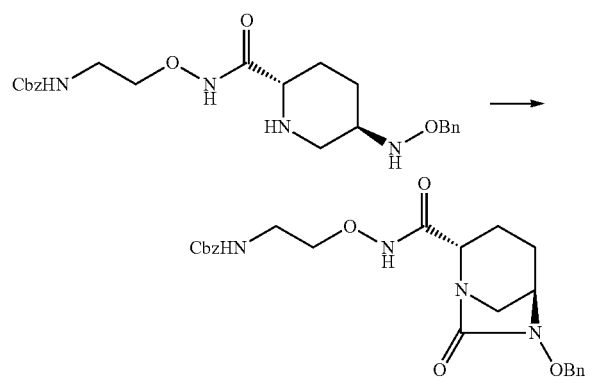

A solution of (2S,5R)-N-(2-benzyloxycarbonylaminoethoxy)-5-(benzyloxyamino)piperidine-2-carboxamide (642 mg, 1.451 mmol) in acetonitrile (66 mL) was ice-cooled, and to which were added triethylamine (709 μL) and chlorotrimethylsilane (203 μL), followed by stirring for 1 h. To this reaction solution was added chloroformate trichloromethyl (105 μL), followed by stirring at the same temperature for 20 min. To this reaction solution was then 4-(dimethylamino)pyridine (18 mg) was added, a temperature was elevated to room temperature, followed by stirring overnight. The reaction mixture was concentrated under reduced pressure, and the resulting residue was diluted with ethyl acetate, and then washed with water, 5% citric acid aqueous solution, 6.5% sodium bicarbonate aqueous solution and saturated brine sequentially. Subsequently, the organic layer was dehydrated over anhydrous magnesium sulfate, and the solvent was distilled off under reduced pressure. The resulting residue was purified by silica gel column chromatography (n-hexane/ethyl acetate=1/3) to afford 407 mg of the title compound (yield 60%).

$^{1}$H NMR (400 MHz, CDCl$_{3}$) δ 1.59-1.65 (m, 1H), 1.91-2.02 (m, 2H), 2.26-2.31 (m, 1H), 2.71-2.74 (d, J=11.6 Hz, 1H), 2.99-3.02 (br d, J=11.2 Hz, 1H), 3.28 (s, 1H), 3.31-3.39 (m, 1H), 3.46-3.49 (m, 1H), 3.88-3.97 (m, 3H), 4.88-4.91 (d, J=11.6 Hz, 1H), 5.03-5.06 (d, J=11.6 Hz, 1H), 5.11 (s, 2H), 5.83 (br s, 1H), 7.27-7.43 (m, 10H), 9.36 (br s, 1H); MS m/z 469 [M+H]$^{+}$.

Example 109

(2S,5R)-N-(2-tert-Butoxycarbonylaminoethoxy)-6-(benzyloxy)-7-oxo-1,6-diazabicyclo[3.2.1]octane-2-carboxamide (IIa-Boc-059)

[Chemical formula 129]

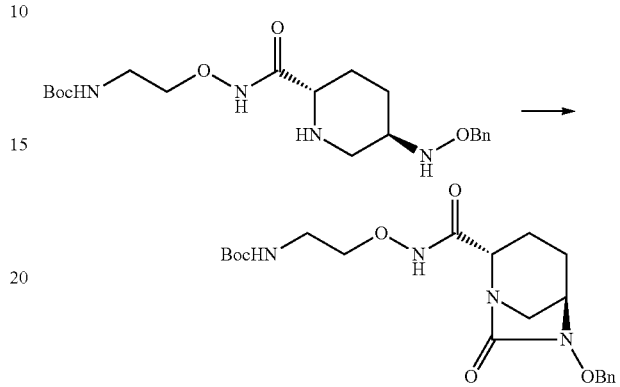

A solution of (2S,5R)-N-(2-tert-butoxycarbonylaminoethoxy)-5-(benzyloxyamino)piperidine-2-carboxamide (368 mg, 0.901 mmol) described in Example 103 or 105 in acetonitrile (40.9 mL) was ice-cooled, and to which were added triethylamine (440 μL) and chlorotrimethylsilane (126 μL), followed by stirring for 1 h. To this reaction solution was added trichloromethyl chloroformate (66.0 μL) was added, followed by stirring at the same temperature for 30 min. Then to this reaction solution was added 4-(dimethylamino)pyridine (10.2 mg), and a temperature was elevated to room temperature, followed by reaction for 4 hr. The reaction mixture was concentrated under reduced pressure, and the resulting residue was diluted with ethyl acetate, and then washed with water, 5% citric acid aqueous solution, 6.5% sodium bicarbonate aqueous solution and saturated brine sequentially. Then, the organic layer was dehydrated over anhydrous magnesium sulfate, and the solvent was distilled off under reduced pressure. The resulting oil residue was purified by silica gel column chromatography (n-hexane/ethyl acetate=2/3) to afford 202 mg of the title compound as a colorless solid (yield 52%). Instrumental data were consistent with those of Example 59.

Example 110 tert-Butyl {2-[({[(2S,5R)-6-hydroxy-7-oxo-1,6-diazabicyclo[3.2.1]oct-2-yl]carbonyl}amino)oxy]ethyl}carbamate (IIb-Boc-059)

[Chemical formula 130]

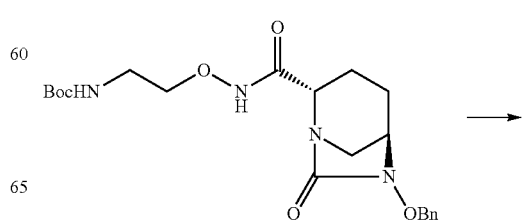

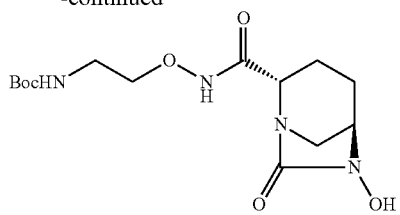

tert-Butyl {2-[({[(2S,5R)-6-benzyloxy-7-oxo-1,6-diazabicyclo[3.2.1]oct-2-yl]carbonyl}amino)oxy]ethyl}carbamate (43.4 g, 100 mmol) was dissolved in tetrahydrofuran (475 mL). After the dissolution was confirmed, water (25 mL) was added, and set under an argon atmosphere. 10% Pd/C (8.68 g, 50% wet) was added, and stirred vigorously under hydrogen atmosphere for 3 h. The end point was confirmed by TLC, and then catalyst was filtered through Celite. The solvent of filtrate was concentrated under reduced pressure. The concentrated residue was subjected to workup of substitution and concentration with ethyl acetate (100 mL) twice, and with methylene chloride (100 mL) once to afford 34.5 g of the title compound (quantitative). Instrumental data were consistent with those of Example 59.

Example 111 tert-Butyl {2-[({[(2S,5R)-6-hydroxy-7-oxo-1,6-diazabicyclo[3.2.1]oct-2-yl]carbonyl}amino)oxy]ethyl}carbamate (IIb-Boc-059): Synthesis from (IIa-Cbz-059)

[Chemical formula 131]

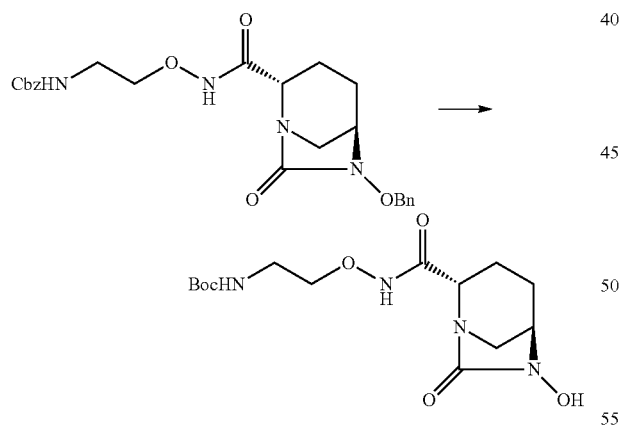

Benzyl {2-[({[(2S,5R)-6-benzyloxy-7-oxo-1,6-diazabicyclo[3.2.1]oct-2-yl]carbonyl}amino)oxy]ethyl}carbamate (468 mg, 1.00 mmol) described in Example 108 and di-tert-butoxycarbonyldicarbonate (240 mg) were dissolved in tetrahydrofuran (6.6 mL), and to which was added 10% Pd/C (93 mg, 50% wet), followed by stirring vigorously under an hydrogen atmosphere for 3 h. The end point was confirmed by TLC, and then catalyst was filtered through Celite. The solvent of filtrate was concentrated under reduced pressure to afford 403.7 mg of the title compound (quantitative). Instrumental data were consistent with those of Example 59.

Example 112

Tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}carbamate (III-Boc-059)

[Chemical formula 132]

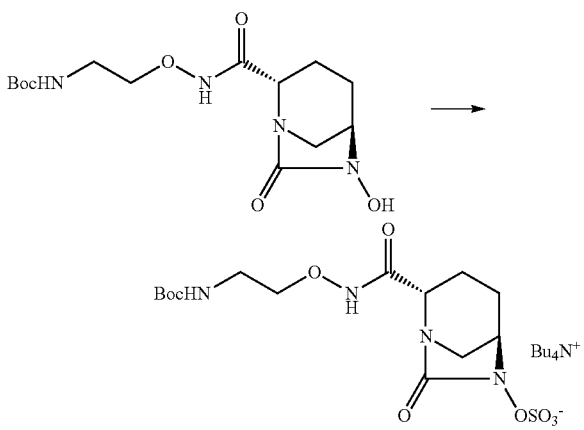

To a solution of tert-butyl {2-[({[(2S,5R)-6-hydroxy-7-oxo-1,6-diazabicyclo[3.2.1]oct-2-yl]carbonyl}amino)oxy]ethyl}carbamate (34.5 g, 100 mmol) in methylene chloride (500 mL) were added 2,6-lutidine (32.8 g) and sulfur trioxide-pyridine complex (51.9 g) sequentially, and stirred for 24 hours. Completion of reaction was confirmed by HPLC, the reaction solution was filtered, and filtrate was added into 8% sodium bicarbonate aqueous solution (1 L), and washed with methylene chloride (500 mL). To the aqueous layer was added ethyl acetate (1 L), followed by addition of tetrabutylammonium hydrogen sulfate (37.34 g) while paying attention to effervescence, and stirred for 30 min. Following liquid separation of the mixture, the aqueous layer was extracted with ethyl acetate (500 ml) twice. The combined organic layers were dried over magnesium sulfate, and the solvent was concentrated under reduced pressure to afford 53.9 g of the title compound (yield 81.1%). Instrumental data were consistent with those of Example 59.

Example 113

(2S,5R)-N-(2-Aminoethoxy)-7-oxo-6-(sulfooxy)-1,6-diazabicyclo[3.2.1]octane-2-carboxamide (III-059)

[Chemical formula 133]

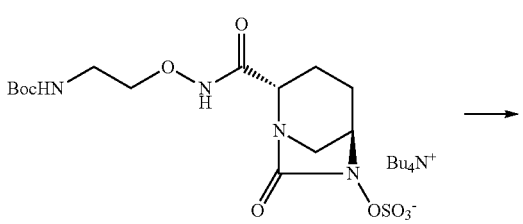

-continued

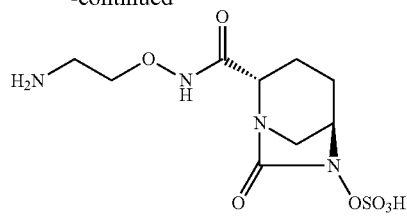

A solution of tetrabutylammonium tert-butyl {2-[({[(2S,5R)-7-oxo-6-(sulfooxy)-1,6-diazabicyclo[3.2.1]oct-2-yl]carbonyl}amino)oxy]ethyl}carbamate (68.9 g, 104 mmol) in methylene chloride (170 mL) solution was cooled to −20° C., and trifluoroacetic acid (170 mL) was added at −15° C. or less over 20 min., followed by stirring at 0° C. for 35 min. To the reaction solution was added diethyl ether (510 mL), and followed by stirring at 0° C. for 40 min. The precipitated solid was filtered through Kiriyama funnel, and washed with diethyl ether (450 mL), subsequently dried under vacuo to afford a crude product (39.5 g). This was added to 0.5M sodium acetate/acetic acid buffer (400 mL, pH 5.6), and further pH was adjusted to pH 5.6 with 5M sodium hydroxide aqueous solution, and then was purified by octadecyl silica gel column chromatography (water) to afford 24.8 g of the title compound (yield 74%). Instrumental data were consistent with those of Example 59.

Example 114

Dihydrochloride of (2S,5R)-methyl 5-(benzyloxyamino)piperidine-2-carboxylate (4b); Synthesis from the compound (2) through hydrochloride of (2S,5S)-5-hydroxypiperidine-2-carboxylic acid (7)

Step 1

Hydrochloride of (2S,5S)-5-hydroxypiperidine-2-carboxylic acid (7)

(2S,5S)-tert-Butyl 5-hydroxypiperidine-2-carboxylate (126.22 g, 0.63 mol) described in Example 1 was gradually added into 5M hydrochloric acid (630 mL) at room temperature, followed by heating to 65° C. and stirring for 2 hours. Subsequently, the reaction solution was cooled to room temperature and the reaction solvent was concentrated under reduced pressure. The residue was dissolved in water (500 mL), and activated carbon (6.5 g) was added, followed by stirring at room temperature for 30 minutes. The activated carbon was filtered through Celite. Celite was washed twice with water (100 mL) and the filtrate was combined, followed by concentrating under reduced pressure. The residue (150 g) was ice-cooled, followed by inoculation and stirring. To the mixture was added dropwise acetone (650 mL) over 30 minutes, followed by stirring for 30 minutes. The deposited crystals were filtered off under an argon stream, followed by washing with acetone. After deliquoring and drying under vacuum overnight, 108.79 g of the title compound was afforded as a colorless powder crystal (yield 96%).

$^1$H NMR (400 MHz, D$_2$O) δ 1.66-2.23 (m, 4H), 3.25 (d, J=3.4 Hz, 1H), 3.38 (d, J=3.4 Hz, 1H), 4.00 (dd, J=11.7, 3.7 Hz, 1H), 4.22 (brs, 1H); MS m/z: 146 (M−HCl+H)$^+$.

Step 2

Hydrochloride salt of (2S,5S)-methyl 5-hydroxypiperidine-2-carboxylate (8)

To (2S,5S)-5-hydroxypiperidine-2-carboxylic acid hydrochloride salt (26.46 g, 0.146 mol) was added 2M hydrogen chloride-methanol (230 mL), followed by heating at reflux. After 1.5 hours, the reaction solution was concentrated, followed by substituting and concentrating with methanol (200 mL) three times. The residue was dried under vacuum to afford 28.55 g of the title compound as a colorless crystalline powder (quantitative yield).

$^1$H NMR (400 MHz, D$_2$O) δ 1.74-2.06 (m, 4H), 3.12 (dd, J=2.0, 13.2 Hz, 1H), 3.25-3.29 (m, 1H), 3.72 (s, 3H), 3.98 (dd, J=3.8, 12.2 Hz, 1H), 4.09 (brs, 1H); MS m/z: 160 (M−HCl+H)$^+$.

Step 3

(2S,5S)-Methyl 5-hydroxy-1-(2,2,2-trifluoroacetyl)piperidine-2-carboxylate (9)

To a suspension of (2S,5S)-methyl 5-hydroxypiperidine-2-carboxylate hydrochloride (26.80 g, 0.137 mol) in dehydrated tetrahydrofuran (440 mL) was added triethylamine (91.0 mL) under ice cooling, followed by adding dropwise trifluoroacetic anhydride (39.5 mL) at 10° C. or less over 1 hour. The reaction suspension was stirred for 70 minutes while the temperature was gradually elevated to room temperature. To the reaction solution was added water (80 mL), followed by stirring at room temperature for 30 minutes. Subsequently, it was added to water (1000 mL) and extracted with ethyl acetate three times (500 mL+2×250 mL). The organic layer was washed with 1M hydrochloric acid (300 mL), a saturated sodium bicarbonate aqueous solution (200 mL) and saturated brine (2×150 mL), dried over anhydrous sodium sulfate, filtered, and then concentrated under reduced pressure to afford 34.65 g of the title compound as an oil (yield 99%).

$^1$H NMR (400 MHz, CDCl$_3$) δ observed as a mixture of 2 rotamers (7:3). 1.34-1.44 (m, 1H), 1.73-1.83 (m, 1H), 2.00-2.10 (m, 2H), 2.39-2.45 (m, 1H), 2.75 (t, J=11.5 Hz, 0.3H), 3.11 (dd, J=5.7, 13.4 Hz, 0.7H), 3.79 (s, 2.1H), 3.81 (s, 0.9H), 4.00-4.06 (m, 0.7H), 4.58-4.67 (m, 0.3H), 4.62 (m, 0.3H), 5.20 (d, J=5.9 Hz, 0.7H); MS m/z: 256 (M+H)$^+$.

Step 4

Hydrochloride of (2S,5R)-methyl 5-(benzyloxyamino)-1-(2,2,2-trifluoroacetyl)piperidine-2-carboxylate (10)

A solution of (2S,5S)-methyl 5-hydroxy-1-(2,2,2-trifluoroacetyl)piperidine-2-carboxylate (32.71 g, 0.128 mol) in dehydrated acetonitrile (250 mL) was cooled to −30° C., followed by adding 2,6-lutidine (16.9 mL) and adding dropwise trifluoromethanesulfonic anhydride (22.5 mL) at −36 to −30° C. over 15 minutes. After stirring at −32° C. for 25 minutes, benzyloxyamine (32.25 g) was added dropwise at −32° C. or less, followed by washing with acetonitrile (10 mL). After the reaction solution was gradually warmed to 0° C., 2,6-lutidine (16.9 mL) was added and stirred at 4° C. for 2 days. The reaction solution was concentrated to 150 mL, followed by diluting with ethyl acetate (750 mL) and washing with water (750 mL), 10% citric acid aqueous solution (3×750 mL), a saturated sodium bicarbonate aqueous solution (375 mL), and saturated brine (400 mL). Each aqueous layer was reextracted with ethyl acetate (400 mL) and the combined organic layers were dried over anhydrous sodium sulfate, filtered, and then concentrated under reduced pressure to afford 46.93 g of the residue. 38.24 g of the resulting residue was taken out and diluted with ethyl acetate (120 mL). At room temperature, 1M hydrogen chloride-ethyl acetate 160 mL (0.160 mol) was added for crystallization, and hexane (560 mL) was added. After stirring at 0° C. for 3 hours, the crystals were filtered, washed with hexane (400 mL), and then dried under vacuum to afford 30.36 g of the title compound as a crystalline powder (yield 73%).

$^1$H NMR (400 MHz, CD$_3$OD) δ observed as a mixture of 2 rotamers. 2.00-2.09 (m, 3H), 2.23-2.24 (m, 1H), 3.33-3.42 (m, 0.5H), 3.74 (dd, J=3.2, 15.6 Hz, 0.5H), 3.79 (s, 2H), 3.81 (s, 1H), 3.89 (brs, 1H), 4.29 (d, J=15.9 Hz, 0.5H), 4.81 (d, J=14.4 Hz, 0.5H), 5.08-5.16 (m, 2.5H); MS m/z: 361 (M−HCl+H)$^+$.

Step 5

Dihydrochloride of (2S,5R)-methyl 5-(benzyloxyamino)piperidine-2-carboxylate (4b)

To (2S,5R)-methyl 5-(benzyloxyamino)-1-(2,2,2-trifluoroacetyl)piperidine-2-carboxylate hydrochloride salt (1.951 g, 4.92 mmol) was added 2M hydrogen chloride-methanol (40 mL), followed by refluxing for 3 days. Subsequently, the reaction solution was concentrated to 14 mL, and ethyl acetate (40 mL) was added to deposit a crystal. The suspension was stirred at room temperature for 1.5 hours, then filtered through Kiriyama funnel, washed with ethyl acetate (80 mL), and dried under vacuum to afford 1.439 g of the title compound as a crystalline powder (yield 87%). The instrumental data were consistent with those of Example 12.

Example 115

Dihydrochloride of (2S,5R)-5-(benzyloxyamino) piperidine-2-carboxylate (4b); Synthesis from commercially available (2S,5S)-5-hydroxypiperidine-2-carboxylic acid (7)

Step 1

Hydrochloride of (2S,5S)-methyl 5-hydroxypiperidine-2-carboxylate (8)

To 2M hydrogen chloride-methanol (12.8 L) was added commercially available (2S,5S)-5-hydroxypiperidine-2-carboxylic acid (content 84%, net 912.22 g, washed with 2M hydrogen chloride-methanol 3.1 L), followed by refluxing for 3 hours (internal temperature 63-67° C.). After the reaction solution was cooled, 1,4-dioxane (12.8 L) was added and the solvent was distilled off under reduced pressure. To the residue (4.1 kg) were added ethyl acetate (18.3 L) and ice-cooled 44% potassium carbonate aqueous solution (23.7 L), followed by layer separation of the organic layer. The aqueous layer was further extracted with ethyl acetate (3×18.3 L). A 50% potassium carbonate aqueous solution (7.3 L) was separated at each organic layer, the organic layers were combined, dried over anhydrous potassium carbonate (2.37 kg) and filtered, and the solvent was distilled off under reduced pressure. The residue was dissolved in toluene (9.1 L), and activated carbon (9.2 g) was added, followed by stirring for 30 minutes and filtering, and the solvent was distilled off under reduced pressure. The residue was substituted with ethyl acetate (9.1 L) and concentrated to afford 1130 g of the title compound as a pale yellow oil (content 78.9%, net 891.57 g, yield 89%).

Step 2

(2S,5S)-Methyl 5-hydroxy-1-(2,2,2-trifluoroacetyl) piperidine-2-carboxylate (9)

A solution of (2S,5S)-methyl 5-hydroxypiperidine-2-carboxylate (content 78.8%, net 459.48 g) in dehydrated ethyl acetate (7.4 L) was cooled to −40° C. and triethylamine (1300 g) and then trifluoroacetic anhydride (1349 g), washed with dehydrated ethyl acetate (100 mL) were added dropwise at −40 to −12° C. for 30 minutes. The temperature was elevated to −2° C. within 15 minutes after completion of the dropwise addition, followed by stirring for 75 minutes. Further, to the mixture was added water (1277 mL), followed by stirring at 25° C. for 1 hour. The mixture was added to water (8.4 L) (washed with ethyl acetate (4.5 L), followed by further extracting with ethyl acetate (2×9.8 L). The combined organic layers were sequentially washed with 1M hydrochloric acid (8.5 L), saturated sodium bicarbonate aqueous solution (8.5 L) and saturated brine (8.5 L), followed by drying over anhydrous sodium sulfate (1.8 kg) and filtering. After the solvent of the organic layer was distilled off under reduced pressure, to the residue was added ethyl acetate (3.6 L), followed by substitution and concentration. The residue was dried under vacuum to afford 793.4 g of the title compound (content 81.5%, net 648.66 g, yield 88%).

Step 3

(2S,5R)-Methyl 5-(benzyloxyamino)-1-(2,2,2-trifluoroacetyl)piperidine-2-carboxylate (10)

A solution of (2S,5S)-methyl 5-hydroxy-1-(2,2,2-trifluoroacetyl)piperidine-2-carboxylate (content 81.5%, net 556.23 g) in dehydrated acetonitrile (4.0 L) was cooled to −40° C., 2,6-lutidine (259.24 g) was added (washed with acetonitrile (100 ml), and trifluoromethane sulfonic acid anhydride (645.72 g) was added dropwise at −43 to −37° C. over 1 hour and 10 minutes (washed with acetonitrile 100 ml). After the reaction solution was stirred at −35° C. for 50 minutes, benzyloxyamine (550.27 g) was added dropwise at −35° C. or less, followed by washing with acetonitrile (500 mL). After the reaction solution was gradually warmed to −5° C., 2,6-lutidine (259.24 g) was added, followed by stirring at 5° C. for 40 hours. The mixture was concentrated to 1.8 L, followed by diluting with ethyl acetate (12.4 L) and washing with water (12.4 L), a 10% citric acid aqueous solution (4×8 L+4.7 L), saturated sodium bicarbonate aqueous solution (6.3 L) and saturated brine (7.2 L). The organic layer was dried over anhydrous sodium sulfate, followed by filtering and then concentrating under reduced pressure. The residue was dried under vacuum to afford 867.73 g of the title compound (content 71.56%, yield 79%).

Step 4

Hydrochloride of (2S,5R)-methyl 5-(benzyloxyamino)-1-(2,2,2-trifluoroacetyl)piperidine-2-carboxylate (10)

(2S,5R)-Methyl 5-(benzyloxyamino)-1-(2,2,2-trifluoroacetyl)piperidine-2-carboxylate (content 70.13%, net 673.20 g) was diluted with ethyl acetate (4.8 L) and activated carbon (48 g) was added, followed by stirring for 1 hour. The mixture was filtered, followed by washing with ethyl acetate (2 L). The filtrate was diluted with ethyl acetate (4.7 L), and 1M hydrogen chloride-ethyl acetate solution (2.7 L) at room temperature was added, followed by stirring for 15 minutes. Then, hexane 28.6 L was added, followed by cooling to 0° C. After stirring and aging for 3 hours, the crystals were filtered, washed with hexane/ethyl acetate=4/1 (3 L), and then dried under vacuum to afford 724.0 g of the title compound (content 91.72%, yield 90%).

Step 5

Dihydrochloride of (2S,5R)-methyl 5-(benzyloxyamino)piperidine-2-carboxylate (4b)

(2S,5R)-Methyl 5-(benzyloxyamino)-1-(2,2,2-trifluoroacetyl)piperidine-2-carboxylate (content 92.01%, net 732.25 g) was dissolved in a 2M hydrogen chloride-methanol solution (15 L), followed by heating at reflux for 27 hours. The mixture was cooled to room temperature and concentrated to 3 L under reduced pressure. To the mixture was added methanol (2.7 L), then ethyl acetate (16.3 L) was added, followed by stirring for 1 hour. The deposited crystals were filtered, washed with ethyl acetate (3×1.1 L), and dried under vacuum to afford 572.0 g of the title compound (content 98.06%, yield 92%). The instrumental data were consistent with those of Example 12.

Example 116

(2S,5R)-5-((Benzyloxy)amino)-1-(tert-butoxycarbonyl)piperidine-2-carboxylic acid (IV-a3)

Dihydrochloride of (2S,5R)-methyl 5-(benzyloxyamino) piperidine-2-carboxylate (4b) described in Example 12 (6.64 g, 20 mmol) was dissolved in water (40 mL) and 1,4-dioxane (27 mL), followed by ice cooling. A 5M aqueous sodium hydroxide (13.2 mL) solution was added, followed by stirring for 1 hour. To the reaction solution were added 5M hydrochloric acid (1.2 mL), potassium carbonate (2.76 g), di-tert-butoxycarbonyl dicarbonate (4.8 g), followed by raising the temperature to room temperature and stirring overnight. The aqueous solution resulting from concentration of the reaction solution was washed with ether, followed by adjusting to pH 3.3 with citric acid.monohydrate, extracting with ethyl acetate (50 mL) twice, washing with saturated brine, drying over anhydrous sodium sulfate, filtering, and concentrating the solvent under reduced pressure. Thereby, 6.87 g of the title compound was afford (quantitative yield). The instrumental data were consistent with those of Example 99.

Example 117

Preparation of β-Lactamase Enzyme

Using *Pseudomonas aeruginosa* ATCCBAA-47 genome, plasmid pBR322, *Klebsiella pneumoniae* ATCCBAA-1705, and *P. aeruginosa* MSC17696 as a template, each DNA for encoding β-lactamase, AmpC, TEM-1, KPC-2 or OXA-2 domain excluding signal peptide was amplified with PCR. Each of the PCR product was incorporated into pET-28b(+) vector (Merck), introduced into *Escherichia coli* BL21 (DE3) (Merck), and, under induction of 1 mM isopropyl-β-D-(−)-thiogalactopyranoside (Nacalai Tesque), cultured overnight at 20° C. to express AmpC, TEM-1, KPC-2, and OXA-2. After the bacterial cell was collected, AmpC was purified from the cell extract obtained by ultrasonic treatment, using CM Sepharose Fast Flow (GE Healthcare) and HiTrap Heparin HP (GE Healthcare) at 4° C. TEM-1 was purified with HiTrap SPHP (GE Healthcare), HiTrap Q (GE Healthcare) and Mono Q (GE Healthcare), and KPC-2 was purified with HiTrap SPHP. OXA-2 was purified with HiTrap SPHP and HiTrap Heparin HP.

Example 118

β-Lactamase Inhibitory Activity

For the measurement of β-lactamase inhibitory activity, 100 μM (final concentration) nitrocefin (Oxoid) was used as a substrate, and 2.5% DMSO, 10 μg/mL bovine serum derived albumin (Sigma-Aldrich) and 50 mM phosphate buffer at pH 7.0 were used as a reaction solution. To each well of a 96-well plate were added test compounds, tazobactam (TAZ, LKT Laboratories), NXL104 (prepared by reference to Patent document 1, purity 99.5%, Meiji Seika Pharma Co., Ltd.) or MK-7655 (prepared by reference to Patent document 3, purity 99.4%, Meiji Seika Pharma Co., Ltd.) and AmpC, TEM-1, KPC-2 or OXA-2 (final concentrations are 0.5 nM, 0.1 nM, 0.5 nM, or 2 nM, respectively), followed by pre-incubation at 30° C. for 10 minutes. Nitrocefin was added to each well to be mixed therein, followed by incubation at 30° C. for 20 minutes, and Multiscan Ascent (Thermo Fisher Scientific) was used to measure 492 nm wavelength, thereby measuring nitrocefin hydrolytic activity of β-Lactamase, to determine enzyme inhibitory activity. As a control, a reaction solution excluding β-lactamase was prepared, and the concentration of a test compound exhibiting 50% inhibition was determined to be IC50 value. As the inhibitory activity strength, less than 0.1 μM, less than 1 μM, less than 3 μM, less than 10 μM, and 10 μM or more were shown with A, B, C, D, and E respectively. The results are as shown in Table 5.

Class A β-Lactamase: KPC-2, TEM-1
Class C β-Lactamase: AmpC
Class D β-Lactamase: OXA-2 (ESBL)

TABLE 5

| Compound | β-Lactamase inhibitory activity | | | |
| --- | --- | --- | --- | --- |
| | AmpC | TEM-1 | KPC-2 | OXA-2 |
| TAZ | B | A | B | A |
| NXL104 | B | A | B | B |
| MK-7655 | B | A | B | B |
| Example 17 | B | A | B | D |
| Example 18 | B | A | B | C |
| Example 19 | B | A | B | NT |
| Example 20 | B | B | C | D |
| Example 21 | B | A | B | C |
| Example 22 | B | A | B | D |
| Example 23 | B | A | B | D |
| Example 24 | B | B | B | NT |
| Example 25 | B | A | A | E |
| Example 26 | C | B | C | NT |
| Example 27 | B | A | C | C |
| Example 28 | A | A | B | D |
| Example 29 | B | A | B | D |
| Example 30 | B | A | B | NT |
| Example 31 | B | A | B | D |
| Example 32 | A | A | B | D |
| Example 33 | B | A | B | D |
| Example 34 | A | A | B | D |
| Example 35 | B | A | D | C |

TABLE 5-continued

| Compound | β-Lactamase inhibitory activity | | | |
|---|---|---|---|---|
| | AmpC | TEM-1 | KPC-2 | OXA-2 |
| Example 36 | B | A | C | D |
| Example 37 | C | A | C | C |
| Example 38 | B | A | B | C |
| Example 39 | A | A | C | C |
| Example 40 | B | A | D | C |
| Example 41 | B | B | C | D |
| Example 42 | B | B | B | C |
| Example 43 | B | A | B | C |
| Example 44 | A | A | A | C |
| Example 45 | A | A | B | C |
| Example 46 | A | A | B | C |
| Example 47 | B | A | B | D |
| Example 48 | A | B | B | D |
| Example 49 | B | A | B | D |
| Example 50 | A | B | B | D |
| Example 51 | B | A | B | C |
| Example 52 | B | A | B | C |
| Example 53 | B | A | B | NT |
| Example 54 | A | A | B | B |
| Example 55 | B | B | C | D |
| Example 56 | B | A | B | C |
| Example 57 | B | A | C | NT |
| Example 58 | A | A | A | B |
| Example 59 | B | A | B | C |
| Example 60 | B | A | B | B |
| Example 61 | B | A | C | C |
| Example 62 | B | A | B | C |
| Example 63 | B | A | B | C |
| Example 64 | B | A | B | C |
| Example 65 | B | B | C | C |
| Example 66 | B | A | C | C |
| Example 67 | B | A | C | C |
| Example 68 | A | A | B | C |
| Example 69 | B | A | C | B |
| Example 70 | B | A | B | B |
| Example 71 | B | A | B | NT |
| Example 72 | A | A | B | B |
| Example 73 | A | A | B | NT |
| Example 74 | A | A | B | B |
| Example 75 | B | A | B | C |
| Example 76 | B | A | B | B |
| Example 77 | B | A | B | B |
| Example 78 | B | A | C | C |
| Example 79 | B | A | C | C |
| Example 80 | B | A | C | B |
| Example 81 | A | A | B | C |
| Example 82 | A | A | B | B |
| Example 83 | A | A | B | B |
| Example 84 | A | A | C | B |
| Example 85 | A | A | B | B |
| Example 86 | A | A | B | NT |
| Example 87 | A | A | A | B |
| Example 88 | B | A | B | B |
| Example 89 | A | A | A | B |
| Example 90 | A | A | B | B |
| Example 91 | A | A | A | B |
| Example 92 | A | A | B | B |
| Example 93 | A | A | B | B |
| Example 94 | A | A | B | B |
| Example 95 | A | A | A | C |
| Example 96 | A | A | B | C |
| Example 97 | A | A | A | B |

NT: Not tested;
A: <0.1 μM,
B: <1 μM,
C: <3 μM,
D: <10 μM,
E: ≥10 μM

Example 119

Synergetic Effect

The synergetic effect of the test compound with a β-lactam agent against bacteria was evaluated using AmpC constitutively-expressing strain, *P. aeruginosa* ATCCBAA-47CR selected from ATCCBAA-47 through agent exposure, KPC-2 producing strain, *K. pneumoniae* ATCCBAA-1705, and CTX-M-15 (ESBL) and OXA-1 producing strain, *E. coli* MSC19503. Using piperacillin (PIPC, Sigma-Aldrich) as a β-lactam agent, minimal inhibitory concentration (MIC) of PIPC was measured by agar plate dilution process based on Clinical and Laboratory Standards Institute (CLSI process). That is, an agar plate containing PIPC at each concentration adjusted in common ratio 2 of dilution series in Mueller-Hinton agar (MHA, Becton, Dickinson and Company) and the test compound having ¼ or ⅛ of respective PIPC concentration was made, and bacteria cultured overnight in cation-adjusted Muller-Hinton broth (CAMHB, Becton, Dickinson and Company) were adjusted in the same medium so as to have $10^4$ CFU/spot and inoculated on a plate containing an agent. This plate containing an agent was cultured overnight at 35° C., and the minimum agent concentration in which no growth of bacteria was observed was determined to be MIC. The antibacterial activities of PIPC alone to AmpC constitutively-expressing, *P. aeruginosa*, KPC-2 producing *K. pneumoniae*, and CTX-M-15 (ESBL) and OXA-1 producing *E. coli* were shown by 64 μg/mL, >128 μg/mL, >128 μg/mL respectively, and those in which antibacterial activities of PIPC were recovered by less than 1/16, less than ¼, and less than 1/1, and were not recovered, by the synergetic effect of the test compounds were shown with A, B, C, and D respectively. The results are as shown in Table 6.

Class A β-Lactamase: KPC-2, CTX-M-15 (ESBL)
Class C β-Lactamase: AmpC
Class D β-Lactamase: OXA-1

TABLE 6

| | | Organism | | |
|---|---|---|---|---|
| | | *P. aeruginosa* | *K. pneumoniae* | *E. coli* |
| | | Bacterial strain | | |
| | | ATCCBAA-47CR | ATCCBAA-1705 | MSC19503 |
| | | Producing enzyme | | |
| Compound | Compound/PIPC ratio | AmpC(++) | KPC-2 | CTX-M-15, OXA-1 |
| | | Enhancing activity | | |
| TAZ | 1/8 | D | D | B |
| NXL104 | 1/8 | B | B | A |
| Example 17 | 1/8 | B | B | A |
| Example 18 | 1/4 | D | C | B |
| Example 19 | 1/4 | C | B | A |
| Example 20 | 1/4 | C | B | A |
| Example 21 | 1/8 | C | A | A |
| Example 22 | 1/8 | C | A | A |
| Example 23 | 1/8 | C | B | A |
| Example 24 | 1/8 | C | C | B |
| Example 25 | 1/4 | C | B | A |
| Example 26 | NT | NT | NT | NT |
| Example 27 | 1/8 | C | A | A |
| Example 28 | 1/8 | C | A | A |
| Example 29 | 1/8 | C | B | A |
| Example 30 | 1/4 | D | C | B |
| Example 31 | 1/8 | C | B | A |

TABLE 6-continued

| Compound | Compound/ PIPC ratio | P. aeruginosa ATCCBAA-47CR AmpC(++) | K. pneumoniae ATCCBAA-1705 KPC-2 | E. coli MSC19503 CTX-M-15, OXA-1 |
|---|---|---|---|---|
| | | Enhancing activity | | |
| Example 32 | 1/4 | C | B | A |
| Example 33 | NT | NT | NT | NT |
| Example 34 | 1/8 | C | B | A |
| Example 35 | 1/8 | B | A | A |
| Example 36 | 1/8 | C | A | A |
| Example 37 | 1/8 | C | B | A |
| Example 38 | 1/8 | C | A | A |
| Example 39 | 1/8 | C | B | A |
| Example 40 | 1/8 | C | B | A |
| Example 41 | 1/8 | C | A | A |
| Example 42 | 1/8 | C | B | A |
| Example 43 | 1/8 | C | B | A |
| Example 44 | 1/8 | C | B | B |
| Example 45 | 1/8 | C | B | A |
| Example 46 | 1/8 | C | B | A |
| Example 47 | 1/8 | C | B | B |
| Example 48 | 1/8 | C | C | B |
| Example 49 | 1/4 | D | B | A |
| Example 50 | 1/8 | C | B | A |
| Example 51 | 1/8 | C | B | A |
| Example 52 | 1/8 | C | B | A |
| Example 53 | 1/4 | C | C | B |
| Example 54 | 1/8 | C | B | A |
| Example 55 | NT | NT | NT | NT |
| Example 56 | 1/8 | C | B | A |
| Example 57 | 1/4 | C | B | A |
| Example 58 | 1/8 | C | C | A |
| Example 59 | 1/8 | B | B | A |
| Example 60 | 1/8 | D | C | B |
| Example 61 | 1/8 | B | A | A |
| Example 62 | 1/8 | C | B | A |
| Example 63 | 1/8 | C | B | A |
| Example 64 | 1/8 | C | A | A |
| Example 65 | 1/8 | C | A | A |
| Example 66 | 1/8 | B | B | A |
| Example 67 | 1/8 | B | A | A |
| Example 68 | 1/8 | B | B | B |
| Example 69 | 1/8 | B | B | A |
| Example 70 | 1/8 | C | B | A |
| Example 71 | 1/8 | D | C | B |
| Example 72 | 1/8 | C | B | A |
| Example 73 | 1/8 | C | B | A |
| Example 74 | 1/8 | C | B | A |
| Example 75 | 1/8 | B | A | A |
| Example 76 | 1/8 | C | A | A |
| Example 77 | 1/8 | B | A | A |
| Example 78 | 1/8 | C | A | A |
| Example 79 | 1/8 | B | B | A |
| Example 80 | 1/8 | C | B | A |
| Example 81 | 1/8 | B | B | B |
| Example 82 | 1/8 | B | B | A |
| Example 83 | 1/8 | C | B | A |
| Example 84 | 1/8 | B | B | A |
| Example 85 | 1/8 | B | B | A |
| Example 86 | 1/8 | C | B | A |
| Example 87 | 1/8 | C | B | A |
| Example 88 | 1/8 | D | B | A |
| Example 89 | 1/8 | C | B | A |
| Example 90 | 1/8 | C | B | A |
| Example 91 | 1/8 | C | B | A |
| Example 92 | 1/8 | B | B | A |
| Example 93 | 1/8 | C | B | A |
| Example 94 | 1/8 | D | C | A |
| Example 95 | 1/8 | C | B | A |
| Example 96 | 1/8 | C | B | A |
| Example 97 | 1/8 | C | B | A |

NT: Not tested;

A: <1/16,

B: <1/4,

C: <1,

D: ≥1

Example 120

The synergetic effect of the test compounds synthesized in Examples 59, 61 and 69 with a β-lactam agent against bacteria was evaluated using KPC-2 producing strain, *K. pneumoniae* ATCCBAA-1705, CTX-M-15 (ESBL) and OXA-1 producing strain, *E. coli* MSC19503, and AmpC constitutively-expressing strain, *P. aeruginosa* ATCCBAA-47CR. Using ampicillin (ABPC, Sigma-Aldrich), amoxicillin (AMPC, Sigma-Aldrich), piperacillin (PIPC), ceftazidime (CAZ, Sigma-Aldrich), cefepime (CFPM, United States Pharmacopeial Convention), cefotaxime (CTX, Sigma-Aldrich), ceftriaxone (CTRX, Sigma-Aldrich), imipenem (IPM, United States Pharmacopeial Convention), biapenem (BIPM, Meiji Seika Pharma Co., Ltd.), meropenem (MEPM, United States Pharmacopeial Convention), doripenem (DRPM, Sequoia Research Products), cefminox (CMNX, Meiji Seika Pharma), flomoxef (FMOX, SHIONOGI & CO., Ltd.), aztreonam (AZT, United States Pharmacopeial Convention) as a β-lactam agent, MIC of each β-lactam agent was measured by broth microdilution method based on CLSI process. That is, a liquid medium containing 4 μg/mL (final concentration) of test compound, TAZ, NXL104, or MK-7655, and β-lactam agent and test compound at each concentration adjusted in common ratio 2 of dilution series in CAMHB was made, and bacteria cultured overnight in CAMHB were adjusted in the same medium so as to have $10^5$ CFU/mL and inoculated on a liquid medium containing an agent. This liquid medium containing an agent was cultured overnight at 35° C., and the minimum agent concentration in which no growth of bacteria was observed was determined to be MIC. The results are as shown in Tables 7 to 9.

TABLE 7

Synergetic MIC (μg/mL)

| Organism, bacterial strain (Producing enzyme) | Antibiotic | alone | Example 59 | Example 61 | Example 69 | TAZ | NXL104 | MK-7655 |
|---|---|---|---|---|---|---|---|---|
| *P. aeruginosa* PAO1CR (AmpC) | ABPC | >64 | 64 | >64 | >64 | >64 | >64 | >64 |
| | AMPC | >64 | 64 | 64 | 64 | >64 | >64 | 64 |
| | PIPC | >64 | 4 | 4 | 4 | >64 | 8 | 8 |
| | CAZ | 64 | 2 | 2 | 2 | 32 | 2 | 2 |
| | CFPM | 16 | 2 | 2 | 2 | 16 | 2 | 2 |
| | CTX | >64 | 16 | 16 | 16 | >64 | 64 | 16 |
| | CTRX | >64 | 16 | 16 | 8 | >64 | 32 | 16 |
| | IPM | 1 | 0.25 | 0.5 | 0.5 | 1 | 0.25 | 0.25 |
| | BIPM | 0.5 | 0.25 | 0.25 | 0.25 | 0.5 | 0.25 | 0.25 |
| | MEPM | 1 | 0.5 | 0.5 | 1 | 1 | 0.5 | 0.5 |
| | DRPM | 1 | 0.25 | 0.5 | 0.5 | 1 | 0.25 | 0.25 |
| | CMNX | >64 | >64 | >64 | >64 | >64 | >64 | >64 |
| | FMOX | >64 | >64 | >64 | >64 | >64 | >64 | >64 |
| | AZT | 32 | 4 | 4 | 8 | 32 | 8 | 4 |

TABLE 8

Synergetic MIC (μg/mL)

| Organism, bacterial strain (Producing enzyme) | Antibiotic | alone | Example 59 | Example 61 | Example 69 | TAZ | NXL104 | MK-7655 |
|---|---|---|---|---|---|---|---|---|
| *K. pneumoniae* MSC19408 (KPC-2) | ABPC | >64 | ≤0.031 | ≤0.031 | ≤0.031 | >64 | 16 | 64 |
| | AMPC | >64 | ≤0.031 | ≤0.031 | ≤0.031 | >64 | 32 | >64 |
| | PIPC | >64 | ≤0.031 | ≤0.031 | ≤0.031 | >64 | 8 | 32 |
| | CAZ | >64 | ≤0.031 | ≤0.031 | ≤0.031 | >64 | 0.5 | 2 |
| | CFPM | >64 | ≤0.031 | ≤0.031 | ≤0.031 | >64 | ≤0.031 | 0.25 |
| | CTX | >64 | ≤0.031 | ≤0.031 | ≤0.031 | >64 | 0.063 | 0.5 |
| | CTRX | >64 | ≤0.031 | ≤0.031 | ≤0.031 | >64 | 0.063 | 0.5 |
| | IPM | 8 | ≤0.031 | ≤0.031 | ≤0.031 | 4 | 0.125 | 0.063 |
| | BIPM | 16 | ≤0.031 | ≤0.031 | ≤0.031 | 8 | 0.125 | 0.063 |
| | MEPM | 16 | ≤0.031 | ≤0.031 | ≤0.031 | 4 | ≤0.031 | ≤0.031 |
| | DRPM | 8 | ≤0.031 | ≤0.031 | ≤0.031 | 4 | ≤0.031 | ≤0.031 |
| | CMNX | 16 | ≤0.031 | ≤0.031 | ≤0.031 | 16 | 0.25 | 2 |
| | FMOX | >64 | ≤0.031 | ≤0.031 | ≤0.031 | 32 | 0.063 | 0.5 |
| | AZT | >64 | ≤0.031 | ≤0.031 | ≤0.031 | >64 | 0.063 | 0.5 |

TABLE 9

Synergetic MIC (μg/mL)

| Organism, bacterial strain (Producing enzyme) | Antibiotic | alone | Example 59 | Example 61 | Example 69 | TAZ | NXL104 | MK-7655 |
|---|---|---|---|---|---|---|---|---|
| *E. coli* MSC19503 (CTX-M-15, OXA-1) | ABPC | >64 | ≤0.031 | ≤0.031 | ≤0.031 | >64 | 4 | >64 |
| | AMPC | >64 | ≤0.031 | ≤0.031 | ≤0.031 | >64 | 4 | >64 |
| | PIPC | >64 | ≤0.031 | ≤0.031 | ≤0.031 | >64 | 4 | >64 |
| | CAZ | >64 | ≤0.031 | ≤0.031 | ≤0.031 | 0.5 | 0.25 | 1 |
| | CFPM | >64 | ≤0.031 | ≤0.031 | ≤0.031 | 0.25 | ≤0.031 | 0.125 |
| | CTX | >64 | ≤0.031 | ≤0.031 | ≤0.031 | 0.25 | ≤0.031 | 1 |
| | CTRX | >64 | ≤0.031 | ≤0.031 | ≤0.031 | 0.25 | ≤0.031 | 1 |
| | IPM | 0.25 | ≤0.031 | ≤0.031 | ≤0.031 | 0.125 | 0.25 | 0.25 |
| | BIPM | 0.25 | ≤0.031 | ≤0.031 | ≤0.031 | 0.125 | 0.25 | 0.25 |
| | MEPM | ≤0.031 | ≤0.031 | ≤0.031 | ≤0.031 | ≤0.031 | ≤0.031 | ≤0.031 |
| | DRPM | ≤0.031 | ≤0.031 | ≤0.031 | ≤0.031 | ≤0.031 | ≤0.031 | ≤0.031 |
| | CMNX | 1 | ≤0.031 | ≤0.031 | ≤0.031 | 1 | 0.125 | 0.5 |
| | FMOX | 0.25 | ≤0.031 | ≤0.031 | ≤0.031 | 0.25 | ≤0.031 | 0.125 |
| | AZT | >64 | ≤0.031 | ≤0.031 | ≤0.031 | 0.25 | 0.063 | 0.5 |

Example 121

The synergetic effect of the test compounds synthesized in Examples 59, 61, and 69 with a β-lactam agent against bacteria was evaluated using 5 strains from each of KPC-2 or 3 producing strain, *K. pneumoniae*, AmpC constitutively-expressing strain, *P. aeruginosa*, AmpC constitutively-expressing strain, Enterobacteriaceae, IMP type metallo-β-lactamase producing strain, Enterobacteriaceae, CTX-M-15 (ESBL) producing strain, *E. coli*. Using PIPC as a β-lactam agent, MIC of the β-lactam agent was measured by agar plate dilution process based on CLSI process. That is, an agar plate containing 4 μg/mL (final concentration) of test compound, TAZ, NXL104 or MK-7655 and β-lactam agent and test compound at each concentration adjusted in common ratio 2 of dilution series in MHA was made, and bacteria cultured overnight in CAMHB were adjusted in the same medium so as to have $10^4$ CFU/spot and inoculated on a plate containing an agent. This plate containing an agent was cultured overnight at 35° C., and the minimum agent concentration in which no growth of bacteria was observed was determined to be MIC. The results are as shown in Tables 1 to 5.

Example 122

Anti-Tubercle *Bacillus* Activity Measurement

The combinatorial effect of the compound of Example 59 with a β-lactam agent against tubercle *bacillus* was evaluated using clinical isolates of multi-drug resistant tuberculosis (MDR-TB), extensively drug-resistant tuberculosis (XDR-TB), and sensitive tuberculosis (H37Rv). Using meropenem (MEPM), biapenem (BIPM), tebipenem (TBPM, Meiji Seika Pharma), ampicillin (ABPC), amoxicillin (AMPC) as a β-lactam agent, MIC of each β-lactam agent was measured by a liquid medium dilution method based on a process of BrothMIC MTB-I (Kyokuto Pharmaceutical Industrial Co., Ltd.) process. That is, a liquid medium containing 4 μg/mL (final concentration) of the compound of Example 59 and β-lactam agent at each concentration adjusted in common ratio 2 of dilution series in a Middlebrook 7H9 liquid medium (Becton, Dichkinson and Company) containing 5% Bovine serum albmin, 2% Dextrose, 0.005% Bovine liver catalase, and 0.05% Tween-80 was made, and bacterial suspension adjusted to $OD_{660}$=0.16-0.2 was inoculated by 200-fold dilution. This was cultured for 7 days at 37° C. under humidified condition, and the minimum agent concentration in which no growth of bacteria was observed was determined to be MIC.

As a result, the antibacterial activities (μg/mL) of β-lactam agent alone to MDR-TB, XDR-TB, and H37Rv were shown by 16, 4, and 1 for MEPM, 16, 2, and 1 for BIPM, 4, 1, and 0.5 for TBPM, 128, 32, and 16 for ABPC, and 128, 64, and 16 for AMPC, and the antibacterial activities in combinatorial use with the compound of Example 59 were shown by 8, 1, and 0.5 for MEPM, 4, 1, and 1 for BIPM, 2, 0.5, and 0.25 for TBPM, 32, 16, and 2 for ABPC, and 64, 16, and 2 for AMPC.

The invention claimed is:

1. A diazabicyclooctane compound represented by the following formula (I):

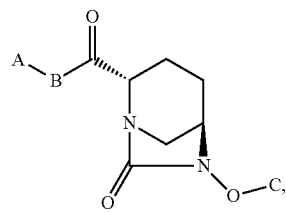

wherein A represents RcO—; B represents NH or $NC_{1-6}$ alkyl; C represents a benzyl group, H or $SO_3M$, wherein M represents H, an inorganic cation or an organic cation; Rc represents a $C_{1-6}$ alkyl group; A is substituted with one substituent Fn1, wherein Fn1 represents an azetidine group; or a pharmaceutically acceptable salt thereof, or a solvate thereof.

2. The compound of claim 1, which further comprises a protecting group $P^1$ and a protecting group $P^3$ and which is represented by a formula selected from the group consisting of

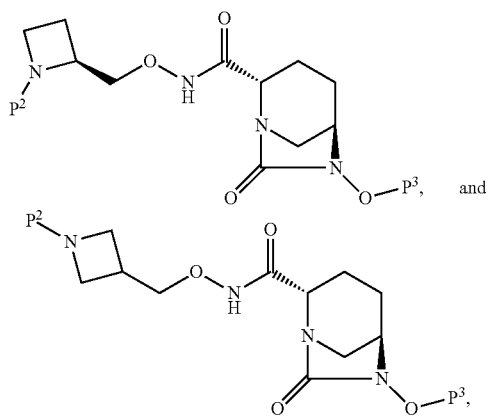

wherein $P^2$ represents tert-butoxycarbonyl, benzyloxycarbonyl or H; $P^3$ represents benzyl, H or $SO_3M$; wherein M represents H, sodium, pyridinium or tetrabutylammonium; or a pharmaceutically acceptable salt thereof, or a solvate thereof.

3. The compound of claim 1, which is selected from the group consisting of
(2S,5R)-N-[(2S)-azetidin-2-ylmethoxy]-7-oxo-6-(sulfooxy)-1,6-diazabicyclo[3.2.1]octane-2-carboxamide and
(2S,5R)-N-(azetidin-3-ylmethoxy)-7-oxo-6-(sulfooxy)-1,6-diazabicyclo[3.2.1]octane-2-carboxamide; or a pharmaceutically acceptable salt thereof, or a solvate thereof.

4. A pharmaceutical composition comprising a pharmaceutically effective amount of the diazabicyclooctane compound represented by the formula (I) of claim 1; or a pharmaceutically acceptable salt thereof, or a solvate thereof, and a pharmaceutically acceptable carrier.

5. A pharmaceutical composition comprising the compound of claim 1 and a β-lactam antibiotic, in a combined pharmaceutically effective amount, and optionally a pharmaceutically acceptable carrier.

6. A method for treating a bacterial infection comprising administering to a patient a pharmaceutically effective amount of the compound of claim 1.

7. The pharmaceutical composition of claim 5, wherein the β-lactam antibiotic is selected from the group consisting of ampicillin, amoxicillin, piperacillin, ticarcillin, flomoxef, cefotaxim, ceftriaxone, ceftazidime, cefepime, ceftaroline, ceftolozane, imipenem, meropenem, biapenem, doripenem, ertapenem and aztreonam.

8. A method for treating a bacterial infection comprising administering to a patient in combination or separately at the same time, the compound of claim 1 and a β-lactam antibiotic, in a pharmaceutically effective amount.

9. The method for treating a bacterial infection of claim 8, wherein the β-lactam antibiotic is selected from the group consisting of ampicillin, amoxicillin, piperacillin, ticarcillin, flomoxef, cefotaxim, ceftriaxone, ceftazidime, cefepime, ceftaroline, ceftolozane, imipenem, meropenem, biapenem, doripenem, ertapenem and aztreonam.

10. The diazabicyclooctane compound of claim 1, wherein the compound is (2S,5R)-N-[(2S)-azetidin-2-ylmethoxy]-7-oxo-6-(sulfooxy)-1,6-diazabicyclo[3.2.1]octane-2-carboxamide.

11. The diazabicyclooctane compound of claim 1, wherein the compound is (2S,5R)-N-[azetidin-3-ylmethoxy]-7-oxo-6-(sulfooxy)-1,6-diazabicyclo[3.2.1]octane-2-carboxamide.

* * * * *